US006271342B1

(12) United States Patent
Lerchen et al.

(10) Patent No.: US 6,271,342 B1
(45) **Date of Patent: *Aug. 7, 2001**

(54) SUGAR-MODIFIED CYTOSTATICS

(75) Inventors: Hans-Georg Lerchen; Karsten von dem Bruch; Uwe Petersen, all of Leverkusen; Jörg Baumgarten, Wuppertal; Norbert Piel, Erkrath; Horst-Peter Antonicek, Bergisch Gladbach; Walter Weichel, Odenthal; Michael Sperzel, Wuppertal; Klaus Dieter Bremm, Recklinghausen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,546

(22) PCT Filed: Mar. 22, 1996

(86) PCT No.: PCT/EP96/01279

§ 371 Date: Sep. 25, 1997

§ 102(e) Date: Sep. 25, 1997

(87) PCT Pub. No.: WO96/31532

PCT Pub. Date: Oct. 10, 1996

(30) Foreign Application Priority Data

Apr. 4, 1995 (DE) ............................................ 195 12 484

(51) Int. Cl.$^7$ .................................................... A61K 38/14

(52) U.S. Cl. ............................ 530/322; 514/25; 514/34; 514/312; 514/19

(58) Field of Search ............................... 514/25, 34, 312; 530/322

(56) References Cited

U.S. PATENT DOCUMENTS

| | | | | |
|---|---|---|---|---|
| 4,757,072 | | 7/1988 | Kabbe et al. | 514/257 |
| 4,975,278 | | 12/1990 | Senter et al. | 424/94.3 |
| 5,399,363 | * | 3/1995 | Liversidge | 424/490 |
| 5,464,796 | | 11/1995 | Petersen et al. | 514/312 |
| 5,561,119 | | 10/1996 | Jacquesy et al. | 514/34 |
| 5,595,732 | * | 1/1997 | Makini | 424/85.7 |
| 5,602,099 | | 2/1997 | Schiller | 514/18 |
| 5,610,145 | | 3/1997 | Horwell et al. | 514/19 |
| 5,614,499 | | 3/1997 | Bylund et al. | 514/19 |
| 5,621,002 | | 4/1997 | Bosslet et al. | 514/451 |
| 5,622,934 | | 4/1997 | Frick et al. | 514/18 |
| 5,624,894 | | 4/1997 | Bodor et al. | 514/2 |
| 5,629,406 | | 5/1997 | Higashida et al. | 530/331 |
| 5,633,232 | | 5/1997 | Matsuo et al. | 514/19 |
| 5,656,722 | | 8/1997 | Dorschug | 530/303 |
| 5,677,286 | * | 10/1997 | Shull | 514/25 |
| 5,741,781 | | 4/1998 | Roques et al. | 514/19 |
| 5,750,648 | | 5/1998 | Chang et al. | 530/331 |
| 5,773,522 | | 6/1998 | Angelucci et al. | 525/329.4 |
| 5,780,589 | | 7/1998 | Lazarus et al. | 530/331 |
| 5,837,685 | | 11/1998 | Strobel et al. | 514/15 |
| 5,872,207 | | 2/1999 | Morgan et al. | 530/300 |
| 6,075,121 | | 6/2000 | Simon et al. | 530/332 |
| 6,143,931 | | 11/2000 | Baldino et al. | 564/123 |

FOREIGN PATENT DOCUMENTS

0097952 * 1/1984 (EP) .

OTHER PUBLICATIONS

Sigma Catalog, p. 447, 1991.*
Chem. Abstr. 100, 192252m, 1984.*
Bradshaw, J. Med. Chem. 37, 1991, 1994.*
Abashev, Bioorg. Khim. 10, 18–24, 1984.*
Proc. Natl. Acad. Sci. USA, vol. 74, Stahl, et al. (1977), p. 1521.
J. Biol. Chem. vol. 243, (1968), p. 155.
Ashwell et al., Annu. Rev. Biochem., vol. 46, (1982), p. 531.
R. Haltiwanger, et al., J. Biol, Chem., vol. 261: 7433–7439 (1986).
R. Jansen, et al., J. Biol. Chem, vol. 266: 3343–3348 (1991).
Derwent abstract of JP 4,253, 973.
Abstract of WO 94/05681 1994.*

* cited by examiner

*Primary Examiner*—Christopher S. F. Low
*Assistant Examiner*—David Lukton
(74) *Attorney, Agent, or Firm*—Norris McLaughlin & Marcus

(57) ABSTRACT

The invention relates to cytostatics which, by modification with sugar, are tumor-specific. Suitable spacers ensure serum stability and at the same time an intracellular action.

9 Claims, 1 Drawing Sheet

SUGAR-MODIFIED CYTOSTATICS

BACKGROUND OF THE INVENTION

Figure 1:
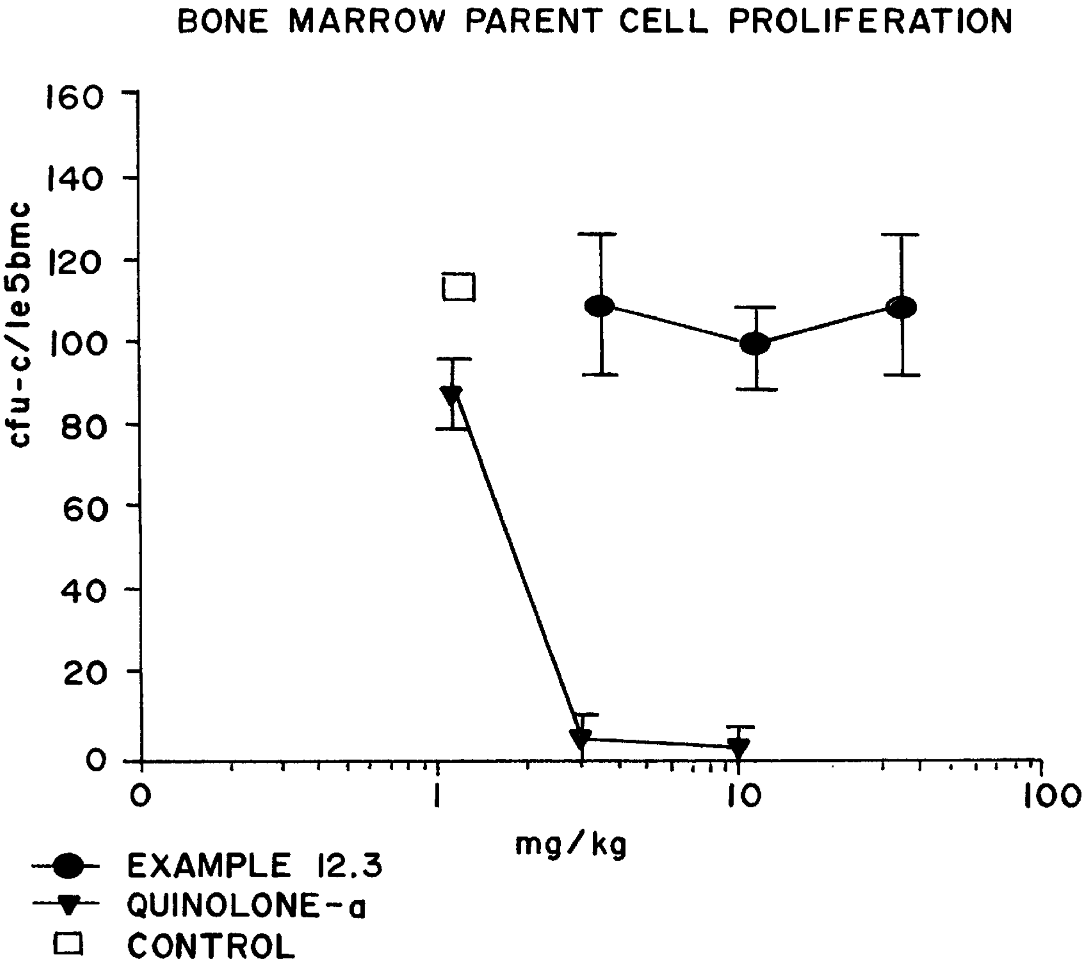

This application is a 371 of PCT/EP96/01279, which was filed on Mar. 11, 1996.

1. Field of the Invention

The invention relates to cytostatics which, due to modification with carbohydrates, are tumour-specific. Suitable spacers ensure serum stability and at the same time an intracellular action.

2. Description of Related Art

Chemotherapy of tumour diseases is accompanied by usually serious side effects caused by the toxicity of chemotherapeutics on proliferating cells of other tissue. For many years, scientists have been addressing the problem of improving the selectivity of the active compounds used. One approach which is often followed is the synthesis of prodrugs, which are liberated more or less selectively in the target tissue, for example by a change in the pH (Tietze et al., for example DE-4 229 903), by enzymes (for example glucuronidases; Jacquesy et al., EP-511 917; Bosslet et al., EP-595 133) or by antibody-enzyme conjugates (Bagshawe et al. WO 88/07378; Senter et al., U.S. Pat. No. 4,975,278; Bosslet et al., EP-595 133). Problems of these approaches are, inter alia, the lack of stability of the conjugates in other tissues and organs and, in particular, the ubiquitous distribution of the active compound, which follows extracellular liberation of the active compound in the tumour tissue.

The pronounced lectin pattern on the surfaces of tumour cells (Gabius; Onkologie 12, (1989), 175) opens up the chief possibility of addressing these specifically on tumour cells by linking the corresponding carbohydrate units to cytostatics. These perspectives are limited by the fact that lectins with similar carbohydrate specificities (galactose, lactose, mannose, N-acetyl-glucosamine, fucose and the like) also occur in other tissues, in particular in the liver (Ashwell et al., Annu. Rev. Biochem. 46 (1982), 531; Stahl et al. Proc. Natl. Acad. Sci. U.S.A. 74 (1977), 1521; Hill et al., J. Biol. Chem. 262 (1986), 7433; Jansen et al., J. Biol. Chem. 266 (1991), 3343). A significant concentration of glycoconjugates containing the active compound in the liver and other lectin-rich organs must consequently be expected if such non-modified sugars are used.

The heterocyclic amine batracyline (1) shows a good antitumoural action in various intestinal cancer models (U.S. Pat. No. 4,757,072).

(1)

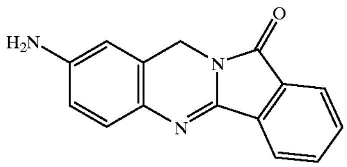

Peptide conjugates of (1) with a good in vitro action and more favourable solubility properties (U.S. Pat. No. 4,180,343) are tolerated more poorly than batracyline in animal studies. The fucose conjugates described in EP-501 250 become very highly concentrated in the liver.

Quinolone-a (2), 7-[(3aRS,4RS,7aSR)-4-amino-1,3,3a,4,7,7a-hexahydro-isoindol-2-yl]-8-chlorol-cyclopropyl-6-fluoro-1,4-dihydro4-oxo-3-quinolinecarboxylic acid also shows, in addition to its outstanding antibacterial activity, a very good activity against various tumour cell lines (EP-520 240, JP-4 253 973). However, this is faced with considerable toxicological problems (for example genotoxicity, bone marrow toxicity, high acute toxicity in vivo and the like).

(2)

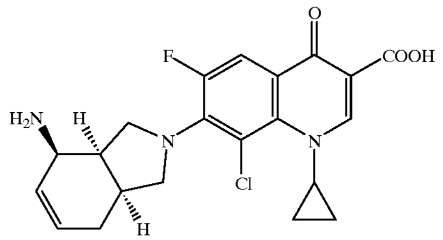

(quinolone-a)

BRIEF SUMMARY OF THE INVENTION

By a novel modification of cytostatics, we have found, surprisingly, a new class of conjugates which are distinguished by the following properties: A novel linkage of carbohydrates with cytostatics (for example batracyline, quinolone-a) leads to glycoconjungates which are serum-stable. The action does not depend on extracellular liberation of the active compound. The in vitro activities against various tumour cell lines are comparable to that of the cytostatic on which they are based. The cell-specific absorption depends on the carbohydrate.

The cell and tissue selectivity (in particular tumour to liver) is significantly improved by the regioselective modifications in the carbohydrate part of the conjugates described.

In vivo, the conjugates according to the invention are distinguished by a significantly improved tolerance compared to the active compound and the corresponding peptide conjugates.

Furthermore, in comparison with the cytostatics on which they are based, the conjugates according to the invention show considerably improved solubility properties.

DETAILED DESCRIPTION OF THE DRAWING

FIG. 1 is a graph showing lack of inhibition of bone marrow parent cell proliferation.

DETAILED DESCRIPTION OF THE INVENTION

The compounds according to the invention are described by the following general formula:

K-Sp-L-AA1-AA2-C (I)

where

K=an unsubstituted or regioselectively modified carbohydrate radical,

Sp=optionally substituted arylene or alkylene,

L= 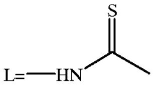 or 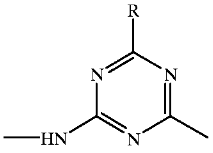

where

R=chlorine or hydroxyalkylamino, the linkage to Sp being via the NH group.

AA1 is an amino acid radical in the D or L configuration, which optionally carries a second grouping K-Sp-L-, in which K, Sp and L, independently of the other grouping K-Sp-L-, can have the abovementioned meanings, or a direct bond. An amino acid radical can be linked to L both via the α-amino group and, where appropriate, via side chain amino or hydroxyl functions, and also via both functions. If AA1 carries further functional groups, these can be present in deblocked form or in a form protected with known protective groups. Suitable protective groups are, for example, acetyl, allyloxycarbonyl, benzyloxycarbonyl, fluorenylmethoxycarbonyl, t-butoxycarbonyl, allyl, benzyl, methyl or tert-butyl.

AA2 is an amino acid radical in the D or L configuration, which optionally carries a second grouping K-Sp-L-, in which K, Sp and L, independently of the other grouping K-Sp-L-, can have the abovementioned meanings, or a direct bond. An amino acid radical can be linked to AA1 both via the α-amino group and, where appropriate, via side chain amino or hydroxyl functions, and also via both functions. If AA2 carries further functional groups, these can be present in deblocked form or in a form protected with known protective groups. Suitable protective groups are, for example, benzyloxycarbonyl, acetyl, allyloxycarbonyl, fluorenylmethoxycarbonyl, t-butoxycarbonyl, allyl, benzyl, methyl or tert-butyl.

C=radicals of a cytostatic or of a cytostatic derivative, which can additionally carry an amino or hydroxyl group. C can be an intercalating substance, a topoisomerase inhibitor, an antimetabolite, an alkylating agent, a tubulin inhibitor, a tyrosine phosphokinase inhibitor, a protein kinase-C-inhibitor or an active compound with another or an unknown cytostatic or cytotoxic action mechanism. C can be, for example, a nucleoside, an endiine antibiotic, a quinolone- or naphthyridone-carboxylic acid or a cytotoxic peptide antibiotic, for example from the class of dolastatins. C can be batracyline, quinolone-a, 5-fluorouracil, cytosine arabinoside, methotrexate, etoposide, camptothecin, daunomycin, doxorubicin, taxol, vinblastine, vincristine, dynemycin, calicheamycin, esperamycin, quercetin, suramin, erbstatin, cyclophosphamide, mitamycin C, melphalan, cisplatin, bleomycin, staurosporin or another active compound having an antineoplastic action.

The structural element -Sp-L-AA1-AA2- in total represents the spacer which connects K and C.

Preferred compounds of the formula (I) are those in which K=a carbohydrate radical having the general formula (II)

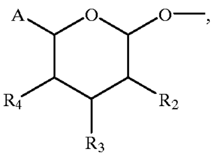

wherein

A=methyl, hydroxymethyl, carboxyl and esters and amides derived therefrom, alkoxymethyl, acyloxymethyl or carboxyalkyloxymethyl and esters and amides derived therefrom. A can also be $CH_2$—B, wherein B in turn can be a carbohydrate radical of the general formula (II) linked via the anomeric centre.

$R_2$, $R_3$, $R_4$=individually or together at the same time, H, hydroxyl, alkyloxy, carboxyalkyloxy and esters and amides derived therefrom, hydroxyalkyloxy, aminoalkyloxy, acyloxy, carboxyalkylcarbonyloxy, sulphato, phosphate, halogen or another carbohydrate radical (II) modified in the same framework and linked via the anomeric centre. $R_2$ can additionally also be amino or acylamino.

Two of the radicals $R_2$, $R_3$ or $R_4$ together can also denote an epoxide group.

The stereochemistry on the anomeric centre of the carbohydrate structural unit can be α or β. The gluco, manno, galacto, gulo, rhamno or fuco configuration can result from the stereochemistry on the other centres.

Sp=an arylene radical which is modified with K and L in the ortho-, meta- or para-position and furthermore can also carry 1 to 4 further substituents which, independently of one another or in an identical manner, can be H, methyl, methoxy, hydroxyl, carboxyl, methoxycarbonyl, cyano, nitro, halogen, sulphonyl or sulphonamide;

Sp can also be a linear or branched alkylene radical.

L= 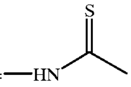 or 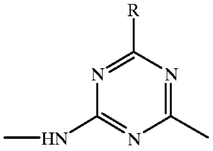

where

R=chlorine or hydroxyalkylamino,

AA1 is an amino acid radical in the D or L configuration, which optionally carries a second grouping K-Sp-L-, in which K, Sp and L, independently of the other grouping K-Sp-L-, can have the abovementioned meanings, or a direct bond. An amino acid radical can be linked with L both via the α-amino group and, where appropriate, via side chain amino or hydroxyl functions and also via both functions. If AA1 carries further functional groups, these can be present in deblocked form or in a form protected with known protective groups. Suitable protective groups are, for example, acetyl, allyloxycarbonyl, benzyloxycarbonyl, fluorenylmethoxycarbonyl, t-butoxycarbonyl, allyl, benzyl, methyl or tert-butyl.

AA2 is an amino acid radical in the D or L configuration, which optionally carries a second grouping K-Sp-L-, in which K, Sp and L, independently of the other grouping K-Sp-L-, can have the abovementioned meanings, or a direct bond. An amino acid radical can be linked with AA1 both via the α-amino group and, where appropriate, via side chain amino or hydroxyl functions, and also via both functions. If AA2 carries further functional groups, these can be present in deblocked form or in a form protected with known protective groups. Suitable protective groups are, for example, benzyloxycarbonyl, allyloxycarbonyl, acetyl, fluorenylmethoxycarbonyl, t-butoxycarbonyl, allyl, benzyl, methyl or tert-butyl.

C can be, for example, the radical of a nucleoside, an endiine antibiotic or a cytotoxic peptide antibiotic, for example from the class of dolastatins, or a quinolone- or naphthyridonecarboxylic acid as defined below. C can be, for example, batracyline, 5-fluorouracil, cytosine arabinoside, methotrexate, etoposide, camptothecin, daunomycin, doxorubicin, taxol, vinblastine, vincristine, dynemycin, calicheamycin, esperamycin, quercetin, suramin, erbstatin, cyclophosphamide, mitamycin C, melphalan, cisplatin, bleomycin, staurosporin or another active compound having an antineoplastic action. The cytostatic is linked with AA2 via amino or hydroxyl functions.

Especially preferred compounds of the formula (I) are those in which

K=a carbohydrate radical of the general formula (II)

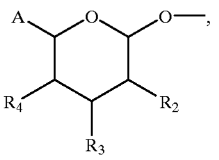

wherein

A=methyl, hydroxymethyl, carboxyl and methoxycarbonylmethyl and $CH_2$—B, wherein B in turn can be a carbohydrate radical of the general formula (II) linked via the anomeric centre.

$R_2$, $R_3$ and $R_4$=individually or together at the same time, H, hydroxyl, $C_1$–$C_3$-alkyloxy, carboxy-$C_1$–$C_3$-alkyloxy and $C_1$–$C_3$-alkyl esters and amides derived therefrom, hydroxyalkyloxy, acyloxy, carboxy-($C_1$–$C_3$-alkyl)-carbonyloxy, sulphato or another carbohydrate radical in position $R_3$ or $R_4$ linked via the anomeric centre.

Two of the radicals $R_2$, $R_3$ and $R_4$ together can also denote an epoxide group.

The stereochemistry on the anomeric centre can be α or β. The D-manno, D-galacto, L-gulo, D-gluco, L-rhamno or L-fuco configuration can result from the stereochemistry on the other centres.

Sp=an arylene radical which is modified with K and L in the ortho- or para-position and furthermore can also carry, in addition to hydrogen atoms, a further substituent, which can be methoxy, nitro or chlorine;

L= 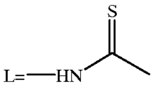 or 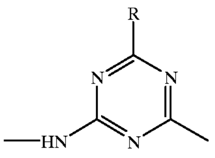

where

R=chlorine or hydroxyalkylamino.

AA1 is an amino acid radical, such as lysine, alanine, aspartic acid, glutamic acid, glycine, ornithine, tyrosine, valine or serine in the D or L configuration, or a direct bond. The amino acid radical can be linked with L both via the α-amino group and, where appropriate, via the side chain amino functions, and also via both functions, and thus optionally carries a further grouping K-Sp-L-, which is identical to or different from the first. If AA1 carries further functional groups, these are preferably deblocked.

AA2 is an amino acid radical, such as alanine, lysine, glycine, serine, ornithine or diaminopropionic acid in the D or L configuration, or a direct bond. The amino acid radical can be linked with AA1 both via the α-amino group and, where appropriate, via the side chain amino functions, and also via both functions, and can thus optionally carry a further grouping K-Sp-L-, which is identical to or different from the first. If AA2 carries further functional groups, these are preferably deblocked.

C can be batracyline, methotrexate, quinolone-a, etoposide, melphalan, taxol, camptothecin, daunomycin or doxorubicin or a quinolone- or naphthyridonecarboxylic acid as defined below. The cytostatic is linked with AA2 via an amino or hydroxyl function.

The quinolone- or naphthyridonecarboxylic acid structural units C used as educts can be represented by the general structure of the formula (III)

T-Q (III)

in which

Q denotes a radical of the formulae

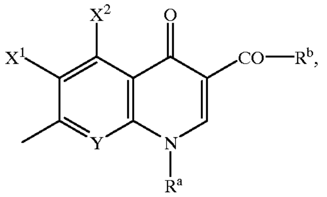

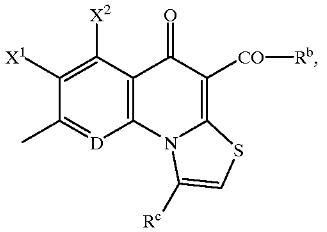

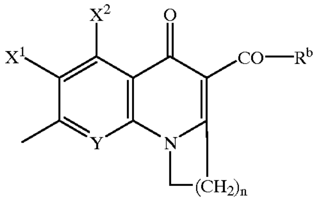 or

-continued

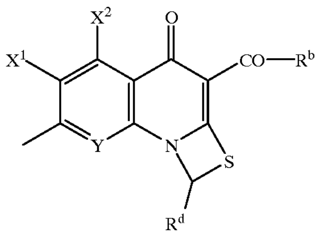

wherein $R^a$ represents alkyl which has 1 to 4 carbon atoms and is optionally mono- or disubstituted by halogen or hydroxyl, vinyl, cycloalkyl which has 3 to 6 carbon atoms and is optionally substituted by 1 or 2 fluorine atoms, bicyclo[1.1.1]pent-1-yl, 1,1-dimethylpropargyl, 3-oxetanyl, methoxy, amino, methylamino, dimethylamino or phenyl which is optionally mono- or disubstituted by halogen, amino or hydroxyl, or, together with $R^e$, can also form a bridge described for that radical, $R^b$ represents hydroxyl, alkoxy having 1 to 3 carbon atoms or nitromethyl, $R^c$ represents hydrogen or methyl or, together with $R^g$, can also form a bridge described for that radical, $R^d$ represents hydrogen, $CH_3$, $CH_2F$ or $=CH_2$, $X^1$ represents hydrogen, halogen or nitro, $X^2$ represents hydrogen, halogen, amino, hydroxyl, methoxy, mercapto, methyl, halogenomethyl or vinyl, Y represents N or C—$R^e$, wherein $R^e$ represents hydrogen, halogen, $CF_3$, $OCH_3$, $OCHF_2$, $CH_3$, CN, CH═$CH_2$ or C═CH, or, together with $R^a$, can also form a bridge of the structure —*O—$CH_2$—CH—$CH_3$, —*S—$CH_2$—$CH_2$—, —*S—$CH_2$—CH—$CH_3$, —*$CH_2$—$CH_2$—CH-$CH_3$ or —*O—$CH_2$—N—$R^f$, wherein the atom marked with is linked with the carbon atom of Y and wherein $R^f$ denotes hydrogen, methyl or formyl, and D represents N or C—$R^g$, wherein $R^g$ represents hydrogen, halogen, $CF_3$, $OCH_3$, $OCHF_2$ or $CH_3$, or, together with $R^c$, can also form a bridge of the structure —*O—$CH_2$—, —*NH—$CH_2$—, —*N($CH_3$)—$CH_2$—, —*N($C_2H_5$)—$CH_2$—, —*N($C_3H_5$)—$CH_2$— or —*S—$CH_2$—, wherein the atom marked with * is linked with the carbon atom of D, n denotes 1, 2 or 3 and T denotes a radical of the formula

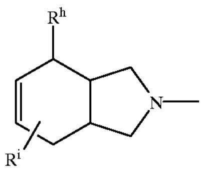

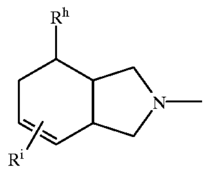

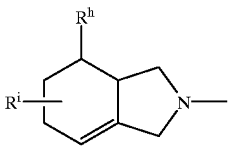

wherein $R^h$ represents

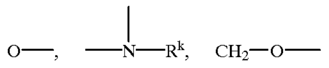

or

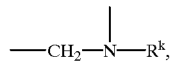

wherein $R^k$ represents hydrogen or methyl and $R^i$ represents hydrogen, $C_1$–$C_3$-alkyl or cyclopropyl.

Compounds of the formula (III) which are particularly preferred as the cytostatic C are those in which Q denotes a radical of the formula

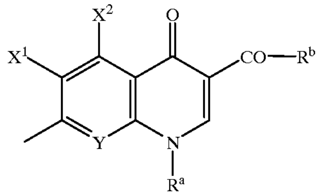

or

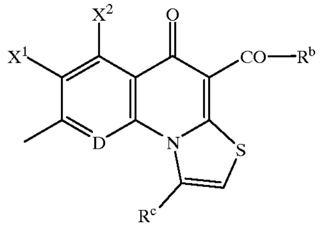

wherein $R^a$ represents alkyl which has 2 to 4 carbon atoms and is optionally substituted by 1 fluorine atom, cyclopropyl which is optionally substituted by 1 fluorine atom or phenyl which is optionally mono- or disubstituted by fluorine, $R^b$ represents hydroxyl or alkoxy having 1 or 2 carbon atoms, $R^c$ represents hydrogen or methyl, or, together with $R^g$, can form a bridge described for that radical, $X^1$ represents fluorine, $X^2$ represents hydrogen or amino, Y represents N or C—$R^e$, wherein $R^e$ represents hydrogen, fluorine, chlorine, $CF_3$, $OCH_3$, $OCHF_2$ or C≡CH, or, together with $R^a$, can form a bridge of the structure —*O—$CH_2$—CH—$CH_3$ or —*O—$CH_2$—N—$R^f$, wherein the atom marked with * is linked with the carbon atom of Y and wherein $R^f$ denotes methyl, D represents N or C—$R^g$, wherein $R^g$ represents hydrogen, fluorine, chlorine, $CF_3$, $OCH_3$ or $CH_3$, or, together with $R^e$, also form a bridge of the structure —*O—$CH_2$—, —*N—$CH_2$—, —N($CH_3$)—$CH_2$— or —*S—$CH_2$—, wherein the atom marked with is linked with the carbon atom of D, and T denotes a radical of the formula

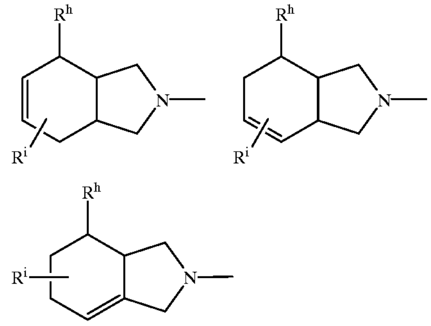

wherein $R^h$ represents

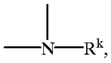, wherein $R^k$ represents hydrogen or methyl, and $R^i$ represents hydrogen or methyl.

Glycoconjugates with camptothecin or derivatives thereof are likewise particularly preferred.

The compounds of the general formula I in which K, Sp and L denote hydrogen and

C represents camptothecin are furthermore of particular importance. These substances are new and can be reacted as intermediate products to give further derivatives of the general formula I, and in turn also show an interesting pharmaceutical action spectrum, in particular as cytostatics.

The compounds according to the invention can be in stereoisomeric forms, for example as enantiomers or diastereomers, or in the form of mixtures thereof, for example as a racemate. The invention relates both to the pure stereoisomers and to mixtures thereof.

If necessary, the stereoisomer mixtures can be separated into the stereoisomerically uniform constituents in a known manner, for example, by chromatography or by crystallization processes.

The compounds according to the invention can also be in the form of their salts. Salts with organic or inorganic bases or acids and inner salts may be mentioned in general here.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Physiologically acceptable salts can likewise be metal or ammonium salts of the compounds according to the invention which have a free carboxyl group. Particularly preferred salts are, for example, sodium, potassium, magnesium or calcium salts, and ammonium salts which are derived from ammonia or organic amines, such as, for example, ethylamine, di- or triethylamine, di- or triethanolamine, dicyclohexylamine, dimethylaminoethanol, arginine, lysine, ethylenediamine or phenethylamine.

EXAMPLE SERIES A

Biological Testing

EXAMPLE A.1

Growth Inhibition Test for Determination of the Cytotoxic Properties of Glycoconjugates of Batracyline and of Quinolone-a The human colon cell lines SW 480 and HT 29 (ATCC no. CCL 228 and HBT-38) and the mouse melanoma cell line B 16 F 10 were cultured in Roux dishes in RPMI 1640 medium with addition of 10% FCS. The cultures were then trypsinized and taken up in RPMI plus 10% FCS to a cell count of 50,000 cells/ml. 100 μl of cell suspension/well were introduced into a 96 microwell plate and incubated for 1 day at 37° C. in a $CO_2$ incubating cabinet. A further 100 μl of RPMI medium and 1 μl of dimethyl sulphoxide with the test substances were then added. The growth was checked after day 3 and day 6. 40 μl of MTT solution (3-(4,5-dimethylthiazol-2-yl)-2,5-diphenyltetrazoline bromide) with an initial concentration of 5 mg/ml of $H_2O$ were added to each microwave. The plate was incubated for 5 hours in a $CO_2$ incubating cabinet at 37° C. The medium was then sucked off and 100 μl of i-propanol/well were added. After shaking for 30 minutes with 100 μl of $H_2O$, the extinction was measured at 540 nm with a Titertek Multiskan MCC/340 (Flow).

The cytotoxic action of the glycoconjugates of batracyline described is shown in Table 1a as the $IC_{50}$ value in each case for the SW 480 and HT 29 cell lines.

The $IC_{50}$ values for the quinolone-a glycoconjugates on the SW 480, HT 29 and B 16 F 10 cell lines are summarized in Table 1b.

TABLE 1a

| Substance | $IC_{50}$ [μM] SW 480 | $IC_{50}$[μM] HT 29 |
|---|---|---|
| Batracyline | 25 | 20 |
| 3.2 | 100 | 75 |
| 3.4 | 100 | 65 |
| 3.7 | 55 | n.m |
| 3.9 | 40 | 55 |
| 3.10 | 100 | 125 |
| 3.11 | 85 | n.m. |
| 3.14 | 40 | n.m. |
| 3.18 | 15 | n.m. |
| 3.19 | 75 | n.m. |
| 3.20 | 100 | n.m. |
| 3.21 | 90 | n.m. |
| 3.23 | 50 | n.m. |
| 3.24 | 95 | n.m. |
| 3.26 | 50 | n.m. |
| 3.27 | 110 | n.m. |
| 3.28 | 60 | n.m. |
| 3.29 | 110 | n.m. |
| 3.30 | >250 | n.m. |
| 3.33 | 90 | 70 |
| 4.1 | 25 | 30 |
| 4.3 | 20 | 20 |
| 4.4 | 30 | 25 |
| 4.5 | 15 | 15 |
| 4.6 | 10 | 10 |
| 4.7 | 15 | 15 |
| 4.8 | 50 | 40 |
| 4.9 | 20 | 30 |
| 4.10 | 30 | 30 |
| 4.11 | 15 | 15 |
| 4.12 | 15 | 9 |
| 5.1 | 55 | 45 |
| 5.2 | 20 | 55 |
| 5.6 | >250 | n.m. |
| 5.8 | 100 | >250 |

TABLE 1a-continued

| Substance | $IC_{50}$ [$\mu$M] SW 480 | $IC_{50}$[$\mu$M] HT 29 |
|---|---|---|
| 5.9 | 70 | 70 |
| 5.12 | 20 | 20 |
| 5.13 | 20 | 40 |
| 5.14 | 20 | 30 |
| 5.15 | >250 | 70 |
| 5.19 | 35 | 25 |
| 5.20 | 50 | 30 |
| 5.21 | 60 | 80 |
| 5.22 | 30 | 40 |
| 5.23 | 25 | 35 |
| 6.2 | 40 | 50 |
| 6.3 | 70 | 105 |
| 6.7 | 60 | >250 |
| 6.10 | 50 | 50 |
| 6.12 | 35 | 50 |
| 6.15 | >250 | >250 |
| 6.20 | 80 | n.m. |
| 6.21 | 150 | n.m. |
| 6.23 | 107 | 45 |
| 6.25 | 50 | 40 |
| 6.28 | 40 | 25 |
| 6.29 | 95 | 130 |
| 6.30 | 60 | 70 |
| 6.32 | 60 | 60 |
| 6.34 | 50 | n.m. |
| 6.35 | 20 | n.m. |
| 6.36 | 70 | 70 |
| 6.40 | 170 | 60 |
| 6.43 | 90 | 80 |
| 6.46 | 120 | 100 |
| 6.59 | 50 | 50 |
| 6.60 | 50 | 40 |
| 6.80 | 40 | 25 |
| 6.81 | 30 | 30 |
| 6.82 | 125 | n.m. |
| 6.83 | 90 | n.m. |
| 6.85 | 22 | n.m. |
| 7.1 | 40 | 40 |
| 7.2 | 40 | 30 |
| 7.3 | 50 | n.m. |
| 7.5 | 80 | n.m. |
| 7.7 | 100 | >250 |
| 7.8 | 40 | 30 |
| 7.11 | 30 | 25 |
| 7.12 | 10 | 10 |
| 8.10 | 70 | n.m. |
| 8.11 | 45 | n.m. |
| 8.12 | 30 | n.m. |

TABLE 1b

| Substance | $IC_{50}$[$\mu$M] SW 480 | $IC_{50}$[$\mu$M] HT 29 | $IC_{50}$[$\mu$M] B 16 F 10 |
|---|---|---|---|
| 10.1 | 50 | >250 | 15 |
| 10.2 | 4 | 3 | 5 |
| 10.3 | 5 | 4 | 0.7 |
| 11.2 | 30 | n.m. | 9 |
| 11.6 | 8 | 9 | 5 |
| 11.7 | 12 | 13 | 15 |
| 11.8 | 12 | 16 | 15 |
| 11.9 | 12 | 12 | 9 |
| 11.10 | 8 | 20 | 2 |
| 11.16 | 10 | 10 | 1.5 |
| 11.17 | 75 | 75 | 8 |
| 11.18 | 4.5 | 3.5 | 0.5 |
| 12.1 | 1 | 1.5 | 0.1 |
| 12.2 | 4 | n.d. | 0.8 |
| 12.3 | 2 | n.d. | 0.3 |
| 12.5 | 1 | 4 | 0.2 |
| 12.6 | 4 | 7 | 0.3 |
| 12.7 | 60 | >250 | 20 |
| 12.8 | 8 | 7 | 1 |

TABLE 1b-continued

| Substance | $IC_{50}$[$\mu$M] SW 480 | $IC_{50}$[$\mu$M] HT 29 | $IC_{50}$[$\mu$M] B 16 F 10 |
|---|---|---|---|
| 12.9 | 4 | 8 | 2 |
| 12.10 | 15 | 15 | 4 |
| 12.11 | 2 | 2 | 0.5 |
| 12.12 | 8 | 13 | 0.5 |
| 12.13 | 35 | 100 | 1 |
| 12.14 | 1 | 2 | 0.3 |
| 12.15 | 0.3 | 1 | 0.1 |
| 14.1 | 0.8 | 1 | 1.5 |
| 14.2 | 1 | 6 | 1.5 |
| 14.3 | 8 | 4 | 4 |
| 14.4 | 1.5 | 1 | 0.4 |
| 15.1 | 20 | 20 | 2 |
| 15.2 | 50 | 70 | 15 |
| 16.1 | 50 | 100 | 200 |
| 16.2 | 50 | 60 | 80 |
| 17.1 | 10 | 5 | 5 |
| 17.2 | 4 | 4 | 4 |
| 18.1 | 0.03 | 0.01 | 0.2 |
| 18.2 | 0.02 | 0.02 | 0.2 |
| 18.4 | 0.02 | 0.02 | 0.3 |
| 18.5 | 0.2 | 0.2 | 1 |
| 18.9 | 0.08 | 0.06 | 0.7 |
| 18.14 | 0.015 | 0.01 | 0.08 |

The dependence of the biological action on the carbohydrate is additionally demonstrated by the inactivity of the carbohydrate-free comparison compounds N-[$N^{\alpha}$,$N^{\epsilon}$-bis-(4-hydroxyphenylamino-thiocarbonyl)-lysyl]-batracyline and N-[$N^{\alpha}$,$N^{\epsilon}$-bis-(4-hydroxyphenylamino-thiocarbonyl)-lysyl-D-alanyl]-batracyline and N-[$N^{\alpha}$,$N^{\epsilon}$-bis-(4-hydroxyphenylamino-thiocarbonyl)-D-lysyl-quinolone-a ($IC_{50}$ values>250), on which Example series 5, 6 and 11 are based.

EXAMPLE A.2

In Vitro Investigation of the Cleavability of the Glycoconjugates

Cleavage Kinetics With Human Blood 1.225 ml of human blood are incubated together with 1.25 ml of PBS and 25 $\mu$l of a substrate stock solution (1 mg/ml in 3% dimethyl sulphoxide in PBS) at 37° C. After 1 hour and 24 hours, samples of in each case 1 ml are taken, mixed with 1 ml of ethanol and left to stand at 4° C. for 20 minutes. After centrifugation (5 minutes at 3500 rpm), 100 $\mu$l of supernatant are taken for the HPLC analysis.

Cleavage Kinetics With Cells 2.25 ml of PBS are incubated together with 225 $\mu$l of a cell suspension (30 mg/ml) and 25 $\mu$l of substrate stock solution (1 mg/ml in 3% dimethyl sulphoxide in PBS) at 37° C. After 1 hour and 24 hours, samples of in each case 1 ml are taken, mixed with 1 ml of ethanol and left to stand at 4° C. for 20 minutes. After centrifugation (5 minutes at 3500 rpm), 100 $\mu$l of supernatant are taken for the HPLC analysis.

HPLC Conditions

Apparatus:
 Waters unit
Column:
 Bischoff Hypersil OCS RP 18 5 $\mu$m 250×4 mm
Eluent:
 A: 10 mM potassium phosphate buffer, pH 4.5
 B: 80% acetonitrile/20% water
Flow:
 1 ml/minute Wavelength:
372 nm
Gradient:
0 minute 10% B
10 minutes 60% B
15 minutes 60% B
18 minutes 10% B
20 minutes 60% B Eluent for Quinolone-a Conjugates A: 100% methanol B: 10 mM potassium phosphate buffer, pH 2.2; 10 mM heptanesulphonic acid TABLE 2a

| Exam- | % cleavage in human blood | | % cleavage in SW-480 | | % cleavage in hepatoma | |
|---|---|---|---|---|---|---|
| ple | 1 hour | 24 hours | 1 hour | 24 hours | 1 hour | 24 hours |
| 3.4 | n.d. | n.d. | 74* | n.d. | 98* | n.d. |
| 3.9 | 0 | 54* | 28* | 100* | 32* | 100* |
| 4.4 | 0 | 0 | 0 | 0 | 0 | 0 |
| 5.9 | 0 | 0 | 0 | 0 | 0 | 0 |
| 6.2 | n.d. | n.d. | 0 | 0 | 0 | 0 |
| 6.12 | n.d. | n.d. | 0 | 0 | 0 | 0 |
| 7.3 | 0 | 0 | 0 | 0 | 0 | 0 |

*Cleavage product is N-[D-alanyl]-batracyline

TABLE 2b

| Exam- | % cleavage in human blood | | % cleavage in SW-480 | | % cleavage in hepatoma | |
|---|---|---|---|---|---|---|
| ple | 1 hour | 24 hours | 1 hour | 24 hours | 1 hour | 24 hours |
| 11.2 | 0 | 0 | 0 | 0 | 0 | 0 |
| 11.6 | 0 | 11% | 0 | 8% | 0 | 12% |
| 11.7 | 0 | 0 | 0 | 0 | 0 | 0 |
| 12.1 | 0 | 0 | 0 | 0 | 0 | 0 |
| 12.3 | 0 | 0 | 0 | 0 | 0 | 0 |
| 12.8 | 0 | 0 | 0 | 0 | 0 | 0 |

EXAMPLE A.3

Investigation of Organ Distribution

Athymic naked mice (strain NMRI nu/nu) bred in "Drug Development Laboratory, Oncotest GmbH", Prof. H. H. Fiebig, Freiburg, were used for all the experiments. The animals were kept in Macrolon cages under laminar flow conditions. Tissue of the cell line SW 480 which had been grown beforehand in several passages in the naked mice, was used as the tumour material.

Two tumours per animal were implanted subcutaneously in the two flanks of the naked mice 6 to 8 weeks old. The animals were kept for 26 to 27 days until the time of randomization. The average tumour size was then 500 mg, corresponding to a tumour diameter of about 10 mm.

The pharmacokinetics themselves proceeded as follows: the substance to be investigated was injected into the naked mice and the mice were then put back in the cages until samples were taken after ½ hour and after 4 hours. The taking of samples itself began with sampling of blood. For this, the mouse was anaesthetized by means of anaesthetic ether (duration ½ to one minute). 0.5 hour and 4 hours after injection of the substance, the abdominal cavity was opened and the mouse was exsanguinated under anaesthesia via the Vena cava caudalis in the course of 1 to 2 minutes and then sacrificed by breaking its neck. As a result, central circulatory arrest occurred and organ perfusion was suppressed.

The individual organs were then exposed and removed, an operation which took about 5 minutes. Immediately thereafter, the organ samples and then the remainder of the body were weighed and frozen in liquid nitrogen.

The substance "conjugate 1" is administered i.p. in an amount of 300 mg/kg of body weight and the substance "conjugate 2" is administered i.v. into the tail vein in an amount of 100 mg/kg. 5 animals are used per substance and time.

The distribution results are summarized in Table 3 for conjugate 1 and in Table 4 for conjugate 2.

A. Calibration Series 5, 10, 50, 100 and 200 μg of substance, dissolved in ethanol/water (1:1, v/v) were added to 1 g of bovine liver. The samples were then ground in a mortar with 1 g of sea sand and 2.5 ml of cooled ethanol/water (1:1, v/v) and centrifuged at 3500 rpm for 2 minutes. After removal of the supernatant, the residue was again mixed with 2.5 ml of ethanol/water and centrifuged and the supernatants were combined. In each case 100 μl were taken and analyzed by HPLC.

HPLC Conditions

Apparatus:
Waters unit
Column:
Bischoff Hypersil OCS RP 18 5 μm 250×4 mm
Eluent:
A: 80% acetonitrile/20% water
B: 10 mM potassium phosphate buffer, pH 4.5
Gradient:
0 minute 90% B
10 minutes 40% B
15 minutes 40% B
18 minutes 90% B
20 minutes 90% B
Flow:
1 ml/minute
Wavelength:
372 nm B. Working up of the Organs The organs were worked up analogously to A, the entire organs being broken down with 2.5 ml of ethanol/water and extracted.

C. Working up of the Blood

The amount of blood taken was mixed with 2 ml of ethanol/water (1:1, v/v) and centrifuged for 2 minutes at 3500 rpm, and the supernatant was decanted. 2 ml of ethanol/water (1:1, v/v) were again added to the residue, the mixture was centrifuged and the supernatants were combined. In each case 100 μl of the combined supernatants were analyzed by HPLC. The HPLC conditions used under A were used.

Conjugate 1 (EP 501 250-A1)

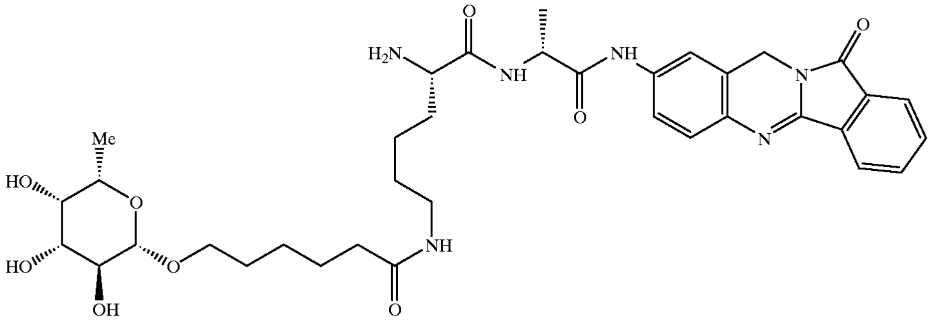

Conjugate 1 (EP 501 250-A1)

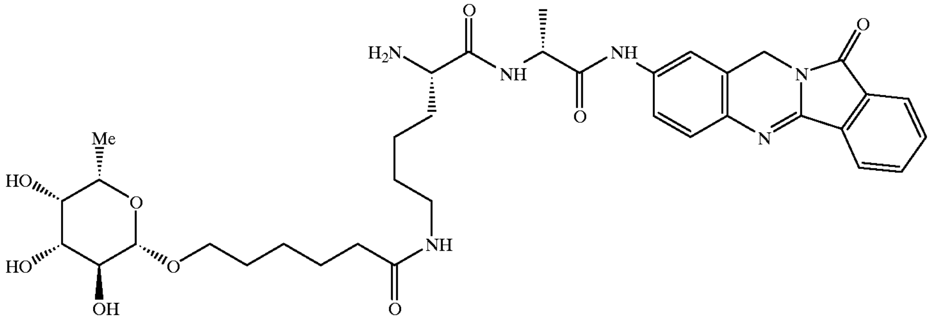

Conjugate 2 (Example 3.9)

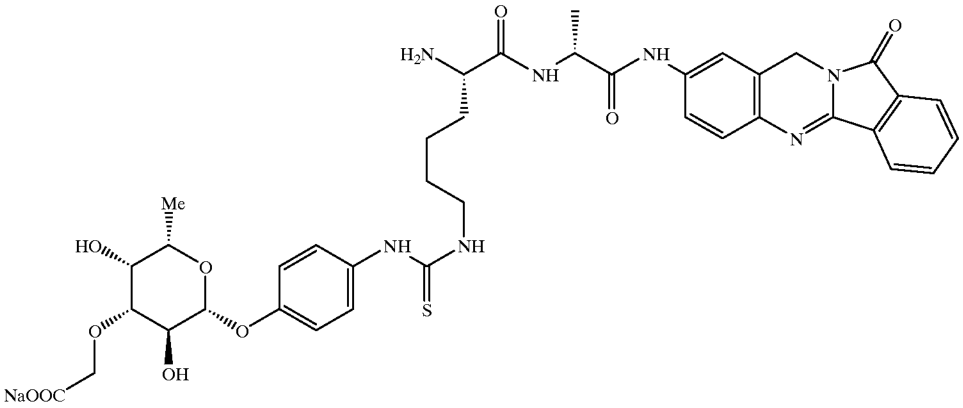

TABLE 3

| Organ | Substance | Evaluation of organ samples Mean 1 hour (μg/g of organ) | Mean 4 hours (μg/g of organ) |
|---|---|---|---|
| Blood | Conjugate 1 | 31.2 | — |
| | Batracyline | — | — |
| Tumour | Conjugate 1 | 56.6 | 24.4 |
| | Batracyline | — | — |
| Liver | Conjugate 1 | 770 | 126 |
| | Batracyline | 34.1 | 22.4 |
| Kidney | Conjugate 1 | 81 | 78.4 |
| | Batracyline | 26.1 | 27.5 |
| Brain | Conjugate 1 | — | — |
| | Batracyline | — | — |

TABLE 4

| Organ | Substance | Evaluation of organ samples Mean 0.5 hour (μg/g of organ) | Mean 4 hours (μg/g of organ) |
|---|---|---|---|
| Blood | Conjugate 2 | 6.5 | — |
| | Batracyline | — | — |
| Tumour | Conjugate 2 | 2.0 | — |
| | Batracyline | 2.5 | 3.12 |
| Liver | Conjugate 2 | 0.9 | 1.2 |
| | Batracyline | — | — |
| Kidney | Conjugate 2 | 17.5 | 0.5 |
| | Batracyline | 10.7 | 0.8 |
| Brain | Conjugate 2 | — | — |
| | Batracyline | — | — |

EXAMPLE A.4

Determination of the Acute Toxicity of Glycoconjugates of Batracyline (Single Administration)

The acute toxicity of the batracyline derivatives was determined on nu/nu naked mice.

The substances administered i.v., as aqueous solutions, and the substances administered i.p., as solutions in dimethyl sulphoxide, were injected once in concentrations of up to 400 mg of substance per kg of mouse.

The individual dose tolerated was calculated from the decrease in the weight of the animals up to 21 days after administration and from the number of animals surviving.

The individual dose of the substances which can be tolerated can be seen from Table 5.

For substances 3.16; 3.33; 3.9; 6.12; 6.14; 6.2; 6.81; and 8.2 it was more than 200 mg of substance per kg of mouse. For substances 3.33; 6.12; 6.14; 6.2; and 6.81, still no acute toxicity was to be detected even with a dose of 400 mg/kg.

In contrast, sugar-free lysyl-D-alanyl-batracyline (2.13) was already significantly toxic at individual doses of between 25 and 50 mg/kg of mouse.

TABLE 5

Maximum individual dose of batracyline derivatives and quinolone-a derivatives which can be tolerated

| Example | Individual dose tolerated in mg/kg of mouse | |
|---|---|---|
| | i.p. | i.v. |
| 2.13 | 50 | 25 |
| 3.4 | 200 | <100 (2 animals died) |
| 3.9 | 200 | 200 |
| 3.16 | >200 | n.d. |
| 3.33 | n.m. | >400 |
| 6.2 | >400 | n.m. |
| 6.12 | n.m. | >400 |
| 6.14 | >400 | n.m. |
| 6.81 | n.m. | >400 |
| 8.2 | >200 | n.d. |
| Quinolone-a | n.d. | <25 |
| 12.3 | n.d. | >200 |

EXAMPLE A.5

Determination of the Acute Toxicity After Several Administrations

The substances were administered partly i.v. and partly i.p., either daily on days 1 to 4 and 7 to 10 or on days 1, 5 and 9. The dosages were 400, 200 and 100 mg/kg/day. The evaluation was made according to the decrease in weight up to day 21 and according to the number of surviving animals. For the experiments, 5 animals were employed per substance and dose. The results are summarized in Table 6.

TABLE 6

Maximum tolerable dose with multiple administrations

| | Administration | Dosage on day | MTD mg/kg day |
|---|---|---|---|
| 3.9 | i.v. | 1–4, 7–10 | ~50 |
| | | 1–4 | ~100 |
| 3.33 | i.v. | 1, 5, 9 | >400 |
| 6.2 | i.p. | 1–4, 7–10 | ~400 |
| | | 1, 5, 9 | >400 |
| 6.12 | i.v. | 1–4, 7–10 | >400 |
| | | 1, 5, 9 | >400 |

TABLE 6-continued

Maximum tolerable dose with multiple administrations

| | Administration | Dosage on day | MTD mg/kg day |
|---|---|---|---|
| 6.14 | i.p. | 1, 5, 9 | >400 |
| 6.81 | i.v. | 1–4, 7–10 | ~200 |
| | | | >400 |
| Batracyline | i.p | 1, 5, 9 | −100 |

EXAMPLE A.6

Haematopoietic Activity of Glycoconjugates of Quinolone-a in Comparison With the Active Compound on Which They Are Based Material and Methods In vitro:

Bone marrow cells are flushed out of the femur of mice. $10^5$ cells are incubated in McCoy SA medium (0.3% agar) together with recombinant murine GM-CSF (Genzyme; parent cell colony formation) and the substances ($10^{-4}$ to 100 μg/ml) at 37° C. and 7% $CO_2$. 7 days later, the colonies (<50 cells) and clusters (17–50 cells) are counted.

In vivo:

Mice are treated subcutaneously with 1, 3, 10 or 30 mg/kg of the compounds. At various times (3, 24, 48, 72 p. inj.) the femurs are removed and the bone marrow cells isolated. $2\times10^5$ cells are incubated with GM-CSF as described above and, after 7 days, the colonies and clusters are counted.

Results

As shown in Table 7, the glycoconjugates investigated show an inhibition of bone marrow parent cell proliferation which is reduced by a factor of $10^5$ to $10^3$ compared with quinolone-a.

In vivo also, no inhibition in parent cell proliferation was to be observed by compound 12.3 up to 30 mg/kg, compared with quinolone-a. A massive suppression of parent cell proliferation was already induced with 3 mg/kg of quinolone-a (FIG. 1).

TABLE 7

CSF-induced proliferation of bone marrow parent cells of the mouse

| Examples | $IC_{50}$ [μg/ml] |
|---|---|
| Quinolone-a | 0.0002 |
| 11.2 | 22.5 |
| 11.7 | 2.9 |
| 12.1 | 0.21 |
| 12.3 | 0.27 |
| 12.6 | 0.3 |
| 12.8 | 0.3 |
| 14.1 | 2.9 |
| 14.2 | 3.6 |
| 14.4 | 3.6 |

EXAMPLE A.7

Antineoplastic Activity of Quinolone-a Conjugates

The in vitro activity of glycoconjugates of quinolone-a was determined on human tumour xenografts in a two-layer soft agar culture system according to Hamburger and Salmon (Science 197: 461–463).

The solid tumours were initially grown in the athymic naked mouse (NMRI nu/nu), obtained by surgery and comminuted mechanically. Individual cells were then obtained by incubation in an enzyme mixture of collagenase 0.05%, DNAse 0.07% and hyaluronidase 0.1% in RPMI at 37° C. for 30 minutes. The cells were washed 2× and then passed through a sieve of 200 μm and 20 μm mesh width.

The following culture method was used:

The base layer comprises 0.2 ml of Iscoves's Modified Dulbeccos Medium with 20% foetal calf serum and 0.7% agar. 40,000 to 200,000 cells in 0.2 ml of the same medium and 0.4% agar were applied to this layer in 24 multiwell plates. The cytostatic substances were added in 0.2 ml of medium.

The cultures were incubated at 37° C. in a 7% $CO_2$ atmosphere for 6 to 15 days. The colonies which had grown were then counted under an inverting microscope, the living colonies being stained with a tetrazolium chloride dyestuff 24 hours before the evaluation.

The effect of the active compound is expressed in per cent of surviving colonies compared with the colony count of untreated plates (T/C=colony count treated×100/control count untreated).

A substance is active if the T/C value is ≦30%.

This value is shown as the $IC_{70}$ value in μg/ml in Table 8.

TABLE 8

| | $IC_{70}$/μg/ml | | | | |
|---|---|---|---|---|---|
| Example | 11.7 | 12.1 | 12.3 | 12.5 | Quinolone-a |
| CXF 280 | >100 | 70 | 5 | <0.3 | 6 |
| HT 29 | 56 | 6 | 5 | 11 | 20 |
| SW 480 | 18 | 8 | 11 | 10 | 3 |
| LXFL 529 | 4 | 0.9 | 2 | 2 | 3 |
| LXFS 538 | 18 | 0.4 | 0.5 | <0.3 | <0.3 |
| MEXF 989 | 3 | <0.3 | <0.3 | 0.5 | <0.3 |
| OVXF 899 | 234 | 45 | 162 | 55 | 2 |
| OVXF 1023 | 136 | 12 | 10 | 9 | 0.5 |

EXAMPLE A.8

In Vivo Tests

Method

Mice are inoculated with $5\times10^6$ B16F10 tumour cells on day 0. The animals in which tumour cells are transplanted develop solid peritoneal tumours and are then treated daily with test substances or with the vehicle control. In the control group, 50% of the animals usually die between day 14 and 20. The test substances are administered in buffer or an organic solvent system comprising 20% methanol and 20% dimethyl sulphoxide in 0.7% sodium chloride solution.

The administration of the vehicle showed no influence on the survival time of the animals. The therapeutic result arises from the prolonging of the survival time of the treated animals. The tolerance of the compounds is analysed in parallel on animals which do not carry tumours. A therapeutic index can be estimated from the tolerance and prolonging of the survival time.

TABLE 9

| | % survivors | | | | |
|---|---|---|---|---|---|
| | Day 0 | Day 20 | Day 25 | Day 30 | Day 35 |
| Control | 100 | 70 | 30 | 10 | 10 |
| 11.12 1 mg/kg | 100 | 90 | 60 | 30 | 30 |
| 11.12 (100 mg/kg) | 100 | 100 | 100 | 90 | 90 |
| Quinolone-a (0.1 mg/kg) | 100 | 100 | 100 | 60 | 40 |
| Etoposide (5 mg/kg) | 100 | 90 | 80 | 80 | 70 |

Table 9 shows the therapeutic activity of the compound from Example 11.12 on mice in which a B16F10 tumour was transplanted.

EXAMPLE A.9

In Vivo Inhibition of Tumour Growth Using a Naked Mouse Model

Material

Athymic naked mice (NMRI nu/nu strain) were used for all the in vivo experiments for investigation of the inhibition of tumour growth. The large-cell lung carcinoma LXFL 529 selected was developed by serial passage in naked mice. The human origin of the tumour was demonstrated by isoenzymatic and immunohistochemical methods.

Experimental Set-up

The tumour was implanted subcutaneously in both flanks of nu/nu naked mice 6 to 8 weeks old. Treatment was started, regardless of the doubling time, as soon as the tumours had reached a diameter of 5–7 mm. The mice were allocated to the treatment group and the control group (5 mice per group with 8–10 evaluable tumours) by randomization. The individual tumours of the control group all grew progressively.

The size of the tumours was measured in two dimensions by means of a sliding gauge. The tumour volume, which correlates well with the cell count, was then used for all the evaluations. The volume was calculated according to the equation "length×breadth×breadth/2" ($[a\times b^2]/2$, a and b represent two diameters at right angles). The values of the relative tumour volume (RTV) were calculated for each individual tumour by dividing the tumour size on day X with the tumour size on day 0 (at the time of randomization). The mean RTV values were then used for the further evaluation.

The inhibition of the increase in the tumour volume (tumor volume of the test group/control group, T/C, in per cent) was the concluding measurement value.

Treatment

All the compounds were administered according to an intermittent plan in each case on day 1, 5 and 9. Furthermore, all the compounds were administered intraperitoneally (i.p.) using water as the solvent.

TABLE 10

| Treatment | Dose[a)] [mg/kg/day] | Survival time (days) | | Number of tumours | Relative tumour volume [% of day 0][b)] | Optimum T/C[b)] |
|---|---|---|---|---|---|---|
| Control group | — | 19<br>>21<br>14 | >21<br>>21 | 10 | 1552 | 100% |

TABLE 10-continued

| Treatment | Dose[a)] [mg/kg/day] | Survival time (days) | | Number of tumours | Relative tumour volume [% of day 0][b)] | Optimum T/C[b)] |
|---|---|---|---|---|---|---|
| 12.6 | 100 | 23 | >26 | 8 | 300.7 | 19.4% |
| | | 26 | >26 | | | |
| | | >26 | | | | |
| 12.8 | 50 | >21 | >21 | 9 | 502.2 | 32.3% |
| | | >21 | >21 | | | |
| | | >21 | | | | |
| 12.14 | 25 | 23 | >26 | | | |
| | | 19 | 26 | 8 | 519.5 | 33.5% |
| | | >26 | | | | |

a) maximum tolerated dose (MTD)
b) on day 19

In this test, the camptohecin compounds of Example series 18 as a rule showed a comparable or better action.

EXAMPLES SERIES B

Synthesis Examples

EXAMPLE 1.1 p-Aminophenyl 2-O-methyl-β-L-fucoside

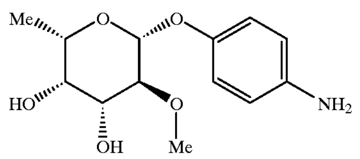

1.1.a) p-Nitrophenyl 3,4-O-isopropylidene-β-L-fucoside 65 mg of p-toluenesulphonic acid and, at 30 minute intervals, 5×100 μl of 2-methoxypropene are added to a solution of p-nitrophenyl β-L-fucoside (750 mg, 2.63 mmol) in 40 ml of dimethylformamide/dioxane 1:2 at 0° C. After the mixture has been stirred at 20° C. for 16 hours, it is concentrated and the residue is purified by flash chromatography (methylene chloride/methanol 99:1). After concentration, 710 mg (83%) of a white solid are obtained.

1.1.b) p-Nitrophenyl 2-O-methyl-3,4-O-isopropylidene-β-L-fucoside 100 mg (0.307 mmol) of the compound from Example 1.1.a are initially introduced into 10 ml of tetrahydrofuran together with 96 μl of methyl iodide, and 11 mg of sodium hydride (80% strength) are then added in portions. After the mixture has been stirred at 20° C. for 3 hours, it is topped up with a further 96 μl of methyl iodide and 11 mg of sodium hydride. After further stirring at 20° C. for 16 hours, a little water and 100 ml of methylene chloride are added. The batch is extracted by shaking twice with water, the organic phase is concentrated and the product is then purified by column chromatography (petroleum ether/ethyl acetate 8:1). Yield: 78 mg (75%).

1.1) p-Aminophenyl 2-O-methyl-β-L-fucoside 78 mg (0.23 mmol) of p-nitrophenyl 2-O-methyl-3,4-O-isopropylidene-β-L-fucoside are stirred in 3 ml of 80% strength acetic acid at 20° C. for 16 hours. The acetic acid is then removed in vacuo, 10 ml of methanol are added to the batch and, after addition of platinum dioxide, hydrogenation is carried out in a hydrogen atmosphere under a slightly increased pressure. The suspension is filtered over Celite and the material on the filter is washed with methanol. After purification by chromatography (methylene chloride/methanol 97.5:2.5), 77 mg (80%) of the target product are obtained. [TLC: methylene chloride/methanol 9:1 $R_f$=0.42].

EXAMPLE 1.2 p-Aminophenyl 3-O-methyl-β-L-fucoside

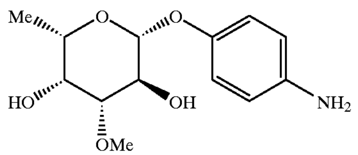

1.2.a) p-Nitrophenyl 3-O-Methyl-β-L-fucoside 784 g (31.5 mmol) of dibutyltin oxide are added to 6 g (21 mmol) of p-nitrophenyl β-L-fucoside in 300 ml of absolute methanol and the mixture is heated under reflux for 2 hours. It is then concentrated and the residue is dried and then taken up in 300 ml of dimethylformamide. After addition of 15.7 ml of methyl iodide, the batch is stirred at 70° C. for 40 hours. The solvent is removed in vacuo and the residue is taken up in 300 ml of methylene chloride. The suspension is filtered, the solution which remains is concentrated again and the residue is subjected to flash chromatography (methylene chloride/methanol 99:1). After concentration, 381.5 mg (61%) of the target product are obtained.

1.2) p-Aminophenyl 3-O-methyl-β-L-fucoside 3.81 g (12.73 mol) of p-nitrophenyl 3-O-methyl-β-L-fucoside are hydrogenated analogously to example 1.1. Yield: 3 g (88%). [TLC: methylene chloride/methanol 9:1 $R_f$=0.53].

EXAMPLE 1.3 p-Aminophenyl 3-O-methyl-α-L-fucoside

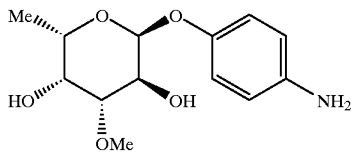

Preparation analogous to Example 1.2 starting from p-nitrophenyl α-L-fucoside. Yield: 63% over 2 stages. [TLC methylene chloride/methanol 9:1 $R_f$=0.39].

EXAMPLE 1.4 p-Aminophenyl 4-O-methyl-β-L-fucoside

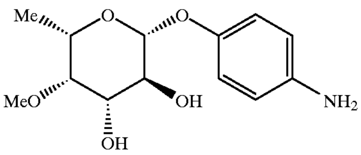

1.4.a) p-Nitrophenyl 2-O-benzyl-4-O-acetyl-β-L-fucoside 31 mg of p-toluenesulphonic acid and 1134 mg (7 mmol) of triethyl orthoacetate are added to 1 g (3.5 mmol) of p-nitrophenyl β-L-fucoside in 100 ml of absolute tetrahydrofuran. After the mixture has been stirred at 20° C. for 15 minutes, the solvent is distilled off in vacuo. The residue is taken up in 50 ml of tetrahydrofuran and 3 ml of dimethylformamide, and 4165 μl of benzyl bromide and 210 mg of sodium hydride (60% strength) are added. After the mixture has been stirred at 20° C. for 1 hour, 10 ml of 80% strength acetic acid are added, the mixture is concentrated and the residue is purified by flash chromatography (methylene chloride/methanol 99:1). After concentration and drying, 1236 mg (85%) of the target product are obtained.

1.4.b) p-Nitrophenyl 2-O-benzyl-3-O-acetyl-4-O-methyl-β-L-fucoside 1000 mg (2.39 mmol) of p-nitrophenyl 2-O-benzyl-4-O-acetyl-β-L-fucoside are dissolved in 60 ml of benzene. After addition of 2988 βl of methyl iodide and 1109 mg of silver oxide, the batch is heated under reflux for 8 hours. The product mixture formed is separated into the components by flash chromatography (methylene chloride/methanol 99:1). 239 mg (23%) of p-nitrophenyl 2-O-benzyl-3-O-acetyl-4-O-methyl-β-L-fucoside are isolated, in addition to 653 mg (63%) of the isomeric p-nitrophenyl 2-O-benzyl-3-O-methyl-4-O-acetyl-β-L-fucoside, as a white solid.

1.4) p-Aminophenyl 4-O-methyl-β-L-fucoside 224 mg (0.52 mmol) of p-nitrophenyl 2-O-benzyl-3-O-acetyl4-O-methyl-β-L-fucoside are dissolved in 20 ml of methanol, and 390 μl of a 1N sodium methylate solution are added. After the mixture has been stirred at 20° C. for 16 hours, it is neutralized with 80% strength acetic acid and concentrated and the residue is taken up in methylene chloride. The organic phase is washed with 1N sodium bicarbonate solution and with water, dried and concentrated. The residue is taken up in 20 ml of methanol and hydrogenated over palladium/active charcoal analogously to Example 1.1. After concentration, the product is taken up in water and lyophilized. 119 mg (88%) of a white amorphous solid are isolated. [TLC: methylene chloride/methanol 9:1 $R_f$=0.38].

EXAMPLE 1.5 p-Aminophenyl 3-O-n-propyl-β-L-fucoside

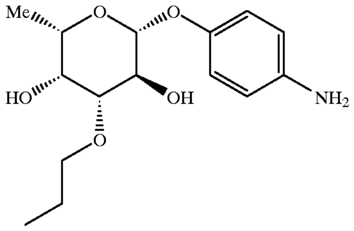

1.5.a) p-Nitrophenyl 2-O-benzyl-3-O-n-propyl-4-O-acetyl-β-L-fucoside

Analogously to Example 1.4.b, the isomeric 3- and 4-propylation products are prepared from compound 1.4.a with propyl iodide and separated by chromatography. p-Nitrophenyl 2-O-benzyl-3-O-n-propyl-4-O-acetyl-β-L-fucoside is obtained in a 49% yield, in addition to p-nitrophenyl 2-O-benzyl-3-O-acetyl-4-O-n-propyl-β-L-fucoside in a 29% yield.

1.5.b) p-Aminophenyl 3-O-n-propyl-β-L-fucoside

Synthesis from Example 1.5.a) fraction 1 analogously to Example 1.4. Yield: 78% [TLC methylene chloride/methanol 9:1 $R_f$=0.42].

EXAMPLE 1.6 p-Aminophenyl 3-deoxy-β-L-fucoside

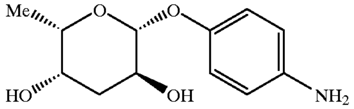

1.6.a) p-Nitrophenyl 3,6-dideoxy-3-chloro-4-O-acetyl-β-L-guloside 31 mg of p-toluenesulphonic acid and 1134 mg (7 mmol) of triethyl orthoacetate are added to 1 g (3.5 mmol) of p-nitrophenyl-β-L-fucoside in 100 ml of tetrahydrofuran. After the mixture has been stirred at 20° C. for 15 minutes, the solvent is distilled off in vacuo. 100 ml of a saturated solution of hydrogen chloride in methylene chloride are added. After a reaction time of 10 minutes, the mixture is concentrated and the product is purified by flash chromatography (methylene chloride/methanol 99:1). 793 mg (65%) of the target product are obtained. [TLC: methylene chloride/methanol 97.5:2.5 $R_f$=0.36].

1.6.b) p-Nitrophenyl 3,6-dideoxy-3-chloro-β-L-guloside 375 mg (1.08 mmol) of p-nitrophenyl 3,6-dideoxy-3-chloro-4-O-acetyl-β-L-guloside are dissolved in 25 ml of methanol, and 10 drops of 1N sodium methylate solution are added. After 20 minutes, the mixture is acidified with acetic acid and concentrated and the residue is partitioned between 400 ml of methylene chloride and 60 ml of water. The organic phase is dried and concentrated and the residue is precipitated from methylene chloride/ether. 315 mg (96%) of the target product are obtained.

1.6) p-Aminophenyl 3-deoxy-β-L-fucoside 315 mg (1.04 mmol) of p-nitrophenyl 3,6-dideoxy-3-chloro-β-L-guloside are dissolved in 40 ml of methanol, 200 mg of palladium-on-active charcoal and 290 μl of triethylamine are added and hydrogenation is carried out in a hydrogen atmosphere under a slightly increased pressure for 4 days. The suspension is filtered, washed and concentrated and the product is purified by flash chromatography (methylene chloride/methanol 97.5:2.5). 160 mg (65%) of the deoxy compound are obtained. [TLC: methylene chloride/methanol 95:5 $R_f$=0.18].

EXAMPLE 1.7 p-Aminophenyl 3,4-dideoxy-β-L-fucoside

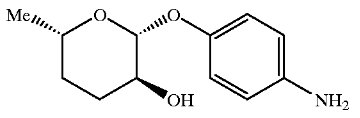

400 mg (1.16 mmol) of p-nitrophenyl 3,6-dideoxy-3-chloro-4-O-acetyl-β-L-guloside (Example 1.6.a) are dissolved in 55 ml of methanol, 323 μl of triethylamine are added and hydrogenation is carried out in a hydrogen atmosphere under a slightly increased pressure over palladium/active charcoal (10%). After the mixture has been stirred at 20° C. for 16 hours, it is filtered over Celite, the material on the filter is rinsed, the filtrate is concentrated and the residue is taken again in 100 ml of methanol. 1.5 ml of a 1N sodium methylate solution are added and the mixture is stirred at room temperature for 16 hours. It is neutralized with acetic acid and concentrated, and the products formed are separated by flash chromatography (methylene chloride/methanol 97.5:2.5). After concentration of the corresponding fractions and reprecipitation from methanol/ether, 120 mg (46%) of the target compound [TLC methylene chloride/methanol 95:5 $R_f$=0.31] are obtained, in addition to 77 mg (28%) of p-aminophenyl 3-deoxy-β-L-fucoside [TLC: methylene chloride/methanol 95:5 $R_f$=0.18].

EXAMPLE 1.8 p-Aminophenyl 3,4-epoxy-β-L-fucoside

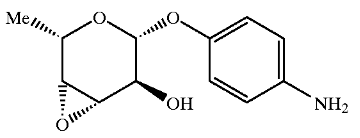

80 mg (0.23 mmol) of p-nitrophenyl 3,6-dideoxy-3-chloro-4-O-acetyl-β-L-guloside (Example 1.6.a) are taken up in 10 ml of methanol, and 345 μl of 1N sodium methylate solution are added. After ultrasonic treatment for 1 hour, the mixture is acidified with 80% strength acetic acid and concentrated and the residue is chromatographed with methylene chloride/methanol 99:1. After concentration of the relevant fractions, the residue is taken up in methanol and hydrogenation is carried out over palladium/active charcoal analogously to Example 1.1. 46 mg (75%) of the target compound are obtained. FAB-MS: m/e=238=M+1.

EXAMPLE 1.9 p-Aminophenyl 4-deoxy-β-L-fucoside

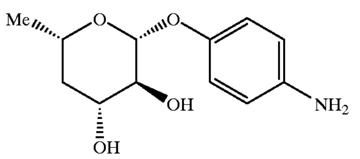

This compound was prepared analogously to the instructions of T. Lindhorst and J. Thiem in Carbohydr. Res. 209 (1991), 119 starting from p-nitrophenyl-β-L-fucoside via p-nitrophenyl 2,3-di-O-benzoyl4,6-dideoxy4-iodo-β-L-fucoside. [TLC: methylene chloride/methanol 90:10 $R_f$=0.3].

EXAMPLE 1.10 p-Aminophenyl 3-O-carboxymethyl-β-L-fucoside

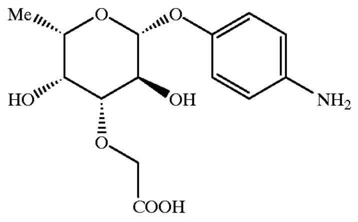

1.10.a) p-Nitrophenyl 3-O-methoxycarbonylmethyl-β-L-fucoside 1 g (3.5 mmol) of p-nitrophenyl β-L-fucoside and 1.3 g (5.2 mmol) of dibutyltin oxide are heated under reflux in 50 ml of methanol for 2 hours. The solution is concentrated, the residue is taken up in 50 ml of dioxane, 2 ml of methyl bromoacetate and 100 mg of tetrabutylammonium iodide are added and the mixture is heated under reflux for 16 hours. The solvent is evaporated off and the product is purified by flash chromatography (methylene chloride/methanol 99:1). After the corresponding fractions have been concentrated and the residue has been reprecipitated from methanol/ether, 455 mg (37%) of the target compound are obtained.

1.10) p-Aminophenyl 3-O-carboxymethyl-β-L-fucoside 282 mg (0.79 mmol) of p-nitrophenyl 3-methoxycarbonylmethyl-β-L-fucoside are dissolved in 20 ml of methanol, and 440 μl of a 2N lithium hydroxide solution are added. After the mixture has been stirred at 20° C. for 2 hours, it is brought to pH 3 with acid ion exchanger SC108 and filtered. 250 mg of palladium-on-active charcoal are added to the filtrate. Hydrogenation is then carried out with hydrogen under a slightly increased pressure for 1.5 hours and the catalyst is removed and washed with methanol. Concentration of the mixture, taking up the residue in water and freeze drying leads to the target product in an 86% yield (212 mg). [TLC: acetonitrile/water/acetic acid 5:1:0.2 $R_f$=0.24].

EXAMPLE 1.11 p-Aminophenyl 3-O-methoxycarbonylmethyl-β-L-fucoside

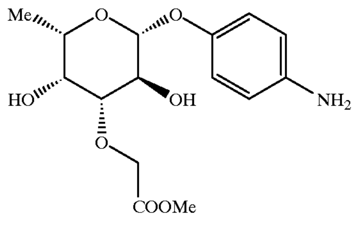

250 mg (0.7 mmol) of p-nitrophenyl 3-methoxycarbonylmethyl-β-L-fucoside (Example 1.10.a) are dissolved in 20 ml of methanol and hydrogenation is carried out with hydrogen over palladium-on-active charcoal under a slightly increased pressure for 1.5 hours. The catalyst is removed and washed with methanol. Concentration, taking up in water and freeze drying lead to 195 mg (85%) of the target product. [TLC methylene chloride/methanol 9:1 $R_f$=0.43; FAB-MS: m/e=328=M+1.]

EXAMPLE 1.12 p-Aminophenyl 3-O-hydroxyethyl-β-L-fucoside

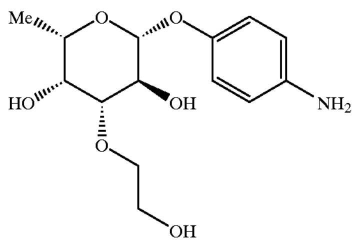

1.12.a) p-Nitrophenyl 3-O-hydroxyethyl-β-L-fucoside 1000 mg (2.8 mmol) of p-nitrophenyl 3-methoxycarbonylmethyl-β-L-fucoside are dissolved in a mixture of 160 ml of tetrahydrofuran and 40 ml of water, and 53 mg of sodium borohydride are added. After 10 minutes, the solvent is evaporated off and the residue is purified by flash chromatography (methylene chloride/methanol 95:5). After the corresponding fractions have been concentrated, the residue has been taken up in water and the mixture has been freeze dried, 362 mg (40%) of the target product are obtained.

1.12) p-Aminophenyl 3-O-hydroxyethyl-β-L-fucoside

After hydrogenation of 362 mg of the compound from Example 1.12.a) analogously to Example 1.1, 270 mg (82%) of the target product are obtained. [TLC: acetonitrile/water 10:1 $R_f$=0.43].

EXAMPLE 1.13 p-Aminophenyl 2-O-carboxymethyl-β-L-fucoside

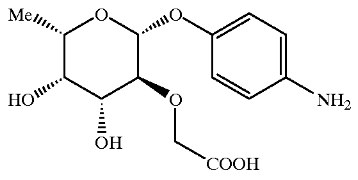

1.13.a) p-Nitrophenyl 2-O-methoxycarbonylmethyl-β-L-fucoside 250 mg (0.88 mmol) of p-nitrophenyl P-L-fucoside are dissolved in 25 ml of absolute tetrahydrofuran and 3 ml of dimethylformamide. 80 mg (2.64 mmol) of 80% strength sodium hydride are added and, after the mixture has been stirred at 20° C. for 10 minutes, 35 μl of benzyl bromoacetate are added. 3 further additions of 35 μl each of benzyl bromoacetate are made at intervals of 10 minutes. The mixture is subsequently stirred for 30 minutes and quenched with methanol. After a further 10 minutes, it is acidified with 5 ml of 80% strength acetic acid. The mixture is concentrated and the residue is subsequently distilled with methylene chloride. Purification by means of flash chromatography is started with the mobile phase system methylene chloride/methanol/glacial acetic acid 90:10:1. The ratio in the same system is later changed to 80:20:2. After the corresponding fractions have been concentrated, the residues are digested with ether and 157 mg (42%) of the target compound are obtained from the early eluate. [TLC: acetonitrile/water/glacial acetic acid 5:1:0.2 $R_f$=0.65]. The isomeric 3-O-alkylated compound is obtained from the late eluates (33%). [TLC: acetonitrile/water/glacial acetic acid 5:1:0.2 $R_f$=0.54].

1.13) p-Aminophenyl 2-O-carboxymethyl-β-L-fucoside

Hydrolysis and hydrogenation of 150 mg of p-nitrophenyl 2-O-methoxycarbonylmethyl-β-L-fucoside by the procedure described in Example 1.10 leads to 109 mg of the target product in an 83% yield [TLC: acetonitrile/water/glacial acetic acid 5:1:0.2 $R_f$=0.35].

EXAMPLE 1.14.a

Synthesis of the regioisomeric monosuccinylation products of p-nitrophenyl β-L-fucoside 1100 mg (3.86 mmol) of p-nitrophenyl β-L-fucoside are dissolved in 50 ml of pyridine, and 580 mg (5.79 mmol) of succinic anhydride are added. After the mixture has been stirred at 20° C. for 16 hours, it is concentrated and the residue is subsequently distilled twice with methylene chloride. The product is precipitated from methylene chloride/ether and 1 g of a substance mixture which cannot be separated is obtained. This is taken up in methanol/water, and 846 mg (2.6 mmol) of caesium carbonate are added. The solvent is evaporated off and the residue is subsequently distilled with dimethylformamide. The residue is taken up in dimethylformamide, and 618 μl of benzyl bromide are added. After ultrasonic treatment for 1 hour, the caesium bromide is filtered off and the filtrate is concentrated. The residue is partitioned between 500 ml of ethyl acetate and 50 ml of water. The organic phase is dried and concentrated. Separation of the components by flash chromatography is achieved in the mobile phase system methylene chloride/methanol 99:1. This gives:

Fraction 1: 87 mg (4.8%) of p-nitrophenyl 3-O-(3-benzyloxycarbonyl-propionyl)-β-L-fucoside [TLC: methylene chloride/methanol 95:5 $R_f$=0.45].

Fraction 2: 27 mg (1.5%) of p-nitrophenyl 2-O-(3-benzyloxycarbonyl-propionyl)-β-L-fucoside [TLC: methylene chloride/methanol 95:5 $R_f$=0.34].

Fraction 3: 190 mg (10.3%) of p-nitrophenyl 4-O-(3-benzyloxycarbonyl-propionyl)-β-L-fucoside [TLC: methylene chloride/methanol 95:5 $R_f$=0.28].

EXAMPLE 1.14 p-Aminophenyl 3-O-succinyl-β-L-fucoside

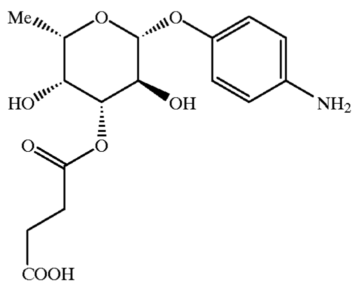

85 mg (0.17 mmol) of fraction 1 from Example 1.14.a are dissolved in 5 ml of tetrahydrofuran and 1 ml of water. 20 mg of platinum dioxide are added and hydrogenation is carried out for 8 hours. The catalyst is filtered off and washed with tetrahydrofuran/water and the filtrate is concentrated. The residue is taken up in water and lyophilized. 57 mg (94%) of the target product are obtained. [TLC: acetonitrile/water/glacial acetic acid 5:1:0.2 $R_f$=0.65].

EXAMPLE 1.15 p-Aminophenyl 2-O-succinyl-β-L-fucoside

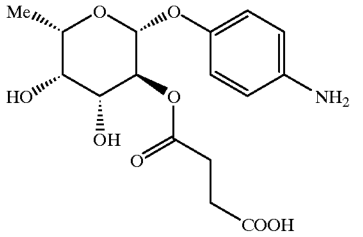

Fraction 2 from Example 1.14.a is hydrogenated analogously to the instructions in Example 1.14. Yield: 16 mg (87%) [TLC: acetonitrile/water/glacial acetic acid 5:1:0.2 $R_f$=0.62].

EXAMPLE 1.16 p-Aminophenyl 4-O-succinyl-β-L-fucoside

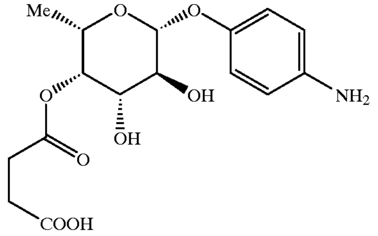

Fraction 3 from Example 1.14.a is hydrogenated analogously to the instructions in Example 1.14. Yield: 125 mg (88%) [TLC: acetonitrile/water/glacial acetic acid 5:1:0.2 $R_f$=0.63].

EXAMPLE 1.17 p-Aminophenyl 3,4-di-O-methyl-β-L-fucoside

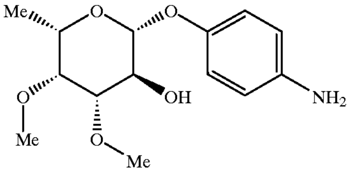

1.17.a) p-Nitrophenyl 2-O-benzyl-3,4-O-isopropylidene-β-L-fucoside 377 mg (1.16 mmol) of the compound from Example 1.1.a are dissolved in 30 ml of absolute tetrahydrofuran, 690 μl of benzyl bromide and 52 mg of sodium hydride are added in succession and the mixture is stirred at 20° C. The mixture is topped up with a further 690 μl of benzyl bromide and sodium hydride after 4 and 6 hours. The batch is worked up analogously to Example 1.1.b. 245 mg (51%) of the target compound are obtained.

1.17.b) p-Nitrophenyl 2-O-benzyl-3,4-di-O-methyl-β-L-fucoside 245 mg (0.59 mmol) of p-nitrophenyl 2-O-benzyl-3,4-O-isopropylidene-β-L-fucoside are stirred in 80% strength acetic acid at 20° C. for 16 hours. The mixture is concentrated and the residue is stirred with ether/pentane. After the mixture have been filtered with suction and the residue dried, the product which remains is taken up in 20 ml of absolute tetrahydrofuran, 45 mg of 80% strength sodium hydride are added and, after 15 minutes, 160 μl of methyl iodide are injected in. After the mixture has been stirred at 20° C. for 20 hours, it is quenched with methanol and glacial acetic acid and concentrated and the residue is partitioned between methylene chloride and water. The organic phase is dried and concentrated and the residue is then purified by flash chromatography (methylene chloride/methanol 100:1). After concentration and drying of the corresponding fractions, 188 mg (79%) of the target product are obtained.

1.17) p-Aminophenyl 3,4-di-O-methyl-β-L-fucoside 180 mg (0.45 mmol) of the compound from Example 1.17.b are hydrogenated in a mixture of 15 ml of methanol and 3 ml of methylene chloride at room temperature for 2 days, after addition of 50 mg of palladium-on-active charcoal. The catalyst is filtered off, the filtrate is concentrated and the residue is purified by flash chromatography (methylene chloride/methanol 97.5:2.5). 86 mg (68%) of the target compound are obtained. [TLC: methylene chloride/methanol 95:5 $R_f$=0.21].

EXAMPLE 1.18 p-Aminophenyl 3-O-carbamoylmethyl-β-L-fucoside

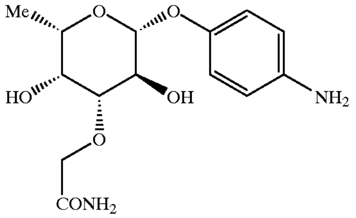

100 mg (0.305 mmol) of the compound from Example 1.11 are dissolved in 10 ml of methanol, and 0.5 ml of 17% strength ammonium hydroxide solution is added. After 4 hours, the mixture is concentrated and the residue is taken up in water and lyophilized. 95 mg (quantitative) of the target compound are obtained. [TLC: acetonitrile/water 10:1 $R_f$=0.43].

EXAMPLE 1.19 p-Aminophenyl 2-O-hydroxyethyl-β-L-fucoside

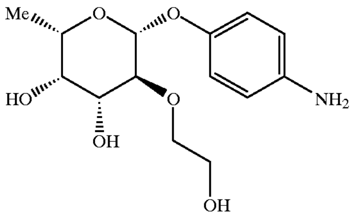

This compound was prepared analogously to Examples 1.12.a and 1.12 starting from 200 mg (0.56 mmol) of p-nitrophenyl 2-O-methoxycarbonylmethyl-β-L-fucoside (Example 1.13.a). Yield: 76 mg (45% over 2 stages) [TLC: methylene chloride/methanol 9:1 $R_f$=0.2].

EXAMPLE 1.20 p-Aminophenyl 3,6-dideoxy-3-chloro-β-L-guloside

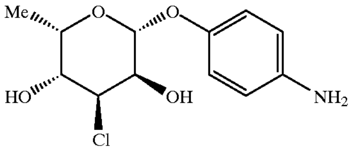

50 mg (0.165 mmol) of the compound from Example 1.6.b are hydrogenated in 5 ml of methanol over palladium/active charcoal for 1 hour. The catalyst is filtered off and rinsed, the filtrate is concentrated and the residue is taken up in water and lyophilized. 45 mg (89%) of the target compound are obtained. [TLC: methylene chloride/methanol 9:1 $R_f$=0.35].

EXAMPLE 1.21 p-Aminophenyl α-L-rhamnoside

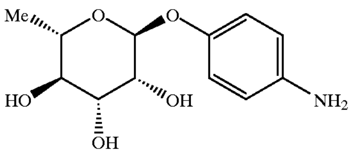

This compound was prepared analogously to Example 1.1 starting from 300 mg of p-nitrophenyl α-L-rhamnoside (Sigma). Yield: 96%

EXAMPLE 1.22 p-Aminophenyl 3-O-carboxymethyl-α-L-rhamnoside

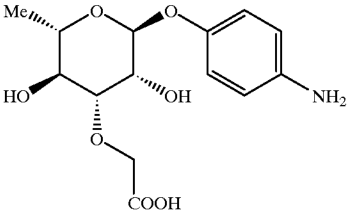

1.22.a) p-Nitrophenyl 3-O-methoxycarbonylmethyl-α-L-rhamnoside 481 mg (1.63 mmol) of p-nitrophenyl α-L-rhamnoside are taken up in 30 ml of methanol, and 629 mg (2.45 mmol) of dibutyltin oxide are added. The mixture is heated under reflux for 2 hours and concentrated and the residue is taken up in 30 ml of dioxane. 85 mg of tetrabutyl-ammonium iodide and 950 μl of methyl bromoacetate are added and the mixture is heated under reflux for 16 hours. If appropriate, it is topped up with a further 1 ml of methyl bromoacetate and the reaction time is prolonged. The mixture is concentrated and the residue is purified by flash chromatography. p-Nitrophenyl 3-O-methoxycarbonylmethyl-α-L-rhamnoside is eluted with methylene chloride/methanol 99:1 and, after drying, 408 mg (70%) are obtained. [TLC: methylene chloride/methanol 95:5 $R_f$=0.36].

1.22) p-Aminophenyl 3-O-carboxymethyl-α-L-rhamnoside

Synthesis completely analogously to Example 1.10 starting from p-nitrophenyl 3-O-methoxycarbonylmethyl-α-L-rhamnoside. The target product is obtained in an 80% yield. [TLC: acetonitrile/water/glacial acetic acid 5:1:0.2 $R_f$=0.26].

EXAMPLE 1.23 p-Aminophenyl β-D-galactopyranoside

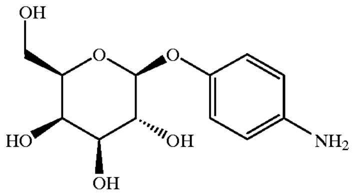

p-Nitrophenyl β-D-galactopyranoside (3.0 g, 10 mmol) is dissolved in methanol/water 1:1 (50 ml) and, after addition of palladium-on-active charcoal (10% of Pd, 200 mg), hydrogenation is carried out in a hydrogen atmosphere under a slightly increased pressure for 3 hours. The suspension is filtered over Celite and the material on the filter is washed with hot methanol/water 1:1 (100 ml). Concentration of the filtrate in vacuo and recrystallization from methanol gives colourless crystals (2.11 g, 78%); TLC [methanol]: $R_f$=0.62; $[\alpha]^{20}$=−39.5° (c=1.0/$H_2O$); melting point=166° C.

EXAMPLE 1.24 p-Aminophenyl 2-O-methyl-β-D-galactopyranoside

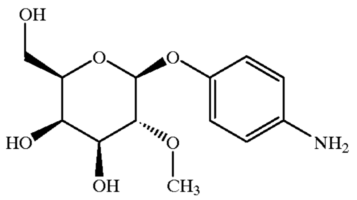

1.24.a) p-Nitrophenyl 6-O-triphenylmethyl-β-D-galactopyranoside

A solution of p-nitrophenyl β-D-galactopyranoside (9.0 g, 30 mmol), chlorotriphenylmethane (16.7 g, 60 mmol) and N,N-dimethylaminopyridine (609 mg, 5 mmol) in absolute pyridine (100 ml) is heated at 60° C. for 4 hours. After concentration in vacuo, the residue is purified by flash chromatography [petroleum ether/ethyl acetate 2:1→3:2, in each case with 0.5% of triethylamine]. Colourless crystals (9.23 g, 57%) are obtained; TLC [methylene chloride/methanol/ammonia (25%) 15:3:0.2]: $R_f$=0.55; melting point=82° C.

1.24.b) p-Nitrophenyl 3,4-O-isopropylidene-6-O-triphenylmethyl-β-D-galactopyranoside Dimethoxypropane (400 ml) and a catalytic amount of (±)-camphor-10-sulphonic acid (400 mg, 1.7 mmol) are added to the above compound (8.7 g, 16 mmol). After 1 hour at room temperature, the reaction is ended by addition of triethylamine (240 ml, 1.7 mmol) and the mixture is concentrated in vacuo. Flash chromatography [petroleum ether/ethyl acetate 2:1] gives a colourless foam (6.2 g, 66%); TLC [petroleum ether/ethyl acetate 1:1]: $R_f$=0.46; $[\alpha]^{20}$=−42.1° (c=0.94/$CH_2Cl_2$).

1.24.c) p-Nitrophenyl 2-O-methyl-3,4-O-isopropylidene-6-O-triphenylmethyl-β-D-galactopyranoside Compound 1.24.b (5.83 g, 10 mmol) is dissolved in dimethylformamide (100 ml), and methyl iodide (2.5 ml, 40 mmol) and, in portions, an 80% strength suspension of sodium hydride in mineral oil (450 mg, 15 mmol) are added. After 2 hours at room temperature, the reaction is ended by dropwise addition of methanol (10 ml) and the mixture is concentrated in vacuo. The residue is taken up in methylene chloride (1000 ml) and the solution is stirred vigorously with water (500 ml). The organic phase is dried over magnesium sulphate (50 g) and concentrated in vacuo and the residue is purified by flash chromatography [petroleum ether/ethyl acetate 12:1→8:1]. A colourless foam (4.72 g, 79%) is obtained; TLC [petroleum ether/ethyl acetate 1:1]: $R_f$=0.72; $[\alpha]^{20}$=−35.7° (c=1.0/$CH_3OH$).

1.24.d) p-Nitrophenyl 2-O-methyl-β-D-galactopyranoside

99% strength trifluoroacetic acid (20 ml) is added to a solution of the above compound (4.48 g, 7.5 mmol) in methylene chloride (200 ml) and the mixture is stirred at room temperature for 3 hours. After the mixture has been concentrated in vacuo, the residue is purified by flash chromatography [petroleum ether/ethyl acetate 5:1→2:1]. Colourless crystals (1.09 g, 46%) are obtained; TLC [methylene chloride/methanol/ammonia (25%) 15:3:0.2]: $R_f$=0.42; melting point 177° C.

1.24) p-Aminophenyl 2-O-methyl-β-D-galactopyranoside

Compound 1.24.d (946 mg, 3 mmol) is dissolved in methanol (50 ml) and, after addition of water (0.5 ml) and basic Raney nickel (about 200 mg), hydrogenation is carried out in a hydrogen atmosphere under a slightly increased pressure for 2 hours. The suspension is filtered over Celite and the material on the filter is washed thoroughly with methanol (100 ml). Concentration of the filtrate in vacuo gives a brownish foam (579 mg, 68%); TLC [methylene chloride/methanol/ammonia (25%) 15:3:0.2]: $R_f$=0.28; $[\alpha]^{20}$=−39.3° (c=0.15/$CH_3OH$).

EXAMPLE 1.25 p-Aminophenyl 3-O-methyl-β-D-galactopyranoside

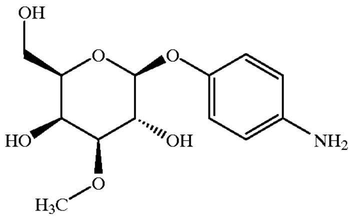

1.25.a) p-Nitrophenyl 3-O-methyl-β-D-galactopyranoside

Dibutyltin oxide (1.87 g, 7.5 mmol) is added to a solution of p-nitrophenyl β-D-galactopyranoside (1.5 g, 5.0 mmol) in absolute methanol (40 ml) and the mixture is heated under reflux. After 3 hours, it is concentrated in vacuo and the residue is dried under an oil pump vacuum for 1 hour. It is taken up in absolute dioxane (40 ml), methyl iodide (1.9 ml, 30 mmol) is added to the resulting solution and the batch is stirred at a bath temperature of 100° C. for 16 hours. The solvent is then distilled off in vacuo and the residue is purified by flash chromatography [ethyl acetate/petroleum ether 2:1→ethyl acetate]. Colourless crystals (1.32 g, 84%) are obtained; TLC [methylene chloride/methanol/ammonia (25%) 15:3:0.2]: $R_f$=0.34; melting point=196° C.; $[\alpha]^{20}$=−53.3° (c=1.0/$CH_3OH$).

1.25) p-Aminophenyl 3-O-methyl-β-D-galactopyranoside

The above compound (946 mg, 3 mmol) is reduced as described in Example 1.24 and the product is worked up. Brownish crystals (656 mg, 77%) are obtained; TLC [methylene chloride/methanol/ammonia (25%) 15:3:0.2]: $R_f$=0.21; melting point=196° C.; $[\alpha]^{20}$=−25.2° (c=1.0/$CH_3OH$).

EXAMPLE 1.26 p-Aminophenyl 4-O-methyl-β-D-galactopyranoside, acetate

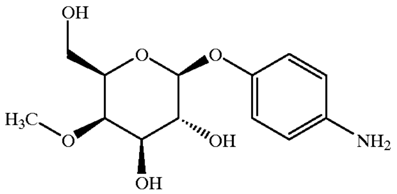

1.26.a) p-Nitrophenyl 3-O-benzyl-β-D-galactopyranoside

Dibutyltin oxide (1.87 g, 7.5 mmol) is added to a solution of p-nitrophenyl β-D-galactopyranoside (1.5 g, 5.0 mmol) in absolute dioxane (40 ml) and the mixture is heated under reflux. After 3 hours, benzyl bromide (3.6 ml, 30 mmol) are added to the solution obtained and the batch is stirred under reflux for a further 48 hours. The solvent is then distilled off in vacuo and the residue is purified by flash chromatography (ethyl acetate/petroleum ether 2:1→1:1]. Colourless crystals (1.58 g 81%) are obtained; TLC [methylene chloride/methanol/ammonia (25%) 15:3:0.2]: $R_f$=0.69; melting point=127° C.

1.26.b) p-Nitrophenyl 3-O-benzyl-4,6-O-isopropylidene-β-D-galactopyranoside

Compound 1.26.a (6.26 g, 16 mmol) is reacted as described in Example 1.24.b. After flash chromatography [petroleum ether/ethyl acetate 5:1→3:1], a colourless foam (6.54 g, 95%) is obtained; TLC [petroleum ether/ethyl acetate 1:1]: $R_f$=0.34; $[\alpha]^{20}$=−38.9° (c=1.0/$CH_2Cl_2$).

1.26.c) p-Nitrophenyl 2,3-di-O-benzyl-4,6-O-isopropylidene-β-D-galactopyranoside Compound 1.26.b (4.31 g, 10 mmol) is dissolved in dimethylformamide (100 ml), and benzyl bromide (12 ml, 100 mmol) and, in portions, an 80% strength suspension of sodium hydride in mineral oil (450 mg, 15 mmol) are added. After 2 hours at room temperature, the reaction is ended by dropwise addition of methanol (10 ml) and the mixture is concentrated in vacuo. The residue is taken up in methylene chloride (1000 ml) and the solution is stirred vigorously with water (500 ml). The organic phase is dried over magnesium sulphate (50 g) and concentrated in vacuo and the residue is purified by flash chromatography [petroleum ether/ethyl acetate 20:1→15:1→10:1]. A colourless oil (2.72 g, 52%), which is still contaminated, is obtained; TLC [petroleum ether/ethyl acetate 1:1]: $R_f$=0.62.

1.26.d) p-Nitrophenyl 2,3-di-O-benzyl-β-D-galactopyranoside

The above compound (2.6 g, 5 mmol) is reacted as described in Example 1.24.d. After concentration in vacuo and extraction of the residue by boiling with diethyl ether, colourless crystals (805 mg, 33%) are obtained; TLC [petroleum ether/ethyl acetate 1:1]: $R_f$=0.23; melting point=160° C.

1.26.e) p-Nitrophenyl 2,3-di-O-benzyl-6-O-triphenylmethyl-β-D-galactopyranoside

Compound 1.26.d (722 mg, 1.5 mmol) is tritylated as described in Example 1.24.a. After flash chromatography [petroleum ether/ethyl acetate 15:1→10:1→5:1], a colourless foam (880 mg, 81%) is obtained; TLC [petroleum ether/ethyl acetate 2:1]: $R_f$=0.79; $[\alpha]^{20}$=−25.3° (c=0.3/$CH_2Cl_2$).

1.26.f) p-Nitrophenyl 2,3-di-O-benzyl-4-O-methyl-6-O-triphenylmethyl-β-D-galactopyranoside The above compound (724 mg, 1 mmol) is methylated as described in Example 1.24.c. After flash chromatography

[petroleum ether/ethyl acetate 10:1→5:1], a colourless foam (662 mg, 90%) is obtained; TLC [petroleum ether/ethyl acetate 5:1]: $R_f$=0.66; $[\alpha]^{20}$=−38.7° (c=0.2/$CH_2Cl_2$).

1.26) p-Aminophenyl 4-O-methyl-β-D-galactopyranoside, acetate

The above compound (590 mg, 0.8 mmol) is dissolved in 90% strength acetic acid (50 ml) and, after addition of palladium-on-active charcoal (10% of Pd, 200 mg), hydrogenation is carried out in a hydrogen atmosphere under a slightly increased pressure for 16 hours. The suspension is filtered over Celite and the material on the filter is washed thoroughly with methanol (100 ml). Concentration of the filtrate in vacuo and reprecipitation of the residue from diethyl ether/petroleum ether gives colourless crystals (253 mg, 92%); TLC [methylene chloride/methanol 5:1]: $R_f$=0.12.

EXAMPLE 1.27 p-Aminophenyl 6-O-methyl-β-D-galactopyranoside

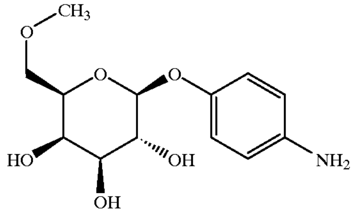

1.27.a) Benzylation of compound 1.24.b

Compound 1.24.b (5.84 g, 10 mmol) is benzylated as described in Example 1.26.c. After flash chromatography [petroleum ether/ethyl acetate 15:1→12:1→5:1→ethyl acetate, in each case with 0.5% of triethylamine], two product fractions are obtained:

Fraction 1: p-nitrophenyl 2-O-benzyl-3,4-O-isopropylidene-6-O-triphenylmethyl-β-D-galactopyranoside; yellowish foam (1.71 g, 25%); TLC [petroleum ether/ethyl acetate 2:1]: $R_f$=0.72; $[\alpha]^{20}$=−8.1° (c=1.0/$CH_2Cl_2$).

Fraction 2: p-nitrophenyl 2-O-benzyl-3,4-O-isopropylidene-β-D-galactopyranoside; yellowish oil (806 g, 19%); TLC [petroleum ether/ethyl acetate 2:1]: $R_f$=0.45; $[\alpha]^{20}$=+2.8° (c=1.2/$CH_3OH$).

1.27.b) p-Nitrophenyl 2-O-benzyl-3,4-O-isopropylidene-6-O-methyl-β-D-galactopyranoside Fraction 2 from Example 1.27.a (777 mg, 1.8 mmol) is methylated as described in Example 1.24.c. After flash chromatography [petroleum ether/ethyl acetate 10:1→8:1], a brownish oil (730 mg, 91%) is obtained; TLC [petroleum ether/ethyl acetate 2:1]: $R_f$=0.54; $[\alpha]^{20}$=−11.6° (c=1.1/$CH_2Cl_2$).

1.27.c) p-Nitrophenyl 2-O-benzyl-6-O-methyl-β-D-galactopyranoside

The above compound (668 mg, 1.5 mmol) is reacted as described in Example 1.24.d. Concentration of the filtrate in vacuo and extraction of the residue by boiling with a little diethyl ether gives, after cooling to room temperature, pale beige crystals (388 mg, 64%); TLC [petroleum ether/ethyl acetate 1:1]: $R_f$=0.15; melting point=143° C.

1.27) p-Aminophenyl 6-O-methyl-β-D-galactopyranoside

Compound 1.27.c (324 mg, 0.8 mmol) is reduced for 16 hours as described in Example 1.24. After concentration of the filtrate in vacuo and extraction of the residue by boiling with a little diethyl ether, beige crystals (184 mg, 81%) are obtained; TLC [ethyl acetate]: $R_f$=0.05; melting point=115° C. (decomposition).

EXAMPLE 1.28 p-Aminophenyl 2,3-di-O-methyl-β-D-galactopyranoside

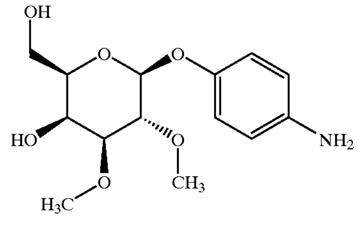

1.28.a) Isopropylidenation of p-nitrophenyl β-D-galactopyranoside

Anhydrous toluenesulphonic acid (500 mg) is added to a solution of p-nitrophenyl β-D-galactopyranoside (7.5 g, 25 mmol) in absolute acetone (1000 ml). Acetone (250 ml) is distilled off under normal pressure in the course of 30 minutes and, immediately thereafter, the mixture is neutralized by addition of potassium carbonate (500 mg). After concentration in vacuo, the residue is stirred with diethyl ether (1000 ml). The mixture is filtered, the filtrate is concentrated and the residue is purified by flash chromatography [petroleum ether/ethyl acetate 2:1→1:1→3:2]. Two product fractions are obtained by this procedure:

Fraction 1: p-Nitrophenyl 3,4-O-isopropylidene-β-D-galactopyranoside; colourless foam (3.74 g, 44%); TLC [methylene chloride/methanol/ammonia (25%) 15:3:0.2]: $R_f$=0.59; $[\alpha]^{20}$=−54.2° (c=0.38/$CH_3OH$).

Fraction 2: p-Nitrophenyl 4,6-O-isopropylidene-β-D-galactopyranoside; colourless foam (4.3 g, 50%); TLC [methylene chloride/methanol/ammonia (25%) 15:3:0.2]: $R_f$=0.54; $[\alpha]^{20}$=−81.0° (c=0.31/$CH_3OH$).

1.28.b) p-Nitrophenyl 2,3-di-O-methyl-4,6-O-isopropylidene-β-D-galactopyranoside Fraction 2 from Example 1.28.a (4.1 g, 12 mmol) is methylated as described in Example 1.24.c. After flash chromatography [petroleum ether/ethyl acetate 5:1→2:1], a colourless foam (2.93 g, 66%) is obtained; TLC [[petroleum ether/ethyl acetate 1:1]: $R_f$=0.42; $[\alpha]^{20}$=−52.6° (c=0.34/$CH_3OH$).

1.28.c) p-Nitrophenyl 2,3-di-O-methyl-β-D-galactopyranoside

The above compound (2.77 g, 7.5 mmol) is reacted as described in Example 1.24.d. After 1 hour at room temperature, the mixture is concentrated in vacuo and the residue is dried under an oil pump vacuum for 1 hour. Digestion with diethyl ether/petroleum ether 1:1 (100 ml) gives colourless crystals (1.11 g, 45%); TLC [ethyl acetate]: $R_f$=0.24; melting point=156° C.

1.28) p-Aminophenyl 2,3-di-O-methyl-β-D-galactopyranoside

Compound 1.28.c (989 mg, 3 mmol) is reduced as described in Example 1.24. A colourless oil (396 mg, 44%) is obtained; TLC [methylene chloride/methanol/ammonia (25%) 15:3:0.2]: $R_f$=0.50; $[\alpha]^{20}$=−19.4° (c=0.16/$CH_3OH$).

EXAMPLE 1.29 p-Aminophenyl 2,4-di-O-methyl-β-D-galactopyranoside

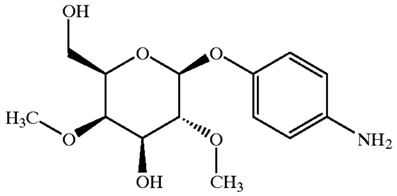

1.29.a) Tritylation of Compound 1.26.a

Compound 1.26.a (11.7 g, 30 mmol) is tritylated as described in Example 1.24.a. After flash chromatography [petroleum ether/ethyl acetate 10:1→7:1→5.1, in each case with 0.5% of triethylamine], two products are obtained:

Fraction 1: triphenylmethyl 2-O-(p-nitrophenyl)-3-O-benzyl-6-O-triphenylmethyl-β-D-galactopyranoside, colourless foam (8.5 g, 32%); TLC [petroleum ether/ethyl acetate 2:1]: $R_f$=0.68; $[\alpha]^{20}$=+42.8° (c=1.0/$CH_2Cl_2$).

Fraction 2: p-nitrophenyl 3-O-benzyl-6-O-triphenylmethyl-β-D-galactopyranoside, colourless foam (9.0 g, 47%); TLC [petroleum ether/ethyl acetate 2:1]: $R_f$=0.22; $[\alpha]^{20}$=−22.6° (c=1.03/$CH_2Cl_2$).

1.29.b) p-Nitrophenyl 2,4-di-O-methyl-3-O-benzyl-6-O-triphenylmethyl-β-D-galactopyranoside Fraction 2 from Example 1.29.a (7.6 g, 12 mmol) is methylated as described in Example 1.24.c. After flash chromatography [petroleum ether/ethyl acetate 15:1→10:1], a colourless foam (7.07 g, 89%) is obtained; TLC [petroleum ether/ethyl acetate 2:1]: $R_f$=0.79; $[\alpha]^{20}$=−35.8° (c=1.09/$CH_3OH$).

1.29.c) p-Aminophenyl 2,4-di-O-methyl-3-O-benzyl-β-D-galactopyranoside

The above compound (6.0 g, 9 mmol) is hydrogenated for 48 hours as described in Example 1.26. Colourless crystals (1.39 g, 40%) are obtained; TLC [ethyl acetate/petroleum ether 2:1]: $R_f$=0.20; melting point=148° C.

1.29) p-Aminophenyl 2,4-di-O-methyl-β-D-galactopyranoside

Compound 1.29.c (779 mg, 2 mmol) is hydrogenated for 5 days as described in

Example 1.24. After evaporation of the combined filtrates in vacuo and extraction of the residue by boiling with diethyl ether (2×50 ml), slightly greenish crystals (391 mg, 65%) are obtained; TLC [ethyl acetate]: $R_f$=0.16; melting point=260° C. (decomposition).

EXAMPLE 1.30 p-Aminophenyl 2,6-di-O-methyl-β-D-galactopyranoside

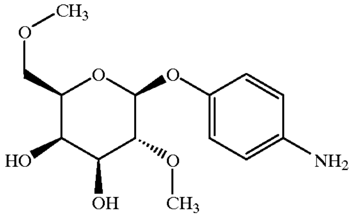

1.30.a) p-Nitrophenyl 2,6-di-O-methyl-3,4-O-isopropylidene-β-D-galactopyranoside Fraction 1 from Example 1.28.a (4.1 g, 12 mmol) is methylated as described in Example 1.24.c. After flash chromatography [petroleum ether/ethyl acetate 10:1→8:1→5:1], a colourless oil (3.25 g, 73%) is obtained; TLC [petroleum ether/ethyl acetate 1:1]: $R_f$=0.65.

1.30.b) p-Nitrophenyl 2,6-di-O-methyl-β-D-galactopyranoside

The above compound (2.77 g, 7.5 mmol) is reacted as described in Example 1.24.d. After flash chromatography [ethyl acetate/petroleum ether 2:1], colourless crystals (1.63 g, 66%) are obtained; TLC [ethyl acetate]: $R_f$=0.31; melting point=222° C.

1.30) p-Aminophenyl 2,6-di-O-methyl-β-D-galactopyranoside

Compound 1.30.b (989 mg, 3 mmol) is reduced as described in Example 1.24. A colourless oil (597 mg, 66%) is obtained; TLC [methylene chloride/methanol/ammonia (25%) 15:3:0.2]: $R_f$=0.56; $[\alpha]^{20}$=−53.1° (c=0.49/$CH_3OH$).

EXAMPLE 1.31 p-Aminophenyl 3,4-di-O-methyl-β-D-galactopyranoside, acetate

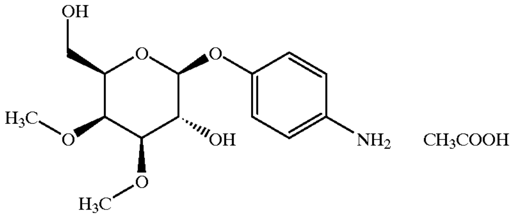

1.31.a) p-Nitrophenyl 2,6-di-O-benzyl-3,4-O-isopropylidene-β-D-galactopyranoside Fraction 1 from Example 1.28.a (4.1 g, 12 mmol) is benzylated as described in Example 1.26.c. After flash chromatography [petroleum ether/ethyl acetate 6:1], a yellowish oil (5.3 g, 85%) is obtained; TLC [ethyl acetate/petroleum ether 2:1]: $R_f$=0.76; $[\alpha]^{20}$=+8.8° (c=1.2/$CH_3OH$).

1.31.b) p-Nitrophenyl 2,6-di-O-benzyl-β-D-galactopyranoside

The above compound (4.69 g, 9 mmol) is reacted as described in Example 1.24.d. After 30 minutes at room temperature, the mixture is concentrated in vacuo and the residue is dried under an oil pump vacuum for 1 hour. Recrystallization from ethanol gives colourless crystals (2.89 g, 67%); TLC [ethyl acetate/petroleum ether 2:1]: $R_f$=0.42; melting point=133° C.; $[\alpha]^{20}$=−64.2° (c=1.0/$CH_3OH$).

1.31.c) p-Nitrophenyl 2,6-di-O-benzyl-3,4-di-O-methyl-β-D-galactopyranoside

The above compound (2.4 g, 5 mmol) is methylated as described in Example 1.24.c. After recrystallization from ethanol/n-hexane, colourless crystals (1.74 g, 69%) are obtained; TLC [petroleum ether/ethyl acetate 1:1]: $R_f$=0.74; melting point=149° C.

1.31) p-Aminophenyl 3,4-di-O-methyl-β-D-galactopyranoside, acetate

Compound 1.31.c (1.52 g, 3 mmol) is hydrogenated as described in Example 1.26. Colourless crystals (664 mg, 62%) are obtained; TLC [methylene chloride/methanol/ammonia (25%) 15:3:0.2]: $R_f$=0.47; melting point=140° C. (decomposition).

EXAMPLE 1.32 p-Aminophenyl 3,6-di-O-methyl-β-D-galactopyranoside

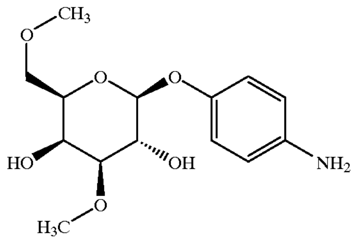

1.32.a) p-Nitrophenyl 3-O-methyl-6-O-(tert-butyldimethylsilyl)-β-D-galactopyranoside Imidazole (1 g, 15 mmol) and tert-butyldimethylsilyl chloride (1.25 g, 8 mmol) are added to a solution of compound 1.25.a (1.58 g, 5 mmol) in dimethylformamide (150 ml) and the mixture is stirred at room temperature for 24 hours. The reaction is then interrupted by addition of water (100 ml). The mixture is diluted with methylene chloride (1000 ml) and the organic phase is washed with water (2×1000 ml), dried over magnesium sulphate (20 g) and concentrated in vacuo. After flash chromatography [petroleum ether/ethyl acetate 15:1→10:1→5:11, a yellowish foam (826 mg, 38%), which is still slightly contaminated, is obtained; TLC [ethyl acetate]: $R_f$=0.59; $[\alpha]^{20}$=−56.3° (c=1.0/$CH_2Cl_2$).

1.32.b) p-Nitrophenyl 2,4-di-O-benzyl-3-O-methyl-6-O-(tert-butyldimethylsilyl)-β-D-galactopyranoside The above compound (773 mg, 1.8 mmol) is benzylated as described in Example 1.26.c. After flash chromatography [petroleum ether/ethyl acetate 30:1→5:1], a colourless foam (810 mg, 74%) is obtained; TLC [petroleum ether/ethyl acetate 5:1]: $R_f$=0.58.

1.32.c) p-Nitrophenyl 2,4-di-O-benzyl-3-O-methyl-β-D-galactopyranoside

Compound 1.32.b (732 mg, 1.2 mmol) is dissolved in tetrahydrofuran (6 ml) and a 1M solution of tetrabutylammonium fluoride in tetrahydrofuran (2.4 ml) is added at 0° C. The mixture is stirred at room temperature for 40 minutes and then concentrated in vacuo. After flash chromatography [petroleum ether/ethyl acetate 5:1→3:1→2:1], colourless crystals (512 mg, 86%) are obtained; TLC [petroleum ether/ethyl acetate 1:1]: $R_f$=0.36; melting point=177° C.

1.32.d) p-Nitrophenyl 2,4-di-O-benzyl-3,6-di-O-methyl-β-D-galactopyranoside

The above compound (446 mg, 0.9 mmol) is methylated as described in Example 1.24.c. After flash chromatography [petroleum ether/ethyl acetate 20:1→10:1→8:1, a colourless oil (401 mg, 87%) is obtained; TLC [petroleum ether/ethyl acetate 1:1]: $R_f$=0.70; $[\alpha]^{20}$=−56.5° (c=0.96/$CH_2Cl_2$).

1.32) p-Aminophenyl 3,6-di-O-methyl-β-D-galactopyranoside

Compound 1.32.d (357 mg, 0.7 mmol) is hydrogenated as described in Example 1.24. After evaporation of the combined filtrates in vacuo and extraction of the residue by boiling with diethyl ether (20 ml), colourless crystals (207 mg, 99%) are obtained; TLC [petroleum ether/ethyl acetate 1:1]: $R_f$=0.02; melting point=>280° C. (decomposition).

EXAMPLE 1.33 p-Aminophenyl 4,6-di-O-methyl-βD-galactopyranoside

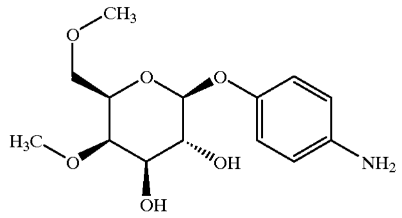

1.33.a) p-Nitrophenyl 2,3-di-O-benzyl-4,6-di-O-methyl-β-D-galactopyranoside

Compound 1.26.d (2.4 g, 5 mmol) is methylated as described in Example 1.24.c. After flash chromatography [petroleum ether/ethyl acetate 5:1→3:1], colourless crystals (1.89 g, (74%) are obtained; TLC [petroleum ether/ethyl acetate 1:1]: $R_f$=0.76; melting point=177° C.

1.33) p-Aminophenyl 4,6-di-O-methyl-β-D-galactopyranoside

Compound 1.33.a (1.53 g, 3 mmol) is hydrogenated as described in Example 1.24. Colourless crystals (890 mg, 99%) are obtained; TLC [methanol/ethyl acetate 1:1]: $R_f$=0.71; melting point=180° C. (decomposition).

EXAMPLE 1.34 p-Aminophenyl 2,3,4-tri-O-methyl-β-D-galactopyranoside

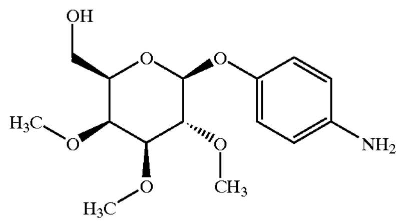

1.34.a) p-Nitrophenyl 2,3,4-tri-O-methyl-6-O-triphenylmethyl-β-D-galactopyranoside Compound 1.24.a (1.63 g, 3 mmol) is methylated as described in Example 1.24.c. After flash chromatography [petroleum ether/ethyl acetate 5:1→3:1], a colourless foam (1.24 g, 71%) is obtained; TLC [petroleum ether/ethyl acetate 1:1]: $R_f$=0.54; $[\alpha]^{20}$=−53.6° (c=0.3/$CH_3OH$).

1.34.b) p-Nitrophenyl 2,3,4-tri-O-methyl-β-D-galactopyranoside

The above compound (1.17 g, 2 mmol) is reacted as described in Example 1.24.d. After flash chromatography [petroleum ether/ethyl acetate 3:1→2:1], colourless crystals (468 mg, 68%) are obtained; TLC [petroleum ether/ethyl acetate 1:1]: $R_f$=0.12; melting point=104° C.; $[\alpha]^{20}$=−68.2° (c=0.47/$CH_3OH$).

1.34) p-Aminophenyl 2,3,4-tri-O-methyl-β-D-galactopyranoside

Compound 1.34.b (343 mg, 1 mmol) is reduced as described in Example 1.24. Beige crystals (224 mg, 71%) are obtained; TLC (methylene chloride/methanol/ammonia (25%) 15:3:0.2]: $R_f$=0.67; melting point=138° C.

EXAMPLE 1.35 p-Aminophenyl 2,3,6-tri-O-methyl-β-D-galactopyranoside

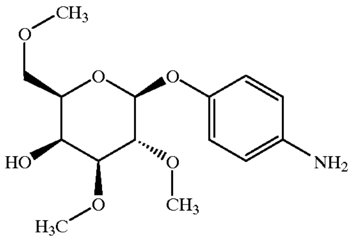

1.35.a) p-Nitrophenyl 2,3,6-tri-O-methyl-β-D-galactopyranoside

Compound 1.30.b (2.63 g, 3 mmol) is methylated selectively as described in Example 1.25.a. After flash chromatography [petroleum ether/ethyl acetate 5:1→2:1], a brownish oil (890 mg, 32%) is obtained; TLC [ethyl acetate]: $R_f$=0.37; $[\alpha]^{20}$=−63.3° (c=0.9/$CH_2Cl_2$).

1.35) p-Aminophenyl 2,3,6-tri-O-methyl-β-D-galactopyranoside

The above compound (858 mg, 2.5 mmol) is reduced as described in Example 1.24. A beige foam (519 mg, 66%) is obtained; TLC [ethyl acetate]: $R_f$0.23; $[\alpha]^{20}$=−34.5° (c=0.86/$CH_3OH$).

EXAMPLE 1.36 p-Aminophenyl 2,4,6-O-methyl-β-D-galactopyranoside

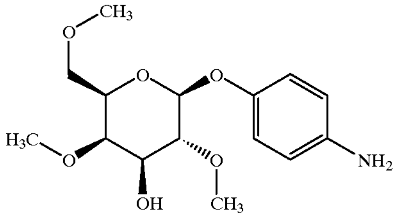

1.36.a) p-Nitrophenyl 2,4,6-tri-O-methyl-3-O-benzyl-β-D-galactopyranoside

Compound 1.26.a (1.96 g, 5 mmol) is methylated as described in Example 1.24.c. After flash chromatography [petroleum ether/ethyl acetate 10:1→8:1], colourless crystals (1.47 g, 68%) are obtained; TLC [petroleum ether/ethyl acetate 2:1]: $R_f$=0.46; melting point=164° C.

1.36) p-Aminophenyl 2,4,6-tri-O-methyl-β-D-galactopyranoside

The above compound (1.3 g, 3 mmol) is reduced as described in Example 1.26. Colourless crystals (642 mg, 68%) are obtained; TLC [ethyl acetate/petroleum ether 2:1]: $R_f$=0.12; melting point=147° C. (decomposition).

EXAMPLE 1.37 p-Aminophenyl 3,4,6-tri-O-methyl-β-D-galactopyranoside

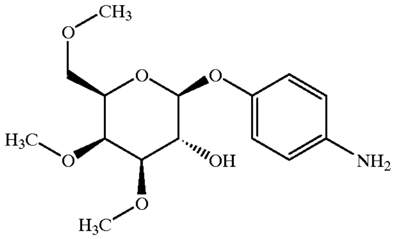

1.37.a) p-Nitrophenyl 2-O-benzyl-β-D-galactopyranoside

Fraction 1 from Example 1.27.a (1.17 g, 2 mmol) is reacted as described in Example 1.24.d. After flash chromatography [petroleum ether/ethyl acetate 3:1→2:1], colourless crystals (468 mg, 68%) are obtained; TLC [petroleum ether/ethyl acetate 1:1]: $R_f$=0.12; melting point=104° C.; $[\alpha]^{20}$=−68.2° (c=0.47/$CH_3OH$).

1.37.b) p-Nitrophenyl 2-O-benzyl-3,4,6-tri-O-methyl-β-D-galactopyranoside

The above compound (391 mg, 1 mmol) is methylated as described in Example 1.24.c. After flash chromatography [petroleum ether/ethyl acetate 10:1→5:1], pale yellow crystals (303 mg, 70%) are obtained; TLC [ethyl acetate]: $R_f$=0.81; $[\alpha]^{20}$=−76.5° (c=1.1/$CH_2Cl_2$).

1.37) p-Aminophenyl 3,4,6-tri-O-methyl-β-D-galactopyranoside

Compound 1.37.b (260 mg, 0.6 mmol) is hydrogenated as described in Example 1.24. Beige crystals (161 mg, 86%) are obtained; TLC [ethyl acetate]: $R_f$=0.20; melting point=132° C.

EXAMPLE 1.38 p-Aminophenyl 2,3,4,6-tetra-O-methyl-β-D-galactopyranoside

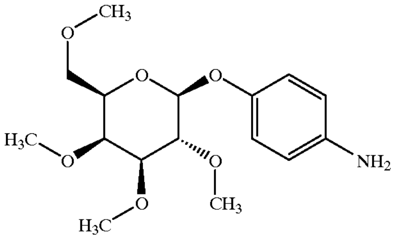

1.38.a) p-Nitrophenyl 2,3,4,6-tetra-O-methyl-β-D-galactopyranoside p-Nitrophenyl β-D-galactopyranoside (904 mg, 3 mmol) is methylated as described in Example 1.24.c. After flash chromatography [petroleum ether/ethyl acetate 8:1→6:1→4:1→2:1], a colourless, waxy solid (633 mg, 59%) is obtained; TLC [ethyl acetate]: $R_f$=0.67; $[\alpha]^{20}$=−55.7° (c=0.9/$CH_2Cl_2$).

1.38) p-Aminophenyl 2,3,4,6-tetra-O-methyl-β-D-galactopyranoside

Compound 1.33.a (536 mg, 1.5 mmol) is hydrogenated as described in Example 1.24. After evaporation of the combined filtrates in vacuo and extraction of the residue by boiling with diethyl ether (20 ml), colourless crystals (412 mg, 84%) are obtained; TLC [ethyl acetate]: $R_f$=0.42; melting point=204° C. (decomposition).

EXAMPLE 1.39 p-Aminophenyl α-D-mannopyranoside

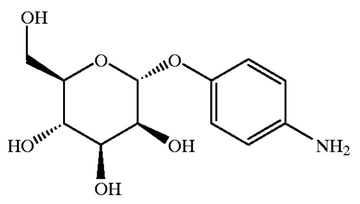

p-Nitrophenyl α-D-mannopyranoside (3.0 g, 10 mmol) is hydrogenated as described in Example 1.23. The precipitation from methanol/diethyl ether gives colourless crystals (2.03 g, 75%); TLC [methanol]: $R_f$=0.69; $[\alpha]^{20}$=+102.7° (c=1.0/$H_2O$); melting point=161° C.

EXAMPLE 1.40 p-Aminophenyl 3-O-methyl-α-D-mannopyranoside

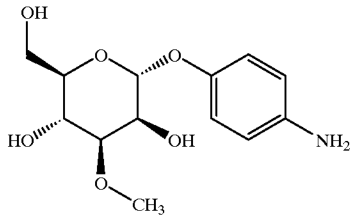

1.40.a) p-Nitrophenyl 6-O-triphenylmethyl-α-D-mannopyranoside p-Nitrophenyl α-D-mannopyranoside (3.0 g, 10 mmol) is tritylated as described in Example 1.24.a. Colourless crystals (4.35 g, 80%) are obtained; TLC [methylene chloride/methanol/ammonia (25%) 15:3:0.2]: $R_f$=0.52; $[\alpha]^{20}$=+104.0° (c=1.0/$CH_3OH$); melting point=102–104° C.

1.40.b) p-Nitrophenyl 3-O-methyl-6-O-triphenylmethyl-α-D-mannopyranoside

The above compound (2.72 g, 5 mmol) is reacted with methyl iodide (2 ml, 30 mmol) as described in Example 1.26.a. After flash chromatography [petroleum ether/ethyl acetate 2:1] and reprecipitation from ethanol/n-hexane, colourless crystals (1.83 g, 66%) are obtained; TLC [methylene chloride/methanol/ammonia (25%) 15:3:0.2]: $R_f$=0.68; $[\alpha]^{20}$=+106.4° (c=1.0/$CH_3OH$); melting point=104° C.

1.40) p-Aminophenyl 3-O-methyl-α-D-mannopyranoside

Compound 1.40.b (1.4 g, 2.5 mmol) is dissolved in methanol (50 ml) and, after addition of palladium-on-active charcoal (10% of Pd, 300 mg), hydrogenation is carried out in a hydrogen atmosphere under a slightly increased pressure for 24 hours. The suspension is filtered over Celite and the material on the filter is washed thoroughly with methanol (100 ml). After concentration of the filtrate in vacuo, the residue is extracted with water (50 ml), the mixture is filtered and the filtrate is lyophilized. A brownish amorphous solid (709 mg, 99%) is obtained; TLC [methylene chloride/methanol/ammonia (25%) 15:3:0.2]: $R_f$=0.33; $[\alpha]^{20}$=+92.9° (c=1.1/$CH_3OH$).

EXAMPLE 1.41 p-Aminophenyl 2,3-di-O-methyl-α-D-mannopyranoside

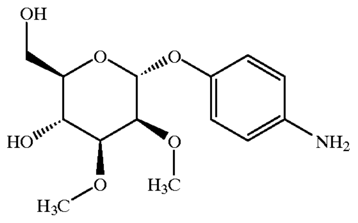

1.41.a) p-Nitrophenyl 4,6-O-benzylidene-α-D-mannopyranoside

Benzaldehyde dimethyl acetal (3.2 ml, 21.4 mmol) and a 54% strength solution of tetrafluoboric acid in diethyl ether (2.7 ml, 20 mmol) are added to a solution of p-nitrophenyl α-D-mannopyranoside (6.0 g, 20 mmol) in dimethylformamide (120 ml). The mixture is stirred at room temperature for 5 hours, the reaction is then interrupted by addition of triethylamine (2.8 ml, 20 mmol) and the mixture is concentrated in vacuo. After flash chromatography [toluene→toluene/ethanol 20:1], colourless crystals (6.48 g, 83%) are obtained; TLC [methylene chloride/methanol/ammonia (25%) 15:3:0.2]: $R_f$=0.82; $[\alpha]^{20}$=+170.7° (c=1.0/$CH_2Cl_2$); melting point=116° C.

1.41.b) p-Nitrophenyl 2,3-di-O-methyl-4,6-O-benzylidene-α-D-mannopyranoside

The above compound (3.9 g, 10 mmol) is methylated as described in Example 1.24.c. After flash chromatography [petroleum ether/ethyl acetate 20:1→7:1] and reprecipitation from ethyl acetate/n-hexane, a colourless foam (3.2 g, 77%) is obtained; TLC [ethyl acetate/petroleum ether 2:1]: $R_f$=0.67; $[\alpha]^{20}$=+167.30 (c=1.05/$CH_3OH$).

1.41) p-Aminophenyl 2,3-di-O-methyl-α-D-mannopyranoside

Compound 1.41.b (1.25 g, 3 mmol) is hydrogenated as described in Example 1.26. After flash chromatography [ethyl acetate/petroleum ether 2:1→ethyl acetate, in each case with 0.5% of triethylamine], a reddish-brown foam (480 mg, 53%) is obtained; TLC [methylene chloride/methanol/ammonia (25%) 15:3:0.2]: $R_f$=0.31; $[\alpha]^{20}$=+83.6° (c=0.76/$CH_3OH$).

EXAMPLE 1.42

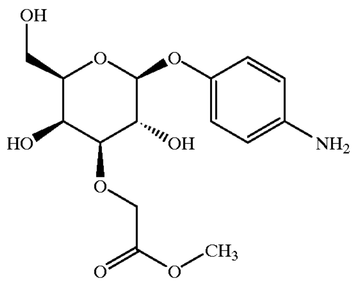

1.42.a) p-Nitrophenyl 3-O-methoxycarbonylmethyl-α-D-galactopyranoside

Dibutyltin oxide (9.3 g, 37.5 mmol) is added to a solution of p-nitrophenyl β-D-galactopyranoside (7.53 g, 25 mmol) in absolute dioxane (180 ml) and the mixture is heated under reflux. After 4 hours, methyl bromoacetate (8.3 ml, 90 mmol) and tetrabutylammonium iodide (9.25 g, 25 mmol) are added to the solution obtained and the batch is stirred under reflux for a further 3 hours. The solvent is then distilled off in vacuo and the residue is purified by flash chromatography [methylene chloride/methanol 50:1→20:1]. In addition to some by-products, the compound 1.42.a is obtained as colourless crystals (4.05 g, 43%); TLC [methylene chloride/methanol/ammonia (25%) 15:3:0.2]: $R_f$=0.54; $[\alpha]^{20}$=−62.0° (c=1.0/$CH_3OH$); melting point 176° C.

1.42) p-Aminophenyl 3-O-methoxycarbonylmethyl-β-D-galactopyranoside

Compound 1.42.a (3.73 g, 10 mmol) is hydrogenated as described in Example 1.24. After reprecipitation from ethanol/-hexane, colourless crystals (2.98 g, 87%) are obtained; TLC [methylene chloride/methanol/ammonia (25%) 15:3:0.2]: $R_f$=0.39; $[\alpha]^{20}$=−36.3° (c=1.07/$CH_3OH$); melting point=155° C.

EXAMPLE 1.43

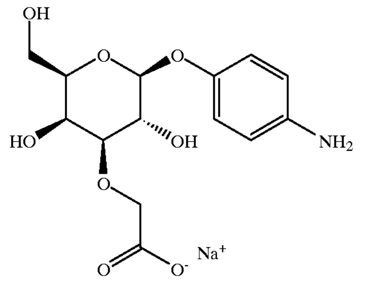

1.43.a) p-Nitrophenyl 3-O-carboxymethyl-β-D-galactopyranoside, sodium salt

A solution of sodium hydroxide (400 mg, 10 mmol) in water (5 ml) is added to a solution of compound 1.42.a (3.73 g, 10 mmol) in methanol (100 ml) and the mixture is stirred at room temperature for 2 hours. After concentration in vacuo, the residue is dried under an oil pump vacuum for 2 hours and ethanol (100 ml) is then added. The mixture is boiled under reflux for 5 minutes and, after cooling in an ice-bath, the solid is filtered off to give colourless crystals (3.66 g, 96%); TLC [methanol]: $R_f$=0.62; $[\alpha]^{20}$=−50.0° (c=1.0/$CH_3OH$); melting point=180–185° C.

1.43) p-Aminophenyl 3-O-carboxymethyl-β-D-galactopyranoside, sodium salt

The above compound (3.05 g, 8 mmol) is hydrogenated as described in Example 1.24. After extraction by boiling with ethanol (50 ml), colourless crystals (2.03 g, 72%) are obtained; TLC [methanol]: $R_f$=0.70; $[\alpha]^{20}$=−22.4° (c=1.0/$CH_3OH$); melting point=180–182° C.

EXAMPLE 1.44 p-Aminophenyl 3-O-carbamoylmethyl-β-D-galactopyranoside

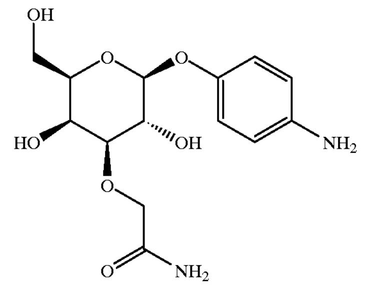

1.44.a) p-Nitrophenyl 3-O-carbamoylmethyl-β-D-galactopyranoside

A 25% strength aqueous solution of ammonia (10 ml) is added to a solution of compound 1.42.a (373 mg, 1 mmol) in methanol (30 ml) and the mixture is stirred at room temperature for 15 minutes. After concentration in vacuo, the residue is dried under an oil pump vacuum for 2 hours and ethanol (30 ml) is then added. The mixture is boiled under reflux for 5 minutes and filtered, after cooling in an ice-bath, to give colourless crystals (306 mg, 85%); TLC [methylene chloride/methanol/ammonia (25%) 15:3:0.2]: $R_f$=0.14; $[\alpha]^{20}$=−41.7° (c=1.0/$CH_3OH$); melting point=229° C. (decomposition).

1.44) p-Aminophenyl 3-O-carbamoylmethyl-β-D-galactopyranoside

The above compound (287 mg, 0.8 mmol) is hydrogenated as described in Example 1.24. After reprecipitation from methanol/diethyl ether, colourless crystals (207 mg, 79%) are obtained; TLC [methylene chloride/methanol/ammonia (25%) 15:3:0.2]: $R_f$=0.10; melting point=205° C. (decomposition).

EXAMPLE 1.45 p-Aminophenyl 3-O-(N-methyl-carbamoylmethyl)-β-D-galactopyranoside

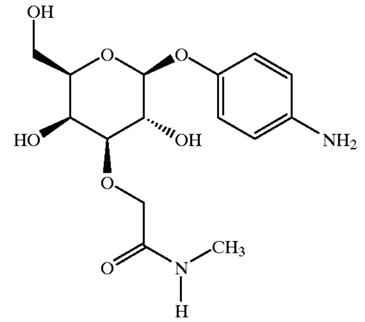

1.45a) p-Nitrophenyl 3-O-(N-methyl-carbamoylmethyl)-β-D-galactopyranoside

A 30% strength aqueous solution of methylamine (10 ml) is added to a solution of compound 1.42.a (373 mg, 1 mmol) in methanol (30 ml) and the mixture is stirred at room temperature for 2 hours. After concentration in vacuo, the residue is dried under an oil pump vacuum for 2 hours and then recrystallized from ethanol. Colourless crystals (372 mg, 100%) are obtained; TLC [methylene chloride/methanol/ammonia (25%) 15:3:0.2]: $R_f$=0.33; $[\alpha]^{20}$=−36.7° (c=1.0/$CH_3OH$); melting point=205° C.

1.45) p-Aminophenyl 3-O-(N-methyl-carbamoylmethyl)-β-D-galactopyranoside

Compound 1.45.a (298 mg, 0.8 mmol) is hydrogenated as described in Example 1.24. After reprecipitation from methanol/diethyl ether, colourless crystals (180 mg, 66%) are obtained; TLC [methylene chloride/methanol/ammonia (25%) 15:3:0.2]: $R_f$=0.16; melting point=239° C.

EXAMPLE 1.46 p-Aminophenyl 3-O-(N-propyl-carbamoylmethyl)-β-D-galactopyranoside

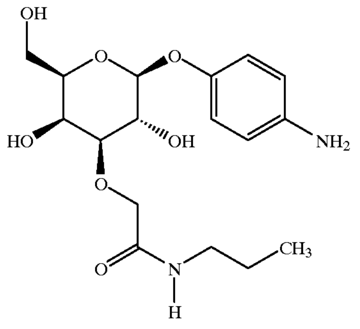

1.46.a) p-Nitrophenyl 3-O-(N-propyl-carbamoylmethyl)-β-D-galactopyranoside

Compound 1.42.a (373 mg, 1 mmol) is reacted with n-propylamine (823 μl, 10 mmol) as described in Example 1.45.a. After concentration in vacuo, the residue is reprecipitated from ethanol/n-hexane. Colourless crystals (340 mg, 85%) are obtained; TLC [methylene chloride/methanol/ammonia (25%) 15:3:0.2]: $R_f$=0.49; $[\alpha]^{20}$=−32.4° (c=1.0/$CH_3OH$); melting point=155° C.

1.46) p-Aminophenyl $^3$-O-(N-propyl-carbamoylmethyl)-β-D-galactopyranoside

Compound 1.46.a (320 mg, 0.8 mmol) is hydrogenated as described in Example 1.24. After reprecipitation from methanol/diethyl ether, colourless crystals (188 mg, 63%) are obtained; TLC [methylene chloride/methanol/ammonia (25%) 15:3:0.2]: $R_f$=0.31; melting point=154° C.

EXAMPLE 1.47 p-Aminophenyl 3-O-(N-butyl-carbamoylmethyl)-β-D-galactopyranoside

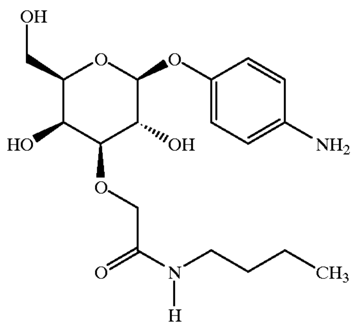

1.47.a) p-Nitrophenyl 3-O-(N-butyl-carbamoylmethyl)-β-D-galactopyranoside

Compound 1.42.a (373 mg, 1 mmol) is reacted with n-butylamine (900 μl, 10 mmol) as described in Example 1.45.a. After concentration in vacuo, the residue is reprecipitated from ethanol/n-hexane. Colourless crystals (413 mg, 100%) are obtained; TLC [methylene chloride/methanol/ammonia (25%) 15:3:0.2]: $R_f$=0.51; $[\alpha]^{20}$=−26.8° (c=1.0/$CH_3OH$); melting point=92° C.

1.47) p-Aminophenyl 3-O-(N-butyl-carbamoylmethyl)-β-D-galactopyranoside

Compound 1.47.a (332 mg, 0.8 mmol) is hydrogenated as described in Example 1.24. After reprecipitation from ethanol/n-hexane, colourless crystals (105 mg, 34%) are obtained; TLC [methylene chloride/methanol/ammonia (25%) 15:3:0.2]: $R_f$=0.32; melting point=135° C.

EXAMPLE 1.48 p-Aminophenyl 3-O-methoxycarbonylmethyl-α-D-mannopyranoside

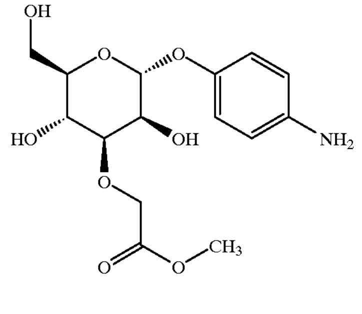

1.48.a) p-Nitrophenyl 3-O-methoxycarbonylmethyl-6-O-triphenylmethyl-α-D-mannopyranoside Compound 1.40.a (13.6 g, 25 mmol) is reacted as described in Example 1.42.a. After flash chromatography [petroleum ether/ethyl acetate 10:1], in addition to some by-products, colourless crystals (2.79 g, 18%) are obtained; TLC [ethyl acetate/petroleum ether 2:1]: $R_f$=0.50; melting point=95–97° C.

1.48) p-Aminophenyl 3-O-methoxycarbonylmethyl-α-D-mannopyranoside

Compound 1.48.a (1.23 g, 2 mmol) is hydrogenated as described in Example 1.40 and the product is worked up. A brownish amorphous solid (250 mg, 36%) is obtained; TLC [methylene chloride/methanol/ammonia (25%) 15:3:0.2]: $R_f$=0.45.

EXAMPLE 1.49 p-Aminophenyl 3-O-carboxymethyl-α-D-mannopyranoside

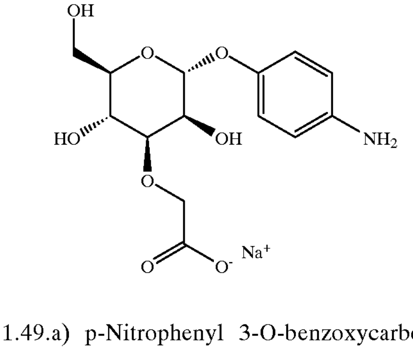

1.49.a) p-Nitrophenyl 3-O-benzoxycarbonylmethyl-6-O-triphenylmethyl-α-D-mannopyranoside Compound 1.40.a (13.6 g, 25 mmol) is reacted with benzyl bromoacetate (14.4 ml, 90 mmol) as described in Example 1.42.a. After flash chromatography [petroleum ether/ethyl acetate 20:1→10:1], in addition to some by-products, a yellowish foam (5.0 g, 29%) is obtained; TLC [ethyl acetate/petroleum ether 2:1]: $R_f$=0.66; $[\alpha]^{20}$=+74.8° (c=1.0/$CH_2Cl_2$).

1.49) p-Aminophenyl 3-O-carboxymethyl-α-D-mannopyranoside

The above compound (2.08 g, 3 mmol) is hydrogenated for 36 hours as described in Example 1.40. After concentration of the filtrate, the residue is reprecipitated from ethanol/n-hexane. Washing with ethyl acetate and renewed reprecipitation from ethanol/diethyl ether gives colourless crystals (495 mg, 50%); TLC [methanol]: $R_f$=0.53; melting point=205–207° C.

EXAMPLE 1.50 p-Aminophenyl 3-O-carbamoylmethyl-α-D-mannopyranoside

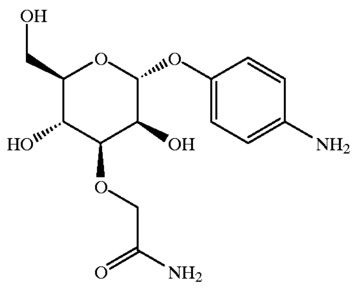

1.50.a) p-Nitrophenyl 3-O-carbamoylmethyl-6-O-triphenylmethyl-α-D-mannopyranoside Compound 1.49.a (1.04 g, 1.5 mmol) is reacted as described in Example 1.44.a. After drying under an oil pump vacuum, the residue is purified by flash chromatography [petroleum ether/ethyl acetate 2:3]. Colourless crystals (561 mg, 62%) are obtained; TLC [methylene chloride/methanol/ammonia (25%) 15:3:0.2]: $R_f$=0.67; $[\alpha]^{20}$=+91.3° (c=1.0/$CH_2Cl_2$); melting point=125–127° C.

1.50) p-Aminophenyl 3-O-carbamoylmethyl-α-D-mannopyranoside

The above compound (541 g, 0.9 mmol) is hydrogenated for 48 hours as described in Example 1.40. After concentration of the filtrate, the residue is washed thoroughly with methanol to give colourless crystals (134 mg, 45%); TLC [methylene chloride/methanol/ammonia (25%) 15:3:0.2]: $R_f$=0.21; melting point=126–128° C.

EXAMPLE 1.51 p-Aminophenyl 3-deoxy-β-D-galactopyranoside

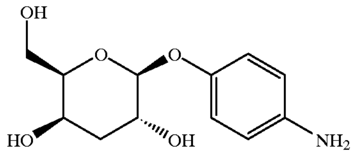

1.51.a) p-Nitrophenyl 2,6-di-O-benzyl-4-O-acetyl-β-D-galactopyranoside

Triethyl orthoacetate (3 ml, 16.3 mmol) and toluenesulphonic acid (20 mg) are added to a solution of compound 1.31.b (2.7 g, 5.6 mmol) in methylene chloride (20 ml). After 30 minutes at room temperature, the batch is diluted with methylene chloride (200 ml) and washed with saturated sodium bicarbonate solution (50 ml), the organic phase is dried over magnesium sulphate and, after filtration, the filtrate is concentrated in vacuo. The resulting colourless foam is dissolved in 80% strength acetic acid (15 ml). After a further 30 minutes at room temperature, the batch is poured into saturated sodium bicarbonate solution (200 ml) and extracted with chloroform (3x75 ml), the combined organic phases are washed with water (100 ml) and dried over magnesium sulphate and, after filtration, the filtrate is concentrated in vacuo. Reprecipitation from ethanol/petroleum ether gives colourless crystals (2.43 g, 83%); TLC [ethyl acetate/petroleum ether 2:1]: $R_f$=0.64; $[\alpha]^{20}$=−62.1° (c=1.0/$CH_2Cl_2$); melting point=83° C.

1.51.b) p-Nitrophenyl 2,6-di-O-benzyl-3-O-trifluoromethanesulphonyl-4-O-acetyl-β-D-galactopyranoside A solution of trifluoromethanesulphonic anhydride (2 ml, 11.8 mmol) in methylene chloride (30 ml) is added dropwise to a solution of compound 1.51.a (2.3 g, 4.4 mmol) in a mixture of methylene chloride (30 ml) and pyridine (3 ml) at −20° C., under argon. After 1 hour at −20° C., the batch is poured into saturated sodium bicarbonate solution (200 ml), the organic phase is separated off and dried over magnesium sulphate and, after filtration, the filtrate is concentrated in vacuo. After flash chromatography [toluene→toluene/ethyl acetate 20:1], colourless crystals (2.39 g, 83%) are obtained; TLC [toluene/ethyl acetate 5:1]: $R_f$=0.55; $[\alpha]^{20}$=−61.4° (c=1.0/$CH_2Cl_2$); melting point=105° C.

1.51.c) p-Nitrophenyl 2,6-di-O-benzyl-3-deoxy-β-D-galactopyranoside

The above compound (1.31 g, 2 mmol) is dissolved in toluene (25 ml), and tetrabutylammonium tetraborohydrate (1.54 g, 6 mmol) is added. After 2 hours at 80° C., the batch is diluted with methylene chloride (200 ml) and washed once with water (50 ml), the organic phase is dried over magnesium sulphate and, after filtration, the filtrate is concentrated in vacuo. After flash chromatography [toluene/ethyl acetate 7:1], colourless crystals (596 mg, 64%) are obtained; TLC [toluene/ethyl acetate 5:1]: $R_f$=0.10; $[\alpha]^{20}$=−81.3° (c=1.0/$CH_2Cl_2$); melting point=114° C.

1.51) p-Aminophenyl 3-deoxy-β-D-galactopyranoside

Compound 1.51.c (465 mg, 1 mmol) is hydrogenated for 6 hours as described in Example 1.40. After concentration of the filtrate, the residue is reprecipitated from ethanol/petroleum ether to give colourless crystals (206 mg, 81%); TLC [methylene chloride/methanol/ammonia (25%) 15:3:0.2]: $R_f$=0.22.

EXAMPLE 1.52 p-Aminophenyl 3,4-dideoxy-β-D-galactopyranoside

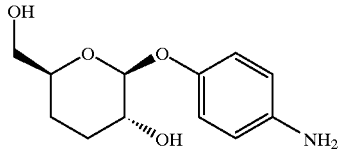

1.52.a) p-Nitrophenyl 2,6-di-O-benzyl-3,4-di-O-trifluoromethanesulphonyl-β-D-galactopyranoside Compound 1.31.b (2.12 g, 4.4 mmol) is reacted with trifluoromethanesulphonic anhydride (4 ml, 23.6 mmol) as in Example 1.51.b. After flash chromatography [toluene→toluene/ethyl acetate 50:1], a yellowish oil (2.75 g, 84%) is obtained; TLC [toluene/ethyl acetate 5:1]: $R_f$=0.67; $[\alpha]^{20}$=−22.5° (c=1.0/$CH_2Cl_2$).

1.52.b) p-Nitrophenyl 2,6-di-O-benzyl-3,4-dideoxy-β-D-galactopyranoside

Compound 1.52.a (1.49 g, 2 mmol) is reacted with tetrabutylammonium tetraborohydrate (2.31 g, 9 mmol) as in Example 1.51.c. After flash chromatography [toluene→toluene/ethyl acetate 50:1], colourless crystals (629 mg, 70%) are obtained; TLC [toluene/ethyl acetate 5:1]: $R_f$=0.53; $[\alpha]^{20}$=−79.1° (c=1.0/$CH_2Cl_2$); melting point=89° C.

1.52) p-Aminophenyl 3,4-dideoxy-β-D-galactopyranoside

Compound 1.52.b (450 mg, 1 mmol) is hydrogenated for 5 hours as described in Example 1.40. After concentration of the filtrate, the residue is reprecipitated from ethanol/petroleum ether to give colourless crystals (183 mg, 76%); TLC [methylene chloride/methanol/ammonia (25%) 15:3:0.2]: $R_f$=0.47; $[\alpha]^{20}$=115.1° (c=1.0/$CH_3OH$); melting point=187° C.

EXAMPLE 1.53 p-Aminophenyl 6-O-acetyl-β-D-galactopyranoside

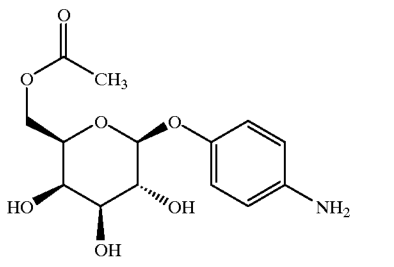

1.53.a) p-Nitrophenyl 6-O-acetyl-β-D-galactopyranoside

A freshly prepared solution of pyridine (2 ml, 25 mmol) and acetyl chloride (1.85 ml, 26 mmol) in acetonitrile (20 ml) is added dropwise to a solution of p-nitrophenyl β-D-galactopyranoside (7.53 g, 25 mmol) in absolute acetonitrile (80 ml) at 0° C. The mixture is stirred at 0° C. for 30 minutes and then concentrated in vacuo.

After flash chromatography [methylene chloride/methanol 50:1→20:1], colourless crystals (4.02 g, 47%) are obtained; TLC [methylene chloride/methanol/ammonia (25%) 15:3:0.2]: $R_f$=0.50.

1.53) p-Aminophenyl 6-O-acetyl-β-D-galactopyranoside

Compound 1.53.a (1.72 g, 5 mmol) is hydrogenated for 2 hours as described in Example 1.40. After concentration of the filtrate, the residue is reprecipitated from methanol/diethyl ether to give colourless crystals (1.34 g, 86%); TLC [methylene chloride/methanol/ammonia (25%) 15:3:0.2]: $R_f$=0.34; $[\alpha]^{20}$=41.0° (c=0.56/$CH_3OH$); melting point=180° C. (decomposition).

EXAMPLE 1.54 p-Aminophenyl 3,4-di-O-methoxycarbonylmethyl-β-D-galactopyranoside

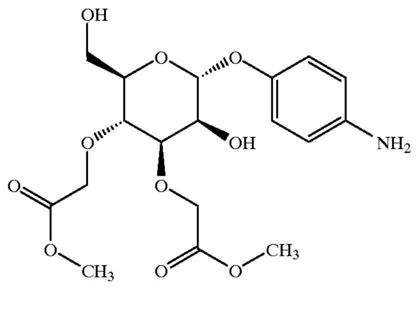

1.54.a) Acylation of compound 1.24.a

Compound 1.24.a (1.36 g, 3 mmol) is dissolved in dimethylformamide (25 ml) and methyl bromoacetate (1 ml, 10.6 mmol) and, in portions, an 80% strength suspension of sodium hydride in mineral oil (300 mg, 10 mmol) are added. After 3.5 hours at room temperature, methyl bromoacetate (250 μl, 2.65 mmol) and sodium hydride in mineral oil (75 mg, 2.5 mmol) are again added. After a further 2 hours, the reaction is ended by dropwise addition of methanol (5 ml) and the mixture is concentrated in vacuo. The residue is taken up in methylene chloride (250 ml) and the solution is stirred vigorously with water (100 ml). The organic phase is dried over magnesium sulphate (10 g) and concentrated in vacuo and the residue is purified by flash chromatography [petroleum ether/ethyl acetate 10:1→7:1→5:1→3:1]. Three product fractions are obtained:

Fraction 1: p-nitrophenyl 2,3,4-tri-O-methoxycarbonylmethyl-β-D-galactopyranoside; colourless foam (401 mg, 21%); TLC [petroleum ether/ethyl acetate 1:1]: $R_f$=0.47; $[\alpha]^{20}$=−51.9° (c=0.26/$CH_3OH$).

Fraction 2: not identified; colourless foam (88 mg); TLC [petroleum ether/ethyl acetate 1:1]: $R_f$=0.39; $[\alpha]^{20}$=−61.5° (c=0.26/$CH_3OH$).

Fraction 3: p-nitrophenyl 3,4-di-O-methoxycarbonylmethyl-β-D-galactopyranoside; colourless foam (275 mg, 16%); TLC [petroleum ether/ethyl acetate 1:1]: $R_f$=0.30; $[\alpha]^{20}$=−38.6° (c=0.28/$CH_3OH$).

1.54) p-Aminophenyl 3,4-di-O-methoxycarbonylmethyl-β-D-galactopyranoside

Fraction 3 from Example 1.54.a (206 mg, 0.3 mmol) is hydrogenated for 16 hours as described in Example 1.40. After concentration of the filtrate, the residue is extracted by boiling with diethyl ether (20 ml) to give grey crystals (45.6 mg, 37%); TLC [petroleum ether/ethyl acetate 1:1]: $R_f$=0.22; melting point=155° C. (decomposition).

EXAMPLE 1.55 p-Aminophenyl 2,3,4-tri-O-methoxycarbonylmethyl-β-D-galactopyranoside

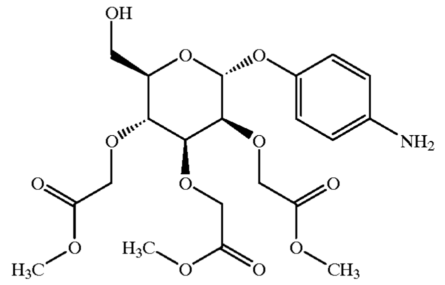

Fraction 1 from Example 1.54.a (380 mg, 0,5 mmol) is hydrogenated for 16 hours as described in Example 1.40. After concentration of the filtrate, the residue is extracted by boiling with diethyl ether (20 ml) to give a yellow-brown oil (46.8 mg, 19%); TLC [petroleum ether/ethyl acetate 1:1]: $R_f$=0.29; melting point=106° C. (decomposition).

EXAMPLE 1.56 p-Aminophenyl 4-O-(β-D-galactopyranosyl)-β-D-glucopyranoside

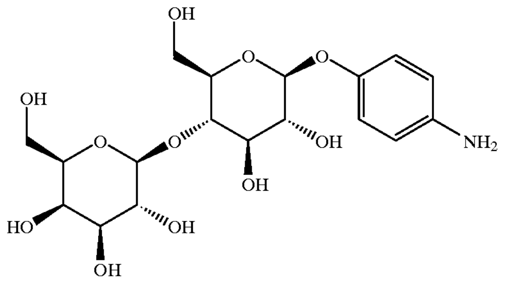

p-Nitrophenyl 4-O-(β-D-galactopyranosyl)-β-D-galactopyranoside (4.63 g, 10 mmol) is hydrogenated as described in Example 1.23. Colourless crystals (3.04 g, 70%) are obtained; TLC [methanol]: $R_f$=0.55, melting point=235–237° C. (decomposition).

EXAMPLE 1.57 p-Aminophenyl 4-O-(3'-sulphato-β-D-galactopyranosyl)-β-D-glucopyranoside, sodium salt

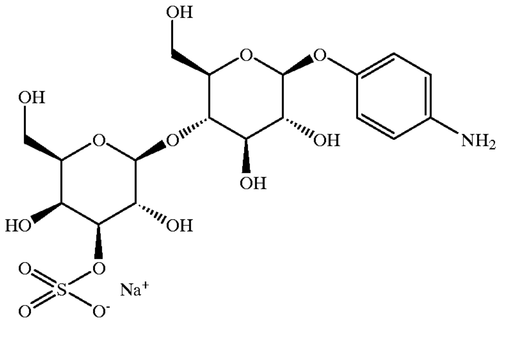

1.57.a) p-Nitrophenyl 4-O-(3',4'-O-isopropylidene-β-D-galactopyranosyl)-β-D-glucopyranoside Dimethoxypropane (400 ml) and a catalytic amount of (±)-camphor-10-sulphonic acid (400 mg, 1.7 mmol) are added to p-nitrophenyl 4-O-(β-D-galactopyranosyl)-β-D-galactopyranoside (23.2 g, 50 mmol). After 3 days at room temperature, the reaction is ended by addition of triethylamine (240 μl, 1.7 mmol), the mixture is concentrated in vacuo and the residue is dried under an oil pump vacuum for 2 hours. The resulting crystals are taken up in methanol/water 10:1 (500 ml) and the mixture is boiled under reflux for 6 hours. After concentration in vacuo and flash chromatography [methylene chloride/methanol 25:1→10:1, in each case with 0.5% of triethylamine], colourless crystals (15.2 g, 60%) are obtained; TLC [methylene chloride/methanol 5:1]: $R_f$=0.49; melting point=253–255° C. (decomposition).

1.57.b) p-Nitrophenyl 2,3,6-tri-O-benzoyl-4-O-(2',6'-di-O-benzoyl-3',4'-O-isopropylidene-β-D-galactopyranosyl)-β-D-glucopyranoside Benzoyl chloride (50 ml, 430 mmol) is slowly added dropwise to a solution of compound 1.57.a (15.1 g, 30 mmol) in pyridine (300 ml) at 0° C. in the course of 30 minutes. The mixture is then stirred at room temperature for a further 2 hours and the batch is subsequently poured into ice-water (2000 ml), while stirring. After 15 minutes, the crystals which have precipitated out are filtered off and taken up in methylene chloride (1500 ml). The solution is washed with water (2×500 ml) and 1N sodium bicarbonate solution (2×500 ml), the organic phase is dried over magnesium sulphate (50 g) and concentrated in vacuo and the residue is purified by recrystallization from methanol. Colourless crystals (26.7 g, 87%) are obtained; TLC [methylene chloride/methanol 50:1]: $R_f$=0.49; $[\alpha]^{20}$=+23.6° (c=1.08/$CH_2Cl_2$); melting point=272–274° C.

1.57.c) p-Nitrophenyl 2,3,6-tri-O-benzoyl-4-O-(2',6'-di-O-benzoyl-β-D-galactopyranosyl)-β-D-glucopyranoside 99% strength trifluoroacetic acid (20 ml) is added to a solution of compound 1.57.b (20.5 g, 20 mmol) in methylene chloride (400 ml) and the mixture is stirred at room temperature for 20 minutes. The solution is then washed with 1N sodium bicarbonate solution (2×200 ml), the organic phase is dried over magnesium sulphate (10 g) and concentrated in vacuo and the residue is purified by reprecipitation from methylene chloride/diethyl ether. Colourless crystals (18.0 g, 91%) are obtained; TLC [methylene chloride/methanol 20:1]: $R_f$=0.18; melting point=234° C.

1.57.d) p-Nitrophenyl 2,3,6-tri--benzoyl-4-O-(2',6'-di-O-benzoyl-4'-O-acetyl-β-D-galactopyranosyl)-β-D-glucopyranoside Compound 1.57.c (5.5 g, 5.6 mmol) is reacted as described in Example 1.51.a. After flash chromatography [petroleum ether/ethyl acetate 3:1→1:1], colourless crystals (4.03 g, 70%) are obtained; TLC [methylene chloride/methanol 20:1]: $R_f$=0.67; melting point=118° C.

1.57.e) p-Nitrophenyl 2,3,6-tri-O-benzoyl4-O-(2',6'-di-O-benzoyl-3'-sulphato-4'-O-acetyl-β-D-galactopyranosyl)-β-D-glucopyranoside, sodium salt Sulphur trioxide-pyridine complex (4.5 g, 28 mmol) is added to a solution of compound 1.57.d (3.59 g, 3.5 mmol) in pyridine (200 ml) and the mixture is stirred first at 60° C. for 2 hours and then at room temperature for 16 hours. The reaction is then ended by dropwise addition of methanol (50 ml) and the mixture is concentrated in vacuo. The residue is purified by flash chromatography [methylene chloride/methanol 10:1]. A solid product is obtained and is taken up in methylene chloride/methanol 1:1 (200 ml), and Amberlite IR120 ($Na^+$ form, 10 g) is added. This mixture is stirred at room temperature for 1 hour and filtered and the filtrate is concentrated in vacuo. Colourless crystals (3.64 g, 92%) are obtained; TLC [methylene chloride/methanol 2:1]: $R_f$=0.87; melting point=168° C.

1.57.f) p-Nitrophenyl 4-O-(3'-sulphato-β-D-galactopyranosyl)-β-D-glucopyranoside, sodium salt Compound 1.57.e (3.4 g, 3 mmol) is dissolved in absolute methanol (150 ml), sodium methylate (200 mg) is added and the mixture is stirred at 60° C. for 7 hours. After cooling to room temperature, the mixture is neutralized with Lewatit SC108 ($H^+$ form) and then filtered. The pH of the filtrate is increased to pH 7–8 by dropwise addition of IN sodium hydroxide solution, the mixture is evaporated in vacuo and reprecipitation of the residue from methanol/diethyl ether gives slightly brownish crystals (1.30 g, 77%); TLC [methylene chloride/methanol 2:1]: $R_f$=0.55; melting point=230° C. (decomposition).

1.57) p-Aminophenyl 4-O-(3'-sulphato-β-D-galactopyranosyl)-β-D-glucopyranoside, sodium salt The above compound (1.13 g, 2 mmol) is reduced as described in Example 1.24. After extraction of the residue by boiling with diethyl ether (50 ml), colourless crystals (983 mg, 92%) are obtained; TLC [methylene chloride/methanol 2:1]: $R_f$=0.22; melting point=176° C. (decomposition).

EXAMPLE 1.58 p-Aminophenyl 4-O-(3'-O-methyl-β-D-galactopyranosyl)-β-D-glucopyranoside

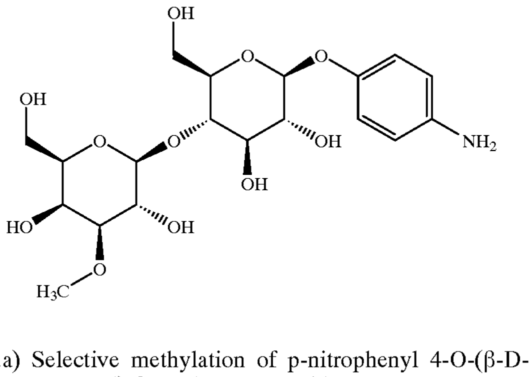

1.58.a) Selective methylation of p-nitrophenyl 4-O-(β-D-galactopyranosyl)-β-D-glucopyranoside p-Nitrophenyl 4-O-(β-D-galactopyranosyl)-β-D-glucopyranoside (2.3 g, 5 mmol) is methylated as described in Example 1.25.a. Flash chromatography [methylene chloride/methanol 20:1→10:1→5:1] gives two products:

Fraction 1: p-nitrophenyl 2-O-methyl-4-O-(3'-O-methyl-β-D-galactopyranosyl)-β-D-glucopyranoside; colourless crystals (264 mg, 11%); TLC [methylene chloride/methanol 5:1]: $R_f$=0.46; $[\alpha]^{20}$=−73.9° (c=1.0/$CH_3OH$); melting point=228° C. (decomposition).

Fraction 2: p-nitrophenyl 4-O-(3'-O-methyl-β-D-galactopyranosyl)-β-D-glucopyranoside; colourless crystals (1.0 g, 42%); TLC [methylene chloride/methanol 5:1]: $R_f$=0.29; $[\alpha]^{20}$=−65.3° (c=1.1/$CH_3OH$); melting point=220° C.

1.58) p-Aminophenyl 4-O-(3'-O-methyl-β-D-galactopyranosyl)-β-D-glucopyranoside

Fraction 2 from Example 1.58.a (955 mg, 2 mmol) is reduced as described in Example 1.24. After washing with diethyl ether (50 ml), colourless crystals (894 mg, 100%) are obtained; TLC [methylene chloride/methanol 5:1]: $R_f$=0.08; melting point=129° C. (decomposition).

EXAMPLE 1.59 p-Aminophenyl 2-O-methyl-4-O-(3'-O-methyl-β-D-galactopyranosyl)-β-D-glucopyranoside

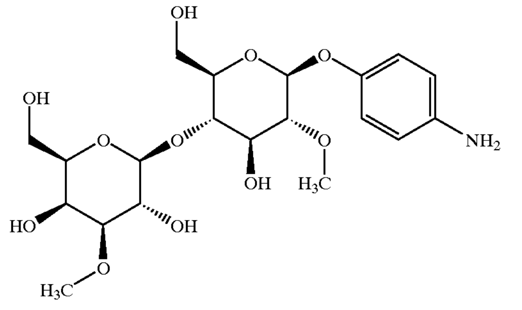

Fraction 1 from Example 1.58.a (246 mg, 0.5 mmol) is reduced as described in Example 1.24. After washing with diethyl ether (20 ml), colourless crystals (186 mg, 81%) are obtained; TLC [methylene chloride/methanol 5:1]: $R_f$=0.13; $[\alpha]^{20}$=−3.6° (c=1.0/$CH_3OH$); melting point=105° C.

EXAMPLE 1.60 p-Aminophenyl 4-O-(3',4'-di-O-methyl-β-D-galactopyranosyl)-β-D-glucopyranoside

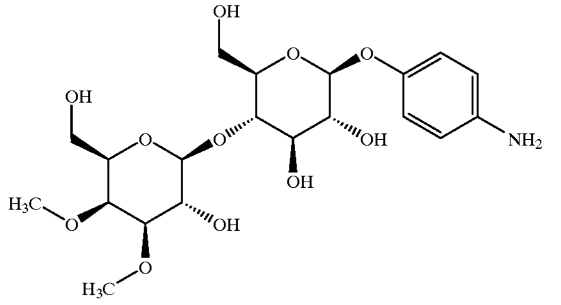

1.60.a) p-Nitrophenyl 2,3,6-tri-O-benzyl-4-O-(2',6'-di-O-benzyl-3',4'-O-isopropylidene-β-D-galactopyranosyl)-β-D-glucopyranoside Compound 1.57.a (5.0 g, 10 mmol) is reacted with benzyl bromide (30 ml, 250 mmol) for 16 hours as described in Example 1.26.c. After concentration in vacuo, the residue is taken up in ethyl acetate (300 ml) and the solution is washed with water (200 ml). The organic phase is dried over magnesium sulphate (10 g) and concentrated in vacuo and the residue is purified by flash chromatography [methylene chloride/petroleum ether 5:1→methylene chloride]. A brownish oil (5.3 g, 56%) is obtained; TLC [methylene chloride/methanol 50:1]: $R_f$=0.70; $[\alpha]^{20}$=−23.2° (c=1.08/$CH_2Cl_2$).

1.60.b) p-Nitrophenyl 2,3,6-tri-O-benzyl-4-O-(2',6'-di-O-benzyl-5-D-galactopyranosyl)-β-D-glucopyranoside The above compound (4.77 g, 5 mmol) is reacted as described in Example 1.57.c. After concentration in vacuo and reprecipitation from diethyl ether/petroleum ether, colourless crystals (3.94 g, 86%) are obtained; TLC [methylene chloride/methanol 50:1]: $R_f$=0.36; melting point=116° C.

1.60.c) p-Nitrophenyl 2,3,6-tri-O-benzyl-4-O-(2',6'-di-O-benzyl-3',4'-di-O-methyl-β-D-galactopyranosyl)-β-D-glucopyranoside Compound 1.60.b (1.8 g, 2 mmol) is methylated as described in Example 1.24.c. Reprecipitation from methylene chloride/petroleum ether gives colourless crystals (1.55 g, 82%); TLC [methylene chloride/methanol 50:1]: $R_f$=0.74; melting point=161–162° C.

1.60) p-Aminophenyl 4-O-(3',4'-di-O-methyl-β-D-galactopyranosyl)-β-D-glucopyranoside Compound 1.60.c (1.41 g, 1.5 mmol) is dissolved in methanol (50 ml) and after addition of palladium hydroxide-on-charcoal (moist, 20% of Pd, 500 mg), hydrogenation is carried out in a hydrogen atmosphere under a slightly increased for 6 days. The suspension is filtered over Celite and the material on the filter is washed thoroughly with methanol (100 ml). Concentration of the filtrate in vacuo and washing of the residue with methylene chloride gives brownish crystals (425 mg, 61 %); melting point=124° C. (decomposition).

EXAMPLE 2.1

N-Alanyl-batracyline

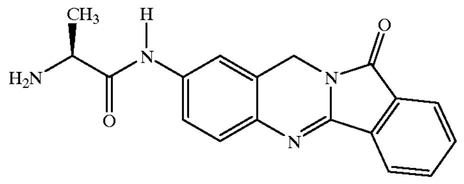

2.1.a) N-[N-(tert-Butoxycarbonyl)-alanyl]-batracyline

N-(tert-Butoxycarbonyl)-alanine (3.3 g, 17.5 mmol) and 2-isobutoxy-1-isobutoxycarbonyl-1,2-dihydro-quinoline (6.8 ml, 23 mmol) are dissolved in 100 ml of methylene chloride. After the mixture has been stirred at room temperature for 20 minutes, a solution of batracyline (4.1 g, 16.5 mmol) in absolute dimethylformamide (350 ml) is added and the batch is stirred at room temperature for a further 48 hours. It is then concentrated to 50 ml in vacuo and the concentrate is topped up to 300 ml with ethyl acetate and immediately heated at the boiling point for 10 minutes. The mixture is then allowed to cool to room temperature and is filtered and the material on the filter is extracted by boiling again with ethyl acetate (200 ml). Cooling to 0° C., while stirring, and filtration gives yellow crystals (6.18 g, 84%); TLC [ethyl acetate]: $R_f$=0.57; melting point=246–247° C. (decomposition).

2.1) N-Alanyl-batracyline

A solution of compound 2.1.a (10.5 g, 25 mmol) in anhydrous trifluoroacetic acid (150 ml) is stirred at room temperature for 15 minutes. After the batch has been concentrated to 30 ml in vacuo, it is poured into saturated sodium bicarbonate solution (1000 ml) while stirring vigorously. Stirring is continued for 10 minutes, the mixture is filtered and the residue is washed with water, a little isopropanol and diethyl ether. The product is obtained in yellow crystals (7.15 g, 89%); TLC [ethyl acetate]: $R_f$=0.06; melting point=261–262° C. (decomposition).

EXAMPLE 2.2

N-[Lysyl-alanyl]-batracyline, di-trifluoroacetate

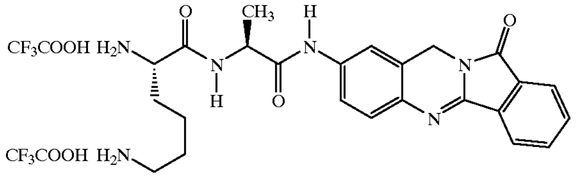

2.2.a) N-[Nα,Nε-Di-(tert-butoxycarbonyl)-lysyl-alanyl]-batracyline

N,N-Di-(tert-butoxycarbonyl)-lysine (2.1 g, 6 mmol) and $^{2}$-isobutoxy-1-isobutoxy-carbonyl-1,2-dihydro-quinoline (2.4 ml, 8 mmol) are dissolved in 20 ml of methylene chloride. After the mixture has been stirred at room temperature for 20 minutes, a solution of compound 2.1 (1.6 g, 5 mmol) in dimethylformamide (40 ml) is added and the batch is stirred at room temperature for a further 16 hours. It is then concentrated in vacuo and the residue is purified by flash chromatography [petroleum ether/ethyl acetate 2:1→1:1→ethyl acetate]. Yellow crystals (2.89 g, 89%) are obtained; TLC [ethyl acetate]: $R_f$=0.52; melting point=203–204° C.

2.2) N-[Lysyl-alanyl]-batracyline, di-trifluoroacetate

Anhydrous trifluoroacetic acid (10 ml) is added to a suspension of the above compound (2.6 g, 4 mmol) in methylene chloride (25 ml) and the resulting solution is stirred at room temperature for 30 minutes. After concentration in vacuo, the residue is crystallized by addition of diethyl ether (100 ml). The precipitate is filtered off and washed intensively with diethyl ether. Yellow crystals (2.68 g, 99%) are obtained; TLC [ethyl acetate]: $R_f$=0.05; melting point=144–146° C. (decomposition).

EXAMPLE 2.3

N-[D-Alanyl]-batracyline

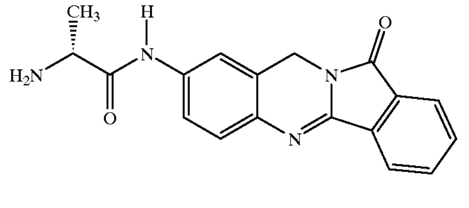

2.3.a) N-[N-Benzyloxycarbonyl-D-alanyl]-batracyline

N-Benzyloxycarbonyl-D-alanine (3.9 g, 17.5 mmol) is reacted as described in Example 2.1.a and the product is worked up. The resulting yellow crystals (6.4 g, 80%) are separated off by filtration, the combined filtrates are concentrated in vacuo and the residue is purified by flash chromatography [petroleum ether/ethyl acetate 3:2→1:1]. A further 1.35 g (17%) are obtained; TLC [ethyl acetate]: $R_f$=0.45; melting point=256° C.; $[\alpha]^{20}$=+75.1° (c=1.0/ $CH_2Cl_2$)+0.5% $CH_3OH$).

2.3) N-[D-Alanyl]-batracyline

Compound 2.3.a (11.4 g, 25 mmol) is dissolved in a 33% strength solution of hydrogen bromide in glacial acetic acid (100 ml). After 30 minutes at room temperature, the batch is concentrated to 30 ml in vacuo and the concentrate is then poured into saturated sodium bicarbonate solution (1000 ml), while stirring vigorously. Stirring is continued for 10 minutes, the mixture is filtered and the residue is washed with water, a little isopropanol and diethyl ether. The product is obtained in yellow crystals (7.87 g, 98%); TLC [ethyl acetate]: $R_f$=0.06; melting point=267° C. (decomposition).

EXAMPLE 2.4

N-[$N^{\alpha}$-(tert-Butoxycarbonyl)-lysyl-D-alanyl]-batracyline

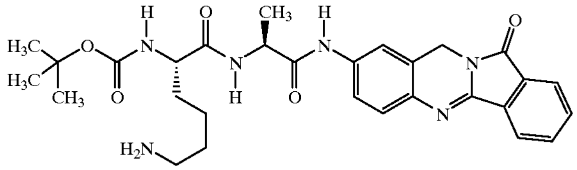

2.4.a) N-[$N^{\alpha}$-(tert-Butoxycarbonyl)-$N^{\epsilon}$-(fluorenyl-9-methoxycarbonyl)-lysyl-D-alanyl]-batracyline $N^{\alpha}$-(tert-Butoxycarbonyl)-$N^{\epsilon}$-(fluorenyl-9-methoxycarbonyl)-lysine (5.3 g, 11.3 mmol) and 2-isobutoxy-1-isobutoxycarbonyl-1,2-dihydro-quinoline (4 ml, 14 mmol) are dissolved in 40 ml of methylene chloride. After the mixture has been stirred at room temperature for 20 minutes, a solution of compound 2.3 (3.2 g, 10 mmol) in dimethylformamide (80 ml) is added and the batch is stirred at room temperature for a further 16 hours. It is then concentrated in vacuo and the residue is suspended in methylene chloride (100 ml). The resulting suspension is topped up with diethyl ether (300 ml). After filtration and washing of the material in the filter with diethyl ether, yellow crystals (5.65 g, 65%) are obtained; TLC [ethyl acetate]: $R_f$=0.45; melting point=186° C.

2.4) N-[$N^{\alpha}$-(tert-Butoxycarbonyl)-lysyl-D-alanyl]-batracyline

The above compound (5.6 g, 7.3 mmol) is dissolved in dimethylformamide (50 ml). After addition of piperidine (50 ml), the mixture is stirred at room temperature for 3 hours and then concentrated in vacuo and the residue is purified by flash chromatography [methylene chloride/methanol/ammonia (25%) 15:3:0.1→15:5:0.1]. Yellow crystals (2.5 g, 62%) are obtained; melting point=217° C. (decomposition).

EXAMPLE 2.5

N-[$N^{\alpha}$-(Fluorenyl-9-methoxycarbonyl)-lysyl-D-alanyl]-batracyline, trifluoroacetate

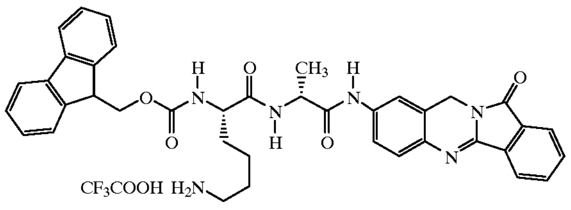

2.5.a) N-[$N^{\alpha}$-(Fluorenyl-9-methoxycarbonyl)-$N^{\epsilon}$-(tert-butoxycarbonyl)-lysyl-D-alanyl]-batracyline $N^{\alpha}$-(Fluorenyl-9-methoxycarbonyl)-$N^{\epsilon}$-(tert-butoxycarbonyl)-lysine (5.3 g, 11.3 mmol) is reacted as described in Example 2.4.a and the product is purified. Yellow crystals (7.0 g, 80%) are obtained; TLC [ethyl acetate]: $R_f$=0.51; melting point=223° C.

2.5) N-[$N^{\alpha}$-(Fluorenyl-9-methoxycarbonyl)-lysyl-D-alanyl]-batracyline, trifluoroacetate Compound 2.5.a (6.17 g, 8 mmol) is reacted as described in Example 2.2. After concentration in vacuo, the residue is reprecipitated from methylene chloride/diethyl ether to give yellow crystals (6.08 g, 97%); TLC [ethyl acetate]: $R_f$=0.05; melting point=224° C. (decomposition).

EXAMPLE 2.6

N-[$N^ε$-(Fluorenyl-9-methoxycarbonyl)-lysyl-D-alanyl]-batracyline, trifluoroacetate

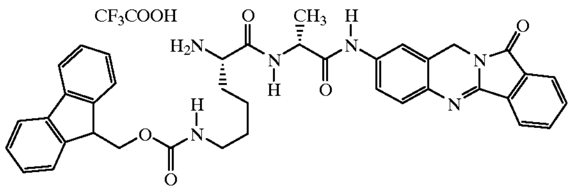

Compound 2.4.a (6.17 g, 8 mmol) is reacted as described in Example 2.2. After concentration in vacuo, the residue is reprecipitated from methylene chloride/diethyl ether to give yellow crystals (5.97 g, 95%); TLC [ethyl acetate]: $R_f$=0.04; melting point=188° C. (decomposition).

EXAMPLE 2.7

N-[Lysyl-D-asparagyl]-batracyline, di-trifluoroacetate

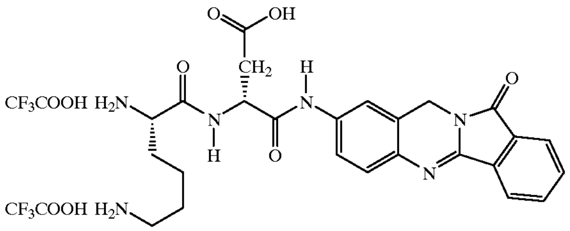

2.7.a) N-[N-(Fluorenyl-9-methoxycarbonyl)-D-asparagyl-(β-tert-butyl ester)]-batracyline N-(Fluorenyl-9-methoxycarbonyl)-D-asparagyl-(β-tert-butyl ester) (7.2 g, 17.5 mmol) is reacted as described in Example 2.1.a. After concentration in vacuo, the residue is taken up in methylene chloride (1000 ml) and the mixture is washed with 1N hydrochloric acid (2×200 ml) and with 1N sodium bicarbonate solution (1×200 ml). After drying over magnesium sulphate (20 g), filtration, concentration to 100 ml and addition of petroleum ether, compound 2.7.a is obtained in the form of yellow crystals (9.7 g, 86%); TLC [ethyl acetate]: $R_f$=0.71; melting point=195° C.

2.7.b) N-[D-Asparagyl-(β-tert-butyl ester)]-batracyline

The above compound (6.4 g, 10 mmol) is dissolved in methylene chloride (100 ml). After addition of morpholine (50 ml), the mixture is stirred at room temperature for 5 hours and then concentrated in vacuo and the residue is purified by flash chromatography [ethyl acetate/petroleum ether 4:1→ethyl acetate→ethyl acetate/ethanol 10:1]. Yellow crystals (3.44 g, 82%) are obtained; TLC [ethyl acetate]: $R_f$=0.21; melting point=209° C. (decomposition).

2.7.c) N-[$N^α$,$N^ε$-Di-(tert-butoxycarbonyl)-lysyl-D-asparagyl-(β-tert-butyl ester)-batracyline Compound 2.7.b (2.1 g, 5 mmol) is reacted as described in Example 2.2.a. Yellow crystals (1.71 g, 46%) are obtained; TLC [ethyl acetate]: $R_f$=0.61; melting point=142° C.

2.7) N-[Lysyl-D-asparagyl]-batracyline, di-trifluoroacetate

Compound 2.7.c (1.65 g, 2.2 mmol) is reacted as described in Example 2.2 and the product is purified. Yellow crystals (1.5 g, 95%) are obtained; TLC [methanol/acetic acid 10:1]: $R_f$=0.29; melting point=154–155° C. (decomposition).

EXAMPLE 2.8

N-[Lysyl-D-glutamyl]-batracyline, di-hydrobromide

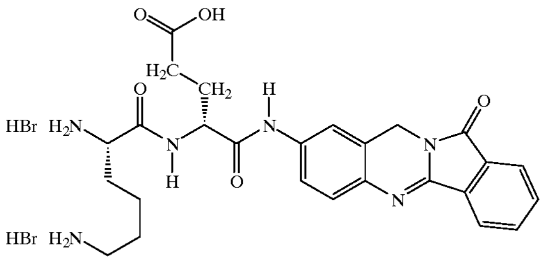

2.8.a) N-[N-(tert-Butoxycarbonyl)-D-glutamyl-(β-benzyl ester)]-batracyline

N-(tert-Butoxycarbonyl)-D-glutamyl-(β-benzyl ester) (5.9 g, 17.5 mmol) is reacted as described in Example 2.1.a. After concentration in vacuo, the residue is purified by flash chromatography [petroleum ether/ethyl acetate 1:1] to give yellow crystals (9.45 g, 95%); TLC [ethyl acetate]: $R_f$=0.61; $[α]^{20}$=+53.1° (c=1.0/$CH_2Cl_2$); melting point=159° C.

2.8.b) N-[D-Glutamyl-(β-benzyl ester)]-batracyline

Compound 2.8.a (9.1 g, 10 mmol) is dissolved in formic acid (100 ml) and the solution is stirred at room temperature for 6 hours. After concentration in vacuo, the residue is taken up in methanol (100 ml) and the pH of the solution is increased to pH 8 by careful addition of 25% strength aqueous ammonia solution. After renewed concentration in vacuo, subsequent flash chromatography [ethyl acetate/ethanol 10:1] gives a yellow oil (4.2 g, 56%); TLC [ethyl acetate]: $R_f$=0.06.

2.8.c) N-[$N^α$,$N^ε$-Di-(tert-butoxycarbonyl)-lysyl-D-glutamyl-(β-benzyl ester)]-batracyline The above compound (3.75 g, 8 mmol) is reacted as described in Example 2.2.a and the product is purified. A yellow amorphous solid (2.26 g, 35%) is obtained; TLC [ethyl acetate]: $R_f$=0.40; $[α]^{20}$=+32.1° (c=1.2/$CH_2Cl_2$).

2.8) N-[Lysyl-D-glutamyl]-batracyline, di-hydrobromide

Compound 2.8.c (2.0 g, 2.5 mmol) is dissolved in a 33% strength solution of hydrogen bromide in glacial acetic acid (50 ml). After 1 hour at room temperature, the batch is concentrated in vacuo and the residue is washed thoroughly with diethyl ether. The product is obtained in yellow-red crystals (1.63 g, 98%); melting point=207–209° C. (decomposition).

EXAMPLE 2.9

N-[Lysyl-glycyl]-batracyline, di-trifluoroacetate

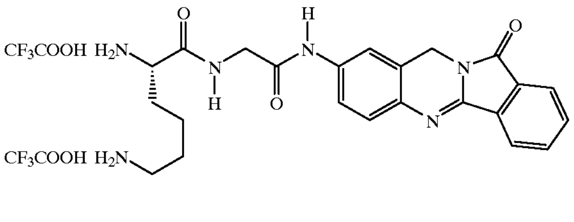

2.9.a) N-[N-(tert-Butoxycarbonyl)-glycyl]-batracyline

N-(tert-Butoxycarbonyl)-glycine (3.07 g, 17.5 mmol) is reacted as described in Example 2.1.a. After 3 days at room temperature, the mixture is concentrated in vacuo and the residue is taken up in ethanol (200 ml). After the mixture has been stirred under reflux for 30 minutes and filtered, after cooling, the target compound is obtained in the form of yellow crystals (4.73 g, 66%); TLC [ethyl acetate]: $R_f$=0.44; melting point=279° C. (decomposition).

2.9.b) N-Glycyl-batracyline, hydrochloride

The above compound (4.1 g, 10 mmol) is dissolved in methylene chloride (1200 ml), while heating in an ultrasonic bath. After addition of hydrogen chloride in diethyl ether (100 ml), the mixture is stirred at room temperature for 30 minutes and concentrated in vacuo, and ethanol (200 ml) is added to the residue. After the mixture has been stirred under reflux for 10 minutes and filtered, after cooling, the product is obtained in the form of yellow crystals (3.21 g, 94%); melting point 297–299° C. (decomposition).

2.9.c) N-[$N^{\alpha}$,$N^{\epsilon}$-Di-(tert-butoxycarbonyl)-lysyl-glycyl]-batracyline N,N-Di-(tert-butoxycarbonyl)-lysine (2.1 g, 6 mmol) and 2-isobutoxy-1-isobutoxycarbonyl-1,2-dihydro-quinoline (2.4 ml, 8 mmol) are dissolved in 20 ml of methylene chloride. After the mixture has been stirred at room temperature for 20 minutes, a solution of compound 2.9.b (1.71 g, 5 mmol), ethyldiisopropylamine (0.86 ml, 5mmol) and dimethylformamide (40 ml) is added and the batch is stirred at room temperature for a further 16 hours. It is then concentrated in vacuo and the residue is purified by flash chromatography [ethyl acetate/petroleum ether 1:1→ethyl acetate]. Yellow crystals (1.69 g, 53%) are obtained; TLC [ethyl acetate]: $R_f$=0.31; melting point=211 ° C. (decomposition).

2.9) N-[Lysyl-glycyl]-batracyline, di-trifluoroacetate

Compound 2.9.c (1.4 g, 2.2 mmol) is reacted as described in Example 2.2 and the product is purified. Yellow crystals (1.33 g, 91%) are obtained; melting point=153° C. (decomposition).

EXAMPLE 2.10

N-[Lysyl-seryl]-batracyline, di-trifluoroacetate

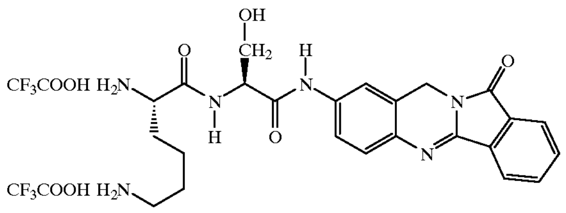

2.10.a) N-[N-(tert-Butoxycarbonyl)-seryl]-batracyline

N-(tert-Butoxycarbonyl)-serine (3.6 g, 17.5 mmol) is reacted as described in Example 2.1.a. After 48 hours, the mixture is concentrated to 100 ml in vacuo and 21 of methylene chloride are added to the concentrate. The resulting solution is washed with water (1x500 ml), with 0.5 N hydrochloric acid (2x250 ml) and with saturated sodium bicarbonate solution (1x250 ml). Drying over magnesium sulphate (50 g), distilling off the solvent in vacuo and flash chromatography [petroleum ether/ethyl acetate 1:1] of the residue gives compound 2.10.a (4.6 g, 64%) in the form of yellow crystals; TLC [ethyl acetate/acetic acid 100:1]: $R_f$=0.38; melting point=219° C. (decomposition); $[\alpha]^{20}$=−61.0° (c=0.5/$CH_2Cl_2$+0.5% $CH_3OH$).

2.10.b) N-Seryl-batracyline, hydrochloride

Concentrated hydrochloric acid (10 ml) is added to a suspension of the above compound (4.6 g, 10.4 mmol) in dioxane (70 ml), while stirring, and the mixture is then stirred vigorously at room temperature for 1 hour. It is subsequently concentrated in vacuo and the residue is dried under an oil pump vacuum for 2 hours. After addition of ethanol (100 ml), the mixture is boiled under reflux for 15 minutes. Cooling and filtration with suction give orange crystals (1.97 g, 96%); TLC [ethyl acetate]: $R_f$=0.05; $[\alpha]^{20}$=+51.8° (c=1.0/$H_2O$H); melting point>270° C. (decomposition).

2.10.c) N-[$N^{\alpha}$,$N^{\epsilon}$-Di-(tert-butoxycarbonyl)-lysyl-seryl]-batracyline Compound 2.10.b (1.86 g, 5 mmol) is reacted as described in Example 2.9.c. After flash chromatography [ethyl acetate/petroleum ether 2:1→ethyl acetate], yellow crystals (1.18 g, 36%) are obtained; TLC [ethyl acetate/acetic acid 100:1]: $R_f$=0.24; melting point=188° C. (decomposition); $[\alpha]^{20}$=−13.1° (c=0.5/$CH_2Cl_2$+0.5% $CH_3OH$).

2.10) N-[Lysyl-seryl]-batracyline, di-trifluoroacetate

Compound 2.10.c (1.0 g, 1.5 mmol) is reacted as described in Example 2.2 and the product is purified. Yellow crystals (1.0 g, 96%) are obtained; TLC [methylene chloride/methanol/ammonia (25%) 15:3:0.2]: $R_f$=0.10; melting point=188–190° C. (decomposition).

EXAMPLE 2.11

N-[Lysyl-D-seryl]-batracyline, di-hydrobromide

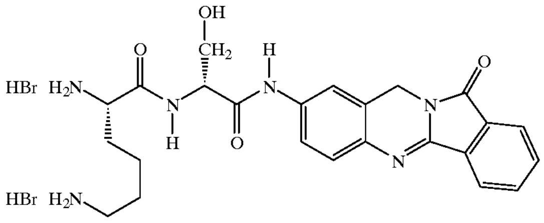

2.11.a) N-[N-(Fluorenyl-9-methoxycarbonyl)-O-(tert-butyl)-D-seryl]-batracyline

N-(Fluorenyl-9-methoxycarbonyl)-O-(tert-butyl)-D-serine (6.7 g, 17.5 mmol) is reacted as described in Example 2.1.a. Concentration in vacuo and flash chromatography [petroleum ether/ethyl acetate 1:1] give the compound 2.11.a (5.64 g, 52%) in the form of yellow crystals; TLC [methylene chloride/methanol/ammonia (25%) 15:3:0.2]: $R_f$=0.87; melting point=225–226° C. (decomposition).

2.11.b) N-[O-(tert-Butyl)-D-seryl]-batracyline

The above compound (2.89 g, 4.7 mmol) is reacted as described in Example 2.7.b. Flash chromatography [petroleum ether/ethyl acetate 3:2→ethyl acetate] gives the product as yellow crystals (1.15 g, 62%); TLC [ethyl acetate]: $R_f$=0.11; melting point=197° C.

2.11.c) N-[$N^{\alpha}$,$N^{\epsilon}$-Di-(tert-butoxycarbonyl)-lysyl-O-(tert-butyl)-D-seryl]-batracyline The above compound (1.1 g, 2.8 mmol) is reacted as described in Example 2.2.a. Yellow crystals (1.94 g, 96%) are obtained; TLC [ethyl acetate]: $R_f$=0.59; melting point=208° C.

2.11.d) N-[Lysyl-O-(tert-butyl)-D-seryl]-batracyline, di-trifluoroacetate

Compound 2.11.c (1.08 g, 1.5 mmol) is reacted as described in Example 2.2 and the product is purified. Yellow crystals (1.1 g, 98%) are obtained; TLC [methanol/acetic acid 10:1]: $R_f$=0.30; melting point=128° C.

2.11) N-[Lysyl-D-seryl]-batracyline, di-hydrobromide

Compound 2.11.d (1.05 g, 1.4 mmol) is reacted as described in Example 2.8 and the product is purified. Yellow-red crystals (846 mg, 96%) are obtained; melting point=247–248° C.

EXAMPLE 2.12

N-[Lysyl-D-threonyl]-batracyline, di-hydrobromide

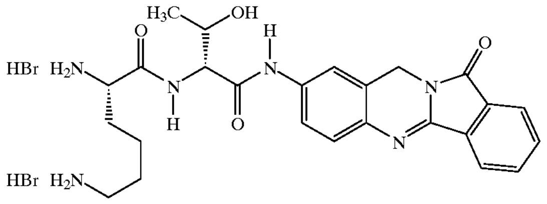

2.12.a) N-[N-(Fluorenyl-9-methoxycarbonyl)-O-(tert-butyl)-D-threonyl]-batracyline N-(Fluorenyl-9-methoxycarbonyl)-O-)tert-butyl)-D-threonine (6.96 g, 17.5 mmol) is reacted as described in Example 2.1.a. Concentration in vacuo and flash chromatography [petroleum ether/ethyl acetate 1:1] give the compound 2.12.a (7.45 g, 68%) in the form of yellow crystals; TLC [ethyl acetate]: $R_f$=0.63; melting point=225–226° C.

2.12.b) N-1O-(tert-Butyl)-D-threonyl]-batracyline

Compound 2.12.a (3.8 g, 6 mmol) is reacted as described in Example 2.7.b. After concentration in vacuo, the product is obtained as yellow crystals (1.9 g, 78%); TLC [ethyl acetate]: $R_f$=0.21; melting point=110–111° C.

2.12.c) N-[$N^{\alpha}$,$N^{\epsilon}$-Di-(tert-butoxycarbonyl)-lysyl-O-(tert-butyl)-D-threonyl]-batracyline Compound 2.12.b (1.8 g, 4.5 mmol) is reacted as described in Example 2.2.a. Yellow crystals (2.6 g, 79%) are obtained; TLC [ethyl acetate]: $R_f$=0.59; melting point=112° C.

2.12.d) N-[Lysyl-O-(tert-butyl)-D-threonyl]-batracyline, di-trifluoroacetate

The above compound (2.5 g, 3.4 mmol) is reacted as described in Example 2.2 and the product is purified. Yellow crystals (2.5 g, 96%) are obtained; TLC [methanol/acetic acid 10:1]: $R_f$=0.30; melting point=142° C. (decomposition).

2.12) N-[Lysyl-D-threonyl]-batracyline, di-hydrobromide

Compound 2.12.d (2.29 g, 3 mmol) is reacted as described in Example 2.8 and the product is purified. Yellow-red crystals (1.86 g, 97%) are obtained; melting point=232° C. (decomposition).

EXAMPLE 2.13

N-[Lysyl-D-alanyl]-batracyline, di-trifluoroacetate

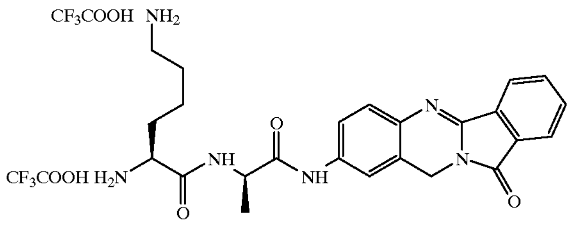

2.13.a) N-[$N^{\alpha}$,$N^{\epsilon}$-Bis-(tert-butoxycarbonyl)-lysyl-D-alanyl]-batracyline 6 g (17.3 mmol) of $N_{\alpha}$,$N^{\epsilon}$-bis-(tert-butoxycarbonyl)-lysine are dissolved in 75 ml of dimethylformamide, and 3 g (26 mmol) of N-hydroxysuccinimide and 4.29 g (20.8 mmol) of N,N'-dicyclohexylcarbodiimide are added at 0° C. After 3 hours, the urea formed is filtered off, 5 g (15.6 mmol) of N-[D-alanyl]-batracyline (Example 2.3) are added to the filtrate and the mixture is stirred at 20° C. for 16 hours. Residual urea is filtered off and discarded. The filtrate is concentrated, the residue is stirred with methanol and the mixture is filtered. The filtrate is concentrated again and the residue is treated again with methanol. The mixture is again filtered and the filter residues are combined. They are dissolved in methylene chloride/methanol 10:1 and the product is precipitated with ether. 8.22 g (81%) of the crystalline target product are obtained.

2.13) N-[Lysyl-D-alanyl]-batracyline, di-trifluoroacetate

Preparation from 8.2 g of compound 2.13.a analogously to Example 2.2. Yield: 7.58 g (89%)

EXAMPLE 2.14

N-[$N^{\epsilon}$-(Fluorenyl-9-methoxycarbonyl)-lysyl]-batracyline, trifluoroacetate

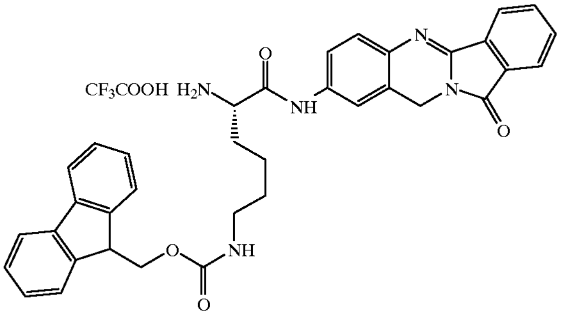

2.14.a) N-[$N^{\alpha}$-(tert-Butoxycarbonyl)-$N^{\epsilon}$-(fluorenyl-9-methoxycarbonyl)-lysyl]-batracyline Preparation analogously to Example 2.4.a from $N^{\alpha}$-(tert-butoxycarbonyl)-$N^{\epsilon}$-(fluorenyl-9-methoxycarbonyl)-lysine and batracyline. Yield: 78%

2.14) N-[$N^{\epsilon}$-(Fluorenyl-9-methoxycarbonyl)-lysyl]-batracyline, trifluoroacetate Preparation analogously to Example 2.5 from compound 2.14.a. Yield: 90%

EXAMPLE 2.15

N-[Lysyl-$N^{\epsilon}$-(fluorenyl-9-methoxycarbonyl)-lysyl]-batracyline, di-trifluoroacetate

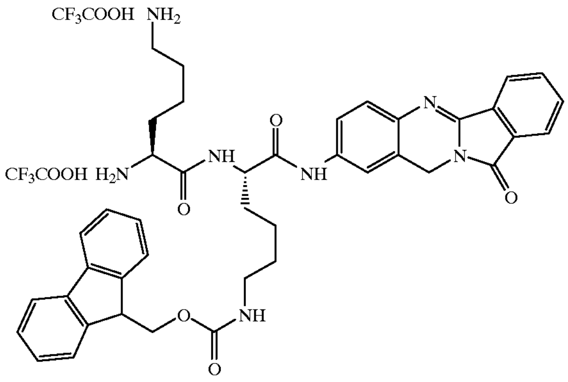

2.15.a) N-[$N^{\alpha}$,$N^{\epsilon}$-Di-(tert-butoxycarbonyl)-lysyl-$N^{\epsilon}$-(fluorenyl-9-methoxycarbonyl)-lysyl]-batracyline 3240 mg (4.54 mmol) of compound 2.14 are dissolved in 50 ml of dimethylformamide, and 2550 mg (5.45 mmol) of $N^{\alpha}$,$N^{\epsilon}$-di-(tert-butoxycarbonyl)-lysine p-nitrophenyl ester and 938 $\mu$l of ethyldiisopropylamine are added. The mixture is stirred at 20° C. for. 16 hours and concentrated and the residue is initially stirred with ether. The mixture is filtered and the filter residue is stirred again, with methanol/ether 1:1. 3881 mg (92%) of the target product are obtained in this way after filtration with suction and drying.

2.15) N-[Lysyl-$N^{\epsilon}$-(fluorenyl-9-methoxycarbonyl)-lysyl]-batracyline, di-trifluoroacetate Deblocking of compound 2.15.a with anhydrous trifluoroacetic acid/methylene chloride 1:1 analogously to Example 2.2. Yield: 95% [TLC: methylene chloride/methanol/ammonia (17%) 15:6:0.6 $R_f$=0.08]

EXAMPLE 2.16

N-[Lysyl-$N^{\beta}$-(fluorenyl-9-methoxycarbonyl)-α,β-diaminopropionyl]-batracyline, di-trifluoroacetate

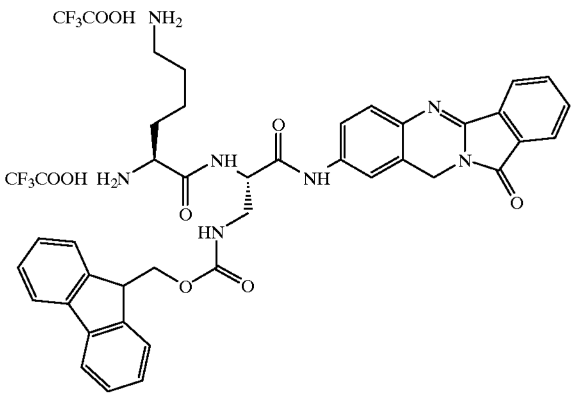

This peptide conjugate was prepared analogously to Examples 2.14 and 2.15 via 4 stages from batracyline and $N^{\alpha}$-(tert-butoxycarbonyl)-$N^{\beta}$-(fluorenyl-9-methoxycarbonyl)-diaminopropionic acid. [TLC: methylene chloride/methanol/glacial acetic acid 5:1:0.2 $R_f$=0.15]

EXAMPLE 2.17

N-[Lysyl]-batracyline

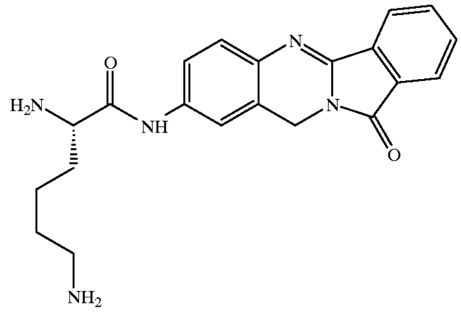

Splitting off of Fmoc analogously to Example 2.4 from N-[$N^{\epsilon}$-(fluorenyl-9-methoxycarbonyl)-lysyl]-batracyline trifluoroacetate (Example 2.14). Yield: 65%

EXAMPLE 2.18

N-[Seryl-D-alanyl]-batracyline, trifluoroacetate

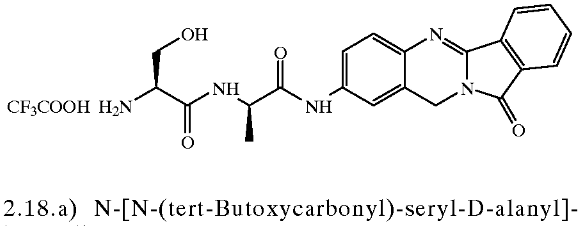

2.18.a) N-[N-(tert-Butoxycarbonyl)-seryl-D-alanyl]-batracyline

Preparation analogously to Example 2.13.a from N-(tert-butoxycarbonyl)-serine and N-[D-alanyl]-batracyline (Example 2.3). Yield: 77%

2.18) N-[Seryl-D-alanyl]-batracyline, trifluoroacetate

Preparation analogously to Example 2.2 from compound 2.18.a. Yield: 98%

EXAMPLE 2.19

N-[D-Alanyl-D-alanyl]-batracyline, trifluoroacetate

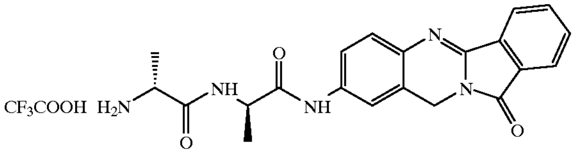

Preparation via 2 stages analogously Example 2.18.

EXAMPLE 2.20

M-[Glutamyl-D-alanyl]-batracyline

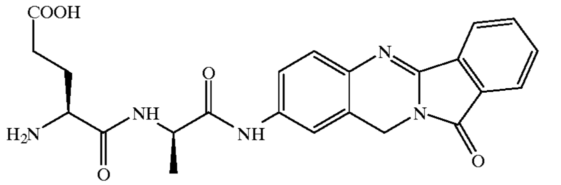

Preparation via 2 stages analogously to Example 2.18 starting from N-tert-butoxycarbonyl-glutamyl-δ-tert-butyl ester and N-[D-alanyl]-batracyline (Example 2.3). After splitting off of the Boc, the mixture is concentrated, the residue is taken up in water, the pH is brought to 7 with 0.1 N sodium hydroxide solution and the betaine is filtered off with suction.

EXAMPLES 3.1–3.34

General Formula

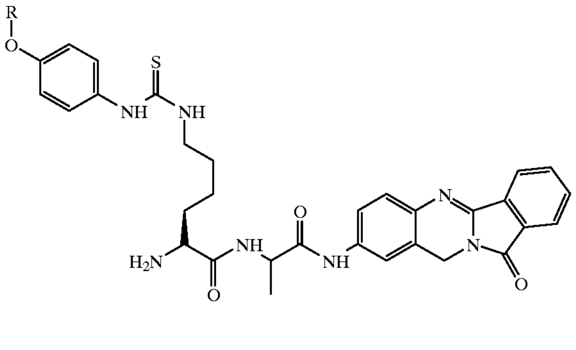

EXAMPLE 3.1

N-{$N^{\epsilon}$-[O-(β-L-Fucosyl)-4-hydroxy-phenylaminothiocarbonyl]-lysyl-D-alanyl}-batracyline 3.1.a) N-{$N^{\alpha}$-(tert-Butoxycarbonyl)-$N^{\epsilon}$-[O-(β-L-fucosyl)-4-hydroxy-phenylaminothiocarbonyl]-lysyl-D-alanyl}-batracyline Thiophosgene (34 μl, 0.44 mmol) is added to 55 mg (0.22 mmol) of p-aminophenyl β-L-fucoside in 10 ml of dioxane/water 1:1, while stirring. After 10 minutes, the mixture is concentrated in vacuo and the residue is dried under a high vacuum for 1 hour. The isothiocyanate obtained is then coupled in absolute dimethylformamide with 109 mg (0.21 mmol) of N-[$N^{\alpha}$-(tert-butoxycarbonyl)-lysyl-D-alanyl]-batracyline (Example 2.4) in the presence of 115 μl of ethyldiisopropylamine. After the crude product has been precipitated twice from methanol/isopropanol, 132 mg (75%) of the target product are obtained. [TLC: methylene chloride/methanol 9:1 $R_f$=0.151.

3.1) N-{N$^\epsilon$-O-(β-L-Fucosyl)-4-hydroxy-phenylamino-thiocarbonyl]-lysyl-D-alanyl}-batracyline 127 mg (0.15 mmol) of the compound from Example 3.1.a are stirred in 10 ml of methylene chloride with 6 ml of anhydrous trifluoroacetic acid at 0° C. for 2 hours. The mixture is concentrated, the residue is subsequently distilled three times with 5 ml of methylene chloride and the product is chromatographed with methylene chloride/methanol/ammonia (17%) 15:2:0.2. After subsequent freeze drying, 80 mg (71%) of the target product are obtained: [TLC: methylene chloride/methanol/ammonia (17% 15:4:0.4 $R_f$=0.3].

Analogously to Example 3.1, the following glycoconjugates are prepared from the partly protected peptide conjugate in Example 2.4 or from the isomeric N-[N$^\alpha$-(tert-butoxycarbonyl)-lysyl-alanyl]-batracyline, which is to be prepared analogously:

EXAMPLE 3.2

N-{N$^\epsilon$-O-(2-O-Methyl-β-L-fucosyl)-4-hydroxy-phenylamino-thiocarbonyl]-lysyl-D-alanyl}-batracyline Educt:

carbohydrate from Example 1.1

Flash chromatography purification of the intermediate stage with methylene chloride/methanol 95:5 and of the final stage with methylene chloride/methanol/ammonia (17%) 15:2:0.2. Yield: 55% [TLC: methylene chloride/methanol/glacial acetic acid 5:1:0.2 $R_f$=0.4].

EXAMPLE 3.3

N-{N$^\epsilon$-[O-(2-O-Methyl-β-L-fucosyl)-4-hydroxy-phenylamino-thiocarbonyl]-lysyl-alanyl}-batracyline Educt:

carbohydrate from Example 1.1

Purification of the into mediate stage by precipitation from methylene chloride/methanol 1:1 with ether and flash chromatography purification of the final stage with methylene chloride/methanol/ammonia (17%) 15:2:0.2. Yield: 65% [TLC: methylene chloride/methanol/ammonia (17%) 15:2:0.2 $R_f$=0.21].

EXAMPLE 3.4

N-{N$^\epsilon$-[O-(3-O-Methyl-β-L-fucosyl)-4-hydroxy-phenylamino-thiocarbonyl]-lysyl-D-alanyl}-batracyline, trifluoroacetate Educt:

carbohydrate from Example 1.2

Flash chromatography purification of the intermediate stage with methylene chloride/methanol 97.5:2.5 and precipitation of the final stage from methanol with ether; yield: 59% [TLC: methylene chloride/methanol/ammonia (17%) 15:2:0.2 $R_f$=0.19].

EXAMPLE 3.5

N-{N$^\epsilon$-[O-(3-O-Methyl-β-L-fucosyl)-4-hydroxy-phenylamino-thiocarbonyl]-lysyl-alanyl}-batracyline Educt:

carbohydrate from Example 1.2

Purification of the intermediate stage by precipitation from methylene chloride/methanol 1:1 with ether and flash chromatography purification of the final stage with methylene chloride/methanol/ammonia (17%) 15:2:0.2. Yield: 36% [TLC: methylene chloride/methanol/ammonia (17%) 15:4:0.5 $R_f$=0.57].

EXAMPLE 3.6

N-{N$^\epsilon$-[O-(3-O-Methyl-α-L-fucosyl)-4-hydroxy-phenylamino-thiocarbonyl]-lysyl-D-alanyl}-batracyline Educt:

carbohydrate from Example 1.3

Purification of the intermediate stage by precipitation from methanol with ether and flash chromatography purification of the final stage with methylene chloride/methanol/ammonia (17%) 15:2:0.2. Yield: 44% [TLC: methylene chloride/methanol/ammonia (17%) 15:2:0.2 $R_f$=0.15].

EXAMPLE 3.7

N-{N$^\epsilon$-[O-(3-Deoxy-β-L-fucosyl)-4-hydroxy-phenylamino-thiocarbonyl]-lysyl-D-alanyl}-batracyline, trifluoroacetate Educt:

carbohydrate from Example 1.6

Flash chromatography purification of the intermediate stage with methylene chloride/methanol 95:5 and precipitation of the final stage from methanol with ether. Yield: 35% [TLC: acetonitrile/water/glacial acetic acid 5:1:0.2 $R_f$=0.42].

EXAMPLE 3.8

N-{N$^\epsilon$-[O-(3,4-Epoxy-β-L-fucosyl)-4-hydroxy-phenylamino-thiocarbonyl]-lysyl-D-alanyl}-batracyline, trifluoroacetate Educt:

carbohydrate from Example 1.8

Flash chromatography purification of the intermediate stage with methylene chloride/methanol 95:5. Several precipitations of the final stage from methanol with ether and subsequent stirring with ethyl acetate. [TLC: acetonitrile/water/glacial acetic acid 5:1:0.2 $R_f$=0.49].

EXAMPLE 3.9

N-{N$^\epsilon$-[O-(3-O-Carboxymethyl-β-L-fucosyl)-4-hydroxy-phenylamino-thiocarbonyl]-lysyl-D-alanyl}-batracyline, sodium salt Educt:

carbohydrate from Example 1.10

Purification of the intermediate stage by stirring with methanol and completion of the precipitation with ether. Flash chromatography purification of the final stage with methylene chloride/methanol/ammonia (17%) 15:3:0.3; later in the same system with 15:6:0.6. The corresponding fractions are concentrated, the residue is taken up in water and the pH is brought to 7 with 0.1N sodium hydroxide solution. The mixture is filtered with suction, the filter residue is taken up in dimethylformamide/water 1:3 and one equivalent of a 0.1N sodium hydroxide solution is added. The mixture is concentrated and the sodium salt is taken up in water and lyophilized. Yield: 43%. [TLC: methylene chloride/methanol/ammonia (17%) 15:4:0.5 $R_f$=0.15].

EXAMPLE 3.10

N-{N$^\epsilon$-[O-(3-O-Carbamoylmethyl-β-L-fucosyl)-4-hydroxy-phenylamino-thiocarbonyl]-lysyl-D-alanyl}-batracyline, sodium salt Educt:

carbohydrate from Example 1.18

Purification of the intermediate stage by stirring with methanol and completion of the precipitation with ether. Flash chromatography purification of the final stage with methylene chloride/methanol/ammonia (17%) 15:2:0.2. [TLC: methylene chloride/methanol/ammonia (17%) 15:3:0.3 $R_f$=0.38]; melting point: 190° C. (decomposition).

EXAMPLE 3.11

N-{N$^\epsilon$-[O-(4-O-Methyl-β-L-fucosyl)-4-hydroxy-phenylamino-thiocarbonyl]-lysyl-D-alanyl}-batracyline, acetate Educt:

carbohydrate from Example 1.4

Flash chromatography purification of the intermediates stage with methylene chloride/methanol 95:5 and of the final stage with methylene chloride/methanol/ammonia (17%) 15:2:0.2. After the concentration, one equivalent of glacial acetic acid and 10 ml of water are added to the residue and the mixture is lyophilized. Yield: 52% [TLC: acetonitrile/water/glacial acetic acid 5:1:0.2 $R_f$=0.43]. FAB-MS: m/z=760=M+1.

EXAMPLE 3.12

N-{$N^\epsilon$-[O-($\alpha$-D-Glucosyl)-4-hydroxy-phenylamino-thiocarbonyl]-lysyl-D-alanyl}-batracyline, trifluoroacetate Educt:

p-aminophenyl $\alpha$-D-glucoside

Purification of the intermediate stage and of the final stage by stirring with methanol and completion of the precipitation with ether. Yield: 83% [TLC: methylene chloride/methanol/ammonia (17%) 15:8:0.8 $R_f$=0.48].

EXAMPLE 3.13

N-{$N^\epsilon$-[O-($\alpha$-D-Glucosyl)-4-hydroxy-phenylamino-thiocarbonyl]-lysyl-alanyl}-batracyline, trifluoroacetate Educt:

p-aminophenyl $\alpha$-D-glucoside

Analogous preparation to that of the isomer in Example 3.12

EXAMPLE 3.14

N-{$N^\epsilon$-[O-(3-O-Methyl-$\beta$-D-galactopyranosyl)-4-hydroxy-phenylamino-thiocarbonyl]-lysyl-D-alanyl}-batracyline, trifluoroacetate 3.14.a) N-{$N^\alpha$-(tert-Butoxycarbonyl)-$N^\epsilon$-[O-(3-O-methyl-$\beta$-D-galactopyranosyl)-4-hydroxy-phenylamino-thiocarbonyl]-lysyl-D-alanyl}-batracyline Thiophosgene (33.5 ml, 0.44 mmol) is added to a solution of compound 1.25 (62.8 mg, 0.22 mmol) in dioxane/water 1:1 (10 ml), while stirring. After 10 minutes, the mixture is concentrated in vacuo and the residue is dried under an oil pump vacuum for 1 hour. The isothiocyanate obtained is dissolved in absolute dimethylformamide (10 ml), and compound 2.4 (109.7 mg, 0.2 mmol) and ethyldiisopropylamine (0.5 ml) are added. The mixture is stirred at room temperature for 16 hours and then concentrated in vacuo and the residue is purified by flash chromatography [methylene chloride/methanol 20:1]. Yellow crystals (108.3 mg, 62 %) are obtained; TLC [methylene chloride/methanol 5:1]: $R_f$=0.42]; melting point=194–195° C. (decomposition).

3.14) N-{$N^\epsilon$-[O-(3-O-Methyl-$\beta$-D-galactopyranosyl)-4-hydroxy-phenylamino-thiocarbonyl]-lysyl-D-alanyl}-batracyline, trifluoroacetate The tert-butoxycarbonyl group is split off from compound 3.14.a (105.1 mg, 0.12 mmol) as described in Example 2.2. After concentration in vacuo and reprecipitation from methanol/diethyl ether, yellow crystals (57.4 mg, 54%) are obtained; TLC [methylene chloride/methanol 5:1]: $R_f$=0.16; melting point=188–189° C. (decomposition).

The following glycoconjugates are prepared analogously to Example 3.14.a and 3.14 from peptide conjugate 2.4 (in each case 109.7 mg, 0.2 mmol):

EXAMPLE 3.15

N-{$N^\epsilon$-[O-($\beta$-D-Galactopyranosyl)-4-hydroxy-phenylamino-thiocarbonyl]-lysyl-D-alanyl}-batracyline, trifluoroacetate Educt:

carbohydrate 1.23 (59.7 mg, 0.22 mmol)

Purification of the intermediate stage by flash chromatography [methylene chloride/methanol 10:1] gives yellow crystals (79.5 mg, 46%); TLC [methanol]: $R_f$=0.74; melting point=182° C.

Purification of the end product as described in Example 3.14 gives yellow crystals (77.1 mg, 44%); TLC [methanol]: $R_f$=0.27; melting point=191–192° C. (decomposition).

EXAMPLE 3.16

N-{$N^\epsilon$-[O-(3,4-Di-O-methyl-$\beta$-D-galactopyranosyl)-4-hydroxy-phenylamino-thiocarbonyl]-lysyl-D-alanyl}-batracyline, trifluoroacetate Educt:

carbohydrate 1.31 (79 mg, 0.22 mmol)

Purification of the intermediate stage by flash chromatography [methylene chloride/methanol 30:1→20:1] gives yellow crystals (150.7 mg, 85%); TLC [methylene chloride/methanol 10:1]: $R_f$=0.35; melting point=197–199° C. (decomposition).

Purification of the end product as described in Example 3.14 gives yellow crystals (137 mg, 76%); TLC [methylene chloride/methanol 10:1]: $R_f$=0.13; melting point=184–186° C. (decomposition).

EXAMPLE 3.17

N-{$N^\epsilon$-[O-(3-O-Methoxycarbonylmethyl-$\beta$-D-galactopyranosyl)-4-hydroxy-phenylamino-thiocarbonyl]-lysyl-D-alanyl}-batracyline, trifluoroacetate Educt:

carbohydrate 1.42 (75.5 mg, 0.22 mmol)

Purification of the intermediate stage by flash chromatography [methylene chloride/methanol 30:1→25:1] gives yellow crystals (124.1 mg, 66%); TLC [methylene chloride/methanol/ammonia (25%) 15:3:0.2]: $R_f$=0.50; melting point=165° C.

Purification of the end product as described in Example 3.14 gives yellow crystals (107.8 mg, 57%); TLC [methylene chloride/methanol 4:1]: $R_f$=0.53; melting point=183° C. (decomposition).

EXAMPLE 3.18

N-{$N^\epsilon$-[O-(3-O-Carboxymethyl-$\beta$-D-galactopyranosyl)-4-hydroxy-phenylamino-thiocarbonyl]-lysyl-D-alanyl}-batracyline, trifluoroacetate Educt:

compound 1.43 (77.3 mg, 0.22 mmol)

Purification of the intermediate stage by reprecipitation from ethanol/diethyl ether gives the sodium salt as yellow crystals (172 mg, 91%); TLC [methanol]: $R_f$=0.71; melting point=225–228° C.

Purification of the end product as described in Example 3.14 gives yellow crystals (136.5 mg, 73%); TLC [methanol]: $R_f$=0.12; melting point=217–220° C. (decomposition).

EXAMPLE 3.19

N-{$N^\epsilon$-[-(3-O-Carbamoylmethyl-$\beta$-D-galactopyranosyl)-4-hydroxy-phenylamino-thiocarbonyl]-lysyl-D-alanyl}-batracyline, trifluoroacetate Educt:

carbohydrate 1.44 (72.2 mg, 0.22 mmol)

Purification of the intermediate stage by flash chromatography [methylene chloride/methanol 10:1] gives yellow crystal (137.7 mg, 75%); TLC [methylene chloride/methanol 4:1]: $R_f$=0.41; melting point=198–201° C. (decomposition).

Purification of the end product as in Example 3.14 gives yellow crystals (140.2 mg, 75%); TLC [methylene chloride/methanol 4:1]: $R_f$=0.16; melting point=188– 190° C. (decomposition).

EXAMPLE 3.20

N-{$N^ε$-[O-(3-O-(N-Methyl-carbamoylmethyl)-β-D-galactopyranosyl)-4-hydroxy-phenylamino-thiocarbonyl]-lysyl-D-alanyl}-batracyline, trifluoroacetate Educt:

carbohydrate 1.45 (75.3 mg, 0.22 mmol)

Purification of the intermediate stage by flash chromatography [methylene chloride/methanol/ammonia (25%) 7:1:0.1] gives yellow crystals (158.4 mg, 85%); TLC [methylene chloride/methanol/ammonia (25%) 15:3:0.2]: $R_f$=0.25; melting point=161–163° C. (decomposition).

Purification of the end product as described in Example 3.14 gives yellow crystals (132.5 mg, 70%); TLC [methylene chloride/methanol/ammonia (25%) 15:3:0.2]: $R_f$=0.10; melting point=191–193° C. (decomposition).

EXAMPLE 3.21

N-{$N^ε$-[O-(3-O-(N-Propyl-carbamoylmethyl)-β-D-galactopyranosyl)-4-hydroxy-phenylamino-thiocarbonyl]-lysyl-D-alanyl}-batracyline, trifluoroacetate Educt:

carbohydrate 1.46 (81.5 mg, 0.22 mmol)

Purification of the intermediate stage by flash chromatography [methylene chloride/methanol/ammonia (25%) 8:1:0.1] gives yellow crystals (153.1 mg, 80%); TLC [methylene chloride/methanol/ammonia (25%) 15:3:0.2]: $R_f$=0.33; melting point=187° C. (decomposition).

Purification of the end product as described in Example 3.14 gives yellow crystals (154.9 mg, 79%); TLC [methylene chloride/methanol/ammonia (25%) 15:3:0.2]: $R_f$=0.21; melting point=179° C.

EXAMPLE 3.22

N-{$N^ε$-[O-(3-O-(N-Butyl-carbamoylmethyl)-β-D-galactopyranosyl)-4-hydroxy-phenylamino-thiocarbonyl]-lysyl-D-alanyl}-batracyline, trifluoroacetate Educt:

carbohydrate 1.47 (84.6 mg, 0.22 mmol)

Purification of the intermediate stage by flash chromatography [methylene chloride/methanol 12:1] gives yellow crystals (132.7 mg, 68%); TLC [methylene chloride/methanol/ammonia (25%) 15:3:0.2]: $R_f$=0.54; melting point=180–182° C.

Purification of the end product as described in Example 3.14 gives yellow crystals (115.2 mg, 58%); TLC [methylene chloride/methanol/ammonia (25%) 15:3:0.2]: $R_f$=0.30; melting point=176° C.

EXAMPLE 3.23

N-{$N^{ε\text{-}[O\text{-}(}$3,4-Dideoxy-β-D-galactopyranosyl)-4-hydroxy-phenylamino-thiocarbonyl]-lysyl-D-alanyl}-batracyline, trifluoroacetate Educt:

carbohydrate 1.52 (52.6 mg, 0.22 mmol)

Purification of the intermediate stage by flash chromatography [methylene chloride/methanol 25:1] gives yellow crystals (127.4 mg, 77%); TLC [methylene chloride/methanol/ammonia (25%) 15:3:0.2]: $R_f$=0.60; melting point=166–167° C.

Purification of the end product as described in Example 3.14 gives yellow crystals (103.1 mg, 61%); TLC [methylene chloride/methanol/ammonia (25%) 15:3:0.2]: $R_f$=0.44; melting point=173–175° C. (decomposition).

EXAMPLE 3.24

N-{$N^ε$-[O-(6-O-Acetyl-β-D-galactopyranosyl)-4-hydroxy-phenylamino-thiocarbonyl]-lysyl-D-alanyl}-batracyline, trifluoroacetate Educt:

carbohydrate 1.53 (78.2 mg, 0.22 mmol)

Purification of the intermediate stage by flash chromatography [methylene chloride/methanol 25:1] gives yellow crystals (88.3 mg, 49%); TLC [methylene chloride/methanol 4:1]: $R_f$=0.61; melting point=196–199° C. (decomposition).

Purification of the end product as described in Example 3.14 gives yellow crystals (89.6 mg, 49%); TLC [methylene chloride/methanol 4:1]: $R_f$=0.31; melting point=186° C. (decomposition).

EXAMPLE 3.25

N-{$N^ε$-[O-(α-D-Mannopyranosyl)-4-hydroxy-phenylamino-thiocarbonyl]-lysyl-D-alanyl}-batracyline, trifluoroacetate Educt:

carbohydrate 1.39 (59.7 mg, 0.22 mmol)

Purification of the intermediate stage by flash chromatography [methylene chloride/methanol 10:1] gives yellow crystals (101.7 mg, 59%); TLC [methanol]: $R_f$=0.79; melting point=180° C. (decomposition).

Purification of the end product as described in Example 3.14 gives yellow crystals (103.1 mg, 59%); TLC [methanol]: $R_f$=0.34; melting point=177–178° C. (decomposition).

EXAMPLE 3.26

N-{$N^ε$[O-(3-O-Methyl-α-D-mannopyranosyl)-4-hydroxy-phenylamino-thiocarbonyl]-lysyl-D-alanyl}-batracyline, trifluoroacetate Educt:

carbohydrate 1.40 (62.8 mg, 0.22 mmol)

Purification of the intermediate stage by flash chromatography [methylene chloride/methanol 20:1] gives yellow crystals (56.6 mg, 32%); TLC [methylene chloride/methanol 5:1]: $R_f$=0.38; melting point=191–192° C. (decomposition).

Purification of the end product as described in Example 3.14 gives yellow crystals (46.6 mg, 26%); TLC [methylene chloride/methanol 5:1]: $R_f$=0.13; melting point=190–191 ° C. (decomposition).

EXAMPLE 3.27

N-{$N^ε$-[O-(2,3-Di-O-methyl-α-D-mannopyranosyl)-4-hydroxy-phenylamino-thiocarbonyl]-lysyl-D-alanyl}-batracyline, trifluoroacetate Educt:

carbohydrate 1.41 (66 mg, 0.22 mmol)

Purification of the intermediate stage by flash chromatography [methylene chloride/methanol 25:1] gives yellow crystals (77.8 mg, 44%); TLC [methylene chloride/methanol 4:1]: $R_f$=0.65; melting point=182–183° C. (decomposition).

Purification of the end product as described in Example 3.14 gives yellow crystals (66.1 mg, 37%); TLC [methylene chloride/methanol 4:1]: $R_f$=0.40; melting point=181° C.

EXAMPLE 3.28

N-{$N^ε$-[O-(3-O-Methoxycarbonylmethyl-α-D-mannopyranosyl)-4-hydroxy-phenylamino-thiocarbonyl]-lysyl-D-alanyl}-batracyline, trifluoroacetate Educt:

carbohydrate 1.48 (75.5 mg, 0.22 mmol)

Purification of the intermediate stage by flash chromatography [methylene chloride/methanol 18:1] gives yellow crystals (62.1 mg, 33%); TLC [methylene chloride/methanol/ammonia (25%) 15:3:0.2]: $R_f$=0.66; melting point=165° C.

Purification of the end product as described in Example 3.14 gives yellow crystals (57.6 mg, 30%); TLC [methylene chloride/methanol/ammonia (25%) 15:3:0.2]: $R_f$=0.43; melting point=183–184° C.

EXAMPLE 3.29

N-{$N^ε$-[O-(3-O-Carboxymethyl-α-D-mannopyranosyl)-4-hydroxy-phenylamino-thiocarbonyl]-lysyl-D-alanyl}-batracyline, trifluoroacetate Educt:

carbohydrate 1.49 (77.3 mg, 0.22 mmol)

Purification of the intermediate stage by reprecipitation from ethanol/diethyl ether gives the sodium salt as yellow crystals (173.4 mg, 92%); TLC [methanol]: $R_f$=0.57; melting point=201–205° C. (decomposition).

Purification of the end product as described in Example 3.14 gives yellow crystals (171.7 mg, 92%); TLC [methanol]: $R_f$=0.29; melting point=196–198° C. (decomposition).

EXAMPLE 3.30

N-{$N^ε$-[O-(3-O-Carbamoylmethyl-α-D-mannopyranosyl)-4-hydroxy-phenylamino-thiocarbonyl]-lysyl-D-alanyl}-batracyline, trifluoroacetate Educt:

carbohydrate 1.50 (72.2 mg, 0.22 mmol)

Purification of the intermediate stage by flash chromatography [methylene chloride/methanol 10:1] gives yellow crystals (106.6 mg, 58%); TLC [methylene chloride/methanol 4:1]: $R_f$=0.34; melting point=192–194° C. (decomposition).

Purification of the end product as described in Example 3.14 gives yellow crystals (107.7 mg, 58%); TLC [methylene chloride/methanol 4:1]: $R_f$=0.13; melting point=186–187° C. (decomposition).

EXAMPLE 3.31

N-{$N^ε$-[O-(3,4-Di-O-methyl-β-D-galactopyranosyl)-4-hydroxy-phenylamino-thiocarbonyl]-lysyl-D-alanyl}-batracyline 3.31.a) N-{$N^α$-(Fluorenyl-9-methoxycarbonyl)-$N^ε$-[O-(3,4-di-O-methyl-β-D-galactopyranosyl)-4-hydroxy-phenylamino-thiocarbonyl]-lysyl-D-alanyl}-batracyline Thiophosgene (33.5 ml, 0.44 mmol) is added to a solution of compound 1.31 (79 mg, 0.22 mmol) in dioxane/water 1:1 (10 ml). After 10 minutes, the mixture is concentrated in vacuo and the residue is dried under an oil pump vacuum for 1 hour. The isothiocyanate obtained is dissolved in absolute dimethylformamide (10 ml), and compound 2.5 (157 mg, 0.2 mmol) and ethyldiisopropylamine (0.5 ml) are added. The mixture is stirred at room temperature for 16 hours and then concentrated in vacuo and the residue is taken up in methylene chloride/methanol 1:1. The product is precipitated by addition of diethyl ether and washed with a little ice-cold methanol. Yellow crystals (191 mg, 94%) are obtained; TLC [methylene chloride/methanol 10:1]: $R_f$=0.35; melting point=203° C. (decomposition).

3.31) N-{$N^ε$-[-(3,4-Di-O-methyl-β-D-galactopyranosyl)-4-hydroxy-phenylamino-thiocarbonyl]-lysyl-D-alanyl}-batracyline The fluorenyl-9-methoxycarbonyl group is split off from compound 3.31.a (182.2 mg, 0.18 mmol) as described in Example 2.4. After concentration in vacuo and dissolving in methanol/methylene chloride 1:1, the product is precipitated by addition of diethyl ether. Yellow crystals (127.1 mg, 89%) are obtained; TLC [methanol]: $R_f$=0.46; melting point=158° C.

The following glycoconjugates are prepared analogously to Examples 3.31.a and 3.31 from peptide conjugate 2.5 (in each case 157 mg, 0.2 mmol):

EXAMPLE 3.32

N-{$N^ε$-[O-(3-O-(Piperidyl-N)-carbonylmethyl-β-D-galactopyranosyl)-4-hydroxy-phenylamino-thiocarbonyl]-lysyl-D-alanyl}-batracyline Educt:

carbohydrate 1.42 (75.5 mg, 0.22 mmol)

Purification of the intermediate stage as described in Example 3.31.a; yellow crystals (191.2 mg, 91%) are obtained; TLC [methylene chloride/methanol 10:1]: $R_f$=0.28; melting point=208° C. (decomposition).

Purification of the end product as described in Example 3.31 gives yellow crystals (155.8 mg, 88%); TLC [methanol]: $R_f$=0.47; melting point=120° C. (decomposition).

EXAMPLE 3.33

N-{$N^ε$-[O-(3-O-Carboxymethyl-β-D-galactopyranosyl)-4-hydroxy-phenylamino-thiocarbonyl]-lysyl-D-alanyl}-batracyline, sodium salt Educt:

carbohydrate 1.43 (77.3 mg, 0.22 mmol)

Purification of the intermediate stage as described in Example 3.31.a; yellow crystals (192 mg, 90%) are obtained; TLC [ethanol/methanol 1:1]: $R_f$=0.05; melting point=211–213° C. (decomposition).

Purification of the end product as described in Example 3.31 gives yellow crystals (110.6 mg, 66%); TLC [methanol]: $R_f$=0.33; melting point=233–235° C. (decomposition).

EXAMPLE 3.34

N-{$N^ε$-[O-(3-O-Carbamoylmethyl-β-D-galactopyranosyl)-4-hydroxy-phenylamino-thiocarbonyl]-lysyl-D-alanyl}-batracyline Educt:

carbohydrate 1.44 (72.2 mg, 0.22 mmol)

Purification of the intermediate stage as described in Example 3.31.a; yellow crystals (159.2 mg, 76%) are obtained; TLC [methylene chloride/methanol 10:1]: $R_f$=0.04; melting point=177° C. (decomposition).

Purification of the end product as described in Example 3.31 gives yellow crystals (125.1 mg, 76%); TLC [methanol]: $R_f$=0.48; melting point=106° C. (decomposition).

EXAMPLES 4.1–4.12

General Formula

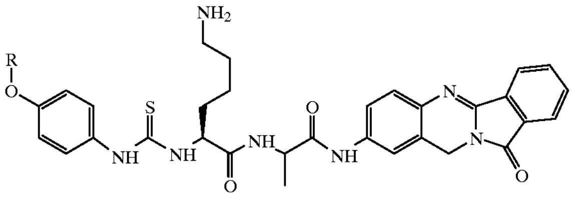

EXAMPLE 4.1

4.1.a) N-{$N^α$-[O-(β-L-Fucosyl)-4-hydroxy-phenylamino-thiocarbonyl]-$N^ε$-(fluorenyl-9-methoxycarbonyl)-lysyl-D-alanyl}-batracyline 140 mg (0.55 mmol) of p-aminophenyl β-L-fucoside are first converted into the isothiocyanate in accordance with the instructions in Example 3.1.a and the product is then coupled with 430 mg (0.55 mmol) of N-[$N^\epsilon$-(fluorenyl-9-methoxycarbonyl)-lysyl-D-alanyl]-batracyline trifluoroacetate (Example 2.5) in the presence of 375 μl of ethyldiisopropylamine. After precipitation from methanol/methylene chloride, the crude product is purified by flash chromatography (acetonitrile/water 10:1). After the residue has been stirred with ether, 358 mg (67%) of the target product are obtained. [TLC: acetonitrile/water 10:1 $R_f$=0.48].

4.1) N-{Nα-[O-(β-L-Fucosyl)-4-hydroxy-phenylamino-thiocarbonyl]-lysyl-D-alanyl}-batracyline 356 mg (0.37 mmol) of the compound from Example 4.1.a are dissolved in 10 ml of dimethylformamide and 5 ml of piperidine and the solution is stirred at 20° C. for 1 hour. It is concentrated and the residue is chromatographed with methylene chloride/methanol/ammonia (17%) 15:6:0.6. The target product is obtained in a 46% yield. [TLC: methylene chloride/methanol/ammonia (17%) 15:4:0.5 $R_f$=0.11].

The following glycoconjugates are prepared analogously to Examples 4.1 from the partly protected peptide conjugate 2.5:

EXAMPLE 4.2

N-{$N^\alpha$-[O-(3-O-Carboxymethyl-β-L-fucosyl)-4-hydroxy-phenylamino-thiocarbonyl]-lysyl-D-alanyl}-batracyline, sodium salt Educt:

carbohydrate from Example 1.10

Chromatographic purification of the intermediate stage with methylene chloride/methanol/ammonia (17%) 15:3:0.3; later in the same system 15:4:0.5.

Purification of the end product at the betaine stage by stirring with water; subsequent conversion into the sodium salt with 0.1N sodium hydroxide solution and freeze drying from dioxane/water. Yield: 65%; melting point: 220° C.

EXAMPLE 4.3

N-{$N^\alpha$-[O-(3-O-Methyl-β-L-fucosyl)-4-hydroxy-phenylamino-thiocarbonyl]-lysyl-D-alanyl}-batracyline Educt:

carbohydrate from Example 1.2

Purification of the intermediate stage by precipitation with methylene chloride with ether; purification of the end product by several precipitations from dimethylformamide with ether. Yield: 88% [TLC: acetonitrile/water/glacial acetic acid 5:1:0.2 $R_f$=0.28].

EXAMPLE 4.4

N-{$N^\alpha$-[O-(4-O-Methyl-β-L-fucosyl)-4-hydroxy-phenylamino-thiocarbonyl]-lysyl-D-alanyl}-batracyline Educt:

carbohydrate from Example 1.4

Purification of the intermediate stage by several precipitations from methylene chloride/methanol 1:1 with ether; column chromatography purification of the end product [methylene chloride/methanol/ammonia (17%) 15:8:0.8], precipitation from methylene chloride/methanol 1:1 with ether. Yield: 74% [TLC: methylene chloride/methanol/ammonia (17%) 10:10:1 $R_f$=0.19].

EXAMPLE 4.5

N-{$N^\alpha$-[O-(3,4-Di-O-methyl-β-D-galactopyranosyl)-4-hydroxy-phenylamino-thiocarbonyl]-lysyl-D-alanyl}-batracyline 4.5.a) N-{$N^\alpha$-[O-(3,4-Di-O-methyl-β-D-galactopyranosyl)-4-hydroxy-phenylamino-thiocarbonyl-$N^\epsilon$-(fluorenyl-9-methoxycarbonyl)]-lysyl-D-alanyl}-batracyline Thiophosgene (33.5 ml, 0.44 mmol) is added to a solution of compound 1.31 (79 mg, 0.22 mmol) in dioxane/water 1:1 (10 ml). After 10 minutes, the mixture is concentrated in vacuo and the residue is dried under an oil pump vacuum for 1 hour. The isothiocyanate obtained is dissolved in absolute dimethylformamide (10 ml), and compound 2.6 (157 mg, 0.2 mmol) and ethyldiisopropylamine (0.5 ml) are added. The mixture is stirred at room temperature for 16 hours and then concentrated in vacuo. Several reprecipitations of the residue from methylene chloride/methanol 1:1 by means of diethyl ether and final washing with a little ice-cold methanol gives yellow crystals (198 mg, 98%); TLC [methylene chloride/methanol 10:1]: $R_f$=0.23; melting point=175° C.

4.5) N-{$N^\alpha$-[O-(3,4-Di-O-methyl-β-D-galactopyranosyl)-4-hydroxy-phenylamino-thiocarbonyl]-lysyl-D-alanyl}-batracyline The fluorenyl-9-methoxycarbonyl group is split off from compound 4.5.a (172.1 mg, 0.17 mmol) as described in Example 2.4. After concentration in vacuo and dissolving in methanol/methylene chloride 1:1, the product is precipitated by addition of diethyl ether. Yellow crystals (114.5 mg, 85%) are obtained; TLC [methylene chloride/methanol 1:1]: $R_f$=0.16; melting point=206° C. (decomposition).

The following glycoconjugates are prepared analogously to Example 4.5.a and 4.5 from peptide conjugate 2.6 (in each case 157 mg, 0.2 mmol):

EXAMPLE 4.6

N-{$N^\alpha$-[O-(β-D-Galactopyranosyl)-4-hydroxy-phenylamino-thiocarbonyl]-lysyl-D-alanyl}-batracyline Educt:

carbohydrate 1.23 (59.7 mg, 0.22 mmol)

Purification of the intermediate stage as described in Example 4.5.a; yellow crystals (185.8 mg, 94%) are obtained; TLC [methylene chloride/methanol 10:1]: $R_f$=0.09; melting point=182° C. (decomposition).

Purification of the end product as described in Example 4.5 gives yellow crystals (134.3 mg, 88%); TLC [methylene chloride/methanol 1:1]: $R_f$=0.04; melting point=221° C. (decomposition).

EXAMPLE 4.7

N-{$N^\alpha$-[O-(3-O-Methyl-β-D-galactopyranosyl)-4-hydroxy-phenylamino-thiocarbonyl]-lysyl-D-alanyl}-batracyline Educt:

carbohydrate 1.25 (62.8 mg, 0.22 mmol)

Purification of the intermediate stage as described in Example 4.5.a; yellow crystals (193.5 mg, 97%) are obtained; TLC [methylene chloride/methanol 10:1]: $R_f$=0.27; melting point=178° C. (decomposition).

Purification of the end product by flash chromatography [methylene chloride/methanol 2:1→1:1] gives yellow crystals (130.5 mg, 84%); TLC [methylene chloride/methanol 1:1]: $R_f$=0.09; melting point=206° C. (decomposition).

EXAMPLE 4.8

N-{$N^\alpha$-[O-(3-O-Methoxycarbonylmethyl-[-D-galactopyranosyl)-4-hydroxy-phenylamino-thiocarbonyl]-lysyl-D-alanyl}-batracyline Educt:

carbohydrate 1.42 (75.5 mg, 0.22 mmol)

Purification of the intermediate stage as described in Example 4.5.a; yellow crystals (209.8 mg, 99%) are obtained; TLC [methylene chloride/methanol 10:1]: $R_f$=0.32; melting point=235° C. (decomposition).

Purification of the end product as described in Example 4.5 gives yellow crystals (164.3 mg, 99%); TLC [methylene chloride/methanol 1:1]: $R_f$=0.05; melting point=217° C. (decomposition).

EXAMPLE 4.9

N-{$N^\alpha$-[O-(3-O-Carboxymethyl-β-D-galactopyranosyl)-4-hydroxy-phenylamino-thiocarbonyl]-lysyl-D-alanyl}-batracyline, sodium salt Educt:

carbohydrate 1.43 (77.3 mg, 0.22 mmol)

Purification of the intermediate stage as described in Example 4.5.a; yellow crystals (210.3 mg, 99%) are obtained; TLC [methylene chloride/methanol 10:1]: $R_f$=0.02; melting point=185° C.

After purification of the product as described in Example 4.5, the residue is suspended in water (10 ml), and 0.05 N sodium hydroxide solution is added dropwise to the suspension, while stirring, until a clear solution forms (pH<10). Lyophilization of the filtered solution gives a yellow amorphous solid (150.8 mg, 90%); TLC [methylene chloride/methanol 1:1]: $R_f$=0.04.

EXAMPLE 4.10

N-{$N^\alpha$-[-(3-O-Carbamoylmethyl-β-D-galactopyranosyl)-4-hydroxy-phenylamino-thiocarbonyl]-lysyl-D-alanyl}-batracyline Educt:

carbohydrate 1.44 (72.2 mg, 0.22 mmol)

Purification of the intermediate stage as described in Example 4.5.a; yellow crystals (152.7 mg, 73%) are obtained; TLC [methylene chloride/methanol 10:1]: $R_f$=0.11; melting point=229° C. (decomposition).

After purification of the product as described in Example 4.5, the residue is suspended in water/dioxane 1:1 (20 ml). Lyophilization of the filtered solution gives a yellow amorphous solid (98.4 mg, 61%); TLC [methylene chloride/methanol 1:1]: $R_f$=0.10; $[\alpha]^{20}$=+44.9° (c=0.2/$H_2O$).

EXAMPLE 4.11

N-{N-[O-(α-D-Mannopyranosyl)-4-hydroxy-phenylamino-thiocarbonyl]-lysyl-D-alanyl}-batracyline Educt:

carbohydrate 1.39 (59.7 mg, 0.22 mmol)

Purification of the intermediate stage as described in Example 4.5.a; yellow crystals (179.6 mg, 91%) are obtained; TLC [methylene chloride/methanol 10:1]: $R_f$=0.07; melting point=176° C. (decomposition).

Purification of the end product as described in Example 4.5 gives yellow crystals (137.5 mg, 90%); TLC [methylene chloride/methanol 1:1]: $R_f$=0.09; melting point=213° C. (decomposition).

EXAMPLE 4.12

N-{$N^\alpha$-[O-(3-O-Methyl-α-D-mannopyranosyl)-4-hydroxy-phenylamino-thiocarbonyl]-lysyl-D-alanyl}-batracyline Educt:

carbohydrate 1.40 (62.8 mg, 0.22 mmol)

Purification of the intermediate stage as described in Example 4.5.a; yellow crystals (94.2 mg, 48%) are obtained; TLC [methylene chloride/methanol 10:1]: $R_f$=0.13; melting point=173° C. (decomposition).

Purification of the end product as described in Example 4.5 gives yellow crystals (66.6 mg, 43%); TLC [methylene chloride/methanol 1:1]: $R_f$=0.07; melting point=215° C. (decomposition).

EXAMPLES 5.1–5.23

General Formula

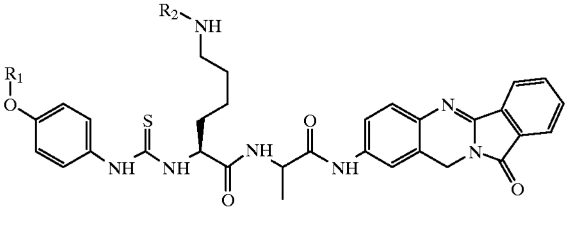

EXAMPLE 5.1

N-{$N^\alpha$-[O-(3-O-Carboxymethyl-β-L-fucosyl)-4-hydroxyphenylaminothiocarbonyl]-$N^\epsilon$-[O-(3-O-methyl-β-L-fucosyl)-4-hydroxyphenylaminothiocarbonyl]-lysyl-D-alanyl}-batracyline 30 μl (0.18 mmol) of thiophosgene are added to 50 mg (0.16 mmol) of p-aminophenyl 3-O-carboxymethyl-β-L-fucoside (Example 1.10) in 10 ml of dioxane/water 1:1, while stirring. After 10 minutes, the mixture is concentrated and the residue is dried under a high vacuum for 1 hour. The isothiocyanate obtained is then coupled in absolute dimethylformamide with 109 mg (0.144 mmol) of the conjugate from Example 3.4 in the presence of 82 μl of ethyldiisopropylamine. The mixture is concentrated and the residue is purified by flash chromatography [methylene chloride/methanol/ammonia (17%) 15:4:0.5]. The substance obtained after concentration is lyophilized from water. Yield: 89 mg (56%). [TLC: methylene chloride/methanol/ammonia (17%) 15:6:0.6 $R_f$=0.22].

The following conjugates with mixed substituents are prepared analogously to Example 5.1:

EXAMPLE 5.2

N-{$N^\alpha$-[O-(3-O-Methyl-β-L-fucosyl)-4-hydroxyphenylamino-thiocarbonyl]-$N^\epsilon$-[O-(3-O-carboxymethyl-β-L-fucosyl)-4-hydroxyphenylamino-thiocarbonyl]-lysyl-D-alanyl}-batracyline Educts:

carbohydrate from Example 1.2, conjugate from Example 3.10

Purification by precipitation of the crude product from methanol with ether. Yield: 78% [TLC: acetonitrile/water/glacial acetic acid 5:1:0.2 $R_f$=0.45].

EXAMPLE 5.3

N-{$N^\alpha$-[O-(3-O-Methyl-β-L-fucosyl)-4-hydroxyphenylamino-thiocarbonyl]-$N^\epsilon$-[4-hydroxyphenylamino-thiocarbonyl]-lysyl-D-alanyl}-batracyline Educts:

conjugate from Example 4.3, 4-hydroxy-aniline

Purification by flash chromatography [methylene chloride/methanol/ammonia (17%) 15:2:0.21; yield: 60% [TLC: methylene chloride/methanol/ammonia (17%) 15:2:0.2 $R_f$=0.31].

EXAMPLE 5.4

N-{$N^\alpha$-[O-(3-O-Carboxymethyl-β-L-fucosyl)-4-hydroxyphenylamino-thiocarbonyl]-$N^\epsilon$-[4-hydroxyphenylamino-thiocarbonyl]-lysyl-D-alanyl}-batracyline Educts:

conjugate from Example 4.2, 4-hydroxy-aniline

Purification by flash chromatography [methylene chloride/methanol/ammonia (17%) 15:4:0.5]. The residue is then stirred with methanol/ether. Yield: 55% [TLC: methylene chloride/methanol/ammonia (17%) 15:6:0.6 $R_f$=0.3].

EXAMPLE 5.5

N-{$N^\alpha$-[O-(4-O-Methyl-β-L-fucosyl)-4-hydroxyphenylamino-thiocarbonyl]-$N^\epsilon$-[4-hydroxyphenylamino-thiocarbonyl]-lysyl-D-alanyl}-batracyline Educts:

conjugate from Example 4.4, 4-hydroxy-aniline

Purification by flash chromatography [methylene chloride/methanol/ammonia (17%) 15:2:0.2]. The residue is then precipitated from methanol/methylene chloride with ether. Yield: 49% melting point: 128° C. [TLC: methylene chloride/methanol/ammonia (17%) 15:2:0.2 $R_f$=0.26].

EXAMPLE 5.6

N-{$N^\alpha$-[4-Hydroxyphenylamino-thiocarbonyl]-$N^\epsilon$-[O-(4-O-methyl-β-L-fucosyl)-4-hydroxyphenylamino-thiocarbonyl]-lysyl-D-alanyl}-batracyline Educts:

conjugate from Example 3.11, 4-hydroxy-aniline

Purification by flash chromatography [methylene chloride/methanol/ammonia (17%) 15:2:0.2]. The residue is then lyophilized from water/dioxane. Yield: 50% [TLC: methylene chloride/methanol/ammonia (17%) 15:2:0.2 $R_f$=0.291.

EXAMPLE 5.7

N-{$N^\alpha$-[4-Hydroxyphenylamino-thiocarbonyl]-$N^\epsilon$-[O-(3-O-methyl-β-L-fucosyl)-4-hydroxyphenylamino-thiocarbonyl]-lysyl-D-alanyl}-batracyline Educts:

conjugate from Example 3.4, 4-hydroxy-aniline

Precipitate the residue from methanol with ether. Yield: 76% [TLC: methylene chloride/methanol/ammonia (17%) 15:2:0.2 $R_f$=0.26].

EXAMPLE 5.8

N-{$N^\alpha$-[O-(3-O-Methyl-β-L-fucosyl)-4-hydroxyphenylamino-thiocarbonyl]-$N^\epsilon$-[4-hydroxyethylamino-2-[O-(3-O-methyl-β-L-fucosyl)-4-hydroxyphenylamino]triazin-6-yl]]-lysyl-D-alanyl}-batracyline Educts:

conjugate from Example 8.10, carbohydrate from Example 1.2

Purification by flash chromatography [methylene chloride/methanol/ammonia (17%) 15:2:0.2]. Yield: 9% FAB-MS: m/z=1165=M+1 [TLC: methylene chloride/methanol/ammonia (17%) 15:3:0.3 $R_f$=0.27].

EXAMPLE 5.9

N-{$N^\alpha$-[O-(3-O-Carboxymethyl-β-L-fucosyl)-4-hydroxyphenylaminothiocarbonyl]-$N^\alpha$-[acetyl]-lysyl-D-alanyl batracyline Educts:

N-[$N^\epsilon$-(acetyl)-lysyl-D-alanyl]-batracyline, carbohydrate from Example 1.10

Purification by flash chromatography [methylene chloride/methanol/ammonia (17%) 15:2:0.2; later in the same system 15:4:0.5]. The residue is then freeze dried from water. Yield: 46% [TLC: acetonitrile/water/glacial acetic acid 5:1:0.2 $R_f$=0.31].

EXAMPLE 5.10

N-{N-[O-(4-O-Methyl-β-L-fucosyl)-4-hydroxyphenylamino-thiocarbonyl]-$N^\epsilon$-[acetyl]-lysyl-D-alanyl}-batracyline 10 μl of acetic anhydride are added to 51 mg (0.067 mmol) of the conjugate from Example 4.4 in 5 ml of dimethylformamide and the mixture is stirred at room temperature for 30 minutes. It is concentrated and the residue is precipitated from methanol with ether. Yield: 46 mg (86%) [TLC: acetonitrile/water/glacial acetic acid 5:1:0.2 $R_f$=0.6].

EXAMPLE 5.11

N-{$N^\alpha$-[O-(β-L-Fucosyl)-4-hydroxyphenylamino-thiocarbonyl]-$N^\epsilon$-[succinyl]-lysyl-D-alanyl}-batracyline, sodium salt 3 mg of succinic anhydride are added to 20 mg (0.027 mmol) of the conjugate from Example 4.1 in 2 ml of dimethylformamide and the mixture is stirred at room temperature for 6 hours. It is concentrated and the residue is precipitated from methanol with ether. The residue is taken up in water, and 27 μl of a 0.1N sodium hydroxide solution are added. Yield: 20 mg (86%); [TLC: methylene chloride/methanol/glacial acetic acid 80:20:2 $R_f$=0.2].

EXAMPLE 5.12

N-{$N^\alpha$-[O-(3-O-Methoxycarbonylmethyl-β-D-galactopyranosyl)-4-hydroxyphenylamino-thiocarbonyl]-$N^\epsilon$-[O-(3,4-di-O-methyl-β-D-galactopyranosyl)-4-hydroxyphenylamino-thiocarbonyl]-lysyl-D-alanyl}-batracyline Carbohydrate 1.42 (37.7 mg, 0.11 mmol) is reacted with peptide conjugate 3.31 (79 mg, 0.1 mmol) as described in Example 3.31.a. After concentration in vacuo and flash chromatography [methylene chloride/methanol 20:1→10:1], yellow crystals (52.9 mg, 45%) are obtained; TLC [methylene chloride/methanol 10:1]: $R_f$=0.14; melting point=178° C. (decomposition).

EXAMPLE 5.13

N-{$N^\alpha$-[-(3-O-Carboxymethyl-β-D-galactopyranosyl)-4-hydroxy-phenylaminothiocarbonyl]-$N^\epsilon$-[O-(3,4-di-O-methyl-β-D-galactopyranosyl)-4-hydroxy-phenylamino-thiocarbonyl]-lysyl-D-alanyl}-batracyline, sodium salt Carbohydrate 1.43 (38.6 mg, 0.11 mmol) is reacted with peptide conjugate 3.31 (79 mg, 0.1 mmol) as described in Example 3.31.a. After concentration in vacuo and dissolving in methanol/methylene chloride 1:1, the product is precipitated by addition of diethyl ether. The residue is suspended in water (10 ml), and 0.05 N sodium hydroxide solution is added dropwise to the suspension, while stirring, until a clear solution forms (pH<10). Lyophilization of the filtered solution gives a yellow amorphous solid (87.9 mg, 74%); TLC [ethanol]: $R_f$=0.17; $[\alpha]^{20}$=+56.0° (c=0.1/$H_2O$).

EXAMPLE 5.14

N-{$N^\alpha$-[O-(3-O-Carboxymethyl-β-D-galactopyranosyl)-4-hydroxy-phenylamino-thiocarbonyl]-$N^\epsilon$-[O-(3,4-di-O-methyl-β-D-galactopyranosyl)-4-hydroxy-phenylamino-thiocarbonyl]-lysyl-D-alanyl}-batracyline Carbohydrate 1.44 (36.1 mg, 0.11 mmol) is reacted with peptide conjugate 3.31 (79 mg, 0.1 mmol) as described in Example 3.31.a. After concentration in vacuo and dissolving in methanol/methylene chloride 1:1, the product is precipitated by addition of diethyl ether. Yellow crystals (45.9 mg, 39%) are obtained; TLC [ethanol]: $R_f$=0.38; melting point=219° C. (decomposition).

EXAMPLE 5.15

N-{$N^\alpha$-[O-(3,4-Di-O-methyl-β-D-galactopyranosyl)-4-hydroxy-phenylamino-thiocarbonyl]-$N^\epsilon$-[O-(3-O-(piperidyl-N)-carbonylmethyl-β-D-galactopyranosyl)-4-hydroxy-phenylamino-thiocarbonyl]-lysyl-D-alanyl}-batracyline Carbohydrate 1.31 (39.5 mg, 0.11 mmol) is reacted with peptide conjugate 3.32 (88.7 mg, 0.1 mmol) as described in Example 3.31.a. After concentration in vacuo and flash chromatography [methylene chloride/methanol 20:1→10:1], yellow crystals (38.8 mg, 32%) are obtained; TLC [methylene chloride/methanol 5:1]: $R_f$=0.79; melting point=205° C. (decomposition).

EXAMPLE 5.16

N-{N$^{\alpha}$-[O-(3-O-Carboxymethyl-β-D-galactopyranosyl)-4-hydroxy-phenylamino-thiocarbonyl]-N$^{\epsilon}$-[O-(3-O-(piperidyl-N)-carbonylmethyl-β-D-galactopyranosyl)-4-hydroxy-phenylamino-thiocarbonyl]-lysyl-D-alanyl}-batracyline, sodium salt Carbohydrate 1.43 (38.6 mg, 0.11 mmol) is reacted with peptide conjugate 3.32 (88.7 mg, 0.1 mmol) as described in Example 3.31.a. After concentration in vacuo and dissolving in methanol/methylene chloride 1:1, the product is precipitated by addition of diethyl ether. The residue is suspended in water (10 ml), and 0.05N sodium hydroxide solution is added dropwise to the suspension, while stirring, until a clear solution forms (pH<10). Lyophilization of the filtered solution gives a yellow amorphous solid (90.3 mg, 71%); TLC [ethanol]: $R_f$=0.05; $[\alpha]^{20}$=+39.0° (c=0.1/$H_2O$).

EXAMPLE 5.17

N-{N$^{\alpha}$-[O-(3-O-Carbamoylmethyl-β-D-galactopyranosyl)-4-hydroxy-phenylamino-thiocarbonyl]-N$^{\epsilon}$-[O-(3-O-(piperidyl-N)-carbonylmethyl-β-D-galactopyranosyl)-4-hydroxy-phenylamino-thiocarbonyl-lysyl-D-alanyl}-batracyline Carbohydrate 1.44 (36.1 mg, 0.11 mmol) is reacted with peptide conjugate 3.32 (88.7 mg, 0.1 mmol) as described in Example 3.31.a. After concentration in vacuo and dissolving in methanol/methylene chloride 1:1, the product is precipitated by addition of diethyl ether. Yellow crystals (44.8 mg, 36%) are obtained; TLC [ethanol]: $R_f$=0.06; melting point=223° C. (decomposition).

EXAMPLE 5.18

N-{N-$^{\alpha}$[O-(3,4-Di-O-methyl-β-D-galactopyranosyl)-4-hydroxy-phenylamino-thiocarbonyl]-N$^{\epsilon}$-[O-(3-O-carboxymethyl-β-D-galactopyranosyl)-4-hydroxy-phenylamino-thiocarbonyl]-lysyl-D-alanyl}-batracyline, sodium salt Carbohydrate 1.31 (39.5 mg, 0.11 mmol) is reacted with peptide conjugate 3.33 (84.2 mg, 0.1 mmol) as described in Example 3.31.a. After concentration in vacuo, methanol/methylene chloride 1:1 (20 ml) is added to the residue and the product is precipitated by addition of diethyl ether. The residue is suspended in water (10 ml), and 0.05N sodium hydroxide solution is added dropwise to the suspension, while stirring, until a clear solution forms (pH<10). Lyophilization of the filtered solution gives a yellow amorphous solid (80.7 mg, 68%); TLC [ethanol]: $R_f$=0.09; $[\alpha]^{20}$=+35.0° (c=0.1/$H_2O$).

EXAMPLE 5.19

N-{N$^{\alpha}$-[O-(3-O-Methoxycarbonylmethyl-β-D-galactopyranosyl)-4-hydroxy-phenylamino-thiocarbonyl]-N$^{\epsilon}$-[O-(3-O-carboxymethyl-β-D-galactopyranosyl)-4-hydroxy-phenylamino-thiocarbonyl]-lysyl-D-alanyl}-batracyline, sodium salt Carbohydrate 1.42 (37.7 mg, 0.11 mmol) is reacted with peptide conjugate 3.33 (84.2 mg, 0.1 mmol) as described in Example 3.31.a. After concentration in vacuo, methanol/methylene chloride 1:1 (20 ml) is added to the residue and the product is precipitated by addition of diethyl ether. The residue is suspended in water (10 ml), and 0.05N sodium hydroxide solution is added dropwise to the suspension, while stirring, until a clear solution forms (pH<10). Lyophilization of the filtered solution gives a yellow amorphous solid (87.5 mg, 71%); TLC [ethanol]: $R_f$=0.10; $[\alpha]^{20}$=+24.6° (c=0.11/$H_2O$).

EXAMPLE 5.20

N-{N$^{\alpha}$-[O-(3-O-Carbamoylmethyl-β-D-galactopyranosyl)-4-hydroxy-phenylamino-thiocarbonyl]-N$^{\epsilon}$-[O-(3-O-carboxymethyl-β-D-galactopyranosyl)-4-hydroxy-phenylamino-thiocarbonyl]-lysyl-D-alanyl}-batracyline, sodium salt Carbohydrate 1.44 (36.1 mg, 0.11 mmol) is reacted with peptide conjugate 3.33 (84.2 mg, 0.1 mmol) as described in Example 3.31.a. After concentration in vacuo, methanol/methylene chloride 1:1 (20 ml) is added to the residue and the product is precipitated by addition of diethyl ether. The residue is suspended in water (10 ml), and 0.05N sodium hydroxide solution is added dropwise to the suspension, while stirring, until a clear solution forms (pH<10). Lyophilization of the filtered solution gives a yellow amorphous solid (78.6 mg, 65%); TLC [ethanol]: $R_f$=0.11; $[\alpha]^{20}$=−44.0° (c=0.13/$H_2O$).

EXAMPLE 5.21

N-{N$^{\alpha}$-[O-(3,4-Di-O-methyl-β-D-galactopyranosyl)-4-hydroxy-phenylamino-thiocarbonyl]-N$^{\epsilon}$-[O-(3-O-carbamoylmethyl-β-D-galactopyranosyl)-4-hydroxy-phenylamino-thiocarbonyl]-lysyl-D-alanyl}-batracyline Carbohydrate 1.31 (39.5 mg, 0.11 mmol) is reacted with peptide conjugate 3.34 (81.9 mg, 0.1 mmol) as described in Example 3.31.a. After concentration in vacuo and flash chromatography [ethanol→ethanol/methanol 2:1], yellow crystals (17.4 mg, 15%) are obtained; TLC [ethanol]: $R_f$=0.20; melting point >290° C. (decomposition).

EXAMPLE 5.22

N-{N$^{\alpha}$-[O-(3-O-Methoxycarbonylmethyl-β-D-galactopyranosyl)-4-hydroxy-phenylamino-thiocarbonyl]-N$^{\epsilon}$-[O-(3-O-carbamoylmethyl-β-D-galactopyranosyl)-4-hydroxy-phenylamino-thiocarbonyl]-lysyl-D-alanyl}-batracyline Carbohydrate 1.42 (37.7 mg, 0.11 mmol) is reacted with peptide conjugate 3.34 (81.9 mg, 0.1 mmol) as described in Example 3.31.a. After concentration in vacuo and dissolving in methanol/methylene chloride 1:1, the product is precipitated by addition of diethyl ether. Yellow crystals (72 mg, 60%) are obtained; TLC [ethanol]: $R_f$=0.21; melting point 222° C. (decomposition).

EXAMPLE 5.23

N-{N$^{\alpha}$-[O-(3-O-Carboxymethyl-β-D-galactopyranosyl)-4-hydroxy-phenylamino-thiocarbonyl]-N$^{\epsilon}$-[O-(3-O-carbamoylmethyl-β-D-galactopyranosyl)-4-hydroxy-phenylamino-thiocarbonyl]-lysyl-D-alanyl}-batracyline, sodium salt Carbohydrate 1.43 (38.6 mg, 0.11 mmol) is reacted with peptide conjugate 3.34 (81.9 mg, 0.1 mmol) as described in Example 3.31.a. After concentration in vacuo, and dissolving in methanol/methylene chloride 1:1, the product is precipitated by addition of diethyl ether. The residue is suspended in water (10 ml), and 0.05N sodium hydroxide solution is added dropwise to the suspension, while stirring, until a clear solution forms (pH<10). Lyophilization of the filtered solution gives a yellow amorphous solid (78.2 mg, 65%); TLC [ethanol]: $R_f$=0.07; $[\alpha]^{20}$=+33.0° (c=0.1/$H_2O$).

EXAMPLES 6.1–6.89

General Formula

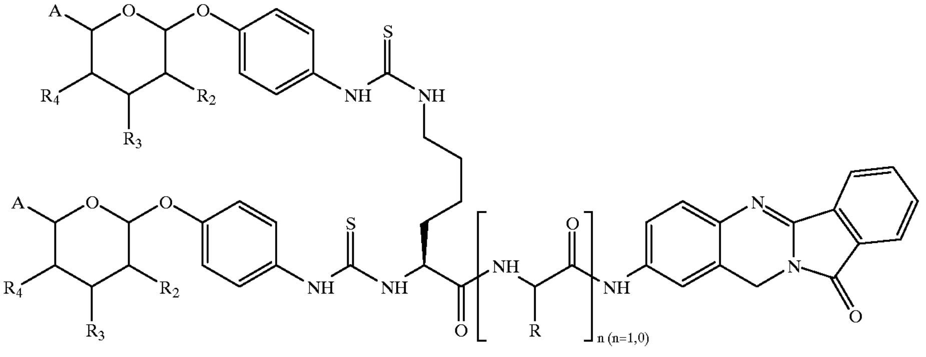

EXAMPLE 6.1

N-{N$^{\alpha}$,N$^{\epsilon}$-Bis-[O-(2-O-methyl-β-L-fucosyl)-4-hydroxy-phenylamino-thiocarbonyl]-lysyl-D-alanyl}-batracyline Thiophosgene (30 μl, 0.4 mmol) is added to a solution of compound 1.1 (50 mg, 0.19 ml) in dioxane/water 1:1 (10 ml), while stirring. After 10 minutes, the mixture is concentrated in vacuo and the residue is dried under an oil pump vacuum for 1 hour. The isothiocyanate obtained is dissolved in absolute dimethylformamide (10 ml), and compound 2.13 (61 mg, 0.09 mmol) and ethyldiisopropylamine (0.5 ml) are added. The mixture is stirred at room temperature for 16 hours and then concentrated in vacuo and the residue is purified by flash chromatography [methylene chloride/methanol/ammonia (17%) 15:2:0.2]. The residue is precipitated from methanol with ether. 48 mg (50%) of the target product are obtained as yellow crystals.

The following glycoconjugates are prepared analogously to Example 6.1 from the peptide conjugate in Example 2.13 or the L-alanyl isomer (Example 2.2):

EXAMPLE 6.2

N-{N$^{\alpha}$,N$^{\epsilon}$-Bis-[O-(3-O-methyl-β-L-fucosyl)-4-hydroxy-phenylamino-thiocarbonyl]-lysyl-D-alanyl}-batracyline Educt:

100 mg (0.38 mmol) of carbohydrate from Example 1.2

Purification by flash chromatography [methylene chloride/methanol/ammonia (17%) 15:0.5:0.05; later 15:1:0.1 in the same system]; subsequent precipitation from methylene chloride/methanol/ether. Yield: 59%. Melting point 178° C. (decomposition) [TLC: acetonitrile/water 10:1 $R_f$=0.51].

EXAMPLE 6.3

N-{N$^{\alpha}$,N$^{\epsilon}$-Bis-[O-(4-O-methyl-β-L-fucosyl)-4-hydroxy-phenylamino-thiocarbonyl]-lysyl-D-alanyl}-batracyline Educt:

115 mg (0.44 mmol) of carbohydrate from Example 1.4

Purification by flash chromatography [methylene chloride/methanol/ammonia (17%) 15:2:0.2]; subsequent precipitation from methylene chloride/methanol (1:1)/ether. Yield: 58%. Melting point 176° C. (decomposition) [TLC: acetonitrile/water 10:1 $R_f$=0.52].

EXAMPLE 6.4

N-{N$^{\alpha}$,N$^{\epsilon}$-Bis-[O-(3-O-methyl-β-L-fucosyl)-4-hydroxy-phenylamino-thiocarbonyl]-lysyl-alanyl}-batracyline Educt:

115 mg (0.44 mmol) of carbohydrate from Example 1.2

Purification by precipitation from methylene chloride/methanol (1: 1)/ether. Yield: 93%. Melting point 192° C. (decomposition) [TLC: acetonitrile/water 10:1 $R_f$=0.46].

EXAMPLE 6.5

N-{N$^{\alpha}$,N$^{\epsilon}$-Bis-[O-(3-O-methyl-α-L-fucosyl)-4-hydroxy-phenylamino-thiocarbonyl]-lysyl-D-alanyl}-batracyline Educt:

100 mg (0.38 mmol) of carbohydrate from Example 1.3

Purification by flash chromatography [methylene chloride/methanol/ammonia (17%) 15:1:0.1]; precipitation from methylene chloride/methanol (1:1)/ether. Melting point: 178° C. (decomposition); FAB-MS: m/z=1071=M+1.

EXAMPLE 6.6

N-{N$^{\alpha}$,N$^{\epsilon}$-Bis-[O-(3-O-n-propyl-β-L-fucosyl)-4-hydroxy-phenylamino-thiocarbonyl]-lysyl-alanyl}-batracyline Educt:

38 mg (0.127 mmol) of carbohydrate from Example 1.5

Purification by flash chromatography [methylene chloride/methanol/ammonia (17%) 15:1:0.1]; precipitation from methylene chloride/methanol (1:1)/ether. Yield: 42%, melting point: 167–170° C. (decomposition), [TLC: methylene chloride/methanol/ammonia (17%) $R_f$=0.34].

EXAMPLE 6.7

N-{N$^{\alpha}$,N$^{\epsilon}$-Bis-[O-(3-O-n-propyl-β-L-fucosyl)-4-hydroxy-phenylamino-thiocarbonyl]lysyl-D-alanyl}-batracyline Educt:

40 mg (0.167 mmol) of carbohydrate from Example 1.6

Purification by flash chromatography [methylene chloride/methanol/ammonia (17%) 15:2:0.2]; precipitation from methanol/ether. Yield: 81% [TLC: acetonitrile/water 10:1 $R_f$=0.46].

EXAMPLE 6.8

N-{N$^{\alpha,N\epsilon}$-Bis-[O-(3,4-dideoxy-β-L-fucosyl)-4-hydroxy-phenylamino-thiocarbonyl]-lysyl-D-alanyl}-batracyline Educt:

41 mg (0.183 mmol) of carbohydrate from Example 1.7

Purification by flash chromatography [methylene chloride/methanol 95:5]; freeze drying from water/dioxane. Yield: 60% [TLC: methylene chloride/methanol 9:1 $R_f$=0.22].

EXAMPLE 6.9

N-{N$^{\alpha}$,N$^{\epsilon}$-Bis-[O-(3-hydroxyethyl-β-L-fucosyl)-4-hydroxy-phenylamino-thiocarbonyl]-lysyl-D-alanyl}-batracyline Educt:

75 mg (0.25 mmol) of carbohydrate from Example 1.12

Purification by flash chromatography [methylene chloride/methanol/ammonia (17%) 15:2:0.2; later in the same system 15:4:0.5]. Precipitation from methanol/ether. Yield: 66%; [TLC: acetonitrile/water 10:1 $R_f$=0.28].

EXAMPLE 6.10

N-{$N^\alpha$,$N^\epsilon$-Bis-[O-(2-hydroxyethyl-β-L-fucosyl)-4-hydroxy-phenylamino-thiocarbonyl]-lysyl-D-alanyl}-batracyline Educt:

50 mg (0.167 mmol) of carbohydrate from Example 1.19

Purification by flash chromatography [methylene chloride/methanol/ammonia (17%) 15:3:0.3]; precipitation from methanol/ether; freeze drying from water/dioxane. Yield: 72%; [TLC: acetonitrile/water/glacial acetic acid 5:1:0.2 $R_f$=0.39].

EXAMPLE 6.11

N-{$N^\alpha$,$N^\epsilon$-Bis-[O-(2-O-carboxymethyl-β-L-fucosyl)-4-hydroxy-phenylamino-thiocarbonyl]-lysyl-D-alanyl}-batracyline, di-sodium salt Educt:

50 mg (0.16 mmol) of carbohydrate from Example 1.13

Purification by flash chromatography [methylene chloride/methanol/ammonia (17%) 15:8:0.8; later in the same system 15:10:1]. Digest the residue with ether, subsequent freeze drying from water/dioxane. Conversion into the di-sodium salt with 2 equivalents of a 0.1N sodium hydroxide solution, subsequently freeze drying from water. Yield: 49% [TLC: acetonitrile/water/glacial acetic acid 5:1:0.5 $R_f$=0.38]. MS-FAB: $FAB^-$; m/z=1157=M−$2Na^+$+$H^+$.

EXAMPLE 6.12

N-{$N^\alpha$,$N^\epsilon$-Bis-[O-(3-O-carboxymethyl-β-L-fucosyl)-4-hydroxy-phenylamino-thiocarbonyl]-lysyl-D-alanyl}-batracyline, di-sodium salt Educt:

200 mg (0.64 mmol) of carbohydrate from Example 1.10

Purification by flash chromatography [methylene chloride/methanol/ammonia (17%) 15:4:0.5; later in the same system 15:8:0.8; and finally 15:10:1]. Digest the residue with ether, subsequently freeze drying from water/dioxane 1:1. Conversion into the di-sodium salt with 2 equivalents of a 0.1N sodium hydroxide solution, subsequently freeze drying from water. Yield: 59%; [TLC: methylene chloride/methanol/ammonia (17%) $R_f$=0.1].

EXAMPLE 6.13

N-[$N^\alpha$,$N^\epsilon$-Bis-[O-(3-O-carbamoylmethyl-β-L-fucosyl)-4-hydroxy-phenylamino-thiocarbonyl]-lysyl-D-alanyl}-batracyline Educt:

60 mg (0.19 mmol) of carbohydrate from Example 1.18

Purification by flash chromatography [methylene chloride/methanol/ammonia (17%) 15:3:0.3]. Precipitate the residue from methylene chloride/methanol (1:1) with ether, filter off with suction and subsequently freeze drying from water/dioxane 1:1. Yield: 36% [TLC: acetonitrile/water/glacial acetic acid 5:1:0.2 $R_f$=0.461. Melting point: 190° (decomposition).

EXAMPLE 6.14

N-{$N^\alpha$,$N^\epsilon$-Bis-[O-(β-L-fucosyl)-4-hydroxy-phenylamino-thiocarbonyl]-lysyl-D-alanyl}-batracyline Educt:

100 mg (0.39 mmol) of p-aminophenyl β-L-fucoside

Purification by flash chromatography [methylene chloride/methanol/ammonia (17%) 15:2:0.2; later in the same system 15:4:0.5]. Precipitate the residue from dimethylformamide with ether, filter off with suction. Yield: 48%; melting point: 195–198° C.

EXAMPLE 6.15

N-{$N^\alpha$,$N^\epsilon$-Bis-[O-(α-L-rhamnosyl)-4-hydroxy-phenylamino-thiocarbonyl]-lysyl-D-alanyl}-batracyline Educt:

158 mg (0.61 mmol) of carbohydrate from Example 1.21

Purification by flash chromatography [methylene chloride/methanol/ammonia (17%) 15:3:0.3; later in the same system 15:4:0.5]. Lyophilize the residue from water/dioxane. Yield: 87% [TLC: methylene chloride/methanol/ammonia (17%) 15:4:0.5 $R_f$=0.25].

EXAMPLE 6.16

N-{$N^\alpha$,$N^\epsilon$-Bis-[O-(3-O-carboxymethyl-α-L-rhamnosyl)-4-hydroxy-phenylamino-thiocarbonyl]-lysyl-D-alanyl}-batracyline, di-sodium salt Educt:

200 mg (0.64 mmol) of carbohydrate from Example 1.22

Purification by flash chromatography [methylene chloride/methanol/ammonia (17%) 15:4:0.5; later in the same system 15:8:0.8; and finally 15:10:1]. Digest the residue with ether, subsequently freeze drying from water/dioxane 1:1.

The following glycoconjugates which contain a completely deblocked lysine structural unit on the amino end are prepared analogously to Example 6.1 from various peptide conjugates of batracyline:

EXAMPLE 6.17

N-{$N^\alpha$,$N^\epsilon$-Bis-[O -(3-O-carboxymethyl-β-L-fucosyl)-4-hydroxy-phenylamino-thiocarbonyl]-lysyl-glycyl}-batracyline, di-sodium salt Educts:

32 mg (0.1 mmol) of carbohydrate from Example 1.10

32 mg (0.045 mmol) of N-[lysyl-glycyl]-batracyline, di-trifluoroacetate (Example 2.9)

Purification by flash chromatography [methylene chloride/methanol/ammonia (17%) 15:8:0.8; later in the same system 15:15:1.51. Precipitation from dimethylformamide/methanol (1:1) with ether, subsequent freeze drying from water/dioxane. Conversion into the di-sodium salt with 2 equivalents of a 0.1N sodium hydroxide solution, subsequently freeze drying from water. Yield: 25%; [TLC: methylene chloride/methanol/ammonia (17%) 15:8:0.8 $R_f$=0.19]. FAB-MS: m/z=1189=M+1.

EXAMPLE 6.18

N-{$N^\alpha$,$N^\epsilon$-Bis-[O-(3-O-methyl-β-L-fucosyl)-4-hydroxy-phenylamino-thiocarbonyl]-lysyl-glycyl}-batracyline Educts:

60 mg (0.22 mmol) of carbohydrate from Example 1.2

66 mg (0.1 mmol) of N-[lysyl-glycyl]-batracyline, di-trifluoroacetate (Example 2.9)

Purification by flash chromatography [methylene chloride/methanol/glacial acetic acid 90:10:1]; precipitation from methanol with ether, subsequently freeze drying from water/dioxane. Yield: 68% [TLC: methylene chloride/methanol/glacial acetic acid 80:20:2 $R_f$=0.62].

EXAMPLE 6.19

N-{$N^\alpha$,$N^\epsilon$-Bis-[O-(β-L-fucosyl)-4-hydroxy-phenylamino-thiocarbonyl]-lysyl-lysyl}-batracyline 6.19.a) N-{$N^{\alpha}$,$N^{\epsilon}$-Bis-[O-(β-L-fucosyl)-4-hydroxy-phenylamino-thiocarbonyl]-lysyl-$N^{\epsilon}$-(fluorenyl-9-methoxycarbonyl)-lysyl}-batracyline Educts:

297 mg (1 mmol) of p-aminophenyl β-L-fucoside 66 mg (0.1 mmol) of N-[lysyl-$N^{\epsilon}$-(fluorenyl-9-methoxycarbonyl)-lysyl]-batracyline, di-trifluoroacetate (Example 2.15)

206 μl of ethyldiisopropylamine

Purification by two precipitations from methanol/methylene chloride (1:1) with ether, washing of the filter residue with ether. Yield: 89% [TLC: methylene chloride/methanol/ammonia (17%) 15:4:0.5 $R_f$=0.31].

6.19) N-{$N^{\alpha}$,$N^{\epsilon}$-Bis-[O-(β-L-fucosyl)-4-hydroxy-phenylamino-thiocarbonyl]-lysyl-lysyl}-batracyline 515 mg (0.39 mmol) of the compound from Example 6.19.a are dissolved in 5 ml of dimethylformamide and 5 ml of piperidine and the solution is stirred at 20° C. for 30 minutes. The batch is concentrated and the residue is digested with ether. The mixture is filtered with suction and the filter residue is taken up in dimethylformamide. After precipitation with ether and rinsing off the filter residue, 335 mg (78%) of crystalline target product remain. FAB-MS: m/z=1100=M+1.

EXAMPLE 6.20

N-{$N^{\alpha}$,$N^{\epsilon}$-Bis-[O-(3-O-methyl-β-L-fucosyl)-4-hydroxy-phenylamino-thiocarbonyl]-lysyl-diaminopropionyl}-batracyline 6.20.a) N-{$N^{\alpha}$,$N^{\epsilon}$-Bis-1O-(3-O-methyl-β-L-fucosyl)-4-hydroxy-phenylamino-thiocarbonyl]-lysyl-$N^{\beta}$-(fluorenyl-9-methoxycarbonyl)-diaminopropionyl }-batracyline Synthesis analogous to Example 6.19:

Educts:

60 mg (0.22 mmol) of carbohydrate from Example 1.2

100 mg (0.1 1 mmol) of N-[lysyl-$N^{\beta}$-(fluorenyl-9-methoxycarbonyl)-diamino-propionyl]-batracyline, di-trifluoroacetate (Example 2.16)

76 μl of ethyldiisopropylamine

Purification by two precipitations from methanol with ether, washing of the filter residue with ether. Yield: 105 mg (73%).

6.20) N-{$N^{\alpha}$,$N^{\epsilon}$-Bis-[O-(3-O-methyl-β-L-fucosyl)-4-hydroxy-phenylamino-thiocarbonyl]-lysyl-diaminopropionyl}-batracyline 103 mg (0.079 mmol) of the compound from Example 6.20.a are deblocked with piperidine analogously to Example 6.19. Purification by flash chromatography (methylene chloride/methanol/ammonia (17%) 15:3:0.3; later in the same system 15:6:0.6). Freeze drying from water/dioxane. Yield: 21%; [TLC: acetonitrile/water/glacial acetic acid 5:1:0.2 $R_f$=0.32].

EXAMPLE 6.21

N-{$N^{\alpha}$,$N^{\epsilon}$-Bis-[O-(3-O-carboxymethyl-β-L-fucosyl)-4-hydroxy-phenylamino-thiocarbonyl]-lysyl-diaminopropionyl}-batracyline, di-sodium salt This compound was prepared analogously to Example 6.20 via 2 stages, starting from the carbohydrate from Example 1.10 and the peptide conjugate from Example 2.16. Chromatographic purification can be omitted since by-products can be removed by digestion with methanol and ether. The product is then converted into the di-sodium salt with 2 equivalents of a 0.1N sodium hydroxide solution. Yield: 66% over 2 stages. [TLC: acetonitrile/water/glacial acetic acid 10:3:1.5 $R_f$=0.3].

EXAMPLE 6.22

N-{$N^{\alpha}$,$N^{\epsilon}$-Bis-[O-(3-O-methyl-β-L-fucosyl)-4-hydroxy-phenylamino-thiocarbonyl]-lysyl-seryl}-batracyline Educt:

60 mg (0.22 mmol) of carbohydrate from Example 1.2

76 mg (0.11 mmol) of N-[lysyl-seryl]-batracyline, di-trifluoroacetate (Example 2.10)

Purification by flash chromatography [methylene chloride/methanol/ammonia (17%) 15:2:0.2]; precipitation from methylene chloride/methanol/ether. Yield: 26%. [TLC: acetonitrile/water 10:1 $R_f$=0.39].

EXAMPLE 6.23

N-{$N^{\alpha}$,$N^{\epsilon}$-Bis-[O-(3-O-methyl-β-L-fucosyl)-4-hydroxy-phenylamino-thiocarbonyl]-lysyl-D-seryl}-batracyline Educt:

60 mg (0.22 mmol) of carbohydrate from Example 1.2

69 mg (0.11 mmol) of N-[lysyl-D-seryl]-batracyline, di-hydrobromide (Example 2.11)

Purification by flash chromatography [methylene chloride/methanol/ammonia (17%) 15:2:0.2]; freeze drying from dioxane/water. Yield: 29%. [TLC: acetonitrile/water 10:1 $R_f$=0.36].

EXAMPLE 6.24

N-{$N^{\alpha}$,$N^{\epsilon}$-Bis-[O-(3-O-methyl-β-L-fucosyl)-4-hydroxy-phenylamino-thiocarbonyl]-lysyl}-batracyline Educt:

80 mg (0.3 mmol) of carbohydrate from Example 1.2

53 mg (0.14 mmol) of N-[lysyl]-batracyline (Example 2.17)

Purification by flash chromatography [methylene chloride/methanol/ammonia (17%) 15:1:0.1; later in the same system 15:2:0.2]; precipitation from methanol/ether. Yield: 26%. [TLC: methylene chloride/methanol/ammonia (17%) 15:2:0.2 $R_f$=0.22].

EXAMPLE 6.25

N-{$N^{\alpha}$,$N^{\epsilon}$-Bis-[O-(3-O-carboxymethyl-β-L-fucosyl)-4-hydroxy-phenylamino-thiocarbonyl]-lysyl}-batracyline Educt:

60 mg (0.19 mmol) of carbohydrate from Example 1.10

24 mg (0.063 mmol) of N-[lysyl]-batracyline (Example 2.17)

Purification by flash chromatography [methylene chloride/methanol/ammonia (17%) 15:2:0.2]; later in the same system 15:4:0.5; freeze drying from water. Yield: 26%. [TLC: acetonitrile/water/glacial acetic acid 5:1:0.2 $R_f$=0.25].

EXAMPLE 6.26

N-{$N^{\alpha}$,$N^{\epsilon}$-Bis-[O-(3,4-di-O-methyl-β-D-galactopyranosyl)-4-hydroxy-phenylamino-thiocarbonyl]-lysyl}-batracyline Thiophosgene (33.5 μl, 0.44 mmol) is added to a solution of compound 1.31 (79 mg, 0.22 mmol) in dioxane/water 1:1 (10 ml), while stirring. After 10 minutes, the mixture is concentrated in vacuo and the residue is dried under an oil pump vacuum for 1 hour. The isothiocyanate obtained is dissolved in absolute dimethylformamide (10 ml), and compound 2.17 (37.7 mg, 0.1 mmol) and ethyldiisopropylamine (0.5 ml) are added. The mixture is stirred at room temperature for 16 hours and then concentrated in vacuo and the residue is purified by flash chromatography [methylene chloride/methanol 30:1→20:1→10.1]. Yellow crystals (56.7 mg, 53%) are obtained; TLC [ethyl acetate/ethanol 2:1]: $R_f$=0.72; melting point=125° C. (decomposition).

EXAMPLE 6.27

N-{$N^{\alpha}$,$N^{\epsilon}$-Bis-[O-(3-O-methoxycarbonylmethyl-β-D-galactopyranosyl)-4-hydroxy-phenylamino-thiocarbonyl]-lysyl}-batracyline Compound 1.42 (75.5 mg, 0.22 mmol) is reacted with peptide conjugate 2.17 (37.7 mg, 0.1 mmol) as described in Example 6.26. Purification by flash chromatography [methylene chloride/methanol 30:1→20:1→10.1] gives yellow crystals (51.1 mg, 44%); TLC [ethanol]: $R_f$=0.80; melting point=176° C. (decomposition).

EXAMPLE 6.28

N-{$N^{\alpha}$,$N^{\epsilon}$-Bis-[O-(3-O-carboxymethyl-β-D-galactopyranosyl)-4-hydroxy-phenylamino-thiocarbonyl]-lysyl}-batracyline, di-sodium salt Compound 1.43 (77.3 mg, 0.22 mmol) is reacted with peptide conjugate 2.17 (37.7 mg, 0.1 mmol) as described in Example 6.26. Purification by reprecipitation from methanol/methylene chloride 1:1 with diethyl ether gives yellow crystals (53 mg, 47 %); TLC [methanol]; $R_f$=0.75; melting point=>260° C. (decomposition).

EXAMPLE 6.29

N-{$N^{\alpha}$,$N^{\epsilon}$-Bis-[O-(3-O-carbamoylmethyl-β-D-galactopyranosyl)-4-hydroxy-phenylamino-thiocarbonyl]-lysyl}-batracyline Compound 1.44 (72.2 mg, 0.22 mmol) is reacted with peptide conjugate 2.17 (37.7 mg, 0.1 mmol) as described in Example 6.26. Purification by reprecipitation from methanol/methylene chloride 1:1 with diethyl ether gives yellow crystals (55.6 mg, 48%); TLC [ethanol]: $R_f$=0.09; melting point=206° C. (decomposition).

EXAMPLE 6.30

N-{$N^{\alpha}$,$N^{\epsilon}$-Bis-[O-(3-O-methyl-β-D-galactopyranosyl)-4-hydroxy-phenylamino-thiocarbonyl]-lysyl-seryl}-batracyline Compound 1.25 (62.8 mg, 0.22 mmol) is reacted with peptide conjugate 2.10 (69.3 mg, 0.1 mmol) as described in Example 6.26. After concentration in vacuo, the residue is taken up in methylene chloride/methanol 1:1 (10 ml) and the product is precipitated by addition of diethyl ether (15 ml) and washed with a little ice-cold methanol. Yellow crystals (46 mg, 41%) are obtained; TLC [ethyl acetate/ethanol 2:11: $R_f$=0.12; melting point=190–191° C.

EXAMPLE 6.31

N-{$N^{\alpha}$,$N^{\epsilon}$-Bis-[O-(β-L-fucopyranosyl)-4-hydroxy-phenylamino-thiocarbonyl]-lysyl-seryl}-batracyline p-Aminophenyl β-L-fucopyranoside (56.2 mg, 0.22 mmol) is reacted with peptide conjugate 2.10 (69.3 mg, 0.1 mmol) as described in Example 6.26. Purification by flash chromatography [ethyl acetate→ethanol] and reprecipitation from methanol/methylene chloride 1:1 with diethyl ether give yellow crystals (73.8 mg, 70%); TLC [ethanol]: $R_f$=0.15; melting point=123° C.

EXAMPLE 6.32

N-{$N^{\alpha}$,$N^{\epsilon}$-Bis-[O-(3,4-di-O-methyl-β-D-galactopyranosyl)-4-hydroxy-phenylamino-thiocarbonyl]-lysyl-seryl}-batracyline Compound 1.31 (79 mg, 0.22 mmol) is reacted with peptide conjugate 2.10 (69.3 mg, 0.1 mmol) as described in Example 6.26. Purification by flash chromatography [ethyl acetate→ethyl acetate/ethanol 7:1] gives yellow crystals (43.8 mg, 38%); TLC [ethyl acetate/ethanol 2:1]: $R_f$=0.31; melting point=176° C.

EXAMPLE 6.33

N-{$N^{\alpha}$,$N^{\epsilon}$-Bis-[-(3-O-methoxycarbonylmethyl-β-D-galactopyranosyl)-4-hydroxy-phenylamino-thiocarbonyl]-lysyl-seryl}-batracyline Compound 1.42 (75.5 mg, 0.22 mmol) is reacted with peptide conjugate 2.10 (69.3 mg, 0.1 mmol) as described in Example 6.26. Purification by flash chromatography [ethyl acetate→ethyl acetate/ethanol 3:1] gives yellow crystals (46.2 mg, 37%); TLC [ethyl acetate/ethanol 2:1]: $R_f$=0.12; melting point=161° C.

EXAMPLE 6.34

N-{$N^{\alpha}$,$N^{\epsilon}$-Bis-[O-(3-O-carboxymethyl-β-D-galactopyranosyl)-4-hydroxy-phenylamino-thiocarbonyl]-lysyl-seryl}-batracyline, di-sodium salt Compound 1.43 (77.3 mg, 0.22 mmol) is reacted with peptide conjugate 2.10 (69.3 mg, 0.1 mmol) as described in Example 6.26 and the product is purified. Yellow crystals (39.2 mg, 31%) are obtained; TLC [methanol]: $R_f$=0.77; melting point=213–215° C. (decomposition).

EXAMPLE 6.35

N-{$N^{\alpha}$,$N^{\epsilon}$-Bis-[O-(3-O-carbamoylmethyl-β-D-galactopyranosyl)-4-hydroxy-phenylamino-thiocarbonyl]-lysyl-seryl}-batracyline Compound 1.44 (72.2 mg, 0.22 mmol) is reacted with peptide conjugate 2.10 (69.3 mg, 0.1 mmol) as described in Example 6.26. Purification by flash chromatography [ethyl acetate/ethanol 2:1] gives yellow crystals (66.1 mg, 53%); TLC [ethyl acetate/ethanol 2:1]: $R_f$=0.14; melting point=192° C. (decomposition).

EXAMPLE 6.36

N-{$N^{\alpha}$,$N^{\epsilon}$-Bis-[O-(3-O-methyl-α-D-mannopyranosyl)-4-hydroxy-phenylamino-thiocarbonyl]-lysyl-seryl}-batracyline Compound 1.40 (62.8 mg, 0.22 mmol) is reacted with peptide conjugate 2.10 (69.3 mg, 0.1 mmol) as described in Example 6.26 and the product is purified. Yellow crystals (48.9 mg, 44%) are obtained; TLC [ethyl acetate/ethanol 2:1]: $R_f$=0.10; melting point=204° C.

EXAMPLE 6.37

N-{$N^{\alpha}$,$N^{\epsilon}$-Bis-[O-(2,3-di-O-methyl-α-D-mannopyranosyl)-4-hydroxy-phenylamino-thiocarbonyl]-lysyl-seryl}-batracyline Compound 1.41 (66 mg, 0.22 mmol) is reacted with peptide conjugate 2.10 (69.3 mg, 0.1 mmol) as described in Example 6.26. Purification by flash chromatography [ethyl acetate→ethyl acetate/ethanol 7:1] gives yellow crystals (52 mg, 45%); TLC [ethyl acetate/ethanol 2:1]: $R_f$=0.28; melting point=164–165° C.

EXAMPLE 6.38

N-{$N^{\alpha}$,$N^{\epsilon}$-Bis-[O-(β-O-(β-D-galactopyranosyl)-β-D-glucopyranosyl)-4-hydroxy-phenylamino-thiocarbonyl]-lysyl-seryl}-batracyline Compound 1.56 (95.4 mg, 0.22 mmol) is reacted with peptide conjugate 2.10 (69.3 mg, 0.1 mmol) as described in Example 6.26. After concentration in vacuo, the product is washed thoroughly with hot methanol (50 ml). Yellow crystals (6.16 mg, 44%) are obtained; TLC [methanol]: $R_f$=0.32; melting point=222° C. (decomposition).

EXAMPLE 6.39

N-{$N^{\alpha}$,$N^{\epsilon}$-Bis-[O-(β-L-fucopyranosyl)-4-hydroxy-phenylamino-thiocarbonyl]-lysyl-D-seryl}-batracyline p-Aminophenyl β-L-fucopyranoside (56.2 mg, 0.22 mmol) is reacted with peptide conjugate 2.11 (62.6 mg, 0.1 mmol) as described in Example 6.26. Purification by flash chromatography [ethyl acetate→ethanol] and reprecipitation of the residue from methanol/methylene chloride 1:1 with diethyl ether give yellow crystals (50.9 mg, 48%); TLC [ethanol]: $R_f$=0.14; melting point=133° C.

EXAMPLE 6.40

N-{$N^{\alpha}$,$N^{\epsilon}$-Bis-[O-(3,4-di-O-methyl-β-D-galactopyranosyl)-4-hydroxy-phenylamino-thiocarbonyl]-lysyl-D-seryl}-batracyline Compound 1.31 (79 mg, 0.22 mmol) is reacted with peptide conjugate 2.11 (62.6 mg, 0.1 mmol) as described in Example 6.26. Purification by flash chromatography [ethyl acetate→ethyl acetate/ethanol 5:1] gives yellow crystals (53.8 mg, 47%); TLC [ethyl acetate/ethanol 2:1]: $R_f$=0.38; melting point=145–146° C.

EXAMPLE 6.41

N-{$N^\alpha$,$N^\epsilon$-Bis-[O-(3-O-methoxycarbonylmethyl-β-D-galactopyranosyl)-4-hydroxy-phenylamino-thiocarbonyl]-lysyl-D-seryl}-batracyline Compound 1.42 (75.5 mg, 0.22 mmol) is reacted with peptide conjugate 2.11 (62.6 mg, 0.1 mmol) as described in Example 6.26. Purification by flash chromatography [ethyl acetate→ethyl acetate/ethanol 3:1] gives yellow crystals (52.4 mg, 42%); TLC [ethyl acetate/ethanol 2:1]: $R_f$=0.12; melting point=168° C.

EXAMPLE 6.42

N-{$N^\alpha$,$N^\epsilon$-Bis-[O-(3-O-carboxymethyl-β-D-galactopyranosyl)-4-hydroxy-phenylamino-thiocarbonyl]-lysyl-D-seryl}-batracyline, di-sodium salt Compound 1.43 (77.3 mg, 0.22 mmol) is reacted with peptide conjugate 2.11 (62.6 mg, 0.1 mmol) as described in Example 6.26 and the product is purified. Yellow crystals (69.2 mg, 55%) are obtained; TLC [methanol]: $R_f$=0.71; melting point=214–216° C. (decomposition).

EXAMPLE 6.43

N-{$N^\alpha$,$N^\epsilon$-Bis-[O-(3-O-carbamoylmethyl-β-D-galactopyranosyl)-4-hydroxy-phenylamino-thiocarbonyl]-lysyl-D-seryl}-batracyline Compound 1.44 (72.2 mg, 0.22 mmol) is reacted with peptide conjugate 2.11 (62.6 mg, 0.1 mmol) as described in Example 6.26. Purification by flash chromatography [ethyl acetate/ethanol 2:1] gives yellow crystals (46.4 mg, 38%); TLC [ethyl acetate/ethanol 2:1]: $R_f$=0.10; melting point=173° C.

EXAMPLE 6.44

N-{$N^\alpha$,$N^\epsilon$-Bis-[O-(β-L-fucopyranosyl)-4-hydroxy-phenylamino-thiocarbonyl]-lysyl-D-asparagyl}-batracyline p-Aminophenyl β-L-fucopyranoside (56.2 mg, 0.22 mmol) is reacted with peptide conjugate 2.11 (72.1 mg, 0.1 mmol) as described in Example 6.26. Purification by reprecipitation from methanol/methylene chloride 1:1 with diethyl ether gives yellow crystals (69.4 mg, 64%); TLC [ethanol]: $R_f$=0.14; melting point=185–187° C.

EXAMPLE 6.45

N-{$N^\alpha$,$N^\epsilon$-Bis-[O-(3,4-di-O-methyl-β-D-galactopyranosyl)-4-hydroxy-phenylamino-thiocarbonyl]-lysyl-D-asparagyl}-batracyline Compound 1.31 (79 mg, 0.22 mmol) is reacted with peptide conjugate 2.7 (72.1 mg, 0.1 mmol) as described in Example 6.26. Purification by flash chromatography [ethyl acetate/acetic acid 200:1→ethyl acetate/ethanol 3:1] gives yellow crystals (99.5 mg, 85%); TLC [ethanol]: $R_f$=0.59; melting point=149° C. (decomposition).

EXAMPLE 6.46

N-{$N^\alpha$,$N^\epsilon$-Bis-[O-(3-O-carboxymethyl-β-D-galactopyranosyl)-4-hydroxy-phenylamino-thiocarbonyl]-lysyl-D-asparagyl}-batracyline, di-sodium salt Compound 1.43 (77.3 mg, 0.22 mmol) is reacted with peptide conjugate 2.7 (72.1 mg, 0.1 mmol) as described in Example 6.26. Purification by reprecipitation from methanol/methylene chloride 1:1 with diethyl ether gives yellow crystals (93.4 mg, 73%); melting point=220° C. (decomposition).

EXAMPLE 6.47

N-{$N^\alpha$,$N^\epsilon$-Bis-[O-(3-O-carbamoylmethyl-β-D-galactopyranosyl)-4-hydroxy-phenylamino-thiocarbonyl]-lysyl-D-asparagyl}-batracyline Compound 1.44 (72.2 mg, 0.22 mmol) is reacted with peptide conjugate 2.7 (72.1 mg, 0.1 mmol) as described in Example 6.26. Purification by flash chromatography [ethyl acetate/ethanol/acetic acid 400:100:2] gives yellow crystals (69.7 mg, 57%); TLC [ethanol]: $R_f$=0.11; melting point=111° C.

EXAMPLE 6.48

N-{$N^\alpha$,$N^\epsilon$-Bis-[O-(β-L-fucopyranosyl)-4-hydroxy-phenylamino-thiocarbonyl]-lysyl-D-asparagyl}-batracyline, sodium salt Compound 6.44 (21.7 mg, 20 mmol) is suspended in water (10 ml), and 0.05N sodium hydroxide solution is added dropwise to the suspension, while stirring, until a clear solution forms (pH<10). Lyophilization of the filtered solution gives a yellow amorphous solid (20.6 mg, 93%).

EXAMPLE 6.49

N-{$N^\alpha$,$N^\epsilon$-Bis-[O-(3,4-di-O-methyl-β-D-galactopyranosyl)-4-hydroxy-phenylamino-thiocarbonyl]-lysyl-D-asparagyl}-batracyline, sodium salt Compound 6.45 (23.5 mg, 20 mmol) is reacted as described in Example 6.48 and the product is worked up. A yellow amorphous solid (23.9 mg, 100%) is obtained.

EXAMPLE 6.50

N-{$N^\alpha$,$N^\epsilon$-Bis-[O-(3-O-carboxymethyl-β-D-galactopyranosyl)-4-hydroxy-phenylamino-thiocarbonyl]-lysyl-D-asparagyl}-batracyline, tri-sodium salt Compound 6.46 (25.6 mg, 20 μmol) is dissolved in water (10 ml), and 0.05N sodium hydroxide solution is added dropwise to the solution, while stirring, until pH 8 is reached. Lyophilization of the filtered solution gives a yellow amorphous solid (24 mg, 92%).

EXAMPLE 6.51

N-{$N^\alpha$,$N^\epsilon$-Bis-[O-(3-O-carbamoylmethyl-β-D-galactopyranosyl)-4-hydroxy-phenylamino-thiocarbonyl]-lysyl-D-asparagyl}-batracyline, sodium salt Compound 6.47 (24.7 mg, 20 μmol) is reacted as described in Example 6.48 and the product is worked up. A yellow amorphous solid (23.0 mg, 92%) is obtained.

EXAMPLE 6.52

N-{$N^\alpha$,$N^\epsilon$-Bis-[O-(β-L-fucopyranosyl)-4-hydroxy-phenylamino-thiocarbonyl]-lysyl-D-glutamyl}-batracyline p-Aminophenyl β-L-fucopyranoside (56.2 mg, 0.22 mmol) is reacted with peptide conjugate 2.8 (66.8 mg, 0.1 mmol) as described in Example 6.26. Purification by flash chromatography [ethyl acetate/acetic acid 200:1→ethyl acetate/ethanol/acetic acid 10:1:0.1] gives yellow crystals (39.5 mg, 36%); TLC [ethanol]: $R_f$=0.09; melting point=138–139° C. (decomposition).

EXAMPLE 6.53

N-{$N^\alpha$,$N^\epsilon$-Bis-[O-(3-O-carboxymethyl-β-D-galactopyranosyl)-4-hydroxy-phenylamino-thiocarbonyl]-lysyl-D-glutamyl}-batracyline, di-sodium salt Compound 1.43 (77.3 mg, 0.22 mmol) is reacted with peptide conjugate 2.8 (66.8 mg, 0.1 mmol) as described in Example 6.26 and the product is purified. Yellow crystals (97.4 mg, 75%) are obtained; melting point=180° C. (decomposition).

EXAMPLE 6.54

N-{$N^{\alpha}$,$N^{\epsilon}$-Bis-O-(3-O-carboxymethyl-β-D-galatopyranosyl)-4-hydroxy-phenylamino-thiocarbonyl]-lysyl-D-glutamyl}-batracyline, tri-sodium salt Compound 6.53 (25.6 mg, 20 μmol) is reacted as described in Example 6.50 and the product is worked up. A yellow amorphous solid (24.3 mg, 92%) is obtained; $[\alpha]^{20}$=+20.0° (c=0.26/$H_2O$).

EXAMPLE 6.55

N-$N^{\alpha}$,$N^{\epsilon}$-Bis-[O-(β-L-fucopyranosyl)-4-hydroxy-phenylamino-thiocarbonyl]-lysyl-glycyl}-batracyline p-Aminophenyl β-L-fucopyranoside is reacted with peptide conjugate 2.9 (66.2 mg, 0.1 mmol) as described in Example 6.26. Purification by flash chromatography [ethyl acetate→ethanol] gives yellow crystals (62.2 mg, 60%); TLC [ethanol]: $R_f$=0.12; melting point=176° C.

EXAMPLE 6.56

N-{$N^{\alpha}$,$N^{\epsilon}$-Bis-[O-(3-O-methyl-p-D-galactopyranosyl)-4-hydroxy-phenylamino-thiocarbonyl]-lysyl-glycyl}-batracyline Compound 1.25 (62.8 mg, 0.22 mmol) is reacted with peptide conjugate 2.9 (66.2 mg, 0.1 mmol) as described in Example 6.26. Purification by flash chromatography [ethyl acetate/ethanol 10:1→2:1] gives yellow crystals (56.2 mg, 52%); TLC [ethyl acetate/ethanol 2:1]: $R_f$=0.22; melting point=197° C.

EXAMPLE 6.57

N-{$N^{\alpha}$,$N^{\epsilon}$-Bis-[O-(3,4-di-O-methyl-β-D-galactopyranosyl)-4-hydroxy-phenylamino-thiocarbonyl]-lysyl-glycyl}-batracyline Compound 1.31 (79 mg, 0.22 mmol) is reacted with peptide conjugate 2.9 (66.2 mg, 0.1 mmol) as described in Example 6.26. Purification by flash chromatography [ethyl acetate/ethanol 10:1→3:1] gives yellow crystals (26.2 mg, 23%); TLC [ethyl acetate/ethanol 2:1]: $R_f$=0.39; melting point=209° C.

EXAMPLE 6.58

N-{$N^{\alpha}$,$N^{\epsilon}$-Bis-[O-(3-O-methoxycarbonylmethyl-β-D-galactopyranosyl)-4-hydroxy-phenylamino-thiocarbonyl]-lysyl-glycyl}-batracyline Compound 1.42 (75.5 mg, 0.22 mmol) is reacted with peptide conjugate 2.9 (66.2 mg, 0.1 mmol) as described in Example 6.26. Purification by flash chromatography [ethyl acetate/ethanol→10:1] gives yellow crystals (22 mg, 18%); TLC [ethyl acetate/ethanol 2:1]: $R_f$=0.06; melting point=194–195° C. (decomposition).

EXAMPLE 6.59

N-{$N^{\alpha}$,$N^{\epsilon}$-Bis-[O-(3-O-carboxymethyl-β-D-galactopyranosyl)-4-hydroxy-phenylamino-thiocarbonyl]-lysyl-glycyl}-batracyline, di-sodium salt Compound 1.43 (77.3 mg, 0.22 mmol) is reacted with peptide conjugate 2.9 (66.2 mg, 0.1 mmol) as described in Example 6.26. After concentration in vacuo, the product is washed thoroughly with methanol, methylene chloride and diethyl ether. Yellow crystals (86.8 mg, 71%) are obtained; melting point=230–232° C. (decomposition).

EXAMPLE 6.60

N-{$N^{\alpha}$,$N^{\epsilon}$-Bis-10-(3-O-carbamoylmethyl-β-D-galactopyranosyl)-4-hydroxy-phenylamino-thiocarbonyl]-lysyl-glycyl}-batracyline Compound 1.44 (72.2 mg, 0.22 mmol) is reacted with peptide conjugate 2.9 (66.2 mg, 0.1 mmol) as described in Example 6.26. After concentration in vacuo, and washing with methanol, methylene chloride and diethyl ether, yellow crystals (40.9 mg, 35%) are obtained; TLC [ethyl acetate/ethanol 2:1]: $R_f$=0.05; melting point=214–216° C. (decomposition).

EXAMPLE 6.61

N-{$N^{\alpha}$,$N^{\epsilon}$-Bis-[O-(3-O-methyl-ϵ-D-mannopyranosyl)-4-hydroxy-phenylamino-thiocarbonyl]-lysyl-glycyl}-batracyline Compound 1.40 (62.8 mg, 0.22 mmol) is reacted with peptide conjugate 2.9 (66.2 mg, 0.1 mmol) as described in Example 6.26. Purification by flash chromatography [ethyl acetate/ethane 10:1→2:1] gives yellow crystals (72.2 mg, 66%); TLC [ethyl acetate/ethanol 2:1]: $R_f$=0.18; melting point=175° C.

EXAMPLE 6.62

N-{$N^{\alpha}$,$N^{\epsilon}$-Bis-[O-(2,3-di-O-methyl-α-D-mannopyranosyl)-4-hydroxy-phenylamino-thiocarbonyl]-lysyl-glycyl}-batracyline Compound 1.41 (66 mg, 0.22 mmol) is reacted with peptide conjugate 2.9 (66.2 mg, 0.1 mmol) as described in Example 6.26. Purification by flash chromatography [ethyl acetate/ethanol 10:1→3:1] gives yellow crystals (66.6 mg, 60%); TLC [ethyl acetate/ethanol 2:1]: $R_f$=0.41; melting point=173° C.

EXAMPLE 6.63

N-{$N^{\alpha}$,$N^{\epsilon}$-Bis-[-(β-L-fucopyranosyl)-4-hydroxy-phenylamino-thiocarbonyl]-lysyl-D-threonyl}-batracyline p-Aminophenyl β-L-fucopyranoside (56.2 mg, 0.22 mmol) is reacted with peptide conjugate 2.12 (64 mg, 0.1 mmol) as described in Example 6.26. Purification by flash chromatography [ethyl acetate→ethanol] and reprecipitation of the product from methanol/methylene chloride 1:1 with diethyl ether give yellow crystals (30.5 mg, 28%); TLC [ethanol]: $R_f$=0.10; melting point=172° C.

EXAMPLE 6.64

N-{$N^{\alpha}$,$N^{\epsilon}$-Bis-[O-(β-D-galactopyranosyl)-4-hydroxy-phenylamino-thiocarbonyl]-lysyl-D-alanyl}-batracyline Compound 1.23 (59.7 mg, 0.22 mmol) is reacted with peptide conjugate 2.13 (67.7 mg, 0.1 mmol) as described in Example 6.26. Purification by flash chromatography [methylene chloride/methanol 10:1→1:1] gives yellow crystals (68.3 mg, 64%); TLC [methylene chloride/methanol 1:1]: $R_f$=0.49; melting point=222–224° C. (decomposition).

EXAMPLE 6.65

N-{$N^{\alpha}$,$N^{\epsilon}$-Bis-[O-(2-O-methyl-β-D-galactopyranosyl)-4-hydroxy-phenylamino-thiocarbonyl]-lysyl-D-alanyl}-batracyline Compound 1.24 (62.8 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (69.6 mg, 63%); TLC [ethanol]: $R_f$=0.24; melting point=208° C. (decomposition).

EXAMPLE 6.66

N-{$N^{\alpha}$,$N^{\epsilon}$-Bis-[O-3-O-methyl-β-D-galactopyranosyl)-4hydroxy-phenylamino-thiocarbonyl]-lysyl-D-alanyl}-batracyline Compound 1.25 (62.8 mg, 0.22 mmol) is reacted with peptide conjugate 2.13 (67.7 mg, 0.1 mmol) as described in Example 6.26. Purification by flash chromatography [methylene chloride/methanol 15:1→10:1→5:1] gives yellow crystals (94.3 mg, 85%); TLC [methylene chloride/methanol 5:1]: $R_f$=0.16; melting point=212° C. (decomposition).

EXAMPLE 6.67

N-{$N^\alpha$,$N^\epsilon$-Bis-[O-(4-O-methyl-β-D-galactopyranosyl)-4-hydroxy-phenylamino-thiocarbonyl]-lysyl-D-alanyl}-batracyline Compound 1.26 (62.8 mg, 0.22 mmol) is reacted with peptide conjugate 2.13 (67.7 mg, 0.1 mmol) as described in Example 6.26. Purification by flash chromatography [methylene chloride/methanol 15:1→10:1→5:1] gives yellow crystals (52.6 mg, 48%); TLC [methylene chloride/methanol]: $R_f$=0.88; melting point=192° C. (decomposition).

EXAMPLE 6.68

N-{$N^\alpha$,$N^\epsilon$-Bis-[O-(6-O-methyl-β-D-galactopyranosyl)-4hydroxy-phenylamino-thiocarbonyl]-lysyl-D-alanyl}-batracyline Compound 1.27 (62.8 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (96.7 mg, 88%); TLC [methylene chloride/methanol 5:1]: $R_f$=0.04; melting point=210° C. (decomposition).

EXAMPLE 6.69

N-{$N^\alpha$,$N^\epsilon$-Bis-[O-(2,3-di-O-methyl-β-D-galactopyranosyl)-4-hydroxy-phenylamino-thiocarbonyl]-lysyl-D-alanyl}-batracyline Compound 1.28 (65.9 mg, 0.22 mmol) is reacted with peptide conjugate 2.13 (67.7 mg, 0.1 mmol) as described in Example 6.26. Purification by flash chromatography [methylene chloride/methanol 20:1] gives yellow crystals (57.4 mg, 51%); TLC [methylene chloride/methanol 5:1]: $R_f$=0.40; melting point=148° C. (decomposition).

EXAMPLE 6.70

N-{$N^\alpha$,$N^\epsilon$-Bis-[O-(2,4-di-O-methyl-β-D-galactopyranosyl)-4-hydroxy-phenylamino-thiocarbonyl]-lysyl-D-alanyl}-batracyline Compound 1.29 (65.9 mg, 0.22 mmol) is reacted with peptide conjugate 2.13 (67.7 mg, 0.1 mmol) as described in Example 6.26. Purification by flash chromatography [methylene chloride/methanol 20:1→15:1→10:1] gives yellow crystals (74.2 mg, 65%); TLC [methylene chloride/methanol 5:11: $R_f$=0.40; melting point=140° C. (decomposition).

EXAMPLE 6.71

N-{$N^\alpha$,$N^\epsilon$-Bis-[O-(2,6-di-O-methyl-β-D-galactopyranosyl)-4-hydroxy-phenylamino-thiocarbonyl]-lysyl-D-alanyl}-batracyline Compound 1.30 (65.9 mg, 0.22 mmol) is reacted with peptide conjugate 2.13 (67.7 mg, 0.1 mmol) as described in Example 6.26. Purification by flash chromatography [methylene chloride/methanol 20:1→15:1] gives yellow crystals (43.9 mg, 40%); TLC [methylene chloride/methanol 5:1]: $R_f$=0.43; melting point=229° C. (decomposition).

EXAMPLE 6.72

N-{$N^\alpha$,$N^\epsilon$-Bis-[O-(3,4-di-O-methyl-β-D-galactopyranosyl)-4-hydroxy-phenylamino-thiocarbonyl]-lysyl-D-alanyl}-batracyline Compound 1.31 (79 mg, 0.22 mmol) is reacted with peptide conjugate 2.13 (67.7 mg, 0.1 mmol) as described in Example 6.26. Purification by flash chromatography [methylene chloride/methanol 10:1] gives yellow crystals (66.2 mg, 59%); TLC [methylene chloride/methanol/ammonia (25%) 15:3:0.2]: $R_f$=0.39; melting point=184° C.

EXAMPLE 6.73

N-{$N^\alpha$,$N^\epsilon$-Bis-[O-(3,6di-O-methyl-D-galactopyranosyl)-4-hydroxy-phenylamino-thiocarbonyl]-lysyl-D-alanyl}-batracyline Compound 1.32 (65.9 mg, 0.22 mmol) is reacted with peptide conjugate 2.13 (67.7 mg, 0.1 mmol) as described in Example 6.26. Purification by flash chromatography [methylene chloride/methanol 15:1→10:13 gives yellow crystals (57.1 mg, 50%); TLC [methylene chloride/methanol 5:1): $R_f$=0.42; melting point=190° C. (decomposition).

EXAMPLE 6.74

N{$N^\alpha$,$N^\epsilon$-Bis-[O-(4,6-di-O-methyl-β-D-galactopyranosyl)-4-hydroxy-phenylamino-thiocarbonyl]-lysyl-D-alanyl}-batracyline Compound 1.33 (79 mg, 0.22 mmol) is reacted with peptide conjugate 2.13 (67.7 mg, 0.1 mmol) as described in Example 6.26. Purification by flash chromatography [methylene chloride/methanol 20:1→10:1→5:1] gives yellow crystals (47.0 mg, 42%); TLC [methylene chloride/methanol 5:1]: $R_f$=0.39; melting point=169° C.

EXAMPLE 6.75

N-{$N^\alpha$,$N^\epsilon$-Bis-[O-(2,3,4-tri-O-methyl-β-D-galactopyranosyl)-4-hydroxy-phenylamino-thiocarbonyl]-lysyl-D-alanyl}-batracyline Compound 1.34 (69 mg, 0.22 mmol) is reacted with peptide conjugate 2.13 (67.7 mg, 0.1 mmol) as described in Example 6.26. Purification by flash chromatography [methylene chloride/methanol 30:1] gives yellow crystals (83.8 mg, 72%); TLC [methylene chloride/methanol 10:1]: $R_f$=0.36; melting point=165° C. (decomposition).

EXAMPLE 6.76

N-{$N^\alpha$,$N^\epsilon$-Bis-[(O-(2,3,6-tri-O-methyl-β-D-galactopyranosyl)-4-hydroxy-phenylamino-thiocarbonyl]-lysyl-D-alanyl}-batracyline Compound 1.35 (69 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (105 mg, 91%); TLC (methylene chloride/methanol 5:1]: $R_f$=0.48; melting point=194° C. (decomposition).

EXAMPLE 6.77

N-{$N^\alpha$,$N^\epsilon$-Bis-[O-(2,4,6-tri-O-methyl-β-D-galactopyranosyl)-4-hydroxy-phenylamino-thiocarbonyl]-lysyl-D-alanyl}-batracyline Compound 1.36 (69 mg, 0.22 mmol) is reacted with peptide conjugate 2.13 (67.7 mg, 0.1 mmol) as described in Example 6.26. Purification by flash chromatography [methylene chloride/methanol 30:1→10:1] gives yellow crystals (67 mg, 58%); TLC (methylene chloride/methanol 5:1]: $R_f$=0.54; melting point=228° C. (decomposition).

EXAMPLE 6.78

N-{$N^\alpha$,$N^\epsilon$-Bis-[O-(3,4,6-tri-O-methyl-β-D-galactopyranosyl)-4-hydroxy-phenylamino-thiocarbonyl]-lysyl-D-alanyl}-batracyline Compound 1.37 (69 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (109.3 mg, 94%); TLC [methylene chloride/methanol 5:1]: $R_f$=0.52; melting point=180° C. (decomposition).

EXAMPLE 6.79

N-{$N^\alpha$,$N^\epsilon$-Bis-[O-(2,3,4,6-tetra-O-methyl-β-D-galactopyranosyl)-4-hydroxy-phenylamino-thiocarbonyl]-lysyl-D-alanyl}-batracyline Compound 1.38 (69 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (99.2 mg, 84%); TLC [methylene chloride/methanol 10:1]: $R_f$=0.73; melting point=188° C. (decomposition).

EXAMPLE 6.80

N-{$N^\alpha$,$N^\epsilon$-Bis-[O-(3-O-methoxycarbonylmethyl-β-D-galactopyranosyl)-4-hydroxy-phenylamino-thiocarbonyl]-lysyl-D-alanyl}-batracyline Compound 1.42 (75.5 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (22 mg, 18%); TLC [methylene chloride/methanol 5:1]: $R_f$=0.33; melting point=194–195° C. (decomposition).

EXAMPLE 6.81

N-{$N^\alpha$,$N^\epsilon$-Bis-[O-(3-O-carboxymethyl-β-D-galactopyranosyl)-4hydroxy-phenylamino-thiocarbonyl]-lysyl-D-alanyl}-batracyline, di-sodium salt Compound 1.43 (77.3 mg, 0.22 mmol) is reacted with peptide conjugate 2.13 (67.7 mg, 0.1 mmol) as described in Example 6.26 and the product is purified. Yellow crystals (99.7 mg, 81%) are obtained; TLC [methanol]: $R_f$=0.80; melting point=230° C. (decomposition).

EXAMPLE 6.82

N-{$N^\alpha$,$N^\epsilon$-Bis-[O-(3-O-carbamoylmethyl-β-D-galactopyranosyl)-4-hydroxy-phenylamino-thiocarbonyl]-lysyl-D-alanyl}-batracyline Compound 1.44 (72.2 mg, 0.22 mmol) is reacted with peptide conjugate 2.13 (67.7 mg, 0.1 mmol) as described in Example 6.26. Purification by flash chromatography [methylene chloride/methanol 7:1] gives yellow crystals (29.4 mg, 25%); TLC [methylene chloride/methanol 3:1]: $R_f$=0.23; melting point=201–202° C.

EXAMPLE 6.83

N-{$N^\alpha$,$N^\epsilon$-Bis-[O-(3,4-O-dideoxy-β-D-galactopyranosyl)-4-hydroxy-phenylamino-thiocarbonyl]-lysyl-D-alanyl}-batracyline Compound 1.52 (52.6 mg, 0.22 mmol) is reacted with peptide conjugate 2.13 (67.7 mg, 0.1 mmol) as described in Example 6.26. Purification by flash chromatography [methylene chloride/methanol 17:1] gives yellow crystals (38.8 mg, 37%); TLC [methylene chloride/methanol/ammonia (25%) 15:3:0.2]: $R_f$=0.40; melting point=175° C.

EXAMPLE 6.84

N-{$N^\alpha$,$N^\epsilon$-Bis-[O-(α-D-mannopyranosyl)-4-hydroxy-phenylamino-thiocarbonyl]-lysyl-D-alanyl}-batracyline Compound 1.39 (59.7 mg, 0.22 mmol) is reacted with peptide conjugate 2.13 (67.7 mg, 0.1 mmol) as described in Example 6.26. Purification by flash chromatography [methylene chloride/methanol 10:1→1:1] gives yellow crystals (52 mg, 48%); TLC [methylene chloride/methanol 1:1]: $R_f$=0.19; melting point 196° C.

EXAMPLE 6.85

N-{$N^\alpha$,$N^\epsilon$-Bis-[O-(3,4-di-O-methyl-β-D-galactopyranosyl)-4-hydroxy-phenylamino-thiocarbonyl]-lysyl-alanyl}-batracyline Compound 1.31 (79 mg, 0.22 mmol) is reacted with peptide conjugate 2.2 (67.7 mg, 0.1 mmol) as described in Example 6.26. Purification by flash chromatography [methylene chloride/methanol 10:1] gives yellow crystals (77.6 mg, 69%); TLC [methylene chloride/methanol/ammonia (25%) 15:3:0.2]: $R_f$=0.33; melting point=186° C.

EXAMPLE 6.86

N-{$N^\alpha$,$N^\epsilon$-Bis-[O-(4-O-β-D-galactopyranosyl)-β-D-glucopyranosyl)-4-hydroxy-phenylamino-thiocarbonyl]-lysyl-D-alanyl}-batracyline Compound 1.56 (95.4 mg, 0.22 mmol) is reacted with peptide conjugate 2.13 (67.7 mg, 0.1 mmol) as described in Example 6.26. After concentration in vacuo, the residue is washed thoroughly with hot methanol (50 ml). Yellow crystals (102.8 mg, 73%) are obtained; TLC [methanol]: $R_f$=0.27; melting point=225–226° C. (decomposition).

EXAMPLE 6.87

N-{$N^\alpha$,$N^\epsilon$-Bis-[O-(4-O-(3'-sulphato-β-D-galactopyranosyl)-D-glucopyranosyl)-4-hydroxy-phenylamino-thiocarbonyl]-lysyl-D-alanyl}-batracyline, disodium salt Compound 1.57 (117.8 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (152.8 mg, 95%); melting point=232° C. (decomposition).

EXAMPLE 6.88

N-{$N^\alpha$,$N^\epsilon$-Bis-[O-(4-O-(3'-O-methyl-β-D-galactopyranosyl)-β-D-glucopyranosyl)-4-hydroxy-phenylamino-thiocarbonyl]-lysyl-D-alanyl}-batracyline Compound 1.58 (98.4 mg, 0.22 mmol) is reacted with peptide conjugate 2.13 (67.7 mg, 0.1 mmol) as described in Example 6.26. Purification by reprecipitation from methanol/methylene chloride 1:1 with diethyl ether gives yellow crystals (118.2 mg, 83%); TLC [methylene chloride/methanol 1:1]: $R_f$=0.58; melting point=221° C. (decomposition).

EXAMPLE 6.89

N-{$N^\alpha$,$N^\epsilon$-Bis-[O-(2-O-methyl-4-O-(3'-O-methyl-β-D-galactopyranosyl)-β-D-glucopyranosyl)-4-hydroxy-phenylamino-thiocarbonyl]-lysyl-D-alanyl}-batracyline Compound 1.59 (101.5 mg, 0.22 mmol) is reacted with peptide conjugate 2.13 (67.7 mg, 0.1 mmol) as described in Example 6.26. Purification by flash chromatography [methylene chloride/methanol 15:1→10:1→5:1] gives yellow crystals (101.3 mg, 70%); TLC [methylene chloride/methanol 2:1]: $R_f$=0.58; melting point=233° C. (decomposition).

EXAMPLES 7.1–7.13

General Formula

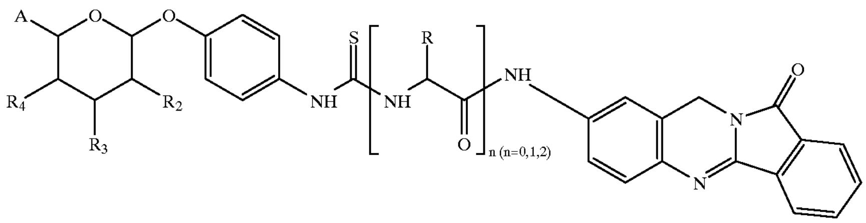

The following glycoconjugates are prepared analogously to Example 4.1.a) starting from other amino acid or peptide conjugates of batracyline or from batracyline:

EXAMPLE 7.1

N-{N-(O-(3-O-Methyl-β-L-fucosyl)-4-hydroxy-phenylamino-thiocarbonyl]-D-alanyl}-batracyline Educts:

carbohydrate from Example 1.2, amino acid conjugate from Example 2.3

Purification by flash chromatography (methylene chloride/methanol/ammonia (17%) 15:1:0.1). Freeze drying from dioxane/water. Yield: 42% [TLC: methylene chloride/methanol/ammonia (17%) 15:2:0.2): $R_f$=0.31].

EXAMPLE 7.2

N-{N-[O-(3-O-Carboxymethyl-β-L-fucosyl)-4-hydroxy-phenylamino-thiocarbonyl]-D-alanyl}-batracyline, sodium salt Educts:

carbohydrate from Example 1.10, amino acid conjugate from Example 2.3

Purification by flash chromatography (methylene chloride/methanol/ammonia (17%) 15:3:0.3). Freeze drying from dioxane/water and subsequent conversion into the sodium salt with 0.1N sodium hydroxide solution. Yield: 43% [TLC: methylene chloride/methanol/ammonia (17%) 15:4:0.5]: $R_f$=0.14].

EXAMPLE 7.3

N-{N-[O-(β-L-Fucosyl)-4-hydroxy-phenylamino-thiocarbonyl]-seryl-D-alanyl]-batracyline Educts:

p-aminophenyl β-L-fucoside, amino acid conjugate from Example 2.18

Purification by flash chromatography (methylene chloride/methanol/ammonia (17%) 15:3:0.3). Freeze drying from dioxane/water. Yield: 93% [TLC: methylene chloride/methanol/ammonia (17%) 15:3:0.31: $R_f$=0.28] FAB-MS: m/z=705=M+1.

EXAMPLE 7.4

N-{N-[O-(β-Fucosyl)-4-hydroxy-phenylamino-thiocarbonyl]-D-alanyl-D-alanyl}-batracyline Educts:

p-aminophenyl β-L-fucoside, amino acid conjugate from Example 2.19

Purification by digestion with methanol and precipitation from methanol/methylene chloride with ether. Yield: 65% [TLC: acetonitrile/water/glacial acetic acid 5:1:0.2 $R_f$=0.78].

EXAMPLE 7.5

N-{N-[O-(β-L-Fucosyl)-4-hydroxy-phenylamino-thiocarbonyl]-glutamyl-D-alanyl}-batracyline Educts:

p-aminophenyl β-L-fucoside, amino acid conjugate from Example 2.20

Purification by flash chromatography (methylene chloride/methanol/ammonia (17%) 15:4:0.4; later in the same system 15:6:0.6). Freeze drying from dioxane/water. Yield: 92% [TLC: methylene chloride/methanol/ammonia (17%) 15:8:0.8: $R_f$=0.55].

EXAMPLE 7.6

N-[O-(3-O-Carboxymethyl-β-L-fucosyl)-4-hydroxy-phenylamino-thio-carbonyl]-batracyline 250 mg (1 mmol) of batracyline are dissolved in 50 ml of dioxane and, after addition of 184 μl of thiophosgene, the mixture is stirred at 20° C. for 2 hours. It is concentrated and the residue is digested with ether and filtered. The filter residue is dried under a high vacuum for 16 hours and then taken up in 30 ml of dimethylformamide. 312 mg (1 mmol) of the carbohydrate from Example 1.10 and 500 μl of ethyldiisopropylamine are added and the mixture is treated with ultrasound for 4 hours. It is then concentrated and the residue is purified by flash chromatography (methylene chloride/methanol/ammonia (17%) 15:2:0.2; later in the same system 15:6:0.6). The relevant fractions are concentrated and lyophilized from dioxane/water. Yield: 363 mg (60%) [TLC: methylene chloride/methanol/ammonia (17%) 15:6:0.6 $R_f$=0.38].

EXAMPLE 7.7

N-[O-(3-O-Methyl-β-L-fucosyl)-4-hydroxy-phenylamino-thiocarbonyl]-batracyline

Preparation analogously to Example 7.6 starting from batracyline and carbohydrate from Example 1.2.

Purification by flash chromatography (methylene chloride/methanol/ammonia (17%) 15:1:0.1); yield: 58% [TLC: methylene chloride/methanol/ammonia (17%) 15:2:0.2 $R_f$=0.39]. FAB-MS: m/z=561=M+1.

EXAMPLE 7.8

N-{N-[O-(3,4-Di-O-methyl-β-D-galactopyranosyl)-4-hydroxy-phenylamino-thio-carbonyl]-D-alanyl}-batracyline Compound 1.31 (37.5 mg, 0.11 mmol) is reacted with peptide conjugate 2.3 (32 mg, 0.1 mmol) as described in Example 6.26. Purification by flash chromatography [methylene chloride/methanol 30:1] gives yellow crystals (49.3 mg, 75%); TLC [ethyl acetate/ethanol 2.1]: $R_f$=0.81; melting point=185° C. (decomposition).

EXAMPLE 7.9

N-{N-[O-(2,3,4-Tri-O-methyl-β-D-galactopyranosyl)-4-hydroxy-phenylamino-thio-carbonyl]-D-alanyl]-batracyline Compound 1.34 (34.5 mg, 0.11 mmol) is reacted with peptide conjugate 2.3 (32 mg, 0.1 mmol) as described in Example 6.26. Purification by flash chromatography [methylene chloride/methanol 40:1–15:1] gives yellow crystals (54.9 mg, 81%); TLC [methylene chloride/methanol 20:1]: $R_f$=0.15; melting point=190° C. (decomposition).

EXAMPLE 7.10

N-{N-[O-(3-O-Methoxycarbonylmethyl-β-D-galactopyranosyl)-4hydroxy-phenylamino-thiocarbonyl]-D-alanyl}-batracyline Compound 1.42 (37.8 mg, 0.11 mmol) is reacted with peptide conjugate 2.3 (32 mg, 0.1 mmol) as described in Example 6.26. Purification by flash chromatography [methylene chloride/methanol 20:1→10:1] gives yellow crystals (44.3 mg, 63%); TLC [ethanol]: $R_f$=0.85; melting point=195° C. (decomposition).

EXAMPLE 7.11

N-{N-[O-(3-O-Carboxymethyl-β-D-galactopyranosyl)-4-hydroxy-phenylamino-thiocarbonyl]-D-alanyl}-batracyline, sodium salt Compound 1.43 (38.6 mg, 0.11 mmol) is reacted with peptide conjugate 2.3 (32 mg, 0.1 mmol) as described in Example 6.26. Purification by reprecipitation from methanol/methylene chloride 1:1 with diethyl ether gives yellow crystals (63.8 mg, 89%); TLC [ethanol]: $R_f$=0.15; melting point=217° C. (decomposition).

EXAMPLE 7.12

N-{N-[O-(3-O-Carbamoylmethyl-β-D-galactopyranosyl)-4-hydroxy-phenylamino-thiocarbonyl]-D-alanyl}-batracyline Compound 1.44 (37.8 mg, 0.11 mmol) is reacted with peptide conjugate 2.3 (32 mg, 0.1 mmol) as described in Example 6.26. Purification by flash chromatography [methylene chloride/methanol 20:1→10:1→5:1] gives yellow crystals (20 mg, 29%); TLC [ethanol]; $R_f$=0.15; melting point=184° C. (decomposition).

EXAMPLE 7.13

N-(N-[O-(β-L-Fucopyranosyl)-4-hydroxy-phenylamino-thiocarbonyl]-D-alanyl}-batracyline p-Aminophenyl β-L-fucopyranoside (28.1 mg, 0.11 mmol) is reacted with peptide conjugate 2.3 (32 mg, 0.1 mmol) as described in Example 6.26. Purification by flash chromatography [ethyl acetate/petroleum ether 2:1→5:1] gives yellow crystals (49.8 mg, 81%); TLC [ethanol]: $R_f$=0.50; meting point –173° C.

EXAMPLES 8.1–8.12

General Formula

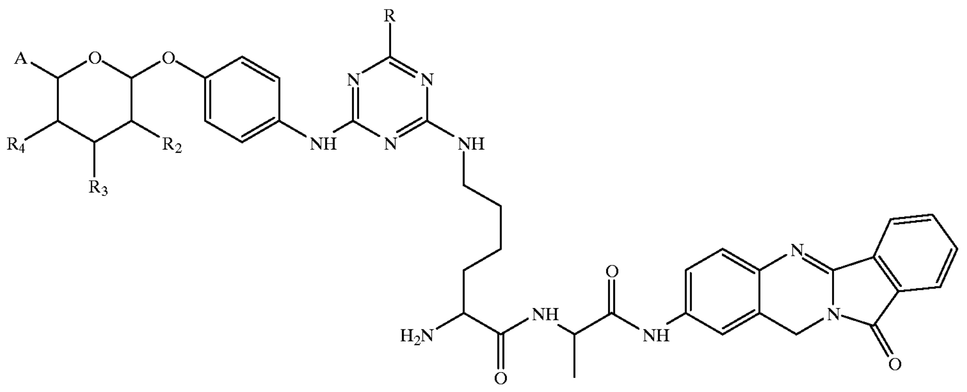

EXAMPLE 8.1

N-{$N^{\epsilon}$-[2-Chloro-4-[O-(3-O-methyl-β-L-fucosyl)-4-hydroxy-phenylamino]-triazin-6-yl]-lysyl-D-alanyl}-batracyline, trifluoroacetate 8.1.a) N-{$N^{\alpha}$-tert-Butoxycarbonyl]-$N^{\epsilon}$-[2-chloro-4-[0–3-O-methyl-β-L-fucosyl)-4-hydroxy-phenylamino]-triazin-6-yl]-lysyl-D-alanyl}-batracyline 265 mg (0.98 mmol) of p-aminophenyl 3-O-methyl-β-L-fucoside (Example 1.2) and 181 mg (0.98 mmol) of cyanuric chloride are taken up in 50 ml of dioxane/water 1:1 and the mixture is cooled to –5° C. and, after addition of 83 mg of sodium bicarbonate, stirred at this temperature for 15 minutes. 538 mg (0.98 mmol) of N-[$N^{\alpha}$-(tert-butoxycarbonyl)-lysyl-D-alanyl]-batracyline (Example 2.4), dissolved in 14 ml of dimethylformamide, and a further 83 mg of sodium bicarbonate are then added and the mixture is allowed to come to room temperature. After stirring at 20° C. for 16 hours, the mixture is concentrated and the residue is treated with water. The mixture is filtered with suction and the filter residue is dried under a high vacuum to give 890 mg (96%) of the target product. [TLC: methylene chloride/methanol 10:1 $R_f$=0.26].

8.1) N-{$N^{\epsilon}$-[2-Chloro-4-[O-(3-O-methyl-β-L-fucosyl)-4-hydroxy-phenylamino]-triazin-6-yl]-lysyl-D-alanyl}-batracyline, trifluoroacetate 100 mg (0.11 mmol) of the compound from ample 8.1.a are stirred in a mixture of 5 ml of anhydrous trifluoroacetic acid and 5 ml of methylene chloride at 0° C. for 30 minutes. The mixture is concentrated and the residue is purified by flash chromatography (methylene chloride/methanol/ammonia 17%) 15:1.5:0.15. Subsequent precipitation from methanol/ether leads to 41 mg (95%) of the target product [TLC: methylene chloride/methanol/ammonia (17%) 15:2:0.2 $R_f$=0.263 FAB-MS: m/z=829=M+1.

EXAMPLE 8.2

N-{$N^{\epsilon}$-[4-Hydroxyethylamino-2-[O-(3-O-methyl-β-L-fucosyl)-4-hydroxy-phenylamino]-triazin-6-yl]-lysyl-D-alanyl}-batracyline, trifluoroacetate 8.2.a) N-[$N^{\alpha}$-[tert-Butoxycarbonyl]-$N^{\epsilon}$-4-hydroxyethylamino-2-[O-(3-O-methyl-β-L-fucosyl)-4-hydroxy-phenylamino]-triazin-6-yl]-lysyl-D-alanyl]-batracyline 100 mg (0.11 mmol) of the compound from Example 8.1.a are dissolved in 3 ml of dioxane. 60 mg of potassium carbonate and 6.5 ml of a 0.1N solution of ethanolamine in dioxane are added and the mixture is stirred at 80° C. for 18 hours. It is then concentrated and the residue is stirred with water. The mixture is filtered and the filter residue is purified by flash chromatography (methylene chloride/methanol/ammonia (17%) 15:1:0.1). After concentration of the relevant fractions and drying under a high vacuum, 83 mg (80%) of the target compound are obtained [TLC: methylene chloride/methanol/ammonia (17%) 15:2:0.2 $R_f$=0.23].

8.2) N-{$N^\alpha$-[4-Hydroxyethylamino-2-10-(3-O-methyl-β-L-fucosyl)-4-hydroxy-phenylamino-triazin-6-yl]-lysyl-D-alanyl}-batracyline, trifluoroacetate 67 mg (0.07 mmol) of the compound from Example 8.2.a are deblocked analogously to Example 8.1. Purification is carried out by flash chromatography (methylene chloride/methanol/ammonia (17%) 15:2:0.2). Subsequent precipitation from methanol/ether leads to the target product in a 90% yield. FAB-MS: m/z=854=M+1.

The following glycoconjugates are prepared analogously to Example 8.1:

EXAMPLE 8.3

N-{$N^\alpha$-[2-Chloro-4-[-(2-O-methyl-β-L-fucosyl)-4hydroxy-phenylamino]-triazin-6-yl]-lysyl-D-alanyl}-batracyline, trifluoroacetate Educt:

carbohydrate from Example 1.1;

Yield: 76%; FAB-MS: m/z=829=M+1.

EXAMPLE 8.4

N-{$N^\epsilon$-[2-Chloro-4-O-(βL-fucosyl)-4-hydroxy-phenylamino]-triazin-6-yl]-lysyl-D-alanyl}-batracyline, trifluoroacetate Educt:

p-aminophenyl β-L-fucoside;

Yield: 36%; FAB-MS: n/z=815=M+1.

[TLC: methylene chloride/methanol/ammonia (17%) 15:4:0, $R_f$=0.44].

EXAMPLE 8.5

N-{$N^\epsilon$-[2-Chloro-4-[O-(3-deoxy-β-L-fucosyl)-4-hydroxy-phenylamino]-triazin-6-yl]-lysyl-D-alanyl}-batracyline, trifluoroacetate Educt:

carbohydrate from Example 1.6;

Yield: 56%; FAB-MS: m/z=799=M+1;

[TLC: acetonitrile/water/glacial acetic acid 15:1:0.2 $R_f$=0.54].

The following glycoconjugates are prepared analogously to Examples 8.1.a, 8.2.a and 8.2 from the batracyline-peptide conjugate in Example 2.4 or from the L-alanyl isomer which is to be prepared in a corresponding manner:

EXAMPLE 8.6

N-{$N^\epsilon$-[4-Hydroxyethylamino-2-[O-(2-O-methyl-β-L-fucosyl)-4-hydroxy-phenylamino]-triazin-6yl]-lysyl-D-allyl}-batracyline, trifluoroacetate Educt:

carbohydrate from Example 1.1;

Yield: 78%; FAB-MS: m/z=854=M+1;

[TLC: methylene chloride/methanol/ammonia (17%) 15:4:0.5 $R_f$=0.33].

EXAMPLE 8.7

N{$N^\epsilon$-[4-Hydroxyethylamino-2-[O-(deoxy-β-L-fucosyl)-4-hydroxy-phenylamino]-triazin-4-yl-lysyl-D-alanyl}-batracyline, trifluoroacetate Educt:

carbohydrate from Example 1.4;

Yield: 38%; [TLC: methylene chloride/methanol/ammonia (17%) 15:4:0.5 $R_f$=0.4].

EXAMPLE 8.8

N-{$N^\epsilon$-[4-Hydroxyethylamino-2-[O-(3-deoxy-β-L-fucosyl)-4-hydroxy-phenylamino]-triazin-6-yl]-lysyl-D-alanyl}-batracyline, trifluoroacetate Educt:

carbohydrate from Example 1.6;

Yield: 77%; FAB-MS: m/z=824=M+1;

[TLC: methylene chloride/methanol/ammonia (17%) 15:4:0.5 $R_f$=0.37].

EXAMPLE 8.9

N-{$N^\epsilon$-[4-Hydroxyethylamino-2-[O-(β-L-fucosyl)-4-hydroxy-phenylamino]-triazin-6-yl]-lysyl-D-alanyl}-batracyline, trifluoroacetate Educt:

p-aminophenyl β-L-fucoside;

Yield: 52%; FAB-MS: m/z=840=M+1;

[TLC: methylene chloride/methanol/ammonia (17%) 15:4:0.5 $R_f$=0.30].

EXAMPLE 8.10

N-{$N^\epsilon$-[4-Hydroxyethylamino-2-[O-(3-O-methyl-β-L-fucosyl)-4-hydroxy-phenylamino]-triazin-6-yl]-lysyl-D-alanyl}-batracyline, trifluoroacetate Educt:

carbohydrate from Example 1.2;

Yield: 88%;

[TLC: methylene chloride/methanol/ammonia (17%) 15:3:0.3 $R_f$=0.35].

EXAMPLE 8.11

N-{$N^\epsilon$-[4-Hydroxyethylamino-2-[O-(2-O-methyl-β-L-fucosyl)-4-hydroxy-phenylamino]-triazin-6-yl]-lysyl-alanyl}-batracyline, trifluoroacetate Educt:

carbohydrate from Example 1.1;

Yield: 58%;

[TLC: methylene chloride/methanol/ammonia (17%) 15:4:0.5 $R_f$=0.40].

EXAMPLES 8–12

N-{$N^\epsilon$-[4-Hydroxyethylamino-2-[O-(4-O-methyl-β-L-fucosyl)-4-hydroxy-phenylamino]-triazin-6-yl]-lysyl-alanyl}-batracyline, trifluoroacetate Educt:

carbohydrate from Example 1.4;

Yield: 66%;

FAB-MS: m/z=854=M+1;

[TLC: methylene chloride/methanol/ammonia (17%) 15:4:0.5 $R_f$=0.37].

EXAMPLE 9.1

N-[D-Alanyl]-quinolone-a, trifluoroacetate

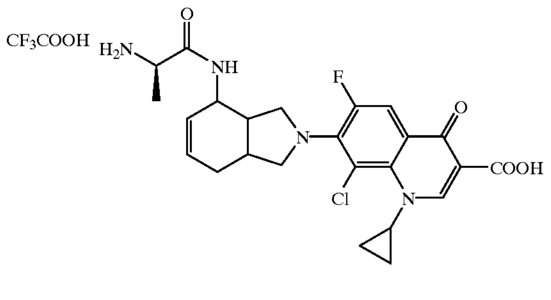

9.1.a) N-[N-(tert-Butoxycarbonyl)-D-alanyl}-quinolone-a

N-(tert-Butoxycarbonyl)-D-alanine (3.6 g, 19.2 mmol) and 2-isobutoxy-1-isobutoxycarbonyl-1,2-dihydro-quinoline (5.8 g, 19.2 mmol) are dissolved in 200 ml of dimethylformamide. After the mixture has been stirred at room temperature for 8 hours, quinolone-a (4 g, 9.6 mmol) and 3.3 ml of ethyldiisopropylamine are added and the batch is treated with ultrasound for 10 hours. It is concentrated, the residue is taken up in methylene chloride and the product is precipitated with ether. After filtration, washing with ether and drying under a high vacuum, 4.58 g (81%) of the target product, which is reacted without further purification, are obtained.

9.1) N-[D-Alanyl]-quinolone-a, trifluoroacetate 4.56 g (7.75 mmol) of the compound from Example 9.1.a are dissolved in 50 ml of methylene chloride and 50 ml of anhydrous trifluoroacetic acid at 0° C. and the solution is stirred at this temperature for 1 hour. It is concentrated, the residue is subsequently distilled with methylene chloride and the product is precipitated from methanol with ether. 4.07 g (87%) of the crystalline target product are obtained. [TLC: acetonitril/water/glacial acetic acid 5:1:0.2 $R_f$=0.34].

EXAMPLE 9.2

N-[Alanyl]-quinolone-a, trifluoroacetate

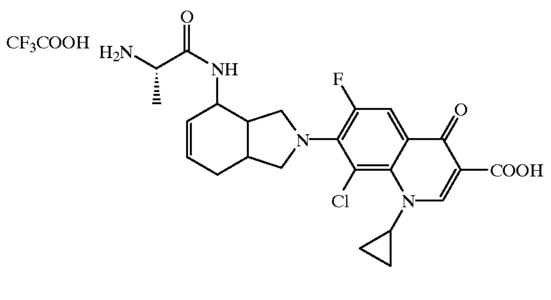

The synthesis proceeds in an identical manner to that of the isomer in Example 9.1.

EXAMPLE 9.3

N-[Lysyl-D-alanyl]-quinolone-a, di-trifluoroacetate

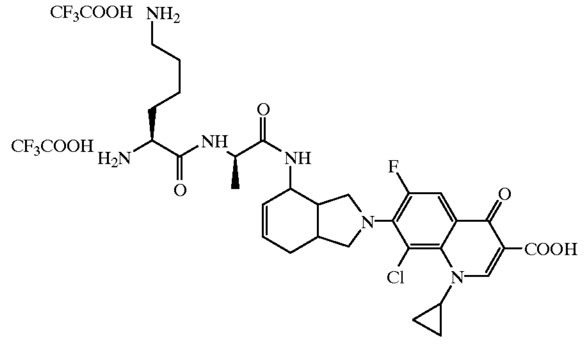

9.3.a) N-[$N^{\alpha}$,$N^{\epsilon}$-Bis-(tert-butoxycarbonyl)-lysyl-D-alanyl]-quinolone-a 341 mg (0.984 mmol) of $N^{\alpha}$,$N^{\epsilon}$-bis-(tert-butoxycarbonyl)-lysine are dissolved in 10 ml of dimethylformamide, and 200 mg (1.48 mmol) of N-hydroxybenzotriazole and 227 mg (1.18 mmol) of N'-(3-dimethylaminopropyl)-N-ethylcarbodiimide hydrochloride are added at 0° C. After the mixture has been stirred at 10° C. for 3 hours, 432 mg (0.82 mmol) of the compound from Example 9.1 are added and the mixture is stirred at 20° C. for a further 2 hours. It is concentrated and the residue is stirred three times with 50 ml of water. The residue is then taken up in methylene chloride and the mixture is dried over sodium sulphate. Precipitation with ether leads to 516 mg (78%) of the target product. [TLC: acetonitrile/water 10:1 $R_f$=0.55].

9.3) N-[Lysyl-D-alanyl]-quinolone-a, di-trifluoroacetate

Deblocking of 512 mg (0.63 mmol) of the compound from Example 9.3.a analogously to Example 9.1. Precipitation from ethyl acetate with ether. Yield: 479 mg (90%); [TLC: acetonitrile/water/glacial acetic acid 10:3:1.5 $R_f$=0.3].

EXAMPLE 9.4

N-[Lysyl-alanyl]-quinolone-a, di-trifluoroacetate

The synthesis proceeds in an identical manner to that of the isomer in Example 9.3.

EXAMPLE 9.5

N-[$N^{\alpha}$-(tert-Butoxycarbonyl)-lysyl-D-alanyl]-quinolone-a

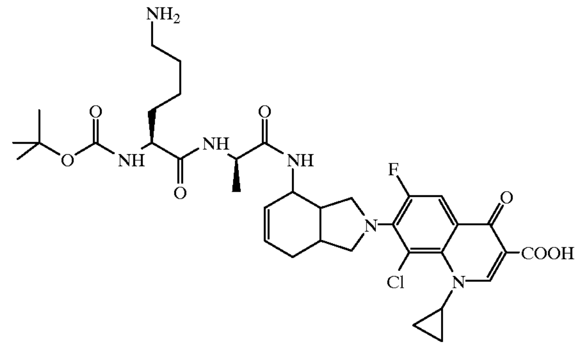

9.5.a) N-[$N^{\alpha}$-(tert--Butoxycarbonyl)-$N^{\epsilon}$-(fluorenyl-9-methoxycarbonyl)-lysyl-D-alanyl]-quinolone-a 1.57 g (3.36 mmol) of $N^{\alpha}$-(tert-butoxy-carbonyl)-$N^{\epsilon}$-(fluorenyl-9-methoxycarbonyl)-lysine are dissolved in 25 ml of dimethylformamide, and 600 mg (5.04 mmol) of N-hydroxysuccinimide and 820 mg (4.03 mmol) of N,N'-dicyclohexylcarbodiimide are added at 0° C. After 3 hours, the urea formed is filtered off, 1.5 g (2.86 mmol) of the compound from Example 9.1 are added to the filtrate and the mixture is stirred at room temperature for 16 hours. Residual urea is filtered off and the filtrate is purified by flash chromatography (methylene chloride/methanol 97.5:2.5; later in the same system 90:10]. The product is then precipitated from methylene chloride/methanol 1:1 with ether. Yield: 1.5 g (56%) [TLC: methylene chloride/methanol 9:1 $R_f$=0.47].

9.5) N-[$N^{\alpha}$-(tert-Butoxycarbonyl)-lysyl-D-alanyl]-quinolone-a

Splitting off of Fmoc from Example 9.5.a) with piperidine in dimethylformamide. Precipitation of the crude product from dimethylformamide with ether. Yield: 72% [TLC: acetonitrile/water/glacial acetic acid 5:1:0.2 $R_f$=0.43].

EXAMPLE 9.6

N-[$N^{\epsilon}$-(Fluorenyl-9-methoxycarbonyl)-lysyl-D-alanyl]-quinolone-a, trifluoroacetate

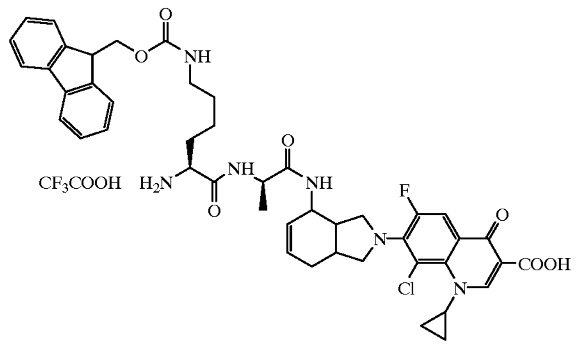

Splitting off of Boc from Example 9.5.a) analogously to Example 9.1. Precipitation of the crude product from methanol/ether. Yield: 80% [TLC: methylene chloride/methanol/ammonia (17%) 15:4:0.5 $R_f$=0.36].

EXAMPLE 9.7

N-[$N^{\alpha}$-(tert-Butoxycarbonyl)-lysyl-alanyl-quinolone-a

The synthesis proceeds in an identical manner to that of the isomer in Example 9.5.

EXAMPLE 9.8

N-[Lysyl]-quinolone-a, di-trifluoroacetate

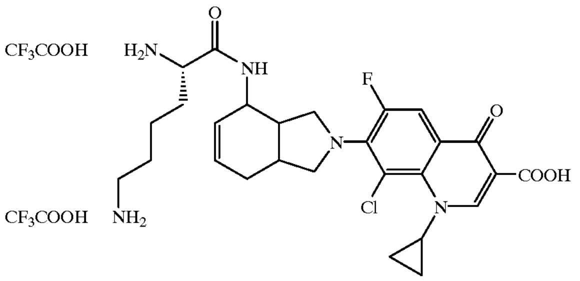

9.8.a) N-[$N^{\alpha}$,$N^{\epsilon}$-Bis-(tert-butoxycarbonyl)-lysyl]-quinolone-a 1317 mg (3.8 mmol) of $N^{\alpha}$,$N^{\epsilon}$-bis-(tert-butoxycarbonyl)-lysine are linked with quinolone-a in accordance with the instructions in Example 9.1.a. Purification is carried out by flash chromatography [methylene chloride/methanol/ammonia (17%) 15:1:0.1]. 1010 mg (71%) of the target product are obtained.

9.8) N-[Lysyl]-quinolone-a, di-trifluoroacetate 1005 mg (1.347 mmol) of the compound from Example 9.8.a are deblocked analogously to Example 9.1. After precipitation from methylene chloride/methanol 1:1 with ether, 966 mg (93%) of the crystalline target product are obtained. [TLC: acetonitrile/water/glacial acetic acid 10:5:3 $R_f$=0.33].

EXAMPLE 9.9

N-[D-Lysyl]-quinolone-a, di-trifluoroacetate

The synthesis proceeds in an identical manner to that of the isomer in Example 9.8.

EXAMPLE 9.10

N-[$N^{\alpha}$-(tert-Butoxycarbonyl-lysyl]-quinolone-a

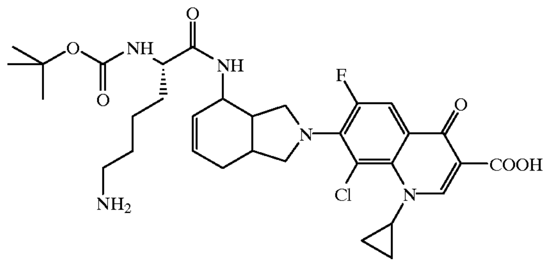

9.10.a) N-[$N^{\alpha}$-tert-Butoxycarbonyl)-$N^{\epsilon}$-(fluorenyl-9-methoxycarbonyl)-lysyl]-quinolone-a 1350 mg (2.88 mmol) of $N^{\alpha}$-(tert-butoxycarbonyl)-$N^{68}$-(fluorenyl-9-methoxycarbonyl)-lysine are linked with quinolone-a in accordance with the instructions in Example 9.8.a. Purification is carried out by flash chromatography [methylene chloride/methanol/ammonia (17%) 15:1:0.1; later in the same system 15:2:0.2]. 1025 mg (82%) of the target product are obtained.

9.10) N-[$N^{\alpha}$-(tert-Butoxycarbonyl)-lysyl]-quinolone-a

Splitting off of Fmoc from Example 9.10.a analogously to Example 9.5. Two precipitations of the crude product from methanol with ether. Yield: 86% [TLC: acetonitrile/water/glacial acetic acid 5:1:0.2 $R_f$=0.48].

EXAMPLE 9.11

N-[$N^{\epsilon}$-(Fluorenyl-9-methoxycarbonyl)-lysyl]-quinolone-a, trifluoroacetate

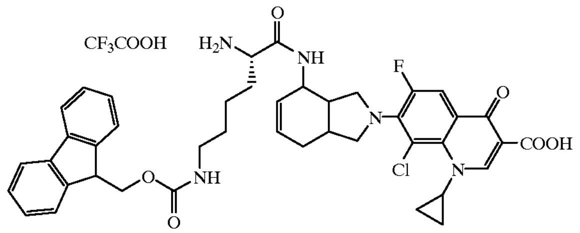

Splitting off of Boc from Example 9.10.a analogously to Example 9.1. Two precipitations of the crude product from methanol/ether. Freeze drying from dioxane/water. Yield: 92% [TLC: methylene chloride/methanol/ammonia (17%) 15:4:0.5 $R_f$=0.44].

EXAMPLES 10.1–10.3

General Formula

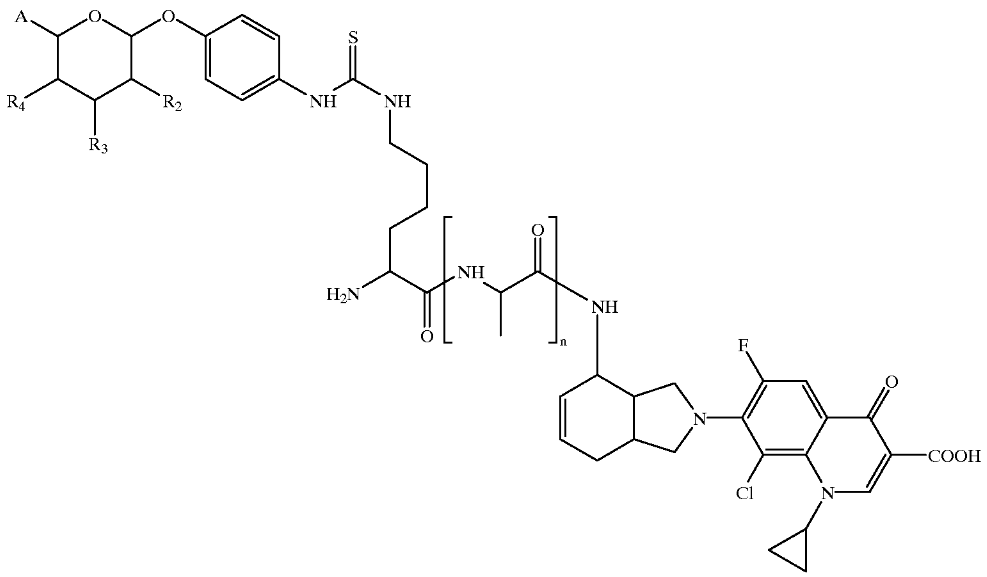

n = 0, 1

EXAMPLE 10.1

N-{$N^ε$-[O(3-O-Carboxymethyl-β-L-fucosyl)-4-hydroxy-phenylamino-thiocarbonyl]-lysyl-D-alanyl}-quinolone-a 10.1.a) N-{$N^α$-(tert-Butoxycarbonyl)-$N^ε$-[O-(3O-carboxymethyl-β-L-fucosyl)-4-hydroxy-phenylamino-thiocarbonyl]-lysyl-D-alanyl}-quinolone-a 47 μl (0.28 mmol) of thiophosgene are added to 78 mg (0.25 mmol) of p-aminophenyl 3-O-carboxymethyl-β-L-fucoside (Example 1.10) in 15 ml of dioxane/water 1:1, while stirring. After the mixture has been stirred at 20° C. for 10 minutes, it is concentrated and the residue is dried under a high vacuum for 1 hour. The isothiocyanate obtained is then coupled in absolute dimethylformamide with 180 mg (0.25 mmol) of N-[$N^α$-(tert-butoxycarbonyl)-lysyl-D-alanyl)-quinolone-a (Example 9.5) in the presence of 86 μl of ethyldiisopropylamine. After two precipitations of the crude product from methylene chloride/ether, subsequent stirring with water and freeze drying from dioxane/water, 210 mg (78%) of the target product are obtained. [TLC: acetonitrile/water/glacial acetic acid 5:1:0.2 $R_f$=0.62].

10.1) N-{$N^ε$-[O-(3-O-Carboxymethyl-β-L-fucosyl)-4-hydroxy-phenylamino-thiocarbonyl]-lysyl-D-alanyl}quinolone-a 208 mg (0.193 mmol) of the compound from Example 1.0.a are stirred with 10 ml of anhydrous trifluoroacetic acid in 10 ml of methylene chloride at 0° C. for 1 hour. The mixture is concentrated and the residue is subsequently distilled with 15 ml of methanol and chromatographed with methylene chloride/methanol/ammonia (17%) 10:10:0.8. After subsequent precipitation from dimethylformamide with ether, 52 mg (28%) of the target product are obtained. [TLC: acetonitrile/water/glacial acetic acid 5:1:0.2 $R_f$=0.53].

The following glycoconjugates are prepared analogously to Example 10.1 from the partly protected peptide conjugates in Examples 9.5, 9.7 and 9.10:

EXAMPLE 10.2

N-{$N^ε$-[O-(3-O-Methyl-β-L-fucosyl)-4-hydroxy-phenylamino-thiocarbonyl]-lysyl-alanyl}-quinolone-a Educts:

carbohydrate from Example 1.2; peptide conjugate from Example 9.7

Purification of the intermediate stage by several precipitations from methanol with ether. Flash chromatographic purification of the final stage with methylene chloride/methanol/ammonia (17%) 15:4:0–5; later in the same system with 15:8:0.8. Yield: 20% [TLC: methylene chloride/methanol/ammonia (17%) 15:8:0.8 $R_f$=0.15].

EXAMPLE 10.3

N-{$N^ε$-[O-(3-O-Methyl-β-L-fucosyl)-4-hydroxy-phenylamino-thiocarbonyl]-lysyl}-quinolone-a Educts:

carbohydrate from Example 1.2; amino acid conjugate from Example 9.10

Purification of the intermediate stage by precipitation from methanol with ether. Flash chromatography purification of the final stage with methylene chloride/methanol/ammonia (17%) 15:8:0.8. Yield: 39% [TLC: acetonitrile/water/glacial acetic acid 5:1:0.2 $R_f$=0.33].

EXAMPLES 11.1–11.18

General Formula

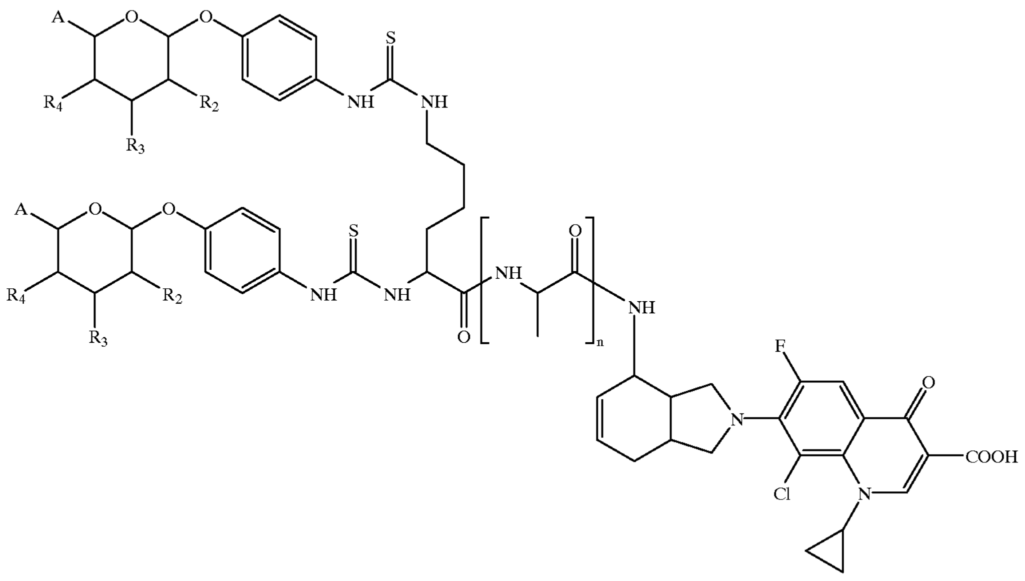

n = 0, 1

EXAMPLE 11.1

N-{$N^{\alpha}$,$N^{\epsilon}$-Bis [O-(3-O-methyl-β-L-fucosyl)-4-hydroxy-phenylamino-thiocarbonyl]-lysyl-D-alanyl}-quinolone-a 50 mg (0.19 mmol) of p-aminophenyl 3-O-methyl-β-L-fucoside (Example 1.2) are first converted into the isothiocyanate in accordance with the instructions in Example 10.1.a and the product is then coupled in 5 ml of dimethylformamide with 68 mg (0.08 mmol) of N-[lysyl-D-alanyl]-quinolone-a, di-trifluoroacetate (Example 9.3) in the presence of 55 μl of ethyldiisopropylamine. The mixture is stirred at room temperature for 16 hours and concentrated and the residue is purified by flash chromatography [methylene chloride/methanol/glacial acetic acid 85:15:1.5]. 62 mg (63%) of the target product are subsequently obtained by precipitation from methanol with ether. [TLC: methylene chloride/methanol/glacial acetic acid 80:20:2 $R_f$=0.5] MS-MALDI: m/z=1242=M+1.

The following glycoconjugates are prepared analogously to Example 11.1 from the peptide conjugates in Examples 9.3, 9.4, 9.8 and 9.9:

EXAMPLE 11.2

N-{$N^{\alpha}$,$N^{\epsilon}$-Bis-[O-(3-O-methyl-β-L-fucosyl)-4-hydroxy-phenylamino-thiocarbonyl]-lysyl-alanyl}-quinolone-a Educts:

50 mg (0.19 mmol) of carbohydrate from Example 1.2;

0.08 mmol of peptide conjugate from Example 9.4

Purification by flash chromatography [methylene chloride/methanol/glacial acetic acid 90:10:1] and precipitation from methanol with ether. Yield: 79% [TLC: acetonitrile/water/glacial acetic acid 5:1:0.2 $R_f$=0.42].

EXAMPLE 11.3

N-{$N^{\alpha}$,$N^{\epsilon}$-Bis-[O-(3-O-carboxymethyl-β-L-fucosyl)-4hydroxy-phenylamino-thiocarbonyl]-lysyl-alanyl}-quinolone-a Educts:

52 mg (0.166 mmol) of carbohydrate from Example 1.10;

0.07 mmol of peptide conjugate from Example 9.4

Purification by flash chromatography [methylene chloride/methanol/glacial acetic acid 80:20:2] and stirring of the residue with methanol [TLC: acetonitrile/water/glacial acetic acid 10:3:1.5 $R_f$=0.62].

EXAMPLE 11.4

N-{$N^{\alpha}$,$N^{\epsilon}$-Bis-[ O-(3-O-carboxymethyl-β-L-fucosyl)-4-hydroxy-phenylamino-thiocarbonyl]-lysyl-D-alanyl}-quinolone-a Educts:

44 mg (0.14 mmol) of carbohydrate from Example 1.10;

0.06 mmol of peptide conjugate 9.3

Purification by flash chromatography [methylene chloride/methanol/glacial acetic acid 80:20:2] and stirring of the residue with methanol. Yield: 57%; [TLC: acetonitrile/water/glacial acetic acid 10:3:1.5 $R_f$=0.62].

EXAMPLE 11.5

N-{$N^{\alpha}$,$N^{\epsilon}$-Bis-[O-(α-L-rhamnosyl)-4-hydroxy-phenylamino-thiocarbonyl]-lysyl-alanyl}-quinolone-a Educts:

44 mg (0.166 mmol) of carbohydrate from Example 1.21;

0.07 mmol of peptide conjugate from Example 9.4

Purification by flash chromatography [methylene chloride/methanol/glacial acetic acid 80:20:1] and stirring of the residue with methanol/ether. Yield: 90 mg (89%); [TLC: acetonitrile/water/glacial acetic acid 5:1:0.2 $R_f$=0.51] MS-ESI: m/z=1212=M+1.

EXAMPLE 11.6

N-{$N^{\alpha}$,$N^{\epsilon}$-Bis-[O-(3-O-methyl-β-L-fucosyl)-4-hydroxy-phenylamino-thiocarbonyl]-lysyl}-quinolone-a Educts:

70 mg (0.258 mmol) of carbohydrate from Example 1.2;

0.11 mmol of amino acid conjugate from Example 9.8

Purification by flash chromatography [methylene chloride/methanol/glacial acetic acid 90:10:1] and precipitation from methylene chloride/methanol 1:1 with ether. Stirring of the residue with water. Yield: 41%. [TLC: acetonitrile/water/glacial acetic acid 5:1:0.2 $R_f$=0.65].

EXAMPLE 11.7

N-{$N^{\alpha}$,$N^{\epsilon}$-Bis-[O-(3--methyl-β-L-fucosyl)-4-hydroxy-phenylamino-thiocarbonyl]-D-lysyl}-quinolone-a Educts:

50 mg (0.19 mmol) of carbohydrate from Example 1.2;

0.08 mmol of amino acid conjugate from Example 9.9

Purification by flash chromatography [methylene chloride/methanol/glacial acetic acid 90:10:1] and precipitation from methylene chloride/methanol 1:1 with ether. Stirring of the residue with water. Yield: 67%. [TLC: acetonitrile/water/glacial acetic acid 5:1:0.2 $R_f$=0.65] MS-FAB: m/z=1169=M+1.

EXAMPLE 11.8

N-{$N^\alpha$,$N^\epsilon$-Bis-[O-(3-O-carboxymethyl-β-L-fucosyl)-4-hydroxy-phenylamino-thiocarbonyl]-lysyl}-quinolone-a, di-sodium salt Educts:

50 mg (0.16 mmol) of carbohydrate from Example 1.10;

0.07 mmol of amino acid conjugate from Example 9.8

After concentration of the reaction batch, taking up of the residue in 10 ml of dimethylformamide and addition of 8 ml of a 0.1N sodium hydroxide solution, the mixture is stirred at 20° C. for 2 hours. After renewed concentration, the residue is taken up in water and the pH is brought to 5. The product is lyophilized and digested with methanol and then with methanol/ether. 68 mg (65%) of the target compound are thus obtained. [TLC: acetonitrile/water/glacial acetic acid 5:1:0.2 $R_f$=0.26].

EXAMPLE 11.9

N-{$N^{\alpha,N\epsilon}$-Bis-[O-(3-O-carboxymethyl-β-L-fucosyl)-4-hydroxy-phenylamino-thiocarbonyl]-D-lysyl}-quinolone-a, di-sodium salt Educts:

100 mg (0.32 mmol) of carbohydrate from Example 1.10;

0.13 mmol of amino acid conjugate from Example 12.9

After concentration of the reaction batch, taking up of the residue in 10 ml of dimethylformamide and addition of 16 ml of a 0.1N sodium hydroxide solution, the mixture is stirred at 20° C. for 2 hours. After renewed concentration, the residue is taken up in water and the pH is brought to 5. The product is lyophilized and digested with methanol and then with methanol/ether. 160 mg (77%) of the target compound are thus obtained. Melting point: 218–220° C. [TLC: acetonitrile/water/glacial acetic acid 10:3:1.5 $R_f$=0.69].

EXAMPLE 11.10

N-{$N^\alpha$,$N^\epsilon$-Bis-[O-(3-O-methyl-α-L-fucosyl)-4hydroxy-phenylamino-thiocarbonyl]-D-lysyl}-quinolone-a Educts:

50 mg (0.19 mmol) of carbohydrate from Example 1.3;

0.08 mmol of amino acid conjugate from Example 9.9

Preparation analogously to Example 11.7. Purification by flash chromatography [methylene chloride/methanol/ammonia (17%) 10:10:1] and subsequent precipitation from methylene chloride/methanol 1:1 with ether. Yield: 66%. [TLC: acetonitrile/water/glacial acetic acid 5:1:0.2: $R_f$=0.62].

EXAMPLE 11.11

N-{$N^\alpha$,$N^\epsilon$-Bis-O-(α-L-rhamnosyl)-4-hydroxy-phenylamino-thiocarbonyl]-D-lysyl}-quinolone-a Educts:

50 mg (0.19 mmol) of carbohydrate from Example 1.21;

0.08 mmol of amino acid conjugate from Example 9.9

Preparation analogously to Example 11.7. Yield: 57%. [TLC: acetonitrile/water/glacial acetic acid 5:1:0.2 $R_f$=0.63].

EXAMPLE 11.12

N-{$N^\alpha$,$N^\epsilon$-Bis-[O-(3-O-methyl-β-L-fucosyl)-4-hydroxy-phenylamino-thiocarbonyl]-D-lysyl}-quinolone-a, sodium salt 58 mg (0.05 mmol) of the compound from Example 11.7 are suspended in water and converted into the sodium salt with one equivalent of a 0.1N sodium hydroxide solution. After freeze drying, 60 mg of the target compound are obtained.

EXAMPLE 11.13

N-{$N^\alpha$,$N^\epsilon$-Bis-[O-(3-O-methyl-β-D-galactopyranosyl)-4-hydroxy-phenylamino-thiocarbonyl]-lysyl}-quinolone-a, sodium salt Thiophosgene (33.5 ml, 0.44 mmol) is added to a solution of compound 1.25 (62.8 mg, 0.22 mmol) in dioxane/water 1:1 (10 ml), while stirring. After 10 minutes, the mixture is concentrated in vacuo and the residue is dried under an oil pump vacuum for 1 hour. The isothiocyanate obtained is dissolved in absolute dimethylformamide (10 ml), and compound 9.8 (77.4 mg, 0.1 mmol) and ethyldiisopropylamine (0.5 ml) are added. The mixture is stirred at room temperature for 16 hours and then concentrated in vacuo and the residue is purified by flash chromatography (methylene chloride/methanol/ammonia (25%) 10:10:1→methanol/ammonia (25%) 20:1]. Yellow crystals are obtained and are suspended in water (10 ml). 0.05N sodium hydroxide solution is added dropwise to the suspension, while stirring, until a clear solution forms (pH<10). Lyophilization of the filtered solution gives a yellow amorphous solid (39.7 mg, 32%); $[\alpha]_D^{20}$=+25.8° (c=0.26/$H_2O$).

EXAMPLE 11.14

N-{$N^\alpha$,$N^\epsilon$-Bis-[O-(4-O-(3'-O-methyl-β-D-galactopyranosyl)-β-D-glucopyranosyl)-4-hydroxy-phenylamino-thiocarbonyl]-lysyl}-quinolone-a, sodium salt Compound 1.58 (98.4 mg, 0.22 mmol) is reacted with peptide conjugate 9.8 (77.4 mg, 0.1 mmol) as described in Example 11.13 and the product is purified. A yellow amorphous solid (62.5 mg, 40%) is obtained; $[\alpha]_D^{20}$=+12.9° (c=0.26/$H_2O$).

EXAMPLE 11.15

N-{$N^\alpha$,$N^\epsilon$-Bis-[O-(2-O-methyl-4-O-(3'-O-Methyl-β-D-galactopyranosyl)-β-D-glucopyranosyl)-4-hydroxy-phenylamino-thiocarbonyl]-lysyl}-quinolone-a, sodium salt Compound 1.59 (101.5 mg, 0.22 mmol) is reacted with peptide conjugate 9.8 (77.4 mg, 0.1 mmol) as described in Example 11.13. Purification by reprecipitation from methanol/methylene chloride 1:1 with diethyl ether and extraction by boiling with ethanol gives yellow crystals, which are converted into the sodium salt as described. A yellow amorphous solid (51.1 mg, 32%) is obtained; $[\alpha]_D^{20}$=+27.9° (c=0.24/$H_2O$).

EXAMPLE 11.16

N-{$N^\alpha$,$N^\epsilon$-Bis-[O-(3-O-methyl-β-D-galactopyranosyl)-4-hydroxy-phenylamino-thiocarbonyl]-D-lysyl}-quinolone, sodium salt Compound 1.25 (62.8 mg, 0.22 mmol) is reacted with peptide conjugate 9.9 (77.4 mg, 0.1 mmol) as described in Example 11.13 and the product is purified. A yellow amorphous solid (77.3 mg, 63%) is obtained; $[\alpha]_D^{20}$=−23.8° (c=0.63/$H_2O$).

EXAMPLE 11.17

N-{$N^\alpha$,$N^\epsilon$-Bis-[O-(3-O-methyl-α-D-mannopyranosyl)-4-hydroxy-phenylamino-thiocarbonyl]-D-lysyl}-quinolone-a, sodium salt Compound 1.40 (62.8 mg, 0.22 mmol) is reacted with peptide conjugate 9.9 (77.4 mg, 0.1 mmol) as described in Example 11.13 and the product is purified. A yellow amorphous solid (33.6 mg, 27%) is obtained; $[\alpha]_D^{20}$=+0.7° (c=0.28/$H_2O$).

EXAMPLE 11.18

N-{$N^\alpha$,$N^\epsilon$-Bis-[O-(4-O-(3'-O-methyl-β-D-galactopyranosyl)-β-D-glucopyranosyl)-4-hydroxy-phenylamino-thiocarbonyl]-D-lysyl}-quinolone-a, sodium salt Compound 1.58 (98.4 mg, 0.22 mmol) is reacted with peptide conjugate 9.9 (77.4 mg, 0.1 mmol) as described in Example 11.13 and the product is purified. A yellow amorphous solid (63.0 mg, 41%) is obtained; $[\alpha]_D^{20}$=−21.8° (c=0.22/$H_2O$).

EXAMPLES 12.1–12.15

General Formula

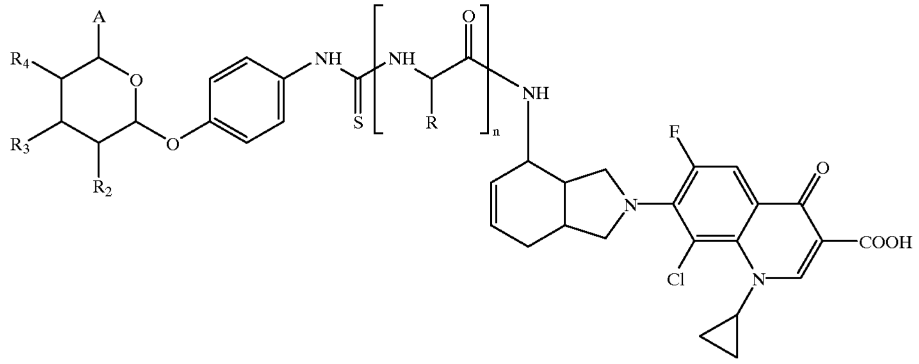

n = 0, 1, 2

EXAMPLE 12.1

N-{N'-[O-(3-O-Methyl-β-L-fucosyl)-4hydroxy-phenylamino-thiocarbonyl]-D-alanyl}-quinolone-a 447 mg (1.66 mmol) of p-aminophenyl 3-O-methyl-β-L-fucoside (Example 1.2) are first converted into the isothiocyanate in accordance with the instructions in Example 10.1.a and the product is then coupled in 40 ml of dimethylformamide with 1 g (1.66 mmol) of N-[D-alanyl]-quinolone-a, trifluoroacetate (Example 9.1) in the presence of 568 μl of ethyldiisopropylamine The mixture is stirred at room temperature for 2 hours and concentrated and the residue is purified by several precipitations from methylene chloride/methanol 1:1 with ether. The filter residue is then stirred twice more with water. 876 mg (66%) of the target product are obtained. Melting point: 198° C.; [TLC: acetonitrile/water/glacial acetic acid 5:1:0.2 $R_f$=0.63].

The following glycoconjugates are prepared analogously to Example 12.1 from the amino acid conjugates in Examples 9.1 and 9.2:

EXAMPLE 12.2

N-{[N'-[O-(3-O-Methyl-β-L-fucosyl)-4hydroxy-phenylamino-thiocarbonyl]-alanyl}-quinolone-a Educt:

25 mg (0.092 mmol) of carbohydrate from Example 1.2

Purification by flash chromatography (methylene chloride/methanol/glacial acetic acid 90:10:1], precipitation from methylene chloride/methanol 1:1 with ether and stirring of the filter residue with water. Yield: 53 mg (52%). [TLC: acetonitrile/water/glacial acetic acid 5:1:0.2 $R_f$=0.65].

EXAMPLE 12.3

N-{N'-[O-(3-O-Carboxymethyl-β-L-fucosyl)-4-hydroxy-phenylamino-thiocarbonyl]-D-alanyl}-quinolone-a, mono-sodium salt Educts:

523 mg (1.67 mmol) of carbohydrate from Example 1.10;

840 mg (1.39 mmol) of the compound from Example 12.1

After a reaction time of 6 hours, the mixture is concentrated and the residue is stirred with water. Flash chromatography [methylene chloride/methanol/ammonia (17%) 15:8:0.8; later in the same system 10:1:1] follows freeze drying from dioxane/water. The product is then taken up in water, one equivalent of a 0.1N sodium hydroxide solution is added and lyophilization is again carried out. Yield: 525 mg (45%). [TLC: acetonitrile/water/glacial acetic acid 5:1:0.2 $R_f$=0.39].

EXAMPLE 12.4

N-{N'-[O-(α-L-Rhamnosyl)-4-hydroxy-phenylamino-thiocarbonyl]-D-alanyl}-quinolone-a Educt:

20 mg (0.076 mmol) of carbohydrate from Example 1.21

Purification by flash chromatography [methylene chloride/methanol/glacial acetic acid 90:10:1] and precipitation from methanol with ether. Yield: 20 mg (34%). [TLC: acetonitrile/water/glacial acetic acid 5:1:0.2 $R_f$=0.42].

The following glycoconjugates are prepared from partly protected N-(lysyl)-quinolone-a conjugates and N-(lysyl-D-alanyl)-quinolone-a conjugates:

EXAMPLE 12.5

N-{$N^\alpha$-[O-(3-O-Methyl-β-L-fucosyl)-4-hydroxy-phenylamino-thiocarbonyl]-lysyl}-quinolone-a 12.5.a) N-{$N^\alpha$-[O-(3-O-Methyl-β-L-fucosyl)-4-hydroxy-phenylamino-thiocarbonyl]-N-$^\epsilon$-[fluorenyl-9-methoxycarbonyl]-lysyl}-quinolone-a 92 mg (0.34 mmol) of p-aminophenyl 3-O-methyl-β-L-fucoside (Example 1.2) are first converted into the isothiocyanate in accordance with the instructions in Example 10.1.a and the product is then coupled in 20 ml of dimethylformamide with 300 mg (0.34 mmol) of N-[$N^\epsilon$-(fluorenyl-9-methoxycarbonyl)-lysyl]-quinolone-a, trifluoroacetate (Example 9.11) in the presence of 116 μl of ethyldiisopropylamine. The mixture is stirred at room temperature for 16 hours and concentrated and the residue is purified by precipitation from methylene chloride with ether. The filter residue is then stirred further with water and lyophilized from dioxane/water. 290 mg (79%) of the target product are obtained. [TLC: acetonitrile/water 10:1 $R_f$=0.6].

12.5) N-{$N^\alpha$-[O-(3-O-Methyl-β-L-fucosyl)-4-hydroxy-phenylamino-thiocarbonyl]-lysyl}-quinolone-a 288 mg (0.267 mmol) of the compound of Example 12.5.a are dissolved in 20 ml of methylene chloride, and 8 ml of piperidine are added. After the mixture has been stirred at 20° C. for 30 minutes, it is concentrated and the residue is precipitated from methylene chloride with ether. The product is purified by flash chromatography [methylene chloride/methanol/ammonia (17%) 10:10:2]. The residue is stirred with ether and lyophilized from water. 90 mg (39%) of the target product are obtained. [TLC: methylene chloride/methanol/ammonia (17%) 10:10:5 $R_f$=0.4].

The following glycoconjugates are prepared analogously to Examples 12.5 from the conjugates in Example 9.11 and 9.6:

EXAMPLE 12.6

N-{$N^{\alpha}$-[O-(3-O-Carboxymethyl-β-L-fucosyl)-4-hydroxy-phenylamino-thiocarbonyl]-lysyl}-quinolone-a, di-sodium salt Educts:

63 mg (0.2 mmol) of carbohydrate from Example 1.10;

158 mg (0.18 mmol) of compound from Example 9.11

Purification of the intermediate stage by flash chromatography [methylene chloride/methanol/ammonia (17%) 15:4:0.5; later in the same system 10:10:1] and of the final stage by stirring several times with methanol and washing of the filter residue with ether. Yield: 44%. The product is then suspended in water, the di-sodium salt is prepared with 2 equivalents of a 0.1N sodium hydroxide solution and the solution is lyophilized. [TLC: acetonitrile/water/glacial acetic acid 10:3:1.5 $R_f$=0.34].

EXAMPLE 12.7

N-{$N^{\alpha}$-[O-(3-O-Carboxymethyl-β-L-fucosyl)-4-hydroxy-phenylamino-thiocarbonyl]-lysyl-D-alanyl}-quinolone-a Educts:

147 mg (0.47 mmol) of carbohydrate from Example 1.10;

448 mg (0.47 mmol) of compound from Example 9.6

Purification of the intermediate stage by two precipitations from methylene chloride/methanol 1:1 with ether; stirring of the filter residue with water (yield: 92%). Purification of the final stage by flash chromatography [methylene chloride/methanol/ammonia (17%) 10:10:2]; precipitation from dimethylformamide with ether. Yield: 59%. [TLC: acetonitrile/water/glacial acetic acid 10:3:1.5 $R_f$=0.4].

EXAMPLE 12.8

N-{$N^{\alpha}$-[O-(3-O-Methyl-β-D-galactopyranosyl4-hydroxy-phenylamino-thio-carbonyl]-lysyl}-quinolone-a, hydrochloride Educts:

compound 1.25 (62.8 mg, 0.22 mmol);

peptide conjugate 9.11 (180.0 mg, 0.2 mmol)

Purification of the intermediate stage by flash chromatography [methylene chloride/methanol 10:1→7:1→2:1]. Yellow crystals (145.7 mg, 67%) are obtained; TLC [methylene chloride/methanol 5:1]: $R_f$=0.48. The fluorenyl-9-methoxycarbonyl group is then split off as described in Example 4.5 and the product is purified. Yellow crystals are obtained and are suspended in water (10 ml). 0.1N hydrochloric acid is added dropwise to the suspension, while stirring, until a clear solution forms (pH>3). Lyophilization of the filtered solution gives a yellow amorphous solid (119.4 mg, 66%); $[\alpha]_D^{20}$=+33.8° (c=0.28/$H_2O$).

EXAMPLE 12.9

N-{$N^{\alpha}$-[O-(3,6-Di-O-methyl-β-D-galactopyranosyl)-4-hydroxy-phenylamino-thiocarbonyl]-lysyl}-quinolone-a, hydrochloride Educts:

compound 1.32 (65.9 mg, 0.22 mmol);

peptide conjugate 9.11 (180.0 mg, 0.2 mmol)

Purification of the intermediate stage by flash chromatography [methylene chloride/methanol 10:1→7:1→1:1]. Yellow crystals (115.0 mg, 52%) are obtained; TLC [methylene chloride/methanol 5:1]: $R_f$=0.44. The fluorenyl-9-methoxycarbonyl group is then split off as described in Example 4.5 and the product is purified. Yellow crystals are obtained and are suspended in water (10 ml). 0.1N hydrochloric acid is added dropwise to the suspension, while stirring, until a clear solution forms (pH>3). Lyophilization of the filtered solution gives a yellow amorphous solid (94.3 mg, 51%); $[\alpha]_D^{20}$=+44.2° (c=0.34/$H_2O$).

EXAMPLE 12.10

N-{$N^{\alpha}$-[O-(3-O-Methyl-α-D-mannopyranosyl)-4-hydroxy-phenylamino-thio-carbonyl]-lysyl}-quinolone-a, hydrochloride Educt:

compound 1.40 (62.8 mg, 0.22 mmol);

peptide conjugate 9.11 (180.0 mg, 0.2 mmol)

Purification of the intermediate stage by flash chromatography [methylene chloride/methanol 10:1→5:1→1:1]. Yellow crystals (96.7 mg, 44%) are obtained; TLC [methylene chloride/methanol 5:1]: $R_f$=0.47. The fluorenyl-9-methoxycarbonyl group is then split off as described in Example 4.5 and the product is purified. Yellow crystals are obtained and are suspended in water (10 ml). 0.1N hydrochloric acid is added dropwise to the suspension, while stirring, until a clear solution forms (pH>3). Lyophilization of the filtered solution gives a yellow amorphous solid (78.2 mg, 43%); $[\alpha]_D^{20}$=−157.2° (c=0.30/$H_2O$).

EXAMPLE 12.11

N-{$N^{\alpha}$-[O-(4-O-(3'-O-Methyl-β-D-galactopyranosyl)-β-D-glucopyranosyl)-4-hydroxy-phenylamino-thiocarbonyl]-lysyl}-quinolone-a hydrochloride Educts:

compound 1.58 (98.4 mg, 0.22 mmol);

peptide conjugate 9.11 (180.0 mg, 0.2 mmol)

Purification of the intermediate stage by flash chromatography [methylene chloride/methanol/ammonia (25%) 20:10:1→10:10:1→methanol/ammonia (25%) 20:1]. Beige crystals (132.1 mg, 53%) are obtained; TLC [methylene chloride/methanol/ammonia (25%) 10:10:3]: $R_f$=0.60. The fluorenyl-9-methoxycarbonyl group is then split off as described in Example 4.5 and the product is purified. Yellow crystals are obtained and are suspended in water (10 ml). 0.1N hydrochloric acid is added dropwise to the suspension, while stirring, until a clear solution forms (pH>3). Lyophilization of the filtered solution gives a yellow amorphous solid (90.0 mg, 42%); $[\alpha]_D^{20}$=+192.2° (c=0.27/$H_2O$).

The following glycoconjugates are prepared in accordance with the instructions in Example 12.1 starting from unsubstituted quinolone-a:

EXAMPLE 12.12

N-[O-(3-O-Carboxymethyl-β-L-fucosyl)-4hydroxy-phenylamino-thiocarbonyl-quinolone-a, di-sodium salt Educts:

78.5 mg (0.25 mmol) of carbohydrate from Example 1.10;

70 mg (0.167 mmol) of quinolone-a

After a reaction time of 6 hours, the mixture is concentrated, the residue is taken up in dimethylformamide and the mixture is stirred with 4 ml of a 0.1N sodium hydroxide solution for 1 hour. Purification by flash chromatography [methylene chloride/methanol/ammonia (17%) 15:4:0.5. The pH is brought to 7 with a 0.1N sodium hydroxide solution and lyophilization is carried out. Yield: 60 mg (44%). [TLC: acetonitrile/water/glacial acetic acid 5:1:0.2 $R_f$=0.42] FAB-MS: m/z=773=M−2Na$^+$+3H$^+$.

EXAMPLE 12.13

N-[O-(3-O-Methyl-β-L-fucosyl)-4-hydroxy-phenylamino-thiocarbonyl]-quinolone-a

Educts:

32 mg (0.12 mmol) of carbohydrate from Example 1.2;

50 mg (0.12 mmol) of quinolone-a

Reaction time of 2 hours; purification by flash chromatography [methylene chloride/methanol/glacial acetic acid 9:10:1]; precipitation from methylene chloride/methanol 1:1 with ether. Yield: 59 mg (51%). [TLC: acetonitril/water 10:1 $R_f$=0.43].

EXAMPLE 12.14

N-{$N^\alpha$-[O-(3-O-Methyl-β-L-fucosyl)-4-hydroxy-phenylamino-thiocarbonyl]-quinolone-a, hydrochloride 86 mg (0.1 mmol) of the compound from Example 12.5 are taken up in water and converted into the salt with one equivalent of 0.1N hydrochloric acid. After freeze drying, 88 mg of the target compound are obtained.

EXAMPLE 12.15

N-{$N^\alpha$-[O-(3-O-Methyl-β-L-fucosyl)-4-hydroxy-phenylamino-thiocarbonyl]-diamino-propionoyl)-quinolone-a, hydrochloride The glycoconjugate 12.5 is prepared analogously to Example 12.14 via several stages starting from $N^\alpha$-(tert-butoxycarbonyl)-$N^\beta$-(fluorenyl-9-methoxycarbonyl)-L-diaminopropionic acid and quinolone-a [TLC: acetonitrile/water/glacial acetic acid 5:1:0.2 $R_f$=0.3].

EXAMPLE 13

General Formula

EXAMPLE 13.1

N-{N'-[O-(3-O-Methyl-β-L-fucosyl)-4-hydroxy-phenylamino-thiocarbonyl]-D-alanyl}-quinolone-b 13.1.a) Quinolone-b: 4-amino-7-[(3aRS,4RS,7aSR)-4-amino-1,3,3a,4,7,7a-hexa-hydro-isoindol-2-yl]-1-cyclopropyl-6-fluoro-1,4-dihydro-8-methoxy-4-oxo-3-quinolinecarboxylic acid 170 mg (1.5 mmol) of 1,4-diazabicyclo[2.2.2]octane and 152 mg (1.1 mmol) of (3aRS,4RS,7aSR -4-amino-1,3,3a,4,7,7a-hexahydro-isoindole are added to 310 mg (I mmol) of 5-amino-1-cyclopropyl-6,7-difluoro-1,4-dihydro-8-methoxy4-oxo-3-quinolinecarboxylic acid in a mixture of 4 ml of acetonitrile and 2 ml of dimethylformamide and the mixture is heated under reflux for 1 hour. It is concentrated in vacuo, the residue is stirred with about 20 ml of water and the residue which has precipitated is filtered off with suction and dried at 100° C. in vacuo.

Yield: 301 mg (70% of theory), Melting point: 237–239° C. (with decomposition).

13.1.b) N-[D-Alanyl]-quinolone-b, trifluoroacetate

The target compound is prepared analogously to Example 9.1 starting from compound 13.1.a and N-(tert-butoxycarbonyl)-D-alanine.

13.1) N-{N'-(O-(3-O-Methyl-β-L-fucosyl)-4-hydroxy-phenylamino-thiocarbonyl]-D-alanyl}-quinolone-b The target compound is prepared analogously to Example 12.1 starting from compound 13.1.b and p-aminophenyl 3O-methyl-β-L-fucoside (Example 1.2).

EXAMPLE 14

General Formula

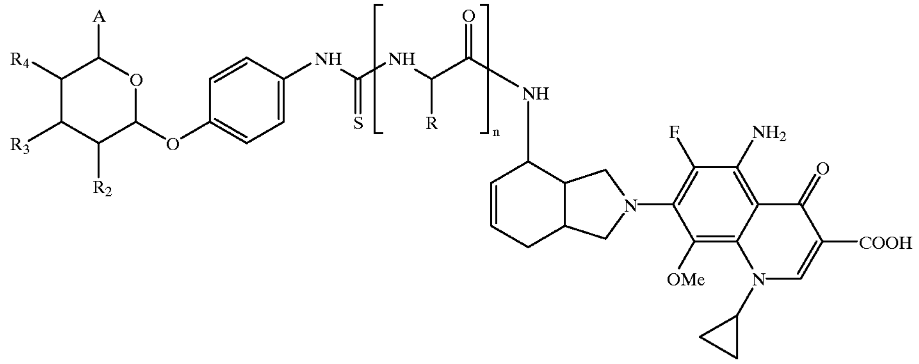

n = 0, 1, 2

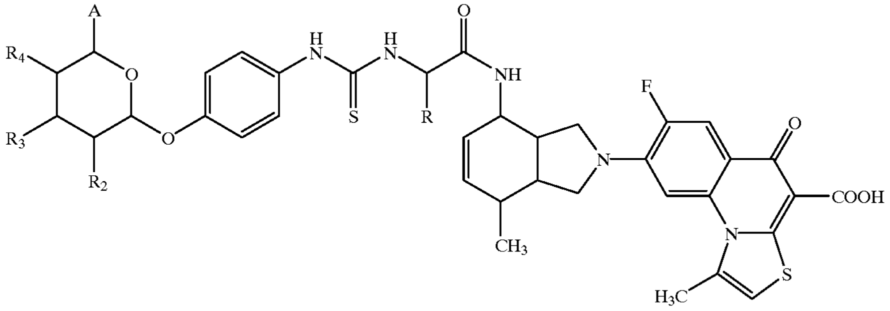

Quinolone-c: 8-(2amino-5-methyl-8-azabicyclo[4.3.0]non-3-en-8-yl)-1-methyl-7-fluoro-5-oxo-5H-thiazolo[3,2-a]quinoline-4-carboxylic acid

EXAMPLE 14.1

N-{-$N^{\alpha}$-[O-(3-O-Methyl-β-D-galactopyranosyl)-4hydroxy-phenylamino-thio-carbonyl]-lysyl}-quinolone-c, hydrochloride 14.1.a) N-[$N^{\epsilon}$-(Fluorenyl-9-methoxycarbonyl)-lysyl]-quinolone-c, trifluoroacetate Educts:

$N^{\alpha}$-(tert-butoxycarbonyl)-$N^{\epsilon}$-(fluorenyl-9-methoxycarbonyl)-lysine (1.4 g, 3.0 mmol);

quinolone-c (820 mg, 1.9 mmol)

The preparation of the intermediate product is carried out analogously to Example 9.1.a. Reprecipitation from ethanol/diethyl ether gives pale yellow crystals (1.37 g, 82%), from which compound 14.1.a is liberated analogously to Example 9.1.b. Orange crystals (1.25 g, 74%) are obtained; TLC [methylene chloride/methanol/ammonia (25%) 30:10:1]: $R_f$=0.7; melting point 180° C.

14.a) N-{$N^{\alpha}$-[O-(3-O-Methyl-β-D-galactopyranosyl)-4-hydroxy-phenylamino-thiocarbonyl]-lysyl}-quinolone-c, hydrochloride Compound 1.25 (62.8 mg, 0.22 mmol) is reacted with peptide conjugate 14.1.a (178.4 mg, 0.2 mmol) analogous to Example 12.5. Purification of the intermediate stage is carried out by flash chromatography [methylene chloride/methanol/ammonia (25%) 30:6:1→30:10:1]. Pale yellow crystals (97.0 mg, 44%) are obtained; TLC [methylene chloride/methanol/ammonia (25%) 30:10:1]: $R_f$=0.23. The fluorenyl-9-methoxycarbonyl group is then split off as described and the product is purified. Yellow crystals are obtained and are suspended in water (10 ml). 0.1N hydrochloric acid is added dropwise to the suspension, while stirring, until a clear solution forms (pH>3). Lyophilization of the filtered solution is a yellow amorphous solid (75.8 mg, 41%); $[\alpha]_D^{20}$=+12.5° (c=0.27/$H_2O$).

The following glycoconjugates are prepared analogously to Example 14.1 from peptide conjugate 14.1.a:

EXAMPLE 14.2

N-{$N^{\alpha}$-[O-(3-O-Methyl-β-L-fucopyranosyl)-4-hydroxy-phenylamino-thio-carbonyl]-lysyl}-quinolone-c, hydrochloride Educts:

compound 1.2 (59.5 mg, 0.22 mmol)

peptide conjugate 14.1.a (178.4 mg, 0.2 mmol)

Purification of the intermediate stage by flash chromatography [methylene chloride/methanol/ammonia (25%) 30:6:1→30:10:1]. Pale yellow crystals (146.6 mg, 67%) are obtained; TLC [methylene chloride/methanol/ammonia (25%) 30:6:1]: $R_f$=0.48. The fluorenyl-9-methoxycarbonyl group is then split off as described and the product is converted into the hydrochloride. A yellow amorphous solid (107.7 mg, 60%) is obtained; $[\alpha]_D^{20}$=+51.6° (c=0.36/$H_2O$).

EXAMPLE 14.3

N-{$N^{\alpha}$-[O-(3-O-Carboxymethyl-β-L-fucosyl)-4-hydroxy-phenylamino-thiocarbonyl]-lysyl}-quinolone-c, di-sodium salt The glycoconjugate 14.4 is prepared analogously to Example 12.6 via several stages starting from compound 14.1.a [FAB-MS: m/z=911=M−2Na+3H].

EXAMPLE 14.4

N-{$N^{\alpha}$-[O-(3-O-Methyl-β-L-fucopyranosyl)-4-hydroxy-phenylamino-thiocarbonyl]-D-lysyl}-quinolone-c, hydrochloride The conjugate is prepared analogously to the isomer in Example 14.2 (FAB-MS: m/z=867=M+H].

EXAMPLE 15

General Formula

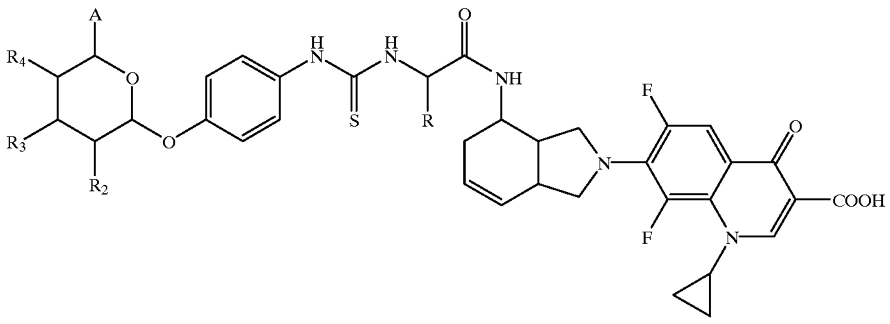

Quinolone-d: 4-(2-amino-8-azabicyclo[4.3.0]non-4-en-8-yl)-1-cyclopropyl-6,8-difluoro-1,4-dihydro-4-oxo-quinoline-3-carboxylic acid

EXAMPLE 15.1

N-{$N^{\alpha}$-[O-(3-O-Methyl-β-D-galactopyranosyl)-4-hydroxy-phenylamino-thiocarbonyl]-lysyl}-quinolone-d, hydrochloride 15.1.a) N-[$N^{\epsilon}$-(Fluorenyl-9-methoxycarbonyl)-lysyl]-quinolone-d, trifluoroacetate $N^{\alpha}$-(tert-Butoxycarbonyl)-$N^{\epsilon}$-(fluorenyl-9-methoxycarbonyl)-lysine (1.4 g, 3.0 mmol) is reacted with quinolone-d, hydrochloride (1.28 mg, 2.8 mmol) as described in Example 9.1.a. Reprecipitation from methylene chloride/methanol 1:1 with diethyl ether gives beige crystals (1.97 g, 83%), from which compound 15.1.a is liberated analogously to Example 9.1.b. Beige crystals (1.7 g, 70%) are obtained; TLC [methylene chloride/methanol/ammonia (25%) 28:14:1]: $R_f$=0.60; melting point=215° C.

15.1) N-{$N^{\alpha}$-[O-(3-O-Methyl-β-D-galactopyranosyl)-4-hydroxy-phenylamino-thio-carbonyl]-lysyl}-quinolone-d, hydrochloride Compound 1.25 (62.8 mg, 0.22 mmol) is reacted with peptide conjugate 15.1.a (173.2 mg, 0.2 mmol) analogously to Example 12.5. Purification of the intermediate stage is carried out by flash chromatography [methylene chloride/methanol/ammonia (25%) 28:14:1→methanol/ammonia (25%) 20:1]. Beige crystals (140.8 mg, 65%) are obtained; TLC [methylene chloride/methanol/ammonia (25%) 28:14:1]: $R_f$=0.06. The fluorenyl-9-methoxycarbonyl group is then split off as described and the product is purified. Beige crystals are obtained and are suspended in water (10 ml). 0.1N hydrochloric acid is added dropwise to the suspension, while stirring, until a clear solution forms (pH>3). Lyophilization of the filtered solution gives a yellow amorphous solid (102.6 mg, 57%); $[\alpha]_D^{20}$=−49.0° (c=0.26/$H_2O$).

The following glycoconjugates are prepared analogously to Example 15.1 from peptide conjugate 15.1.a:

EXAMPLE 15.2

N-{$N^{\alpha}$-[O-(4-O-(3'-O-Methyl-β-D-galactopyranosyl)-β-D-glucopyranosyl)-4-hydroxy-phenylamino-thiocarbonyl]-lysyl}-quinolone-d, hydrochloride Educts:

compound 1.58 (98.4 mg, 0.22 mmol)

peptide conjugate 15.1.a (173.2 mg, 0.2 mmol)

Purification of the intermediate stage by flash chromatography [methylene chloride/methanol/ammonia (25%) 20:10:1→10:10:1→methanol/ammonia (25%) 20:1]. Beige crystals (106.5 mg, 43%) are obtained; TLC [methylene chloride/methanol/ammonia (25%) 10:10:3]: $R_f$=0.51. The fluorenyl-9-methoxycarbonyl group is then split off as described and the product is converted into the hydrochloride. A yellow amorphous solid (82.0 mg, 39%) is obtained; $[\alpha]_D^{20}$=+22.8° (c=0.29/$H_2O$).

EXAMPLE 16

Glycoconjugates With Melphalan

General Formula

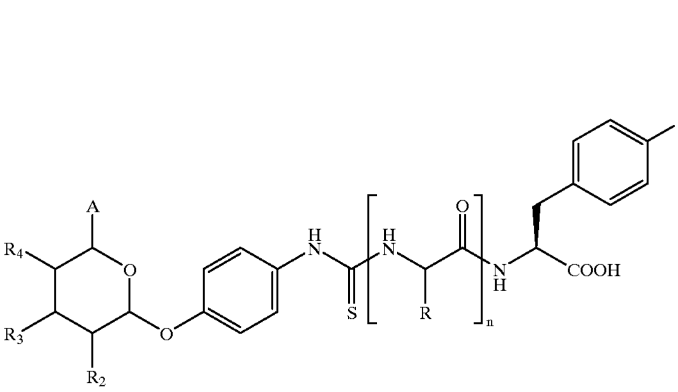

n = 1, 2

EXAMPLE 16.1

N-{N'-[O-3-O-Methyl-β-L-fucopyranosyl)-4-hydroxy-phenylamino-thiocarbonyl]-D-alanyl}-melphalan 16.1.a) N-tert-Butoxycarbonyl-D-alanyl-melphalan 114 mg (0.6 mmol) of N-tert-butoxycarbonyl-D-alanine are dissolved in 10 ml of dimethylformamide, and 138 mg of N'-(3-dimethylaminopropyl)-N-ethyl-carbodiimide, hydrochloride and 1-hydroxy-benzotriazole are added at 0° C. After 10 minutes, 153 mg of melphalan are added and the mixture is stirred at room temperature for 16 hours. It is concentrated and the residue is partitioned between methylene chloride and water. The organic phase is washed, dried over sodium sulphate and concentrated and the residue is then subjected to flash chromatography with methylene chloride/methanol/ammonia (17%) 15:2:0.2→15:4:0.5. 134 mg (56%) of the target compound are obtained [TLC: methylene chloride/methanol/ammonia (17%) 15:4:0.5 $R_f$=0.45].

16.1) N-{N'-[O-(3-O-Methyl-β-L-fucopyranosyl)-4-hydroxy-phenylamino-thiocarbonyl]-D-alanyl}-melphalan Splitting off of the protective group and coupling with the carbohydrate are carried out as described in Examples 9.1 and 12.1. [TLC: acetonitrile/water 10:1 $R_f$=0.26; FAB-MS: m/z=685=M−H.

EXAMPLE 16.2

N-{N'-[O-(3-O-Methyl-β-L-fucopyranosyl)-4-hydroxy-phenylamino-thiocarbonyl]-alanyl-alanyl}-melphalan This compound can be prepared analogously to Example 16.1 via several stages (TLC: acetonitrile/water 10:1 $R_f$=0.2; FAB-MS: m/z=756=M−H).

EXAMPLES 17

Glycoconjugates With Doxorubicin (Adriamycin)

General Formula

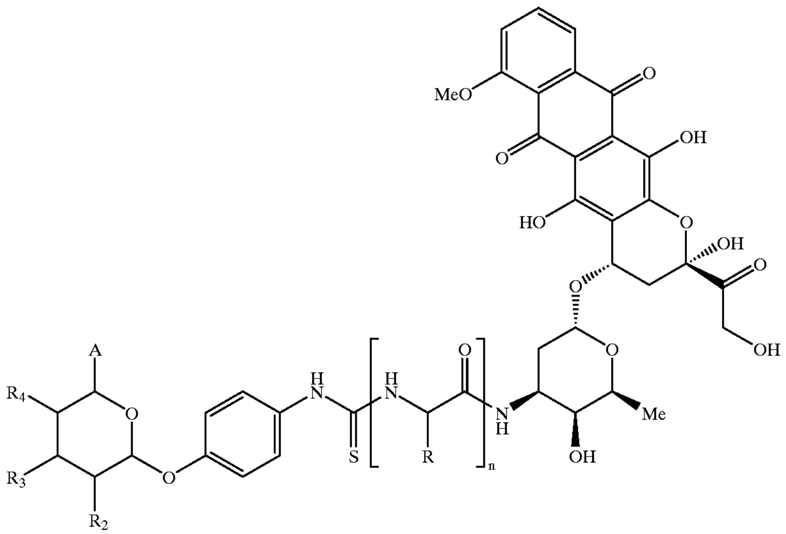

n = 1, 2

EXAMPLE 17.1

N-{N'-[O-(3--Methyl-β-L-fucopyranosyl)-4-hydroxy-phenylamino-thiocarbonyl]-alanyl-alanyl}-doxorubicin 17.1.a) N-[O-(3-O-Methyl-β-L-fucopyranosyl)-4-hydroxy-phenylamino-thiocarbonyl]-alanyl-alanine 160 mg (1 mmol) of alanyl-alanine are taken up in 20 ml of dioxane/water 1:1, and 1 ml of Hünig base is added. 1.2 mmol of p-aminophenyl 3-O-methyl-β-L-fucoside (Example 1.2) are first converted into the isothiocyanate in accordance with instructions 10.1.a and the product is then added to the solution of the dipeptide. The mixture is stirred at room temperature for 16 hours and the residue is purified by flash chromatography (acetonitrile/water 15:1). After concentration of the corresponding fractions, the product is precipitated from methanol/ether. Yield: 267 mg (57%).

17.1) N-{N'-[O-(3-O-Methyl-β-L-fucopyranosyl)-4-hydroxy-phenylamino-thiocarbonyl]-alanyl-alanyl}-doxorubicin 48 mg (0.1 mmol) of the compound from Example 17.1.a are dissolved in 10 ml of dimethylformamide, and 23.1 mg of N'-(3-dimethylaminopropyl)-N-ethyl-carbodiimide, hydrochloride and 21 mg of 1-hydroxy-benzotriazole are added. After 5 minutes, 30 mg of doxorubicin and 35 μl of Hünig base are added and the mixture is stirred at room temperature for 30 minutes. It is concentrated and the residue is purified by flash chromatography (methylene chloride/methanol 88:12). The corresponding fractions are concentrated and the residue is lyophilized from dioxane/water. 20 mg (40%) of the target compound are obtained. [TLC: methylene chloride/methanol 10:1 $R_f$=0.17; ESI: m/z=997=M+H].

EXAMPLE 17.2

N-{$N^{\alpha}$,$N^{\epsilon}$-Bis-[O-(3-O-methyl-β-L-fuccopyranosyl)-4-hydroxy-phenylamino-thiocarbonyl]-D-lysyl-alanyl}-doxorubicin 17.2.a) $N^{\alpha}$,$N^{\epsilon}$-Bis-[O-(3-O-methyl-β-L-fucopyranosyl)-4-hydroxy-phenylamino-thiocarbonyl]-D-lysyl-alanine 580 mg (1.31 mmol) of the bis-trifluoroacetate of D-lysyl-alanine are linked with 2.2 equivalents of the carbohydrate from Example 1.2 in the presence of 1.3 ml of Hünig base as described in Example 17.1.a. Purification by flash chromatography is carried out with acetonitrile/water 10:1. 446 mg (41%) of the target compound are obtained.

17.2) N-{$N^{\alpha}$,$N^{\epsilon}$-Bis-[O-(3-O-methyl-β-L-fucopyranosyl)-4-hydroxy-phenylamino-thiocarbonyl]-D-lysyl-alanyl}-doxorubicin Linking of 59 mg of the compound from Example 17.2.a with 20 mg of doxorubicin is carried out as described in Example 17.1. 15 mg of the conjugate are obtained. [TLC: methylene chloride/methanol 85:15 $R_f$=0.43; FAB-MS: m/z=1365=M+H].

EXAMPLES 18

Glycoconjugates With Camptothecin

General Formula

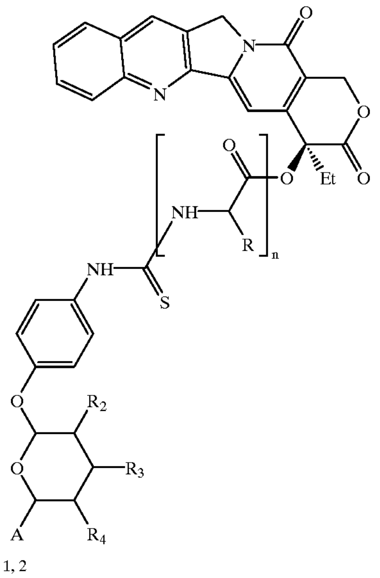

n = 1, 2

EXAMPLE 18.1

20-O-{$N^{\alpha}$,$N^{\epsilon}$-Bis-[O-(3-O-methyl-β-L-fucopyranosyl)-4-hydroxy-phenylamino-thiocarbonyl]-lysyl-alanyl}-camptothecin 18.1.a) 20-O-(Alanyl)-camptothecin, trifluoroacetate 500 mg (1.44 mmol) of camptothecin are dissolved in 20 ml of dimethylformamide, and 50 mg of 4-dimethylaminopyridine and N-tert-butoxycarbonyl-alanine N-carboxy-anhydride are then added. After 3 hours, a further 775 mg of N-tert-butoxycarbonyl-alanine-N-carboxy-anhydride are added and the suspension is treated with ultrasound for 16 hours. The mixture is concentrated, the crude material is taken up in 50 ml of methylene chloride, and 5 ml of trifluoroacetic acid are added at 0° C. After the mixture has been stirred for 30 minutes, it is concentrated again and the product is purified by flash chromatography (acetonitrile/water 20:1). The corresponding fractions are collected and concentrated and the residue is lyophilized from dioxane/water. 712 mg (93%) of the target compound are obtained [FAB-MS: m/z=420=M+H].

18.1.b) 20-O-(Lysyl-alanyl)-camptothecin, bis-trifluoroacetate

The conjugate from Example 18.1.a is linked with $N^{\alpha}$,$N^{\epsilon}$-bis-(tert-butoxycarbonyl)-lysine in accordance with the standard instructions and the product is then deblocked. The target compound is obtained in a 65% yield.

18.1) 20-O-{$N^{\alpha}$,$N^{\epsilon}$-Bis-[O-(3-O-methyl-β-L-fucopyranosyl)-4-hydroxy-phenylamino-thiocarbonyl]-lysyl-alanyl}-camptothecin p-Aminophenyl 3-O-methyl-β-L-fucoside (Example 1.2) is linked with the conjugate of Example 1 8.1.b analogously to the instructions in Example 11.1. Yield: 40% [TLC: acetonitrile/water 10:1 $R_f$=0.44].

EXAMPLE 18.2

20-O-{$N^{\alpha}$-[O-(3-O-Carboxymethyl-β-fucopyranosyl)-4hydroxy-phenylamino-thiocarbonyl]-lysyl-alanyl}-camptothecin 18.2.a) 20-O-[N-(Fluorenyl-9-methoxycarbonyl)-lysyl-alanyl]-camptothecin, trifluoroacetate The conjugate from Example 18.1.a is linked with $N^{\alpha}$-(tert-butoxycarbonyl)-$N^{\epsilon}$-(fluorenyl-9-methoxycarbonyl)-lysine in accordance with the standard instructions and the product is then deblocked on the α-amino function. The target compound is obtained in a 24% yield. [TLC: acetonitrile/water 20.1 $R_f$=0.15].

18.2.b) 20-O-($N^{\alpha}$-[O-(3-O-Carboxymethyl-β-L-fucopyranosyl)-4-hydroxy-phenylamino-thiocarbonyl]-$N^{\epsilon}$-[fluorenyl-9-methoxycarbonyl]-lysyl-alanyl}-camptothecin The compound from Example 18.1.a is modified with the carbohydrate derivative from Example 1.10 analogously to Example 12.6 and 12.5. The crude product can be purified by digestion with water and is then lyophilized from dioxane/water and employed in the next stage without further characterization.

18.2) 20-O-{$N^{\alpha}$-[O-(3-O-Carboxymethyl-β-L-fucopyranosyl)-4-hydroxy-phenylamino-thiocarbonyl]-lysyl-alanyl}-camptothecin The conjugate 18.2.b is deblocked with piperidine in dimethylformamide. After 30 minutes, the mixture is concentrated and the residue is digested twice with methylene chloride. It is then taken up in dimethylformamide and precipitated with methanol/ether. The product is filtered off with suction, washed with ether and then lyophilized from dioxane/water. Yield: 86% [TLC: acetonitrile/water/glacial acetic acid 5:1:0.2 $R_f$=0.17].

EXAMPLE 18.3

20-O-{$N^{\alpha}$-[O-3-O-Carboxymethyl-β-L-fucopyranosyl)-4-hydroxy-phenylamino-thiocarbonyl]-lysyl-alanyl}-camptothecin, sodium salt 62 mg (0.074 mmol) of the conjugate from Example 18.2 are taken up in dioxane/water and converted into the sodium salt with one equivalent of a 0.1N sodium hydroxide solution. Yield: quantitative [TLC: acetonitrile/water/glacial acetic acid 5:1:0.2 $R_f$=0.17].

The following glycoconjugates of camptothecin are prepared analogously to Examples 18.1 and 18.2:

EXAMPLE 18.4

20-O-{$N^{\alpha}$,$N^{\epsilon}$-Bis-[O-(3-O-methyl-β-L-fucopyranosyl)-4-hydroxy-phenylamino-thiocarbonyl]-lysyl-D-alanyl}-camptothecin

EXAMPLE 18.5

20-O-{$N^{\alpha}$,$N^{\epsilon}$-Bis-[O-(3-O-methyl-β-L-fucopyranosyl)-4-hydroxy-phenylamino-thiocarbonyl]-lysyl-valinyl}-camptothecin

EXAMPLE 18.6

20-O-{$N^{\alpha}$-[O-3-O-Carboxymethyl-β-L-fucopyranosyl)-4-hydroxy-phenylamino-thiocarbonyl]-lysyl-valinyl}-camptothecin

EXAMPLE 18.7

20-O-{$N^{\alpha}$-[O-(3-O-Methyl-β-D-galactopyranosyl)-4-hydroxy-phenylamino-thio-carbonyl]-lysyl-valinyl}-camptothecin

EXAMPLE 18.8

20-O-{$N^{\alpha}$-[O-(3-O-Methyl-β-D-galactopyranosyl)-4-hydroxy-phenylamino-thio-carbonyl]-lysyl-alanyl}-camptothecin

EXAMPLE 18.9

20-O-{$N^{\alpha}$[O-(3-O-Carboxymethyl-β-L-fucopyranosyl)-4-hydroxy-phenylamino-thiocarbonyl]-lysyl-valinyl}-camptothecin, hydrochloride Compound 18.6 is converted into the hydrochloride with one equivalent of 0.01N hydrochloric acid.

EXAMPLE 18.10

20-O-{$N^{\alpha}$[O-(3-O-Carboxymethyl-β-fucopyranosyl)-4-hydroxy-phenylamino-thiocarbonyl]-lysyl-alanyl}-camptothecin, hydrochloride Compound 18.2 is converted into the hydrochloride with one equivalent of 0.01N hydrochloric acid.

EXAMPLE 18.11

20-O-{$N^{\alpha}$[O-(3-O-Carboxymethyl-β-L-fucopyranosyl)-4-hydroxy-phenylamino-thiocarbonyl]-lysyl-phenylalanyl}-camptothecin, hydrochloride

EXAMPLE 18.12

20-O-{$N^{\alpha}$,$N^{\epsilon}$-Bis-[O-(3-O-carboxymethyl-β-L-fucopyranosyl)-4-hydroxy-phenylamino-thiocarbonyl]-lysyl-alanyl}-camptothecin, sodium salt

EXAMPLE 18.13

20-O-{$N^{\alpha}$,$N^{\epsilon}$-Bis-[O-(3-O-carboxymethyl-β-L-fucopyranosyl)-4-hydroxy-phenylamino-thiocarbonyl]-lysyl-valinyl}-camptothecin, sodium salt

EXAMPLE 18.14

20-O-{$N^{\alpha}$-[O-(3-O-Methyl-β-L-fucopyranosyl)-4-hydroxy-phenylamino-thiocarbonyl]-lysyl-alanyl}-camptothecin, hydrochloride

We claim:

1. A compound of the formula (I):

K-Sp-L-AA1-AA2-C (I)

wherein

K represents an unsubstituted or regioselectively modified monosaccharide or oligosaccharide moiety of the formula (II):

(II)

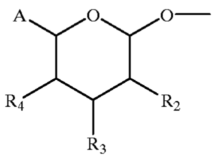

wherein

A represents methyl, hydroxymethyl, carboxyl or an ester or amide derived therefrom, alkoxymethyl, acyloxymethyl or carboxyalkoxymethyl or an ester or amide derived therefrom; or A represents $CH_2$—B, wherein B represents a monosaccharide or oligosaccharide moiety of the formula (II) linked via the anomeric center thereof;

$R_2$, $R_3$ and $R_4$ independently represent hydrogen, hydroxyl, alkoxy, carboxyalkoxy or an ester or amide derived therefrom, hydroxyalkoxy, aminoalkoxy, acyloxy, carboxyalkylcarbonyloxy, sulphato, phosphato, halogen or another monosaccharide or oligosaccharide moiety (II) modified in the same framework and linked via the anomeric center; or $R_3$ and $R_4$ have the meaning given above and $R_2$ represents amino or acylamino; or one of $R_2$, $R_3$ or $R_4$ has the meaning given above and two of the radicals $R_2$, $R_3$ and $R_4$ together represent an epoxide group;

Sp represents optionally substituted arylene or alkylene;

L represents a radical of the formula:

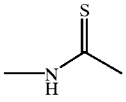

or

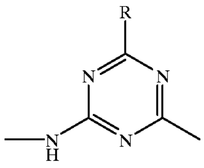

wherein

R represents chlorine or hydroxyalkylamino;

AA1 represents a direct bond or an amino acid radical in the D or L configuration, wherein said amino acid radical is optionally protected with a protective group or said amino acid radical optionally carries a second K-Sp-L-group in which K, Sp and L, independent of the K-Sp-L-group depicted in formula (I), has the above mentioned meanings;

AA2 represents a direct bond or an amino acid radical in the D or L configuration, wherein said amino acid radical is optionally protected with a protective group or said amino acid radical optionally carries a second K-Sp-L-group in which K, Sp and L, independent of the K-Sp-L-group depicted in formula (I), has the above mentioned meanings; and C represents the radical of a cytostatic or a derivative thereof that retains cytostatic activity, which optionally carries an amino or hydroxyl group;

or a stereoisomer of said compound, or a salt of said compound or stereoisomer.

2. A compound of the formula (I) according to claim 1, wherein

Sp represents an arylene radical wherein K and L are bound thereto in the ortho-, meta- or para-position relative to one another, and said arylene is optionally substituted 1 to 4 times by substituents independently selected from the group consisting of hydrogen, methyl, methoxy, hydroxyl, carboxyl, methoxycarbonyl, cyano, nitro, halogen, sulphonyl and sulphonamide; or Sp represents a linear or branched alkylene radical; and K, L, AA1, AA2 and C are defined as in claim 1;

or a stereoisomer of said compound, or a salt of said compound or stereoisomer.

3. A compound of the formula (I) according to claim 1, wherein

C represents the radical of a nucleoside, an endiine antibiotic, a cytotoxic peptide antibiotic, a quinolone- or naphthyridonecarboxylic acid or batracyline, 5-fluorouracil, cytosine arabinoside, methotrexate, etoposide, camptothecin, daunomycin, doxorubicin, taxol, vinblastine, vincristine, dynemycin, calicheamycin, esperamycin, quercetin, suramin, erbstatin, cyclophosphamide, mitomycin C, melphalan, cisplatin, bleomycin, staurosporin or another active compound having an antineoplastic action; and K, Sp, L, AA1 and AA2 are defined as in claim 1;

or a stereoisomer of said compound, or a salt of said compound or stereoisomer.

4. A compound of the formula (I) according to claim 1, wherein

AA1 represents a direct bond or an amino acid radical derived from lysine, alanine, aspartic acid, glutamic acid, glycine, ornithine, tyrosine, valine or serine in the D or L configuration, wherein said amino acid radical optionally carries a second K-Sp-L-group: and K, Sp, L, AA1, AA2 and C are defined as in claim 1, or a stereoisomer of said compound, or a salt of said compound or stereoisomer.

5. A compound of the formula (I) according to claim 1, wherein

AA2 represents a direct bond or an amino acid radical derived from lysine, alanine, glycine, ornithine, diaminopropionic acid or serine in the D or L configuration, wherein said amino acid radical optionally carries a second K-Sp-L-group; and K, Sp, L, AA1 and C are defined as in claim 1;

or a stereoisomer of said compound, or a salt of said compound or stereoisomer.

6. A compound of the formula (I) according to claim 1, wherein

C represents a radical of the formula (III):

T-Q (III)

in which

Q represents a radical of the formula:

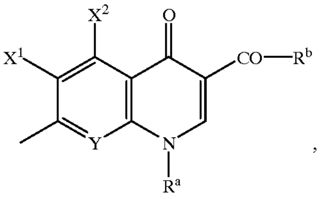

,

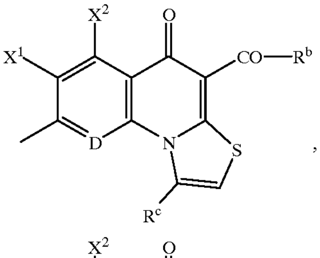

,

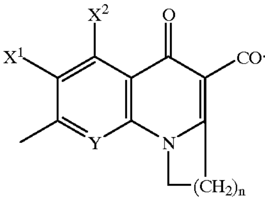

or

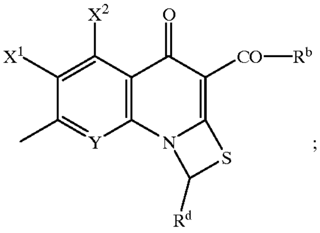

;

wherein $R^a$ represents alkyl which has 1 to 4 carbon atoms and is optionally mono- or disubstituted by halogen or hydroxyl, vinyl, cycloalkyl which has 3 to 6 carbon atoms and is optionally substituted by 1 or 2 fluorine atoms, bicyclo[1.1.1]pent-1-yl, 1,1-dimethylpropargyl, 3-oxetanyl, methoxy, amino, methylamino, dimethylamino or phenyl which is optionally mono- or disubstituted by halogen, amino or hydroxyl; or $R^a$ together with $R^e$ forms a bridge of the structure —*O—$CH_2$—$CH(CH_3)$—, —*S—$CH_2$—$CH_2$—, —*S—$CH_2$—$CH(CH_3)$—, —*$CH_2$—$CH_2$—$CH(CH_3)$— or *O—$CH_2$—$N(R^f)$—, wherein the atom marked with * is bonded to the carbon atom of Y; and wherein $R^f$ represents hydrogen, methyl or formyl;

$R^b$ represents hydroxyl, alkoxy having 1 to 3 carbon atoms or nitromethyl;

$R^c$ represents hydrogen or methyl; or $R^c$ together with $R^g$ forms a bridge of the structure —*O—$CH_2$—, —*NH—$CH_2$—, —*$N(CH_3)$—$CH_2$—, —*$N(C_2H_5)$—$CH_2$—, —*$N(C_3H_5)$—$CH_2$— or —*S—$CH_2$—, wherein the atom marked with * is bonded to the carbon atom of D;

$R^d$ represents hydrogen, $CH_3$, $CH_2F$ or =$CH_2$;

$X^1$ represents hydrogen, halogen or nitro;

$X^2$ represents hydrogen, halogen, amino, hydroxyl, methoxy, mercapto, methyl, halogenomethyl or vinyl;

Y represents N or C—$R^e$;

wherein $R^e$ represents hydrogen, halogen, $CF_3$, $OCH_3$, $OCHF_2$, $CH_3$, CN, CH=$CH_2$ or C≡CH; or $R^e$ together with $R^a$ forms a bridge of the structure —*O—$CH_2$—$CH(CH_3)$—, —*S—$CH_2$—$CH_2$—, —*S—$CH_2$—$CH(CH_3)$—, —*$CH_2$—$CH_2$—$CH(CH_3)$— or *O—$CH_2$—$N(R^f)$—, wherein the atom marked with * is bonded to the carbon atom of Y; and wherein $R^f$ represents hydrogen, methyl or formyl; and D represents N or C—$R^g$;

wherein $R^g$ represents hydrogen, halogen, $CF_3$, $OCH_3$, $OCHF_2$, or $CH_3$; or $R^g$ together with $R^c$ forms a bridge of the structure —*O—$CH_2$—, —*NH—$CH_2$—, —*$N(CH_3)$—$CH_2$—, —*$N(C_2H_5)$—$CH_2$—, —*$N(C_3H_5)$—$CH_2$— or —*S—$CH_2$—, wherein the atom marked with * is bonded to the carbon atom of D;

n represents 1, 2 or 3; and

T represents a radical of the formula:

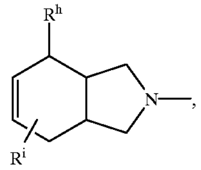

,

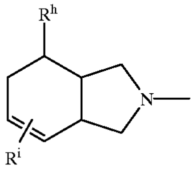

or

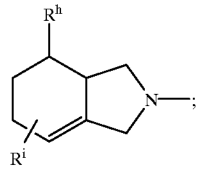

;

wherein $R^h$ represents —$N(R^k)$—, —$CH_2$—O— or —$CH_2$—$N(R^k)$—;

wherein $R^k$ represents hydrogen or methyl; and $R^i$ represents hydrogen, $C_1$–$C_3$-alkyl or cyclopropyl; and K, Sp, L, AA1 and AA2 are defined as in claim 1;

or a stereoisomer of said compound, or a salt of said compound or stereoisomer.

7. A compound of the formula (I) according to claim 6, in which

Q represents a radical of the formula:

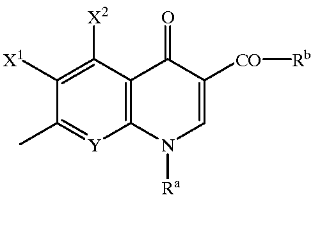

or

-continued

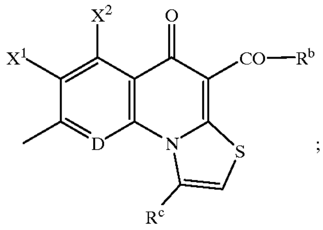

;

wherein $R^a$ represents alkyl which has 2 to 4 carbon atoms and is optionally substituted by 1 fluorine atom, cyclopropyl which is optionally substituted by 1 fluorine atom, or phenyl which is optionally mono- or disubstituted by fluorine; or $R^a$ together with $R^e$ forms a bridge of the structure —*O—$CH_2$—$CH(CH_3)$— or *O—$CH_2$—$N(R^f)$—, wherein the atom marked with * is bonded to the carbon atom of Y; and wherein $R^f$ represents methyl;

$R^b$ represents hydroxyl or alkoxy having 1 or 2 carbon atoms;

$R^c$ represents hydrogen or methyl; or $R^c$ together with $R^g$ forms a bridge of the structure of the structure —*O—$CH_2$—, —*NH—$CH_2$—, —*$N(CH_3)$—$CH_2$— or —*S—$CH_2$—, wherein the atom marked with * is bonded to the carbon atom of D;

$X^1$ represents fluorine;

$X^2$ represents hydrogen or amino;

Y represents N or C—$R^e$;

wherein $R^e$ represents hydrogen, fluorine, chlorine, $CF_3$, $OCH_3$, $OCHF_2$ or C≡CH; or $R^e$ together with $R^a$ forms a bridge of the structure —*O—$CH_2$—$CH(CH_3)$— or *O—$CH_2$—$N(R^f)$—, wherein the atom marked with * is bonded to the carbon atom of Y; and wherein $R^f$ represents methyl; and D represents N or C—$R^g$;

wherein $R^g$ represents hydrogen, fluorine, chlorine, $CF_3$, $OCH_3$ or $CH_3$; or $R^g$ together with $R^c$ forms a bridge of the structure —*O—$CH_2$—, —*NH—$CH_2$—, —*$N(CH_3)$—$CH_2$— or —*S—$CH_2$—, wherein the atom marked with * is bonded to the carbon atom of D; and T represents a radical of the formula:

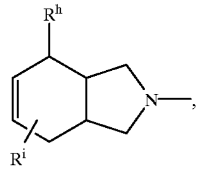

,

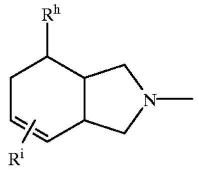

or

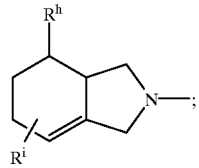

;

wherein $R^h$ represents —$NR^k$;

wherein $R^k$ represents hydrogen or methyl; and $R^i$ represents hydrogen or methyl;

or a stereoisomer of said compound, or a salt of said compound or stereoisomer.

8. A composition for treating a mammal afflicted with a tumor comprising an effective amount therefor of a compound according to any one of claims 1–7 and a pharmaceutically acceptable carrier.

9. A method of treating a mammal afflicted with a tumor comprising administering to said mammal an effective amount therefor of a compound according to any one of claims 1–7.

* * * * *